US008058050B2

(12) United States Patent
Calvert et al.

(10) Patent No.: US 8,058,050 B2

(45) **Date of Patent: *Nov. 15, 2011**

(54) CELLULAR PERMISSIVITY FACTOR FOR VIRUSES AND USES THEREOF

(75) Inventors: Jay Gregory Calvert, Otsego, MI (US); Shelly Shields, Plainwell, MI (US); David E Slade, Portage, MI (US); Siao-Kun Welch, Kalamazoo, MI (US)

(73) Assignee: Pharmacia and Upjohn Company LLC, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/775,283

(22) Filed: May 6, 2010

(65) Prior Publication Data

US 2010/0273238 A1 Oct. 28, 2010

Related U.S. Application Data

(63) Continuation of application No. 11/113,751, filed on Apr. 25, 2005, now Pat. No. 7,754,464.

(60) Provisional application No. 60/565,214, filed on Apr. 23, 2004, provisional application No. 60/634,736, filed on Dec. 9, 2004.

(51) Int. Cl.
*C12N 7/00* (2006.01)
*A61K 39/12* (2006.01)

(52) U.S. Cl. .................... 435/239; 435/69.1; 435/235.1; 424/204.1

(58) Field of Classification Search ........................ None
See application file for complete search history.

(56) References Cited

U.S. PATENT DOCUMENTS

| | | | | |
|---|---|---|---|---|
| 4,366,241 | A | 12/1982 | Tom et al. | 435/7 |
| 4,376,110 | A | 3/1983 | David et al. | 436/513 |
| 4,517,288 | A | 5/1985 | Giegel et al. | 435/7 |
| 4,837,168 | A | 6/1989 | deJaeger et al. | 436/533 |
| 5,118,937 | A | 6/1992 | Hillenkamp et al. | 250/282 |
| 5,514,545 | A | 5/1996 | Eberwine | 435/6 |
| 5,591,645 | A | 1/1997 | Rosenstein | 436/514 |
| 5,622,871 | A | 4/1997 | May et al. | 436/514 |
| 5,698,203 | A | 12/1997 | Visser et al. | 424/218.1 |
| 5,719,060 | A | 2/1998 | Hutchens et al. | 436/174 |
| 5,840,563 | A | 11/1998 | Chladek et al. | 435/235.1 |
| 2003/0186236 | A1 | 10/2003 | Kapil et al. | 435/6 |

FOREIGN PATENT DOCUMENTS

| | | |
|---|---|---|
| EP | A-0367566 | 5/1997 |
| WO | WO 91/09955 | 7/1991 |
| WO | WO 91/18982 | 12/1991 |
| WO | WO 92/20808 | 11/1992 |
| WO | WO 94/12650 | 6/1994 |
| WO | WO95/35505 | 12/1995 |
| WO | WO03/010200 | 2/2003 |

OTHER PUBLICATIONS

Result 3 (sequence search comparison) SEQ ID# 2 v M130 antigen precursor from Law et al. Eu. J. Immun. vol. 23, pp. 2320-2325, date 1993.*
Asai, ed., Methods in Cell Biology vol. 37: Antibodies in Cell Biology,. Academic Press, Inc. New York (1993).
Ausubel et al., supra, [e.g., Chapter 11], 1993.
Ausubel et al., eds., Current Protocols in Molecular Biology, Section 10.11.8, John Wiley & Sons, New York , 1993.
Ausubel, et al. (Eds.), Protocols in Molecular Biology, John Wiley & Sons (1994), pp. 6.0.3 to 6.4.10.
Bolton and Hunter, Biochem. J. 133, 529 (1973).
Cole et al., p. 77-96 in Monoclonal Antibodies and Cancer Therapy, Alan R. Liss, Inc. (1985).
Cosman et al. *Mol. Immunol*. 23:935 (1986).
Cosman et al. *Nature* 312:768 (1984).
Creighton,T. E., Proteins-Structure and Molecular Properties, 2nd Ed., W. H. Freeman and Company, New York, 1993.
Dea,S., Gagnon,C.A., Mardassi,H., Pirzadeh,B., and Rogan,D. (2000). Arch. Virol. 145, 659-688.
Delputte,P.L., Vanderheijden,N., Nauwynck,H.J., and Pensaert,M.B. (2002). J. Virol. 76, 4312-4320.
Duan,X., Nauwynck,H.J., and Pensaert,M.B. (1997a). Arch. Virol. 142, 2483-2497.
Duan,X., Nauwynck,H.J., and Pensaert,M.B. (1997b). Vet. Microbiol. 56, 9-19.
Duan,X.B., Nauwynck,H.J., Favoreel,H.W., and Pensaert,M.B. (1998). J. Virol. 72, 4520-4523.
Erlich, H. A. ed., PCR Technology, Stockton Press, New York, 1989; PCR Protocols: A Guide to Methods and Applications, M. A. Innis, David H. Gelfand, John J. Sninsky, and Thomas J. White, eds., Academic Press, Inc., New York, 1990.
Evan et al., Molecular and CellularBiology, 5:3610-3616 (1985).
Field et al., Mol. Cell. Biol., 8:2159-2165 (1988).
Graversen,J.H., Madsen,M., and Moestrap,S.K. (2002). International Journal of Biochemistry & Cell Biology 34, 309-314.
Gronlund J. Vitved L. Lausen M. Skjodt K. Holmskov U. Journal of Immunology 165(11):6406-6415, 2000.
Harlow et al. (Eds), Antibodies a Laboratory Manual; Cold Spring Harbor Laboratory; Cold Spring Harbor, NY (1988), Chapter 6.
Harlow and Lane, supra [e.g., Chapter 14], 1988.
Henikoff and Henikoff (Proc. Nat. Acad. Sci. USA 89:10915-10919. 1992).
Hopp et al., BioTechnology, 6:1204-1210 (1988).
Kim,H.S., Kwang,J., Yoon,I.J., Joo,H.S., and Frey,M.L. (1993). Arch. Virol. 133, 477-483.
Kohler, G. and Milstein, C., Nature 256: 495-497 (1975).
Kozbor et al., Immunology Today 4: 72 (1983).
Kreutz,L.C. (1998). Virus Res. 53, 121-128.
Kreutz,L.C. and Ackermann,M.R. (1996). Virus Res. 42, 137-147.

(Continued)

*Primary Examiner* — Mary E Mosher
*Assistant Examiner* — Myron G Hill
(74) *Attorney, Agent, or Firm* — Brandon Boss; Michael J. Moran; E. Victor Donahue

(57) ABSTRACT

The present invention provides methods and compositions related to the generation of host cells permissive for virus growth, particularly Porcine Reproductive and Respiratory Syndrome (PRRS) virus.

13 Claims, 24 Drawing Sheets

OTHER PUBLICATIONS

Law, S.K., Micklem, K.J., Shaw, J.M., Zhang, X.P., Doug, Y., Willis, A.C. and Mason, D.Y. (1993), European Journal of Immunology 23 (9), 2320-2325).
Lutz-Freyermuth et al., Proc. Natl. Acad. Sci. USA, 87:6393-6397(1990).
Maddox et al., 1983, J. Exp. Med., 158:1211.
Martin et al., Science, 255:192-194 (1992).
Mengeling,W.L. and Lager,K.M. (2000). Veterinary Research 31, 61-69.
Meulenberg,J.J.M. (2000). PRRSV, the virus. Veterinary Research 31, 11-21.
Murtaugh,M.P., Xiao,Z.G., and Zuckermann,F. (2002). Viral Immunology 15, 533-547.
Morrison, Methods in Enzymology 32b, 103 (1974).
Nauwynck,H.J., Duan,X., Favoreel,H.W., Van Oostveldt,P., and Pensaert,M.B. (1999). J. Gen. Virol. 80, 297-305.
Nodelijk,G. (2002). Vet. Quart. 24, 95-100.
Okayama and Berg (*Mol. Cell. Biol.* 3:280 (1983).
Paborsky et al., Protein Engineering, 3(6):547-553(1990).
Philippidis,P., Mason,J.C., Evans,B.J., Nadra,I., Taylor,K.M., Haskard,D.O., and Landis,R.C. (2004). Circulation Research 94, 119-126.
Plagemann,P.G.W. (2003). Emerging Infectious Diseases 9, 903-908.
Rattan Et al., Ann NY Acad Sci (1992) 663:4842).
Ritter,M., Buechler,C., Langmann,T., and Schmitz,G. (1999). Biochemical & Biophysical Research Communications 260, 466-474.
Sambrook, et al., (Eds.), Molecular Cloning: A Laboratory Manual, Cold Spring Harbor Laboratory Press: Cold Spring Harbor, New York (1989), pp. 9.47 to 9.51.
Sanchez-Torres,C., Gomez-Puertas,P., Gomez-del-Moral,M., Alonso,F., Escribano,J.M., Ezquerra,A., and Dominguez,J. (2003). Arch. Virol. 148, 2307-2323.
Seifter et al., Meth Enzymol (1990) 182:626-646.
Shanmukhappa,K. and Kapil,S. (2001). Adv. Exp. Med. Biol. 494, 641-646.
Skinner et al.,J. Biol. Chem., 266:15163-15166 (1991).
Snijder,E.J. and Meulenberg,J.J.M. (2001). Arteriviruses. In Fields Virology, D.M.Knipe, P.M.Howley, D.E.Griffin, M.A.Martin, R.A. Lamb, B.Roizman, and S.E.Straus, eds. (Philadelphia: Lippincott Williams & Wilkins), pp. 1205-1220.
Stites & Terr, eds. Basic and Clinical Immunology 7th Edition, (1991).
Syvanen et al., J. Biol. Chem. 284, 3762 (1973).
Tatusova TA and TL Madden, (1999) FEMS Microbiol Lett. 174:247-250.
Therrien,D., St Pierre,Y., and Dea,S. (2000). Arch. Virol. 145, 1099-1116.
Vanderheijden,N., Delputte,P.L., Favoreel,H.W., Vandekerckhove,J., Van Damme,J., van Woensel,P.A., and Nauwynck,H.J. (2003). J. Virol. 77, 8207-8215.
Weingartl,H.M., Sabara,M., Pasick,J., van Moorlehem,E., and Babiuk,L. (2002). J. Virol. Methods 104, 203-216.
Wissink,E.H.J., van Wijk,H.A.R., Pol,J.M.A., Godeke,G.J., van Rijn,P.A., Rottier,P.J.M., and Meulenberg,J.J.M. (2003). Arch. Virol. 148, 177-187.
Wold, F., Post-translational Protein Modifications: Perspectives and Prospects, pp. 1-12 in Postranslational Covalent Modification of Proteins, B. C. Johnson, Ed., Academic Press, New York, 1983.
AAH51281; Genbank Jun. 30, 2004.
AF274883; Genbank May 10, 2001.
AJ311716; Genbank Apr. 15, 2001.
BC051281; Genbank Jun. 30, 2004.
CAA80543; Genbank Apr. 18, 2005.
M96262; Genbank Nov. 8, 2000.
U87392; Genbank Nov. 17, 2000.
Z22968; Genbank Apr. 18, 2005.
Z22969; Genbank Apr. 18, 2005.
Bautista et al. Archives in Virology, 1999, vol. 144, pp. 117-134.
Lopez-Fuertes et al. Veterinary Research, 2000, vol. 31, pp. 42-43.
Frings et al. FEBS Letters, 2002, vol. 526, pp. 93-96.
Kristiansen et al. Nature, Jan. 2001, vol. 409, pp. 198-201.
Sanchez et al. The Journal of Immunology, 1999, vol. 162, pp. 5230-5237.
Seuberlich et al., Nucleocapsid Protein-Based Enzyme-Linked Immunosorbent Assay for Dection and Differentiation of Antibodies against European and North American Porcine Reproductive and Respiratory Syndrome Virus Clinical and Diagnostic Laboratory Immunology, 9(6): 1183-1191, 2002.

* cited by examiner

CD163
d1
67 bp
3333 bp
AAA
44 adenosines
235 bp
2568 bp
738 bp deletion
27 bp
15 bp extension
41 bp

Figure 2A

```
                    1                                                          60
AJ311716(porcine)   .....MVLLEDSGSADFRRCSAHLSSFTFAVVAVLSACLVTSSLGGKDKELRLTGGENKC
Pfizer_susCD163v1   MDKLRMVLHENSGSAD............................................

                    61                                                        120
AJ311716(porcine)   SGRVEVKVQEEWGTVCNNGWDMDVVSVVCRQLGCPTAIKATGWANFSAGSGRIWMDHVSC
Pfizer_susCD163v1   ............................................................

                    121                                                       180
AJ311716(porcine)   RGNESALWDCKHDGWGKHNCTHQQDAGVTCSDGSDLEMRLVNGGNRCLGRIEVKFQERWG
Pfizer_susCD163v1   ............................................................

                    181                                                       240
AJ311716(porcine)   TVCDDNFNINHASVVCKQLECGSAVSFSGSANFGEGSGPIWFDDLVCNGNESALWNCKHE
Pfizer_susCD163v1   ............................................................

                    241                                                       300
AJ311716(porcine)   GWGKHNCDHAEDAGVICLNGADLKLRVVDGLTECSGRLEVKFQGEWGTICDDGWDSDDAA
Pfizer_susCD163v1   ......................LKLRVVDGVTECSGRLEVKFQGEWGTICDDGWDSDDAA

                    301                                                       360
AJ311716(porcine)   VACKQLGCPTAVTAIGRVNASEGTGHIWLDSVSCHGHESALWQCRHHEWGKHYCNHNEDA
Pfizer_susCD163v1   VACKQLGCPTAVTAIGRVNASEGTGHIWLDSVSCHGHESALWQCRHHEWGKHYCNHNEDA

                    361                                                       420
AJ311716(porcine)   GVTCSDGSDLELRLKGGGSHCAGTVEVEIQKLVGKVCDRSWGLKEADVVCRQLGCGSALK
Pfizer_susCD163v1   GVTCSDGSDLELRLKGGGSHCAGTVEVEIQKLVGKVCDRSWGLKEADVVCRQLGCGSALK

                    421                                                       480
AJ311716(porcine)   TSYQVYSKTKATNTWLFVSSCNGNETSLWDCKNWQWGGLSCDHYDEAKITCSAHRKPRLV
Pfizer_susCD163v1   TSYQVYSKTKATNTWLFVSSCNGNETSLWDCKNWQWGGLSCDHYDEAKITCSAHRKPRLV

                    481                                                       540
AJ311716(porcine)   GGDIPCSGRVEVQHGDTWGTVCDSDFSLEAASVLCRELQCGTVVSLLGGAHFGEGSGQIW
Pfizer_susCD163v1   GGDIPCSGRVEVQHGDTWGTVCDSDFSLEAASVLCRELQCGTVVSLLGGAHFGEGSGQIW
```

Figure 2B

```
                    541                                                        600
AJ311716(porcine)   AEEFQCEGHESHLSLCPVAPRPDGTCSHSRDVGVVCSRYTQIRLVNGKTPCEGRVELNIL
Pfizer_susCD163v1   AEEFQCEGHESHLSLCPVAPRPDGTCSHSRDVGVVCSRYTQIRLVNGKTPCEGRVELNIL

                    601                                                        660
AJ311716(porcine)   GSWGSLCNSHWDMEDAHVLCQQLKCGVALSIPGGAPFGKGSEQVWRHMFHCTGTEKHMGD
Pfizer_susCD163v1   GSWGSLCNSHWDMEDAHVLCQQLKCGVALSIPGGAPFGKGSEQVWRHMFHCTGTEKHMGD

                    661                                                        720
AJ311716(porcine)   CSVTALGASLCSSGQVASVICSGNQSQTLSPCNSSSSDPSSSIISEESGVACIGSGQLRL
Pfizer_susCD163v1   CSVTALGASLCSSGQVASVICSGNQSQTLSPCNSSSSDPSSSIISEENGVACIGSGQLRL

                    721                                                        780
AJ311716(porcine)   VDGGGRCAGRVEVYPGASWGTICDDSWDLNDAHVVCKQLSCGWAINATGSAHFGEGTGPI
Pfizer_susCD163v1   VDGGGRCAGRVEVYHEGSWGTICDDSWDLNDAHVVCKQLSCGWAINATGSAHFGEGTGPI
                    781                                                        840
AJ311716(porcine)   WLDEINCNGKESHIWQCHSHGWGRHNCRHKEDAGVICSEFMSLRLISENSRETCAGRLEV
Pfizer_susCD163v1   WLDEINCNGKESHIWQCHSHGWGRHNCRHKEDAGVICSEFMSLRLISENSRETCAGRLEV

                    841                                                        900
AJ311716(porcine)   FYNGAWGSVGRNSMSPATVGVVCRQLGCADRGDISPASSDKTVSRHMWVDNVQCPKGPDT
Pfizer_susCD163v1   FYNGAWGSVGKNSMSPATVGVVCRQLGCADRGDISPASSDKTVSRHMWVDNVQCPKGPDT

                    901                                                        960
AJ311716(porcine)   LWQCPSSPWKKRLASPSEETWITCANKIRLQEGNTNCSGRVEIWYGGSWGTVCDDSWDLE
Pfizer_susCD163v1   LWQCPSSPWKKRLASPSEETWITCANKIRLQEGNTNCSGRVEIWYGGSWGTVCDDSWDLE

                    961                                                       1020
AJ311716(porcine)   DAQVVCRQLGCGSALEAGKEPAFGQGTGPIWLNEVKCKGNEPSLWDCPARSWGHSDCGHK
Pfizer_susCD163v1   DAQVVCRQLGCGSALEAGKEAAFGQGTGPIWLNEVKCKGNETSLWDCPARSWGHSDCGHK

                    1021                                                        1080
AJ311716(porcine)   EDAAVTCSEIAKSRESLHATGRSSFVALAIFGVILLACLIAFLIWTQKRRQRQRLSVFSG
Pfizer_susCD163v1   EDAAVTCSEIAKSRESLHATGRSSFVALAIFGVILLACLIAFLIWTQKRRQRQRLSVFSG

                    1081                                  1116
AJ311716(porcine)   GENSVHQIQYREMNSCLKADETDMLNPSGDHSEVQ.
Pfizer_susCD163v1   GENSVHQIQYREMNSCLKADETDMLNPSGDHSEVQ.
```

Figure 3A

```
Martinez/Needleman-Wunsch DNA Alignment
Minimum Match: 9; Gap Penalty: 1.10; Gap Length Penalty: 0.33

Genbank AJ311716 porcine CD163 cDNA       --------------------------------------------------------
Insert from plasmid pSport-susCD163d1     GTAATAATACAAGAAGATTTAAATGGGCATAAAACCTTGGAATGGACAAACTCAGA

ATGGTGCTACTTGAAGACTCTGGATCTGCAGACTTTAGAAGATGTTCTGCCCATTTAAGTTCCTTCACTTTTGCTGTAGTCGCTGTTCTCAGTGCCTGCT
ATGGTGCTACATGAAAACTCTGGATCT-------------------------------------------------------------------------

TGGTCACTAGTTCTCTTGGAGGAAAAGACAAGGAGCTGAGGCTAACGGGTGGTGAAAACAAGTGCTCTGGAAGAGTGGAGGTGAAAGTGCAGGAGGAGTG
----------------------------------------------------------------------------------------------------

GGGAACTGTGTGTAATAATGGCTGGGACATGGATGTGGTCTCTGTTGTTTGTAGGCAGCTGGGATGTCCAACTGCTATCAAAGCCACTGGATGGGCTAAT
----------------------------------------------------------------------------------------------------

TTTAGTGCAGGTTCTGGACGCATTTGGATGGATCATGTTTCTTGTCGAGGGAATGAGTCAGCTCTCTGGGACTGCAAACATGATGGATGGGGAAAGCATA
----------------------------------------------------------------------------------------------------

ACTGTACTCACCAACAGGATGCTGGAGTAACCTGCTCAGATGGATCTGATTTAGAGATGAGGCTGGTGAATGGAGGAAACCGGTGCTTAGGAAGAATAGA
----------------------------------------------------------------------------------------------------

AGTCAAATTTCAAGAGCGGTGGGGAACAGTGTGTGATGATAACTTCAACATAAATCATGCTTCTGTGGTTTGTAAACAACTTGAATGTGGAAGTGCTGTC
----------------------------------------------------------------------------------------------------

AGTTTCTCTGGTTCAGCTAATTTTGGAGAAGGTTCTGGACCAATCTGGTTTGATGATCTTGTATGCAATGGAAATGAGTCAGCTCTCTGGAACTGCAAAC
----------------------------------------------------------------------------------------------------

ATGAAGGATGGGGAAAGCACAATTGCGATCATGCTGAGGATGCTGGAGTGATTTGCTTAAATGGAGCAGACCTGAAACTGAGAGTGGTAGATGGACTCAC
-----------------------------------------------------------------GCAGACCTGAAACTGAGAGTGGTAGATGGAGTCAC

TGAATGTTCAGGAAGATTGGAAGTGAAATTCCAAGGAGAATGGGGAACAATCTGTGATGATGGCTGGGATAGTGATGATGCCGCTGTGGCATGTAAGCAA
TGAATGTTCAGGAAGATTGGAAGTGAAATTCCAAGGAGAATGGGGAACAATCTGTGATGATGGCTGGGATAGTGATGATGCCGCTGTGGCATGTAAGCAA

CTGGGATGTCCAACTGCTGTCACTGCCATTGGTCGAGTTAACGCCAGTGAGGGAACTGGACACATTTGGCTTGACAGTGTTTCTTGCCATGGACACGAGT
CTGGGATGTCCAACTGCTGTCACTGCCATTGGTCGAGTTAACGCCAGTGAGGGAACTGGACACATTTGGCTTGACAGTGTTTCTTGCCATGGACACGAGT

CTGCTCTCTGGCAGTGTAGACACCATGAATGGGGAAAGCATTATTGCAATCATAATGAAGATGCTGGTGTGACATGTTCTGATGGATCAGATCTGGAACT
CTGCTCTCTGGCAGTGTAGACACCATGAATGGGGAAAGCATTATTGCAATCATAATGAAGATGCTGGTGTGACATGTTCTGATGGATCAGATCTGGAACT
```

Figure 3B

```
GAGACTTAAAGGTGGAGGCAGCCACTGTGCTGGGACAGTGGAGGTGGAAATTCAGAAACTGGTAGGAAAAGTGTGTGATAGAAGCTGGGGACTGAAAGAA
GAGACTTAAAGGTGGAGGCAGCCACTGTGCTGGGACAGTGGAGGTGGAAATTCAGAAACTGGTAGGAAAAGTGTGTGATAGAAGCTGGGGACTGAAAGAA

GCTGATGTGGTTTGCAGGCAGCTGGGATGTGGATCTGCACTCAAAACATCATATCAAGTTTATTCCAAAACCAAGGCAACAAACACATGGCTGTTTGTAA
GCTGATGTGGTTTGCAGGCAGCTGGGATGTGGATCTGCACTCAAAACATCATATCAAGTTTATTCCAAAACCAAGGCAACAAACACATGGCTGTTTGTAA

GCAGCTGTAATGGAAATGAAACTTCTCTTTGGGACTGCAAGAATTGGCAGTGGGGTGGACTTAGTTGTGATCACTATGACGAAGCCAAAATTACCTGCTC
GCAGCTGTAATGGAAATGAAACTTCTCTTTGGGACTGCAAGAATTGGCAGTGGGGTGGACTTAGTTGTGATCACTATGACGAAGCCAAAATTACCTGCTC

AGCCCACAGGAAACCCAGGCTGGTTGGAGGGGACATTCCCTGCTCTGGTCGTGTTGAAGTACAACATGGAGACACGTGGGGCACCGTCTGTGATTCTGAC
AGCCCACAGGAAACCCAGGCTGGTTGGAGGGGACATTCCCTGCTCTGGTCGTGTTGAAGTACAACATGGAGACACGTGGGGCACCGTCTGTGATTCTGAC

TTCTCTCTGGAGGCGGCCAGCGTGCTGTGCAGGGAACTACAGTGCGGCACTGTGGTTTCCCTCCTGGGGGGAGCTCACTTTGGAGAAGGAAGTGGACAGA
TTCTCTCTGGAGGCGGCCAGCGTGCTGTGCAGGGAACTACAGTGCGGCACTGTGGTTTCCCTCCTGGGGGGAGCTCACTTTGGAGAAGGAAGTGGACAGA

TCTGGGCTGAAGAATTCCAGTGTGAGGGGCACGAGTCCCACCTTTCACTCTGCCCAGTAGCACCCCGCCCTGACGGGACATGTAGCCACAGCAGGGACGT
TCTGGGCTGAAGAATTCCAGTGTGAGGGGCACGAGTCCCACCTTTCACTCTGCCCAGTAGCACCCCGCCCTGACGGGACATGTAGCCACAGCAGGGACGT

CGGCGTAGTCTGCTCAAGATACACACAAATCCGCTTGGTGAATGGCAAGACCCCATGTGAAGGAAGAGTGGAGCTCAACATTCTTGGGTCCTGGGGGTCC
CGGCGTAGTCTGCTCAAGATACACACAAATCCGCTTGGTGAATGGCAAGACCCCATGTGAAGGAAGAGTGGAGCTCAACATTCTTGGGTCCTGGGGGTCC

CTCTGCAACTCTCACTGGGACATGGAAGATGCCCATGTTTTATGCCAGCAGCTTAAATGTGGAGTTGCCCTTTCTATCCCGGGAGGAGCACCTTTTGGGA
CTCTGCAACTCTCACTGGGACATGGAAGATGCCCATGTTTTATGCCAGCAGCTTAAATGTGGAGTTGCCCTTTCTATCCCGGGAGGAGCACCTTTTGGGA

AAGGAAGTGAGCAGGTCTGGAGGCACATGTTTCACTGCACTGGGACTGAGAAGCACATGGGAGATTGTTCCGTCACTGCTCTGGGCGCATCACTCTGTTC
AAGGAAGTGAGCAGGTCTGGAGGCACATGTTTCACTGCACTGGGACTGAGAAGCACATGGGAGATTGTTCCGTCACTGCTCTGGGCGCATCACTCTGTTC

TTCAGGGCAAGTGGCCTCTGTAATCTGCTCAGGGAACCAGAGTCAGACACTATCCCCGTGCAATTCATCATCCTCGGACCCATCAAGCTCTATTATTTCA
TTCAGGGCAAGTGGCCTCTGTAATCTGCTCAGGGAACCAGAGTCAGACACTATCCCCGTGCAATTCATCATCCTCGGACCCATCAAGCTCTATTATTTCA

GAAGAAAGTGGTGTTGCCTGCATAGGGAGTGGTCAACTTCGCCTGGTCGATGGAGGTGGTCGTTGTGCTGGGAGAGTAGAGGTCTATCCTGGGGCATCCT
GAAGAAAATGGTGTTGCCTGCATAGGGAGTGGTCAACTTCGCCTGGTCGATGGAGGTGGTCGTTGTGCTGGGAGAGTAGAGGTCTATCATGAGGGCTCCT

GGGGCACCATCTGTGATGACAGCTGGGACCTGAATGATGCCCATGTGGTGTGCAAACAGCTGAGCTGTGGATGGGCCATTAATGCCACTGGTTCTGCTCA
GGGGCACCATCTGTGATGACAGCTGGGACCTGAATGATGCCCATGTGGTGTGCAAACAGCTGAGCTGTGGATGGGCCATTAATGCCACTGGTTCTGCTCA

TTTTGGGGAAGGAACAGGGCCCATTTGGCTGGATGAGATAAACTGTAATGGAAAAGAATCTCATATTTGGCAATGCCACTCACATGGTTGGGGGCGGCAC
TTTTGGGGAAGGAACAGGGCCCATTTGGCTGGATGAGATAAACTGTAATGGAAAAGAATCTCATATTTGGCAATGCCACTCACATGGTTGGGGGCGGCAC
```

Figure 3C

```
AATTGCAGGCATAAGGAGGATGCAGGAGTCATCTGCTCAGAGTTCATGTCTCTGAGACTGATCAGTGAAAACAGCAGAGAGACCTGTGCAGGGCGCCTGG
AATTGCAGGCATAAGGAGGATGCAGGAGTCATCTGCTCGGAGTTCATGTCTCTCAGACTGATCAGTGAAAACAGCAGAGAGACCTGTGCAGGGCGCCTGG

AAGTTTTTTACAACGGAGCTTGGGGCAGCGTTGGCAGGAATAGCATGTCTCCAGCCACAGTGGGGGTGGTATGCAGGCAGCTGGGCTGTGCAGACAGAGG
AAGTTTTTTACAACGGAGCTTGGGGCAGCGTTGGCAAGAATAGCATGTCTCCAGCCACAGTGGGGGTGGTATGCAGGCAGCTGGGCTGTGCAGACAGAGG

GGACATCAGCCCTGCATCTTCAGACAAGACAGTGTCCAGGCACATGTGGGTGGACAATGTTCAGTGTCCTAAAGGACCTGACACACTATGGCAGTGCCCC
GGACATCAGCCCTGCATCTTCAGACAAGACAGTGTCCAGGCACATGTGGGTGGACAATGTTCAGTGTCCTAAAGGACCTGACACGCTATGGCAGTGCCCA

TCATCTCCATGGAAGAAGAGACTGGCCAGCCCCTCAGAGGAGACATGGATCACATGTGCCAACAAAATAAGACTTCAAGAAGGAAACACTAATTGTTCTG
TCATCTCCATGGAAGAAGAGACTGGCCAGCCCCTCAGAGGAGACATGGATCACATGTGCCAACAAAATAAGACTTCAAGAAGGAAACACTAATTGTTCTG

GACGTGTGGAGATCTGGTACGGAGGTTCCTGGGGCACTGTGTGTGACGACTCCTGGGACCTTGAAGATGCTCAGGTGGTGTGCCGACAGCTGGGCTGTGG
GACGTGTGGAGATCTGGTACGGAGGTTCCTGGGGCACTGTGTGTGACGACTCCTGGGACCTTGAAGATGCTCAGGTGGTGTGCCGACAGCTGGGCTGTGG

CTCAGCTTTGGAGGCAGGAAAAGAGCCCGCATTTGGCCAGGGGACTGGGCCCATATGGCTCAATGAAGTGAAGTGCAAGGGGAATGAACCCTCCTTGTGG
CTCAGCTTTGGAGGCAGGAAAAGAGGCCGCATTTGGCCAGGGGACTGGGCCCATATGGCTCAATGAAGTGAAGTGCAAGGGGAATGAAACCTCCTTGTGG

GATTGTCCTGCCAGATCCTGGGGCCACAGTGACTGTGGACACAAGGAGGATGCTGCTGTGACGTGCTCAGAAATTGCAAAGAGCCGAGAATCCCTACATG
GATTGTCCTGCCAGATCCTGGGGCCACAGTGACTGTGGACACAAGGAGGATGCTGCTGTGACGTGTTCAGAAATTGCAAAGAGCCGAGAATCCCTACATG

CCACAGGTCGCTCATCTTTTGTTGCACTTGCAATCTTTGGGGTCATTCTGTTGGCCTGTCTCATCGCATTCCTCATTTGGACTCAGAAGCGAAGACAGAG
CCACAGGTCGCTCATCTTTTGTTGCACTTGCAATCTTTGGGGTCATTCTGTTGGCCTGTCTCATCGCATTCCTCATTTGGACTCAGAAGCGAAGACAGAG

GCAGCGGCTCTCAGTTTTCTCAGGAGGAGAGAATTCTGTCCATCAAATTCAATACCGGGAGATGAATTCTTGCCTGAAAGCAGATGAAACGGATATGCTA
GCAGCGGCTCTCAGTTTTCTCAGGAGGAGAGAATTCTGTCCATCAAATTCAATACCGGGAGATGAATTCTTGCCTGAAAGCAGATGAAACGGATATGCTA

AATCCCTCAGGAGACCACTCTGAAGTACAATGAAAAGGAAAATGGGAATTATAACCTGGTGAGTTCAGCCTTTAAGATACCTTGATGAAGACCTGGACTA
AATCCCTCAGGAGACCACTCTGAAGTACAATGAAAAGGAAAATGGGAATTATAACCTGGTGAGTTCAGCCTTTAAGATACCTTGATGAAGACCTGGACTA

----------------------------------------------------------------------------------------------------
TTGAATGAGCAAGAATCTGCCTCTTACACTGAAGATTACAATACAGTCCTCTGTCTCCTGGTATTCCAAAGACTGCTGTTGAATTTCTAAAAAaTAGATT

----------------------------------------------------------------------------------------------------
GGTGAATGTGACTACTCAAAGTTGTATGTAAGACTTTCAAGGGCATTAAATAAAAAAGAATATTGCTGAAAAAAAAAAAAAAAAAAAAAAAAAAAAAAAA

------------
AAAAAAAAAAAA
```

Figure 14

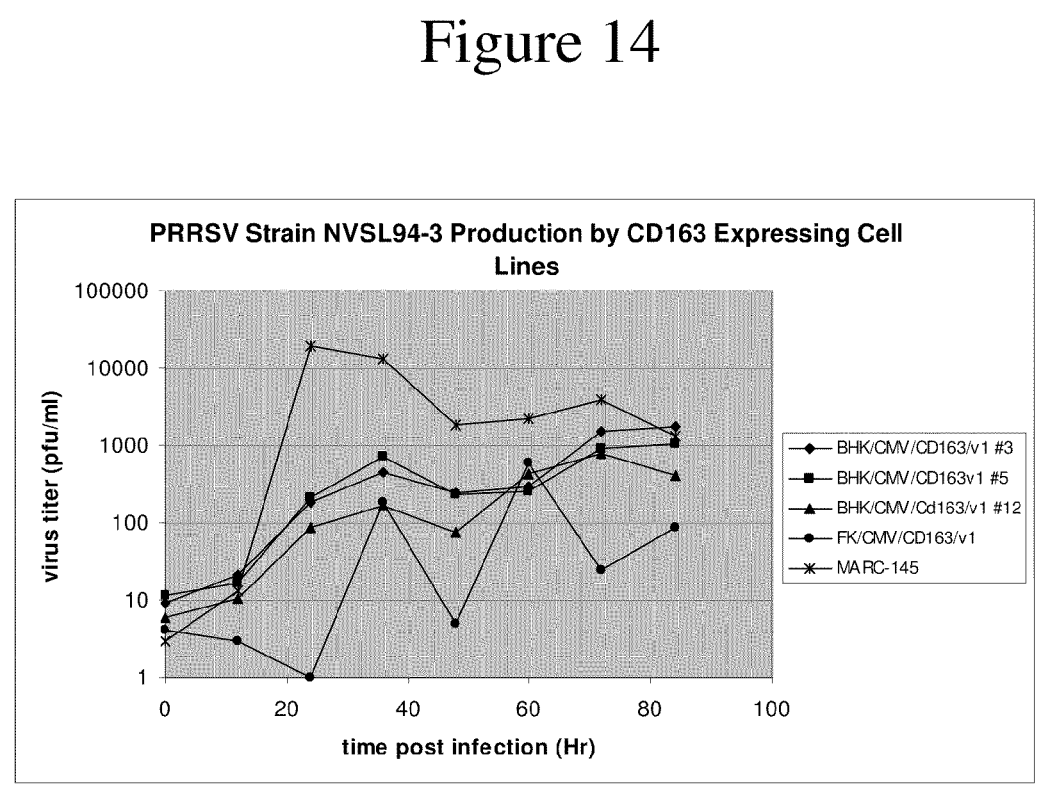

PRRSV Strain NVSL94-3 Production by CD163 Expressing Cell Lines virus titer (pfu/ml): 1, 10, 100, 1000, 10000, 100000 time post infection (Hr): 0, 20, 40, 60, 80, 100

BHK/CMV/CD163/v1 #3
BHK/CMV/CD163v1 #5
BHK/CMV/Cd163/v1 #12
FK/CMV/CD163/v1
MARC-145

Figure 15

Inhibition of PRRSV infection by anti-CD163 antibody

% infected

Micrograms IgG

CD163

NGS 0 1 2 3 4 5

Inhibition of PRRSV infection by anti-CD163 antibody

% infected

Micrograms IgG

CD163

NGS 0 1 2 3 4

0 2 4 6 8 10 12

CELLULAR PERMISSIVITY FACTOR FOR VIRUSES AND USES THEREOF

CROSS REFERENCE TO RELATED APPLICATIONS

The present application is a continuation of U.S. Ser. No. 11/113,751, filed Apr. 25, 2005, now U.S. Pat. No. 7,754,464, and claims benefit of U.S. Provisional Patent Application Ser. Nos. 60/565,214, filed Apr. 23, 2004, and 60/634,736, filed Dec. 9, 2004. The complete disclosure of the Ser. No. 11/113,751 parent application is incorporated by reference herein, as if fully set forth.

FIELD OF THE INVENTION

The present invention provides methods and compositions related to the generation of host cells permissive for virus growth for viruses of the family Asfarviridae and Arteriviridae.

BACKGROUND OF THE INVENTION

Asfarviridae

Asfarviridae is a family of icosohedral enveloped viruses whose genome consists of a single molecule of linear double-stranded DNA of about 150000-190000 nucleotides long. The name of the family is derived from African Swine Fever And Releted Viruses. African Swine Fever Virus (ASFV) is the type species of the Asfivirus genus and is the sole member of the family. Recently, porcine CD163 polypeptide has been surmised by implication to be the cellular receptor for African swine fever virus (ASFV) (Sanchez-Tones et al., 2003)

Arteriviridae

Viruses of the family of Arteriviridae includes equine arteritis virus (EAV), lactate dehydrogenase-elevating virus (LDV) and simian hemorrhagic fever virus (SHFV). The Arterivirus having the greatest economic importance is Porcine Reproductive and Respiratory Syndrome Virus (PRRSV).

PRRSV

Porcine Reproductive and Respiratory Syndrome (PRRS) is one of the most economically important diseases of swine. The syndrome appeared almost simultaneously in North America and in Western Europe in the late 1980s, and has since spread to become endemic in the major swine producing nations of Europe, Asia, and the Americas. The etiologic agent of PRRS is a virus that has been designated PRRS virus or PRRSV. For both European and North American PRRS, the disease is characterized by reproductive failure in sows and gilts (late term abortions, still births, and mummies), high mortality among nursery pigs, and respiratory disease in swine of all ages. The disease has been the subject of recent reviews (Mengeling and Lager, 2000; Murtaugh et al., 2002; Nodelijk, 2002; Plagemann, 2003).

In the pig, PRRSV infection is limited to a subset of cells of the monocyte/macrophage lineage. Fully differentiated porcine alveolar macrophage (PAM) cells are the primary target cells for viral replication (Duan et al., 1997a; Duan et al., 1997b). Immortalization of PAM cells is technically challenging, and when successful, has resulted in cell lines that are not permissive for PRRS virus growth (Weingartl et al., 2002). PRRS virions are specifically bound by macrophages and internalized in clathrin-coated pits by endocytosis. Release from endocytic vesicles requires acidic pH (Nauwynck et al., 1999). Initial binding of virions is mediated by interaction of the viral matrix protein with heparin sulfate glycosaminoglycans (Delputte et al., 2002). Internalization can be facilitated by a 210 or 220 kDa membrane glycoprotein, as incubation of PAM cells with monoclonal antibodies to this polypeptide blocks infection with PRRS virus (Duan et al., 1998; Wissink et al., 2003). The 210 kDa glycoprotein has recently been identified as sialoadhesin, a member of siglec family of sialic acid binding immunoglobulin-like lectins (Pensaert et al., 2003). Transfection of the non-permissive PK-15 (porcine kidney) cell line with porcine sialoadhesin conferred the ability to internalize PRRSV particles, but there remained an apparent block at the uncoating stage, as virions entered into cellular vesicles but did not undergo nucleocapsid disintegration and vesicle membrane fusion. Viral genes were not expressed, and the transfected PK-15 cells were not rendered permissive for the PRRS virus (Vanderheijden et al., 2003). To our knowledge, transfection with sialoadhesin has not been shown to be sufficient to convert any PRRSV non-permissive cell line to a PRRSV-permissive phenotype.

Apart from primary porcine cells of the monocyte/macrophage lineage, the only other cell type known to be permissive for the growth of PRRSV in cell culture is the immortalized monkey kidney cell line MA-104 (Chladek et al., 1998) and derivatives such as MARC-145 (Kim et al., 1993) and CL-2621. It is not known why this one particular cell line is permissive, yet other mammalian cell lines are not. The PRRS virus binds specifically to a number of different cell types, but does not initiate infection (Kreutz, 1998; Therrien et al., 2000). In MARC-145 cells, the internalization of the virus by endocytosis and subsequent uncoating in low pH vesicles seems to mimic similar events in PAM cells (Kreutz and Ackermann, 1996). However, a number of monoclonal antibodies that bind to porcine sialoadhesin fail to detect a homologous protein on the surface of MARC-145 cells (Duan et al., 1998; Wissink et al., 2003), suggesting that MARC-145 cells may use a divergent member of the same protein family or a different receptor altogether.

Current PRRSV vaccines are propagated on simian cell lines, which is a potentially dangerous activity. The use of simian cell lines for vaccine production has the potential to introduce primate viruses of significance into swine lines intended for xenotransplant purposes. Because swine are being increasingly explored as a source of xenotransplanted organs for humans, the introduction of primate cell lines to swine populations may ultimately pose a risk to humans receiving xenotransplanted organs. Thus, it would be prudent to avoid the use of simian cell lines in swine vaccine preparations. It would be therefore desirable to identify or generate non-simian cells or cell lines capable of supporting PRRSV replication. Towards this goal, it is essential to identify the gene product(s) which may be responsible for conferring the permissivity for PRRSV replication as seen in certain simian cells lines as well as PAM cells. Once such gene products are identified, non-permissive cells might be rendered permissive by, for example, transfection of the essential gene into them, thereby affording a wider array of production lines for a vaccine.

One lab has reported that the tetraspanin protein CD151 from MARC-145 cells, when transfected into non-permissive BHK-21 cells, confers permissivity to the PRRS virus (Kapil and Shanmukhappa, 2003; Shanmukhappa and Kapil, 2001). This observation has yet to be confirmed by an independent lab.

We describe here an unrelated polypeptide, which when introduced into non-permissive cells, confers permissivity to the PRRS virus.

REFERENCES CITED

Chladek, D. W., Harris, L. L., and Gorcyca, D. E. Method of growing and attenuating a viral agent associated with mystery swine disease. Boehringer Ingelheim Animal Health, Inc. 677,585 [U.S. Pat. No. 5,840,563], 1-24. Nov. 24, 1998. USA. Jul. 9, 1996. Ref Type: Patent Dea, S., Gagnon, C. A., Mardassi, H., Pirzadeh, B., and Rogan, D. (2000). Current knowledge on the structural proteins of porcine reproductive and respiratory syndrome (PRRS) virus: comparison of the North American and European isolates [Review]. Arch. Virol. 145, 659-688.

Delputte, P. L., Vanderheijden, N., Nauwynck, H. J., and Pensaert, M. B. (2002). Involvement of the matrix protein in attachment of porcine reproductive and respiratory syndrome virus to a heparinlike receptor on porcine alveolar macrophages. J. Virol. 76, 4312-4320.

Duan, X., Nauwynck, H. J., and Pensaert, M. B. (1997a). Effects of origin and state of differentiation and activation of monocytes/macrophages on their susceptibility to porcine reproductive and respiratory syndrome virus (PRRSV). Arch. Virol. 142, 2483-2497.

Duan, X., Nauwynck, H. J., and Pensaert, M. B. (1997b). Virus quantification and identification of cellular targets in the lungs and lymphoid tissues of pigs at different time intervals after inoculation with porcine reproductive and respiratory syndrome virus (PRRSV). Vet. Microbiol. 56, 9-19.

Duan, X. B., Nauwynck, H. J., Favoreel, H. W., and Pensaert, M. B. (1998). Identification of a putative receptor for porcine reproductive and respiratory syndrome virus on porcine alveolar macrophages. J. Virol. 72, 4520-4523.

Graversen, J. H., Madsen, M., and Moestrup, S. K. (2002). CD163: a signal receptor scavenging haptoglobin-hemoglobin complexes from plasma. [Review][19 refs]. International Journal of Biochemistry & Cell Biology 34, 309-314.

Gronlund J. Vitved L. Lausen M. Skjodt K. Holmskov U. Cloning of a novel scavenger receptor cysteine-rich type I transmembrane molecule (M160) expressed by human macrophages. Journal of Immunology 165(11):6406-6415, 2000.

Kapil, S, and Shanmukhappa, K. Host susceptibility factor(s) for porcine reproductive and respiratory syndrome virus and uses in swine breeding, as a target for antiviral compounds, and development of a non-simian recombinant cell line for propagation of the virus. none. US 2003/0186236 A1, 1-45. Oct. 2, 2003. USA. Jan. 28, 2002. Ref Type: Patent Kim, H. S., Kwang, J., Yoon, I. J., Joo, H. S., and Frey, M. L. (1993). Enhanced replication of porcine reproductive and respiratory syndrome (PRRS) virus in a homogenous subpopulation of MA-104 cell line. Arch. Virol. 133, 477-483.

Kreutz, L. C. (1998). Cellular membrane factors are the major determinants of porcine reproductive and respiratory syndrome virus tropism. Virus Res. 53, 121-128.

Kreutz, L. C. and Ackermann, M. R. (1996). Porcine reproductive and respiratory syndrome virus enters cells through a low pH-dependent endocytic pathway. Virus Res. 42, 137-147.

Mengeling, W. L. and Lager, K. M. (2000). A brief review of procedures and potential problems associated with the diagnosis of porcine reproductive and respiratory syndrome. Veterinary Research 31, 61-69.

Meulenberg, J. J. M. (2000). PRRSV, the virus. Veterinary Research 31, 11-21.

Murtaugh, M. P., Xiao, Z. G., and Zuckermann, F. (2002). Immunological responses of swine to porcine reproductive and respiratory syndrome virus infection [Review]. Viral Immunology 15, 533-547.

Nauwynck, H. J., Duan, X., Favoreel, H. W., Van Oostveldt, P., and Pensaert, M. B. (1999). Entry of porcine reproductive and respiratory syndrome virus into porcine alveolar macrophages via receptor-mediated endocytosis. J. Gen. Virol. 80, 297-305.

Nodelijk, G. (2002). Porcine Reproductive and Respiratory Syndrome (PRRS) with special reference to clinical aspects and diagnosis—A review [Review]. Vet. Quart. 24, 95-100.

Pensaert, M., Nauwynck, H., and Vanderheijden, N. Nucleic acid encoding polypeptide involved in cellular entrance of the PRRS virus. Akzo Nobel N.V. and Universiteit Gent. WO 03/010200 A2, 1-24. Feb. 6, 2003. Jul. 18, 2002. Ref Type: Patent Philippidis, P., Mason, J. C., Evans, B. J., Nadra, I., Taylor, K. M., Haskard, D. O., and Landis, R. C. (2004). Hemoglobin scavenger receptor CD163 mediates interleukin-10 release and heme oxygenase-1 synthesis—Antiinflammatory monocyte-macrophage responses in vitro, in resolving skin blisters in vivo, and after cardiopulmonary bypass surgery. Circulation Research 94, 119-126.

Plagemann, P. G. W. (2003). Porcine reproductive and respiratory syndrome virus: Origin hypothesis. Emerging Infectious Diseases 9, 903-908.

Ritter, M., Buechler, C., Langmann, T., and Schmitz, G. (1999). Genomic organization and chromosomal localization of the human CD 163 (M130) gene: a member of the scavenger receptor cysteine-rich superfamily. Biochemical & Biophysical Research Communications 260, 466-474.

Sanchez-Torres, C., Gomez-Puertas, P., Gomez-del-Moral, M., Alonso, F., Escribano, J. M., Ezquerra, A., and Dominguez, J. (2003). Expression of porcine CD163 on monocytes/macrophages correlates with permissiveness to African swine fever infection. Arch. Virol. 148, 2307-2323.

Shanmukhappa, K. and Kapil, S. (2001). Cloning and identification of MARC-145 cell proteins binding to 3'UTR and partial nucleoprotein gene of porcine reproductive and respiratory syndrome virus. Adv. Exp. Med. Biol. 494, 641-646.

Snijder, E. J. and Meulenberg, J. J. M. (2001). Arteriviruses. In Fields Virology, D. M. Knipe, P. M. Howley, D. E. Griffin, M. A. Martin, R. A. Lamb, B. Roizman, and S. E. Straus, eds. (Philadelphia: Lippincott Williams & Wilkins), pp. 1205-1220.

Therrien, D., St Pierre, Y., and Dea, S. (2000). Preliminary characterization of protein binding factor for porcine reproductive and respiratory syndrome virus on the surface of permissive and non-permissive cells. Arch. Virol. 145, 1099-1116.

Vanderheijden, N., Delputte, P. L., Favoreel, H. W., Vandekerckhove, J., Van Damme, J., van Woensel, P. A., and Nauwynck, H. J. (2003). Involvement of sialoadhesin in entry of porcine reproductive and respiratory syndrome virus into porcine alveolar macrophages. J. Virol. 77, 8207-8215.

Weingartl, H. M., Sabara, M., Pasick, J., van Moorlehem, E., and Babiuk, L. (2002). Continuous porcine cell lines developed from alveolar macrophages—Partial characterization and virus susceptibility. J. Virol. Methods 104, 203-216.

Wissink, E. H. J., van Wijk, H. A. R., Pol, J. M. A., Godeke, G. J., van Rijn, P. A., Rottier, P. J. M., and Meulenberg, J. J. M. (2003). Identification of porcine alveolar macrophage glycoproteins involved in infection of porcine respiratory and reproductive syndrome virus. Arch. Virol. 148, 177-187.

SUMMARY OF THE INVENTION

The invention includes a method of facilitating infection of one or more cells by a virus that is selected from the group consisting of Arteriviridae and Asfarviridae, which comprises the step of increasing expression of a CD163 polypeptide within said cell. In a preferred embodiment the CD163 is membrane bound. In one embodiment the virus is selected from the group consisting of Arteriviridae. In a preferred embodiment the virus is PRRSV. In another embodiment said virus is equine arteritis virus (EAV). In yet another embodiment said virus is African Swine Fever virus (ASFV).

Increased expression of a CD163 polypeptide may be accomplished by methods such as introduction of exogenous nucleic acids encoding CD163 polypeptides. Such methods include but are not limited to transfection, electroporation and fusion with a carrier of a polynucleotide comprising a polynucleotide encoding a CD163 polypeptide. Increased expression may also be accomplished by induction of expression of endogenous CD163 by chemical treatment.

The method may render previously non PRRSV-permissive cells to be PRRSV permissive. The method may render a cell that was previously PRRSV permissive to be more PRRSV permissive. The method also includes rendering one or more cells that previously did not express a CD163 polypeptide into cells that are induced to express a CD163 polypeptide. The method also includes rendering one or more cells that previously expressed a CD163 polypeptide to express a higher level of CD163 polypeptide.

The cells in a preferred embodiment are animal cells. They may be vertebrate or invertebrate cells. The cells may be mammalian. The cells or cell line may be an insect cell line. The cells may be BHK21 cells. The cells may be derived from porcine kidney cells. The cells or cell line may be derived from feline kidney cells. The cells or cell line may be but are not limited to BHK-21, NLST-1, NLFK-1, Vero, swine testicle, or rabbit lung cells. The cells or cell line may be derived from avian cells. The PRRSV may be of the European or North American genotype.

As noted above, increased expression of a CD163 polypeptide may be accomplished by methods which include but are not limited to: transfection, electroporation and fusion with a carrier of a polynucleotide comprising a polynucleotide encoding a CD163 polypeptide. In addition, viral vectors may be used to introduce a polynucleotide encoding a CD163 polypeptide. Any CD163 polypeptides are contemplated. Those containing a transmembrane region are preferred. Exemplary polynucleotide encoding CD163 polypeptides that may be used in the method are selected from the group consisting of the polynucleotides listed below.

One such polynucleotide comprises a polynucleotide encoding a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO: 2 or fragments thereof.

One such polynucleotide comprises a polynucleotide encoding a polypeptide differing from SEQ ID NO: 2 by no more than 20 conservative amino acid substitutions.

One such polynucleotide comprises a polynucleotide encoding a polypeptide differing from SEQ ID NO: 2 by no more than 10 conservative amino acid substitutions.

One such polynucleotide comprises a polynucleotide encoding a polypeptide comprising SEQ ID NO: 2.

One such polynucleotide comprises a polynucleotide with the sequence set forth in SEQ ID NO: 1.

One such polynucleotide comprises a polynucleotide encoding a polypeptide that has at least 70% identity to a polypeptide set forth in SEQ ID NO: 14 or fragments thereof.

One such polynucleotide comprises a polynucleotide encoding a polypeptide that has at least 90% identity to a polypeptide set forth in SEQ ID NO: 14 or fragments thereof.

One such polynucleotide comprises a polynucleotide encoding a polypeptide that has at least 99% identity to a polypeptide set forth in SEQ ID NO: 14 or fragments thereof.

One such polynucleotide comprises a polynucleotide encoding a polypeptide differing from SEQ ID NO: 14 by no more than 15 conservative amino acid substitutions.

One such polynucleotide comprises a polynucleotide encoding a polypeptide differing from SEQ ID NO: 14 by no more than 10 conservative amino acid substitutions.

One such polynucleotide comprises a polynucleotide encoding a polypeptide comprising SEQ ID NO: 14.

One such polynucleotide comprises a polynucleotide with the sequence set forth in SEQ ID NO: 13.

One such polynucleotide comprises a polynucleotide encoding a polypeptide that has at least 90% identity to a polypeptide set forth in SEQ ID NO: 19 or fragments thereof.

One such polynucleotide comprises a polynucleotide encoding a polypeptide differing from SEQ ID NO: 19 by no more than 2 conservative amino acid substitutions.

One such polynucleotide comprises a polynucleotide encoding a polypeptide comprising SEQ ID NO: 19.

One such polynucleotide comprises a polynucleotide with the sequence set forth in SEQ ID NO: 18.

One such polynucleotide comprises a polynucleotide encoding a polypeptide differing from SEQ ID NO: 24 by no more than 2 conservative amino acid substitutions.

One such polynucleotide comprises a polynucleotide encoding a polypeptide comprising SEQ ID NO: 24.

One such polynucleotide comprises a polynucleotide with the sequence set forth in SEQ ID NO: 23.

One such polynucleotide comprises a polynucleotide encoding a polypeptide having at least 96%, 97%, 98%, or 99% identity to a polypeptide set forth in SEQ ID NO: 27 or fragments thereof.

One such polynucleotide comprises a polynucleotide encoding a polypeptide differing from SEQ ID NO: 27 by no more than 20 conservative amino acid substitutions.

One such polynucleotide comprises a polynucleotide encoding a polypeptide differing from SEQ ID NO: 27 by no more than 10 conservative amino acid substitutions.

One such polynucleotide comprises a polynucleotide encoding a polypeptide comprising SEQ ID NO: 27.

One such polynucleotide comprises a polynucleotide with the sequence set forth in SEQ ID NO: 26.

One such polynucleotide comprises a polynucleotide encoding a polypeptide that has at least 98% or 99% identity to a polypeptide set forth in SEQ ID NO: 32 or fragments thereof.

One such polynucleotide comprises a polynucleotide encoding a polypeptide differing from SEQ ID NO: 32 by no more than 15 conservative amino acid substitutions.

One such polynucleotide comprises a polynucleotide encoding a polypeptide differing from SEQ ID NO: 32 by no more than 10 conservative amino acid substitutions.

One such polynucleotide comprises a polynucleotide encoding a polypeptide comprising SEQ ID NO: 32.

One such polynucleotide comprises a polynucleotide with the sequence set forth in SEQ ID NO: 31.

One such polynucleotide comprises a polynucleotide encoding a polypeptide that has at least 95%, 96%, 97%, 98%, or 99% identity to a polypeptide set forth in SEQ ID NO: 34 or fragments thereof.

One such polynucleotide comprises a polynucleotide encoding a polypeptide differing from SEQ ID NO: 34 by no more than 15 conservative amino acid substitutions.

One such polynucleotide comprises a polynucleotide encoding a polypeptide differing from SEQ ID NO: 34 by no more than 10 conservative amino acid substitutions.

One such polynucleotide comprises a polynucleotide encoding a polypeptide comprising SEQ ID NO: 34.

One such polynucleotide comprises a polynucleotide with the sequence set forth in SEQ ID NO: 33.

One such polynucleotide comprises a polynucleotide encoding a polypeptide that has at least 95%, 96%, 97%, 98%, or 99% identity to a polypeptide set forth in SEQ ID NO: 36 or fragments thereof.

One such polynucleotide comprises a polynucleotide encoding a polypeptide differing from SEQ ID NO: 36 by no more than 15 conservative amino acid substitutions.

One such polynucleotide comprises a polynucleotide encoding a polypeptide differing from SEQ ID NO: 36 by no more than 10 conservative amino acid substitutions.

One such polynucleotide comprises a polynucleotide encoding a polypeptide comprising SEQ ID NO: 36.

One such polynucleotide comprises a polynucleotide with the sequence set forth in SEQ ID NO: 35.

One such polynucleotide comprises a polynucleotide encoding a polypeptide that has at least 90%, 91%, 92%, 93%, 94%, 95%, 96%, 97%, 98%, or 99% identity to a polypeptide set forth in SEQ ID NO: 42 or fragments thereof.

One such polynucleotide comprises a polynucleotide encoding a polypeptide differing from SEQ ID NO: 42 by no more than 15 conservative amino acid substitutions.

One such polynucleotide comprises a polynucleotide encoding a polypeptide differing from SEQ ID NO: 42 by no more than 10 conservative amino acid substitutions.

One such polynucleotide comprises a polynucleotide encoding a polypeptide comprising SEQ ID NO: 42.

One such polynucleotide comprises a polynucleotide with the sequence set forth in SEQ ID NO: 41.

One such polynucleotide comprises a polynucleotide encoding a polypeptide that has at least 90%, 91%, 92%, 93%, 94%, 95%, 96%, 97%, 98%, or 99% identity to a polypeptide set forth in SEQ ID NO: 44 or fragments thereof.

One such polynucleotide comprises a polynucleotide encoding a polypeptide differing from SEQ ID NO: 44 by no more than 15 conservative amino acid substitutions.

One such polynucleotide comprises a polynucleotide encoding a polypeptide differing from SEQ ID NO: 44 by no more than 10 conservative amino acid substitutions.

One such polynucleotide comprises a polynucleotide encoding a polypeptide comprising SEQ ID NO: 44.

One such polynucleotide comprises a polynucleotide with the sequence set forth in SEQ ID NO: 43.

One such polynucleotide comprises a polynucleotide encoding a polypeptide that has at least 95%, 96%, 97%, 98%, or 99% identity to a polypeptide set forth in SEQ ID NO: 46 or fragments thereof.

One such polynucleotide comprises a polynucleotide encoding a polypeptide differing from SEQ ID NO: 46 by no more than 15 conservative amino acid substitutions.

One such polynucleotide comprises a polynucleotide encoding a polypeptide differing from SEQ ID NO: 46 by no more than 10 conservative amino acid substitutions.

One such polynucleotide comprises a polynucleotide encoding a polypeptide comprising SEQ ID NO: 46.

One such polynucleotide comprises a polynucleotide with the sequence set forth in SEQ ID NO: 45.

One such polynucleotide comprises a polynucleotide encoding a polypeptide that has at least 90%, 91%, 92%, 93%, 94%, 95%, 96%, 97%, 98%, or 99% identity to a polypeptide set forth in SEQ ID NO: 48 or fragments thereof.

One such polynucleotide comprises a polynucleotide encoding a polypeptide differing from SEQ ID NO: 48 by no more than 15 conservative amino acid substitutions.

One such polynucleotide comprises a polynucleotide encoding a polypeptide differing from SEQ ID NO: 48 by no more than 10 conservative amino acid substitutions.

One such polynucleotide comprises a polynucleotide encoding a polypeptide comprising SEQ ID NO: 48.

One such polynucleotide comprises a polynucleotide with the sequence set forth in SEQ ID NO: 47.

The method of facilitating infection described above may further comprise the step of producing a culture of virus. The invention also comprises the step of isolating the virus from said culture.

The invention further comprises the culture isolated by the method described above.

The invention further comprises the virus isolated by the method described above.

Any of the methods described above may further comprise the step of producing a PRRSV or other viral vaccine. The vaccine may comprise killed or live attenuated virus. The invention further comprises the vaccines produced by said method.

The invention also comprises a cell or cell line wherein the ability of one or more cells to be infected by a virus selected from the group consisting of Arteriviridae and Asfarviridae has been modified by increasing expression of a CD163 polypeptide within said cells. In another embodiment the virus is PRRSV. In another embodiment said virus is equine arteritis virus (EAV). In yet another embodiment said virus is African Swine Fever virus (ASFV).

In a preferred embodiment the CD163 polypeptide comprises a transmembrane region. In one embodiment the virus is selected from the group consisting of Arteriviridae. In a preferred embodiment the virus is PRRSV. In another embodiment said virus is equine arteritis virus (EAV). In yet another embodiment said virus is African Swine Fever virus (ASFV).

The cell or cell line of the invention may have been previously PRRSV non-permissive and is rendered PRRSV permissive by directing increased expression of a CD163 polypeptide within said cell or cell line. The cell or cell line of the invention may have been previously PRRSV permissive and is rendered to be more PRRSV permissive by directing increased expression of a CD163 polypeptide within said cell or cell line.

The cell or cell line of the invention includes cells or cell lines that did not express a CD163 polypeptide and is induced to express a CD163 polypeptide. The cell or cell line of the invention includes cells or cell lines that previously expressed a CD163 polypeptide and is induced to express a higher level of CD163 polypeptide.

The cells in a preferred embodiment are animal cells. They may be vertebrate or invertebrate cells. The cells may be mammalian. The cell or cell line may be an insect cell or cell line. The cells may be BHK21 cells. The cells may be derived from porcine kidney cells. The cell or cell line may be derived from feline kidney cells. The cells may be, but are not limited to, BHK-21, NLST-1, NLFK-1, Vero, swine testicle (ST), or rabbit lung (RL) cells. The PRRSV may be North American or European.

The invention includes a method for measuring the propensity of a test cell or cell line to allow infection by a virus selected from the group consisting of Arteriviridae and Asfarviridae comprising:

a) providing a sample containing nucleic acids from the test cell or cell line;

b) determining the amount of polynucleotide encoding a CD163 polypeptide or its complement in said sample;

wherein an increased amount of polynucleotide encoding a CD163 polypeptide relative to a control sample derived from a control cell or cell line known not to support the growth of said virus indicates a propensity of the test cell or cell line to support the replication of said virus.

In one embodiment the virus is selected from the group consisting of Arteriviridae. In a preferred embodiment the virus is PRRSV. In another embodiment said virus is equine arteritis virus (EAV). In yet another embodiment said virus is African Swine Fever virus (ASFV).

The amount of polynucleotide encoding a CD163 polypeptide may be determined by hybridization.

The amount of polynucleotide encoding a CD163 polypeptide may be determined by PCR.

The invention also includes a method for measuring the propensity of a test cell or cell line to allow infection by a virus selected from the group consisting of Arteriviridae and Asfarviridae comprising:

(a) providing a sample containing polypeptides from the test cell or cell line;

(b) determining the amount of CD163 polypeptide in said sample;

wherein an increased amount of a CD163 polypeptide relative to a control sample derived from a control cell or cell line known not to support the growth of said virus indicates a propensity of the test cell or cell line to support the replication of said virus.

In one embodiment the virus is selected from the group consisting of Arteriviridae. In a preferred embodiment the virus is PRRSV. In another embodiment said virus is equine arteritis virus (EAV). In yet another embodiment said virus is African Swine Fever virus (ASFV).

In one embodiment the determining is accomplished by contacting a CD163 polypeptide with an antibody specific for the CD163 polypeptide, under conditions wherein the antibody binds the CD163 polypeptide.

The invention includes a method for measuring the propensity of a first pig to become infected by a virus selected from the group consisting of Arteriviridae and Asfarviridae comprising:

a) providing a sample containing nucleic acids from the pig to be tested;

b) determining the amount of polynucleotide encoding a CD163 polypeptide or its complement in said sample;

wherein an increased amount of polynucleotide encoding a CD163 polypeptide relative to the amount of polynucleotide encoding a CD163 polypeptide in a sample from a second pig indicates a greater propensity of the first pig to be infected by said virus.

In one embodiment the virus is selected from the group consisting of Arteriviridae. In a preferred embodiment the virus is PRRSV. In another embodiment said virus is equine arteritis virus (EAV). In yet another embodiment said virus is African Swine Fever virus (ASFV).

In one embodiment the determining is accomplished by hybridization. In another embodiment the determining is accomplished by PCR.

The invention also includes a method for measuring the propensity of a first pig to become infected by a virus selected from the group consisting of Arteriviridae and Asfarviridae comprising:

(a) providing a sample containing polypeptides from pig to be tested;

(b) determining the amount of CD163 polypeptide in said sample;

wherein an increased amount of a CD163 polypeptide relative to the amount of CD163 polypeptide in a sample from a second pig indicates a greater propensity of the first pig to be infected by said virus.

In one embodiment the virus is selected from the group consisting of Arteriviridae. In a preferred embodiment the virus is PRRSV. In another embodiment said virus is equine arteritis virus (EAV). In yet another embodiment said virus is African Swine Fever virus (ASFV).

In one embodiment the determining is accomplished by contacting a CD163 polypeptide with an antibody specific for the CD163 polypeptide, under conditions wherein the antibody binds the CD163 polypeptide.

The invention also includes an isolated polypeptide wherein the polypeptide is selected from the group consisting of the polypeptides described below.

Therefore the invention also includes an isolated polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO: 2 or fragments thereof.

One such polypeptide is a polypeptide differing from SEQ ID NO: 2 by no more than 20 conservative amino acid substitutions.

One such polypeptide is a polypeptide differing from SEQ ID NO: 2 by no more than 10 conservative amino acid substitutions.

One such polypeptide comprises SEQ ID NO: 2.

The invention also includes an isolated polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to a polypeptide set forth in SEQ ID NO: 14 or fragments thereof.

One such polypeptide is a polypeptide differing from SEQ ID NO: 14 by no more than 15 conservative amino acid substitutions.

One such polypeptide is a polypeptide differing from SEQ ID NO: 14 by no more than 10 conservative amino acid substitutions.

One such polypeptide comprises SEQ ID NO: 14.

The invention also includes an isolated polypeptide having at least 90%, 91%, 92%, 93%, 94%, 95%, 96%, 97%, 98%, or 99% identity to a polypeptide set forth in SEQ ID NO: 19 or fragments thereof.

The invention also includes an isolated polypeptide differing from SEQ ID NO: 19 by no more than 2 conservative amino acid substitutions.

One such polypeptide comprises SEQ ID NO: 19.

The invention also includes an isolated polypeptide having at least 90%, 91%, 92%, 93%, 94%, 95%, 96%, 97%, 98%, or 99% identity to a polypeptide set forth in SEQ ID NO: 24 or fragments thereof.

The invention also includes an isolated polypeptide differing from SEQ ID NO: 24 by no more than 2 conservative amino acid substitutions.

One such polypeptide comprises SEQ ID NO: 24.

The invention also includes an isolated polypeptide having at least 96%, 97%, 98%, or 99% identity to a polypeptide set forth in SEQ ID NO: 27.

One such polypeptide is a polypeptide differing from SEQ ID NO: 27 by no more than 20 conservative amino acid substitutions.

One such polypeptide is a polypeptide differing from SEQ ID NO: 27 by no more than 10 conservative amino acid substitutions.

One such polypeptide is a polypeptide comprising SEQ ID NO: 27.

The invention also includes an isolated polypeptide having at least 90%, 91%, 92%, 93%, 94%, 95%, 96%, 97%, 98% or 99% identity to a polypeptide set forth in SEQ ID NO: 32 or fragments thereof.

One such polypeptide is a polypeptide differing from SEQ ID NO: 32 by no more than 15 conservative amino acid substitutions.

One such polypeptide is a polypeptide differing from SEQ ID NO: 32 by no more than 10 conservative amino acid substitutions.

One such polypeptide is a polypeptide comprising SEQ ID NO: 32.

The invention also includes an isolated polypeptide having at least 95%, 96%, 97%, 98%, or 99% identity to a polypeptide set forth in SEQ ID NO: 34 or fragments thereof.

One such polypeptide is a polypeptide differing from SEQ ID NO: 34 by no more than 15 conservative amino acid substitutions.

One such polypeptide is a polypeptide differing from SEQ ID NO: 34 by no more than 10 conservative amino acid substitutions.

One such polypeptide is a polypeptide comprising SEQ ID NO: 34.

The invention also includes an isolated polypeptide having at least 95%, 96%, 97%, 98%, or 99% identity to a polypeptide set forth in SEQ ID NO: 36 or fragments thereof.

One such polypeptide is a polypeptide differing from SEQ ID NO: 36 by no more than 15 conservative amino acid substitutions.

One such polypeptide is a polypeptide differing from SEQ ID NO: 36 by no more than 10 conservative amino acid substitutions.

One such polypeptide is a polypeptide comprising SEQ ID NO: 36.

The invention also includes an isolated polypeptide having at least 95%, 96%, 97%, 98%, or 99% identity to a polypeptide set forth in SEQ ID NO: 38 or fragments thereof.

One such polypeptide is a polypeptide differing from SEQ ID NO: 38 by no more than 15 conservative amino acid substitutions.

One such polypeptide is a polypeptide differing from SEQ ID NO: 38 by no more than 10 conservative amino acid substitutions.

One such polypeptide is a polypeptide comprising SEQ ID NO: 38.

The invention also includes an isolated polypeptide having at least 95%, 96%, 97%, 98%, or 99% identity to a polypeptide set forth in SEQ ID NO: 40 or fragments thereof.

One such polypeptide is a polypeptide differing from SEQ ID NO: 40 by no more than 15 conservative amino acid substitutions.

One such polypeptide is a polypeptide differing from SEQ ID NO: 40 by no more than 10 conservative amino acid substitutions.

One such polypeptide is a polypeptide comprising SEQ ID NO: 40.

The invention also includes an isolated polypeptide having at 90%, 91%, 92%, 93%, 94%, 95%, 96%, 97%, 98%, or 99% identity to a polypeptide set forth in SEQ ID NO: 42 or fragments thereof.

One such polypeptide is a polypeptide differing from SEQ ID NO: 42 by no more than 15 conservative amino acid substitutions.

One such polypeptide is a polypeptide differing from SEQ ID NO: 42 by no more than 10 conservative amino acid substitutions.

One such polypeptide is a polypeptide comprising SEQ ID NO: 42.

The invention also includes an isolated polypeptide having at least 90%, 91%, 92%, 93%, 94%, 95%, 96%, 97%, 98%, or 99% identity to a polypeptide set forth in SEQ ID NO: 44 or fragments thereof.

One such polypeptide is a polypeptide differing from SEQ ID NO: 44 by no more than 15 conservative amino acid substitutions.

One such polypeptide is a polypeptide differing from SEQ ID NO: 44 by no more than 10 conservative amino acid substitutions.

One such polypeptide is a polypeptide comprising SEQ ID NO: 44.

The invention also includes an isolated polypeptide having at least 90%, 91%, 92%, 93%, 94%, 95%, 96%, 97%, 98%, or 99% identity to a polypeptide set forth in SEQ ID NO: 46 or fragments thereof.

One such polypeptide is a polypeptide differing from SEQ ID NO: 46 by no more than 15 conservative amino acid substitutions.

One such polypeptide is a polypeptide differing from SEQ ID NO: 46 by no more than 10 conservative amino acid substitutions.

One such polypeptide is a polypeptide comprising SEQ ID NO: 46.

Therefore the invention also includes an isolated polypeptide having at least 90%, 91%, 92%, 93%, 94%, 95%, 96%, 97%, 98%, or 99% identity to a polypeptide set forth in SEQ ID NO: 48 or fragments thereof.

One such polypeptide is a polypeptide differing from SEQ ID NO: 48 by no more than 15 conservative amino acid substitutions.

One such polypeptide is a polypeptide differing from SEQ ID NO: 48 by no more than 10 conservative amino acid substitutions.

One such polypeptide is a polypeptide comprising SEQ ID NO: 48.

The invention also includes an isolated CD163 polynucleotide wherein said polynucleotide is selected from the group consisting of the polynucleotides enumerated below.

Therefore the invention also includes an isolated polynucleotide comprising:

(a) a polynucleotide sequence set forth in SEQ ID NOs: 1 or 5;

(b) a polynucleotide that encodes a polypeptide that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity and/or similarity to a polypeptide set forth in SEQ ID NO: 2 or fragments thereof;

(c) a polynucleotide encoding a polypeptide of SEQ ID NO: 2;

(d) a polynucleotide which is the complement of any of (a), (b), or (c).

Therefore the invention also includes an isolated polynucleotide comprising:

(a) a polynucleotide sequence set forth in SEQ ID NOs: 12 or 13;

(b) a polynucleotide that encodes a polypeptide that has at least 99% identity and/or similarity to a polypeptide set forth in SEQ ID NO: 14 or fragments thereof;

(c) a polynucleotide encoding a polypeptide of SEQ ID NO: 14;

(d) a polynucleotide that is the complement of any of (a), (b), or (c).

Therefore the invention also includes an isolated polynucleotide comprising:

(a) a polynucleotide sequence set forth in SEQ ID NOs: 17 or 18;

(b) a polynucleotide encoding a polypeptide of SEQ ID NO: 19 or fragments thereof;

(c) a polynucleotide which is the complement of (a) or (b).

Therefore the invention also includes an isolated polynucleotide comprising:

(a) a polynucleotide sequence set forth in SEQ ID NOs: 22 or 23;

(b) a polynucleotide that encodes a polypeptide that has at least 99%, 99.9% identity to a polypeptide set forth in SEQ ID NO: 24 or fragments thereof;

(c) a polynucleotide encoding a polypeptide of SEQ ID NO: 24;

(d) a polynucleotide which is the complement of any of (a), (b), or (c).

Therefore the invention also includes an isolated polynucleotide comprising:

(a) a polynucleotide sequence set forth in SEQ ID NOs: 25 or 26;

(b) a polynucleotide that encodes a polypeptide that has at least 96%, 97%, 98%, or 99% identity and/or similarity to a polypeptide set forth in SEQ ID NO: 27 or fragments thereof;

(c) a polynucleotide encoding a polypeptide of SEQ ID NO: 27;

(d) a polynucleotide which is the complement of any of (a), (b), or (c).

Therefore the invention also includes an isolated polynucleotide comprising:

(a) polynucleotide sequence set forth in SEQ ID NOs: 30 or 31;

(b) a polynucleotide that encodes a polypeptide that has at least 96%, 96.2%, 97%, 98% or 99% identity and/or similarity to a polypeptide set forth in SEQ ID NO: 32 or fragments thereof;

(c) a polynucleotide encoding a polypeptide of SEQ ID NO: 32;

(d) a polynucleotide which is the complement of any of (a), (b), or (c).

Therefore the invention also includes an isolated polynucleotide comprising:

(a) polynucleotide sequence set forth in SEQ ID NO: 33;

(b) a polynucleotide that encodes a polypeptide that has at least 95%, 96%, 97%, 98%, or 99% identity and/or similarity to a polypeptide set forth in SEQ ID NO: 34 or fragments thereof;

(c) a polynucleotide encoding a polypeptide of SEQ ID NO: 34;

(d) a polynucleotide which is the complement of any of (a), (b), or (c).

Therefore the invention also includes an isolated polynucleotide comprising:

(a) polynucleotide sequence set forth in SEQ ID NO: 35;

(b) a polynucleotide that encodes a polypeptide that has at least 95%, 96%, 97%, 98%, or 99% identity and/or similarity to a polypeptide set forth in SEQ ID NO: 36 or fragments thereof;

(c) a polynucleotide encoding a polypeptide of SEQ ID NO: 36;

(d) a polynucleotide which is the complement of any of (a), (b), or (c).

Therefore the invention also includes an isolated polynucleotide comprising:

(a) polynucleotide sequence set forth in SEQ ID NO: 37;

(b) a polynucleotide that encodes a polypeptide that has at least 95%, 96%, 97%, 98%, or 99% identity and/or similarity to a polypeptide set forth in SEQ ID NO: 38 or fragments thereof;

(c) a polynucleotide encoding a polypeptide of SEQ ID NO: 38;

(d) a polynucleotide that is the complement of any of (a), (b), or (c).

Therefore the invention also includes an isolated polynucleotide comprising:

(a) polynucleotide sequence set forth in SEQ ID NO: 39;

(b) a polynucleotide that encodes a polypeptide that has at least 95%, 96%, 97%, 98%, or 99% identity and/or similarity to a polypeptide set forth in SEQ ID NO: 40 or fragments thereof;

(c) a polynucleotide encoding a polypeptide of SEQ ID NO: 40;

(d) a polynucleotide that is the complement of any of (a), (b), or (c).

Therefore the invention also includes an isolated polynucleotide comprising:

(a) polynucleotide sequence set forth in SEQ ID NO: 41;

(b) a polynucleotide that encodes a polypeptide that has at least 95%, 96%, 97%, 98%, or 99% identity and/or similarity to a polypeptide set forth in SEQ ID NO: 42 or fragments thereof;

(c) a polynucleotide encoding a polypeptide of SEQ ID NO: 42;

(d) a polynucleotide that is the complement of any of (a), (b), or (c).

Therefore the invention also includes an isolated polynucleotide comprising:

(a) polynucleotide sequence set forth in SEQ ID NO: 43;

(b) a polynucleotide that encodes a polypeptide that has at least 95%, 96%, 97%, 98%, or 99% identity and/or similarity to a polypeptide set forth in SEQ ID NO: 44 or fragments thereof;

(c) a polynucleotide encoding a polypeptide of SEQ ID NO: 44;

(d) a polynucleotide that is the complement of any of (a), (b), or (c).

Therefore the invention also includes an isolated polynucleotide comprising:

(a) polynucleotide sequence set forth in SEQ ID NO: 45;

(b) a polynucleotide that encodes a polypeptide that has at least 85%, 85.5%, 86%, 87%, 88%, 89%, 90%, 91%, 92%, 93%, 94%, 95%; 96%, 97%, 98%; or 99% identity and/or similarity to a polypeptide set forth in SEQ ID NO: 46 or fragments thereof;

(c) a polynucleotide encoding a polypeptide of SEQ ID NO: 46;

(d) a polynucleotide which is the complement of any of (a), (b), or (c).

The invention also includes an isolated polynucleotide comprising:

(a) polynucleotide sequence set forth in SEQ ID NO: 47;

(b) a polynucleotide that encodes a polypeptide that has at least 90%, 91%, 92%, 93%, 94%, 95%, 96%, 97%, 98%, or 99% identity and/or similarity to a polypeptide set forth in SEQ ID NO: 48 or fragments thereof;

(c) a polynucleotide encoding a polypeptide of SEQ ID NO: 49;

(d) a polynucleotide which is the complement of any of (a), (b), or (c).

Therefore the invention also includes a CD163 polypeptide in which the transmembrane region is deleted.

Therefore the invention also includes a polynucleotide encoding a CD163 polypeptide in which the transmembrane region is deleted.

In addition to the foregoing, the invention includes, as an additional aspect, all embodiments of the invention narrower in scope in any way than the variations specifically mentioned above.

BRIEF DESCRIPTION OF THE SEQUENCE LISTINGS

SEQ ID NO: 1—cDNA sequence encoding porcine susCD163v1

SEQ ID NO: 2—predicted amino acid sequence of porcine susCD163v1

SEQ ID NO: 3—cDNA sequence, Genbank accession number AJ311716

SEQ ID NO: 4—predicted amino acid sequence derived from Genbank accession number AJ311716

SEQ ID NO: 5—cDNA sequence of susCD163v1 containing flanking (non-coding) sequence SEQ ID NO: 6-11—primer sequences SEQ ID NO: 12—cDNA sequence encoding porcine susCD163v2 containing flanking (non-coding) sequence SEQ ID NO: 13—cDNA sequence encoding porcine susCD163v2

SEQ ID NO: 14—predicted amino acid sequence of porcine susCD163v2

SEQ ID NO: 15-16—primer sequences

SEQ ID NO: 17—cDNA sequence encoding human CD163v2 containing flanking (non-coding) sequence SEQ ID NO: 18—cDNA sequence encoding human CD163v2

SEQ ID NO: 19—predicted amino acid sequence of human CD163v2

SEQ ID NO: 20-21—primer sequences

SEQ ID NO: 22—cDNA sequence encoding murine CD163v2 containing flanking (non-coding) sequence SEQ ID NO: 23—cDNA sequence encoding murine CD163v2

SEQ ID NO: 24—predicted amino acid sequence of murine CD163v2

SEQ ID NO: 25—cDNA sequence encoding murine CD163v3 containing flanking (non-coding) sequence SEQ ID NO: 26—cDNA sequence encoding murine CD163v3

SEQ ID NO: 27—predicted amino acid sequence of murine CD163v3

SEQ ID NO: 28-29—primer sequences

SEQ ID NO: 30—cDNA sequence encoding MARC-145 CD163v2 containing flanking (non-coding) sequence SEQ ID NO: 31—cDNA sequence encoding MARC-145 CD163v2

SEQ ID NO: 32—predicted amino acid sequence of MARC-145 CD163v2

SEQ ID NO: 33—cDNA sequence encoding Vero cell CD163v2 transcript

SEQ ID NO: 34—predicted amino acid sequence of Vero cell CD163v2

SEQ ID NO: 35—cDNA sequence encoding Vero cell CD163v3 transcript

SEQ ID NO: 36—predicted amino acid sequence of Vero cell CD163v3

SEQ ID NO: 37—cDNA sequence encoding Vero cell CD163v4 transcript

SEQ ID NO: 38—predicted amino acid sequence of Vero cell CD163v4

SEQ ID NO: 39—cDNA sequence encoding Vero cell CD163v5 transcript

SEQ ID NO: 40—predicted amino acid sequence of Vero cell CD163v5

SEQ ID NO: 41—cDNA sequence encoding Vero cell CD163v6 transcript

SEQ ID NO: 42—predicted amino acid sequence of Vero cell CD163v6

SEQ ID NO: 43—cDNA sequence encoding Vero cell CD163v7 transcript

SEQ ID NO: 44—predicted amino acid sequence of Vero cell CD163v7

SEQ ID NO: 45—cDNA sequence encoding canine CD163v2 transcript

SEQ ID NO: 46—predicted amino acid sequence of canine CD163v2

SEQ ID NO: 47—cDNA sequence encoding canine CD163v3 transcript

SEQ ID NO: 48—predicted amino acid sequence of canine CD163v3

BRIEF DESCRIPTION OF THE DRAWINGS

FIG. 2 Amino acid sequence alignment of susCD163v1 (SEQ ID NO: 2) with AJ311716 (SEQ ID NO: 4)

FIG. 3 Nucleotide sequence alignment of susCD163v1 (SEQ ID NO:1) with AJ311716 (SEQ ID NO:3).

FIG. 14 The amount of progeny PRRSV produced by four recombinant cell lines stably expressing susCD163v1, and by MARC-145 cells, was determined in a growth curve experiment using the NVSL 94-3 isolate of PRRSV. Samples harvested at 12-hour intervals were titrated on MARC-145 cell monolayers.

FIG. 15 Flow cytometry analysis of PRRSV infection in the presence of CD163 specific antibody. BHK-21 cells expressing MARC-145 CD163 from transient transfection were incubated with either CD163 specific antibody or normal goat IgG (NGS) and infected with a GFP-expressing PRRSV. Each data point represents the results of triplicate wells.

FIG. 16 Flow cytometry analysis of PRRSV infection in the presence of CD163 specific antibody. NLFK cells stably expressing human CD163 were incubated with either CD163 specific antibody or normal goat IgG (NGS) and infected with a GFP expressing PRRSV. At 24 hours post infection the percentage of GFP expressing infected cells was determined. Each data point represents the result from a single well of cells FIG. 17. Graphical depiction of six alternative splicing variants of CD163 mRNA recovered from Vero cells. The six variants differ in the presence or absence of three exons, designated E6, E105, and E83. Exons E6 and E105 have lengths that are multiples of three, and therefore do not result in a change in reading frame when absent. In contrast, the absence of E83 results in a shifted reading frame and an alternative amino acid sequence at the carboxy terminus of the protein (indicated by a hatched pattern in the figure). The hydrophobic transmembrane (TM) region is encoded within E105.

DETAILED DESCRIPTION OF THE INVENTION

General Definitions

Figure 1:
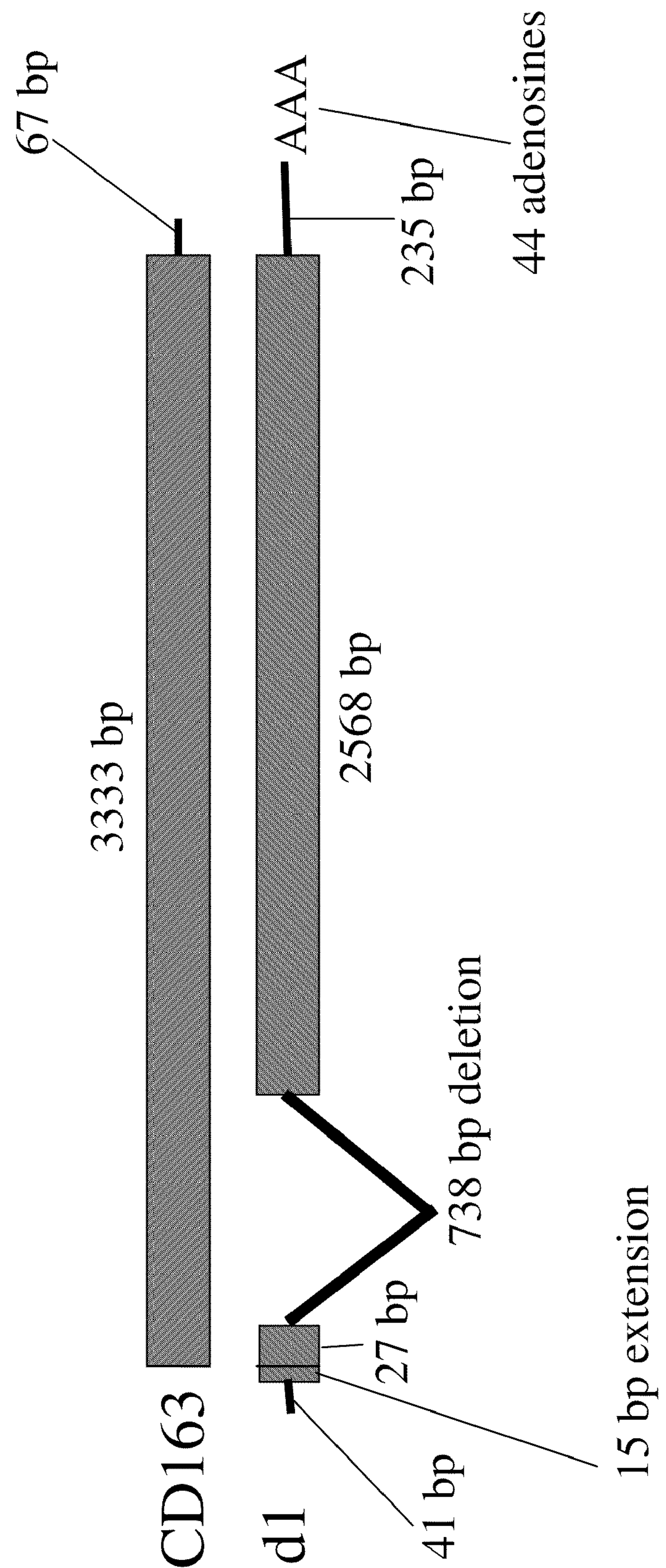
FIG. 1 Schematic comparison of susCD163v1 with AJ311716

Cells and cell lines can be either "virus permissive" or "virus non-permissive". For example, a cell or cell line that is virus permissive is capable of allowing virus infection, subsequent replication, and virus production. A cell or cell line that is virus non-permissive is incapable of allowing virus infection, subsequent replication, and virus production. A cell line that is already somewhat permissive may be rendered more permissive by the methods of the invention.

Arteriviridae refers to a family of enveloped, positive-stranded RNA viruses belonging to the order Nidovirales. The family includes lactate dehydrogenase-elevating virus (LDV) of mice, equine arteritis virus (EAV), simian hemorrhagic fever virus (SHFV), and PRRSV.

Asfarviridae is a family of icosohedral, enveloped viruses whose genomes consist of single molecules of linear double-stranded DNA about 150000-190000 nucleotides long. The name of the family is derived from African Swine Fever And Releted Viruses. African Swine Fever Virus (ASFV) is the type species of the Asfivirus genus and is the sole member of the family.

The term "PRRSV" or PRRS virus refers to both European and North American PRRS virus genotypes. Within each genotype, isolates typically share 85% or higher nucleotide identity. Between genotypes, however, the level of sequence identity is only about 60%. The North American genotype of PRRSV is exemplified by the prototype isolate VR2332. The genomic sequence of VR2332 is found in Genbank accession number U87392, which is incorporated herein by reference. The European genotype of PRRSV is exemplified by the prototype isolate "Lelystad virus". The genomic sequence of Lelystad virus is found in Genbank accession number M96262, which is incorporated herein by reference.

The PRRS virus is a member of the family Arteriviridae. The genome of the arteriviruses is single-stranded RNA of positive polarity between 12 and 16 kb in length, capped at the 5' end and polyadenylated at the 3' end. Over two-thirds of the genome is dedicated to open reading frames (ORFs) 1a and 1b, which encode the non-structural functions of the virus. ORF1b is an extension of ORF1a, and is the result of a ribosomal frameshift. ORFs 1a and 1b are translated directly from the genomic RNA. These large polypeptide products are cleaved by viral proteases to yield 12 or 13 discrete smaller peptides. The remaining ORFs, which encode viral structural proteins, are expressed from a series of 3' co-terminal subgenomic RNAs (sgRNAs). The sgRNAs are produced by discontinuous transcription of negative-stranded RNA, such that a common 5' leader sequence becomes fused to each transcript. The major structural proteins are the nucleocapsid (N, encoded by ORF7), the matrix protein (M, encoded by ORF6), and the major envelope glycoprotein (GP5, encoded by ORF5). The remaining proteins, GP4 (ORF4), GP3 (ORF3), GP2 (ORF2a), and E (ORF2b) are minor structural components of the virion, whose functions have not yet been elucidated. The molecular biology of PRRSV has been the subject of recent review articles (Dea et al., 2000; Meulenberg, 2000; Snijder and Meulenberg, 2001).

As used herein, the term "CD163 polypeptide" means a protein encoded by a mammalian CD163 gene, including allelic variants containing conservative or non-conservative changes. A cDNA sequence that encodes a porcine CD163 polypeptide has been reported (Genbank accession number AJ311716). A murine CD163 polypeptide has also been reported (Genbank access number AF274883), as well as multiple human variants, exemplified by Genbank access numbers AAH51281 and CAA80543. We report herein polynucleotides that encode porcine, human, murine, canine, and african green monkey CD163 polypeptides and which comprise the sequences set forth in SEQ ID NO: 1, 5, 12, 13, 17, 18, 22, 23, 25, 26, 30, 31, 33, 35, 37, 39, 41, 43, 45, and 47. A "CD163 polypeptide" is a member of the scavenger receptor cysteine-rich (SRCR) family of transmembrane glycoproteins, and is thought to be expressed exclusively on monocytes and macrophages. One identified role of CD163 is to inhibit oxidative tissue damage following hemolysis by consuming hemoglobin:haptoglobin complexes by endocytosis. The subsequent release of interleukin-10 and synthesis of heme oxygenase-1 results in antiinflammatory and cytoprotective effects (Philippidis et al., 2004; Graversen et al., 2002). The human CD163 gene spans 35 kb on chromosome 12, and consists of 17 exons and 16 introns. A number of isoforms of the CD163 polypeptide, including membrane bound, cytoplasmic and secreted types, are known to be generated by alternative splicing (Ritter et al., 1999). Isoforms that comprise a transmembrane domain are particularly preferred.

A transmembrane domain is characterized by a polypeptide segment of a larger sequence that is exposed on both sides of a membrane. The cytoplasmic and extracellular domains are separated by at least one membrane-spanning segment that traverses the hydrophobic environment of the lipid bilayer. The membrane-spanning segment is composed of amino acid residues with nonpolar side chains, usually in the form of an alpha helix. Segments that contain about 20-30 hydrophobic residues are long enough to span a membrane as an alpha helix, and they can often be identified by means of a hydropathy plot. The predicted transmembrane domain of SEQ ID NOs:2 and 14 are indicated by bolding in the specification. To determine whether other CD163 sequences contain a similar sequence feature is easily determined by inspection of the sequence or hydropathy plots. SEQ ID NOs: 37-40 are representative of variant CD163 proteins which do not contain a transmembrane domain and their encoding nucleic acids.

As used hereinafter, "polynucleotide" generally refers to any polyribonucleotide or polydeoxyribonucleotide, which may be unmodified RNA or DNA or modified RNA or DNA. "Polynucleotides" include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides. Polynucleotide and nucleic acid are used synonymously herein.

As used hereinafter, "polypeptide" refers to any peptide or protein comprising amino acids joined to each other by peptide bonds or modified peptide bonds. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications or modified forms include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation prenylation, racemization, selenoylation, sulfation, transfer-RNA mediated addition of amino acids to proteins such as arginylation, and ubiquitination (see, for instance, Proteins-Structure and Molecular Properties, 2nd Ed., T. E. Creighton, W. H. Freeman and Company, New York, 1993; Wold, F., Post-translational Protein Modifications: Perspectives and Prospects, pgs. 1-12 in Postranslational Covalent Modification of Proteins, B. C. Johnson, Ed., Academic Press, New York, 1983; Seifter et al., "Analysis for protein modifications and nonprotein cofactors", Meth Enzymol (1990) 182:626-646 and Rattan et al., "Protein Synthesis: Post-translational Modifications and Aging", Ann NY Acad Sci (1992) 663:4842).

A "fragment" of a polypeptide as used herein means a segment of at least about 25 consecutive amino acids of a polypeptide of the invention. In another embodiment, a "fragment" as used herein means a segment of at least about 50 consecutive amino acids of a polypeptide of the invention. In another embodiment, a "fragment" as used herein means a segment of at least about 100 consecutive amino acids of a polypeptide of the invention.

As used hereinafter, "isolated" means altered by the hand of man from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein. Therefore "isolated" as used herein and as understood in the art, whether referring to "isolated" polynucleotides or polypeptides, is taken to mean separated from the original cellular environment in which the polypeptide or nucleic acid is normally found. As used herein therefore, by way of example only, a transgenic animal or a recombinant cell line constructed with a polynucleotide of the invention makes use of the "isolated" nucleic acid. Specifically excluded from the definition of isolated polynucleotides of the invention are entire isolated chromosomes from native host cells from which the polynucleotide was originally derived.

In the disclosure to follow we will often make use of the term "identity" or similarity as applied to the amino acid sequences of polypeptides. Percent amino acid sequence "identity" with respect to polypeptides is defined herein as the percentage of amino acid residues in the candidate sequence that are identical with the residues in the target sequences after aligning both sequences and introducing gaps, if necessary, to achieve the maximum percent sequence identity, and not considering any conservative substitutions as part of the sequence identity. Percent sequence identity is determined by conventional methods. For example, BLASTP 2.2.6 [Tatusova T A and T L Madden, "BLAST 2 sequences—a new tool for comparing protein and nucleotide sequences." (1999) FEMS Microbiol Lett. 174:247-250.]

Briefly, as noted above, two amino acid sequences are aligned to optimize the alignment scores using a gap opening penalty of 10, a gap extension penalty of 0.1, and the "blosum62" scoring matrix of Henikoff and Henikoff (Proc. Nat. Acad. Sci. USA 89:10915-10919. 1992).

The percent identity is then calculated as:

$$\frac{\text{Total number of identical matches}}{[\text{length of the longer sequence} + \text{number of gaps introduced into the longer sequence to align the two sequences}]} \times 100$$

Percent sequence "similarity" (often referred to as "homology") with respect to a polypeptide of the invention is defined herein as the percentage of amino acid residues in the candidate sequence that are identical with the residues in the target sequences after aligning the sequences and introducing gaps, if necessary, to achieve the maximum percent sequence identity (as described above), and also considering any conservative substitutions as part of the sequence identity.

$$\frac{\text{Total number of identical matches and conservative substitutions}}{[\text{length of the longer sequence} + \text{number of gaps introduced into the longer sequence to align the two sequences}]} \times 100$$

Amino acids can be classified according to physical properties and contribution to secondary and tertiary protein structure. A conservative substitution is recognized in the art as a substitution of one amino acid for another amino acid that has similar properties.

Exemplary conservative substitutions are set out in Tables 1, 2, and 3 below.

TABLE 1

| Conservative Substitutions I | |
|---|---|
| SIDE CHAIN CHARACTERISTIC | AMINO ACID |
| Aliphatic | |
| Non - polar | G A P |
| | I L V |
| Polar - uncharged | C S T M |
| | NQ |
| Polar - charged | D E |
| | K R |
| Aromatic | H F W Y |
| Other | N Q D E |

Alternatively, conservative amino acids can be grouped as described in Lehninger, [Biochemistry, Second Edition; Worth Publishers, Inc. NY:N.Y. (1975), pp. 71-77] as set out in Table 2, immediately below

TABLE 2

| Conservative Substitutions II | |
|---|---|
| SIDE CHAIN CHARACTERISTIC | AMINO ACID |
| Non - polar (hydrophobic) | |
| A. Aliphatic: | A L I V P |
| B. Aromatic: | F W |
| C. Sulfur - containing: | M |
| D. Borderline: | G |
| Uncharged - polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | DE |

As still another alternative, exemplary conservative substitutions are set out in Table 3, immediately below.

TABLE 3

| Conservative Substitutions III | |
|---|---|
| Original Residue | Exemplary Substitution |
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

Methods Directed to the Production of Virus and Host Cells of the Invention

The invention provides a method of modifying production of a virus that is a member of the family Arteriviridae and Asfarviridae in a cell comprising the step of directing said cell to express a CD163 polypeptide. This may include rendering a virus non-permissive cell into a virus permissive cell, or may involve rendering a cell more permissive to the virus.

In one embodiment, the virus that is a member of the family Arteriviridae or Asfarviridae is selected from the group consisting of LDV of mice, equine arteritis virus (EAV), simian hemorrhagic fever virus (SHFV), PRRSV of swine, and ASFV of swine.

In a preferred embodiment the virus is PPRSV.

The invention further provides a method of preparing a culture of a virus that is a member of the family Arteriviridae or Asfarviridae comprising the steps of: providing a cell line; directing said cell line to express a CD163 polypeptide; infecting said cell line with virus; and causing said cell line to produce viral progeny.

In one embodiment, the virus that is a member of the family Arteriviridae is selected from the group consisting of LDV of mice, equine arteritis virus (EAV), simian hemorrhagic fever virus (SHFV), PRRSV of swine and ASFV of swine.

In a preferred embodiment the virus is PRRSV.

All of the above methods utilize cells and cell lines expressing a CD163 polypeptide. Expression of CD163 may be facilitated or increased by methods that involve the introduction of exogenous nucleic acid into the cell. Such a cell may comprise a polynucleotide or vector in a manner that permits expression of an encoded CD163 polypeptide.

Polynucleotides that encode CD163 may be introduced into the host cell as part of a circular plasmid, or as linear DNA comprising an isolated protein-coding region, or in a viral vector. Methods for introducing exogenous nucleic acid into the host cell are well known and routinely practiced in the art, including transformation, transfection, electroporation, nuclear injection, or fusion with carriers such as liposomes, micelles, ghost cells, and protoplasts. Host cell systems of the invention include invertebrate and vertebrate cells systems. Hosts may include, but are not limited to, the following: insect cells, porcine kidney (PK) cells, feline kidney (FK) cells, swine testicular (ST) cells, African green monkey kidney cells (MA-104, MARC-145, VERO, and COS cells), Chinese hamster ovary (CHO) cells, baby hampster kidney cells, human 293 cells, and murine 3T3 fibroblasts. Insect host cell culture systems may also be used for the expression of CD163 polypeptides. In another embodiment, the CD163 polypeptides are expressed using a drosophila expression system.

The choice of a suitable expression vector for expression of the CD163 polypeptides will of course depend upon the specific host cell to be used, and is within the skill of the ordinary artisan. Examples of suitable expression vectors include pSport and pcDNA3 (Invitrogen), pCMV-Script (Stratagene), and pSVL (Pharmacia Biotech). Expression vectors for use in mammalian host cells may include transcriptional and translational control sequences derived from viral genomes. Commonly used promoter sequences and modifier sequences which may be used in the present invention include, but are not limited to, those derived from human cytomegalovirus (CMV), Rous sarcoma virus (RSV), Adenovirus 2, Polyoma virus, and Simian virus 40 (SV40). Methods for the construction of mammalian expression vectors are disclosed, for example, in Okayama and Berg (*Mol. Cell. Biol.* 3:280 (1983)); Cosman et al. (*Mol. Immunol.* 23:935 (1986)); Cosman et al. (*Nature* 312:768 (1984)); EP-A-0367566; and WO 91/18982.

Because CD163 sequences are known to exist in cells from various species, the endogenous gene may be modified to permit, or increase, expression of the CD163 polypeptide. Cells can be modified (e.g., by homologous recombination) to provide increased expression by replacing, in whole or in part, the naturally occurring CD163 promoter with all or part of a heterologous promoter, so that the cells express CD163 polypeptide at higher levels. The heterologous promoter is inserted in such a manner that it is operatively linked to endogenous CD163 encoding sequences. [See, for example, PCT International Publication No. WO 94/12650, PCT International Publication No. WO 92/20808, and PCT International Publication No. WO 91/09955.] It is also contemplated that, in addition to heterologous promoter DNA, amplifiable marker DNA (e.g., ada, dhfr, and the multifunctional cad gene, which encodes for carbamyl phosphate synthase, aspartate transcarbamylase, and dihydroorotase) and/or intron DNA may be inserted along with the heterologous promoter DNA. If linked to the CD163 coding sequence, amplification of the marker DNA by standard selection methods results in co-amplification of the CD163 coding sequences in the cells.

CD163 expression may also be induced by chemical treatment. Phorbol esters, especially phorbol myristyl acetate (PMA), activate one or more isozymes of the ubiquitous membrane receptor, protein kinase C (PKC) and are particularly preferred means of increasing CD163 expression. Other methods of intracellular calcium mobilization are also contemplated.

Vaccine Production

The methods described above may be used to produce any virus that is a member of the family Arteriviridae or Asfarviridae for the purpose of vaccine production or diagnostics.

In one embodiment the virus that is a member of the family Arteriviridae is selected from the group consisting of LDV of mice, equine arteritis virus (EAV), simian hemorrhagic fever virus (SHFV), and PRRSV of swine.

In a preferred embodiment the virus is PRRSV.

Vaccine Production

The methods described above may be used to produce virus for the purpose of vaccine production or diagnostics.

Killed (inactivated) or live vaccines can be produced. Therefore, to make a live vaccine, a viral isolate, or an attenuated or mutated variant thereof, is grown in cell culture. The virus is harvested according to methods well known in the art.

The virus may then be concentrated, frozen, and stored at −70° C., or freeze-dried and stored at 4° C. Prior to vaccination the virus is mixed at an appropriate dosage, (which is from about $10^3$ to $10^8$ tissue culture infectious doses per ml ($TCID_{50}$/ml)), with a pharmaceutically acceptable carrier such as a saline solution, and optionally an adjuvant.

The vaccine produced might also comprise an inactivated or killed virus comprising a virus grown by the methods of the invention. The inactivated vaccine is made by methods well known in the art. For example, once the virus is propagated to high titers, it would be readily apparent by those skilled in the art that the virus antigenic mass could be obtained by methods well known in the art. For example, the virus antigenic mass may be obtained by dilution, concentration, or extraction. All of these methods have been employed to obtain appropriate viral antigenic mass to produce vaccines. The virus is then inactivated by treatment with formalin, betapropriolactone (BPL), binary ethyleneimine (BEI), or other methods known to those skilled in the art. The inactivated virus is then mixed with a pharmaceutically acceptable carrier such as a saline solution, and optionally an adjuvant. Examples of adjuvants include, but not limited to, aluminum hydroxide, oil-in-water and water-in-oil emulsions, AMPHIGEN, saponins such as QuilA, and polypeptide adjuvants including interleukins, interferons, and other cytokines.

Inactivation by formalin is performed by mixing the viral suspension with 37% formaldehyde to a final formaldehyde concentration of 0.05%. The virus-formaldehyde mixture is mixed by constant stirring for approximately 24 hours at room temperature. The inactivated virus mixture is then tested for residual live virus by assaying for growth on a suitable cell line.

Inactivation by BEI is performed by mixing the viral suspension of the present invention with 0.1 M BEI (2-bromo-ethylamine in 0.175 N NaOH) to a final BEI concentration of 1 mM. The virus-BEI mixture is mixed by constant stirring for approximately 48 hours at room temperature, followed by the addition of 1.0 M sodium thiosulfate to a final concentration of 0.1 mM. Mixing is continued for an additional two hours. The inactivated virus mixture is tested for residual live virus by assaying for growth on a suitable cell line.

Virus permissive cells that have been directed to express CD163 can also be used to quantify live virus. Two common methods, which are well known to those skilled in the art, are the plaque assay and the limiting dilution assay.

CD163-expressing cell lines of the present invention can be used to grow virus for the purpose of producing viral antigen for diagnostic kits. For example lysates from infected cells (with optional purification of viral particles or extraction of selected viral proteins) may be coated on ELISA plates in order to detect and quantify antibodies to the virus in swine sera.

Live or inactivated virus grown in CD163-expressing cells can be used after optional separation of the viral proteins to immunize animals in order to generate polyclonal, monospecific or monoclonal antibodies. These in turn can be used as the basis of diagnostic assays for the detection and quantification of virus in swine serum and other biological samples.

Assays of the Invention

The invention provides methods for determining the propensity of an animal to be infected by a virus that is a member of the family Arteriviridae or Asfarviridae, or of a cell line to support the replication of a virus that is a member of the family Arteriviridae or Asfarviridae. Samples from either source are obtained and assayed for expression of CD163. The level of CD163 gene expression can be compared with levels of controls known not to support replication of the virus, where an increased amount of CD163 gene expression relative to levels from the controls indicates a greater propensity of the non-control to be infected by said virus.

In the case of an animal, samples can be any sample comprising sample nucleic acid molecules or proteins, and obtained from any bodily tissue expressing CD163, including, but not limited to, alveolar macrophages, cultured cells, biopsies, or other tissue preparations. The level of expression can be assessed at the level of genomic DNA, messenger RNA, and/or protein produced. In a preferred embodiment the member of the virus of the family Arteriviridae or Asfarviridae is selected from the group consisting of LDV of mice, equine arteritis virus (EAV), simian hemorrhagic fever virus (SHFV), PRRSV of swine, and ASFV of swine.

Nucleic Acid Based Assays

Methods of determining CD163 levels may be nucleic acid based as noted above. CD163-derived nucleic acids may be in solution or on a solid support. In some embodiments, they may be employed as array elements in microarrays alone or in combination with other array element molecules. Nucleic acid based methods generally require the isolation of DNA or RNA from the sample and subsequent hybridization or PCR amplification using specific primers derived from any known CD163 encoding sequences in the art or those specifically disclosed as SEQ ID NOs: 1, 3, 5, 12, 13, 17, 18, 22, 23, 25, 26, 30, 31, 33, 35, 37, 39, 41, 43, 45, and 47. DNA or RNA can be isolated from the sample according to any of a number of methods well known to those of skill in the art. For example, methods of purification of nucleic acids are described in Tijssen, P. (1993) Laboratory Techniques in Biochemistry and Molecular Biology Hybridization With Nucleic Acid Probes, Part I. Theory and Nucleic Acid Preparation, Elsevier, New York, N.Y. In one preferred embodiment, total RNA is isolated using the TRIZOL total RNA isolation reagent (Life Technologies, Inc., Gaithersburg Md.) and mRNA is isolated using oligo d(T) column chromatography or glass beads. When sample nucleic acid molecules are amplified it is desirable to amplify the sample nucleic acid molecules and maintain the relative abundances of the original sample, including low abundance transcripts. RNA can be amplified in vitro, in situ, or in vivo (See Eberwine U.S. Pat. No. 5,514,545).

It is also advantageous to include controls within the sample to assure that amplification and labeling procedures do not change the true distribution of nucleic acid molecules in a sample. For this purpose, a sample is spiked with an amount of a control nucleic acid molecule predetermined to be detectable upon hybridization to its complementary arrayed nucleic acid molecule and the composition of nucleic acid molecules includes reference nucleic acid molecules which specifically hybridize with the control arrayed nucleic acid molecules. After hybridization and processing, the hybridization signals obtained should reflect accurately the amounts of control arrayed nucleic acid molecules added to the sample.

Prior to hybridization, it may be desirable to fragment the sample nucleic acid molecules. Fragmentation improves hybridization by minimizing secondary structure and cross-hybridization to other sample nucleic acid molecules in the sample or noncomplementary nucleic acid molecules. Fragmentation can be performed by mechanical or chemical means.

Labeling

The sample nucleic acid molecules or probes may be labeled with one or more labeling moieties to allow for detection of hybridized arrayed/sample nucleic acid molecule complexes. The labeling moieties can include compositions that can be detected by spectroscopic, photochemical, biochemical, bioelectronic, immunochemical, electrical, optical, or chemical means. The labeling moieties include radioisotopes, such as (32)P, (33)P or (35)S, chemiluminescent compounds, labeled binding proteins, heavy metal atoms, spectroscopic markers, such as fluorescent markers and dyes, magnetic labels, linked enzymes, mass spectrometry tags, spin labels, electron transfer donors and acceptors, and the like. Preferred fluorescent markers include Cy3 and Cy5 fluorophores (Amersham Pharmacia Biotech, Piscataway N.J.).

Hybridization

The nucleic acid molecule sequence of SEQ ID NOs: 1, 3, 5, 12, 13, 17, 18, 22, 23, 25, 26, 30, 31, 33, 35, 37, 39, 41, 43, 45, and 47 or other CD163 encoding sequences in the art and fragments thereof can be used in various hybridization technologies for various purposes. Hybridization probes may be designed or derived from any mammalian CD163 sequence but may make use of those sequences disclosed in SEQ ID NOs: 1, 3, 5, 12, 13, 17, 18, 22, 23, 25, 26, 30, 31, 33, 35, 37, 39, 41, 43, 45, and 47. Such probes may be made from a highly specific region or from a conserved motif, and used in protocols to quantify CD163 message, allelic variants, or related sequences. The hybridization probes of the subject invention may be DNA or RNA and may be derived from any mammalian CD163 sequence known in the art or from those sequences disclosed herein as SEQ ID NOs: 1, 3, 5, 12, 13, 17, 18, 22, 23, 25, 26, 30, 31, 33, 35, 37, 39, 41, 43, 45, and 47 or from genomic sequences including promoters, enhancers, and introns of the mammalian gene. Hybridization or PCR probes may be produced using oligolabeling, nick translation, end-labeling, or PCR amplification in the presence of the labeled nucleotide. A vector containing the nucleic acid sequence may be used to produce an mRNA probe in vitro by addition of an RNA polymerase and labeled nucleic acid molecules. These procedures may be conducted using commercially available kits such as those provided by Amersham Pharmacia Biotech.

The stringency of hybridization is determined by the G+C content of the probe, salt concentration, and temperature. In particular, stringency can be increased by reducing the concentration of salt or raising the hybridization temperature. In solutions used for some membrane-based hybridizations, additions of an organic solvent such as formamide allows the reaction to occur at a lower temperature. Hybridization can be performed at low stringency with buffers, such as 5× saline sodium citrate (SSC) with 1% sodium dodecyl sulfate (SDS) at 60° C., which permits the formation of a hybridization complex between nucleotide sequences that contain some mismatches. Subsequent washes are performed at higher stringency with buffers such as 0.2×SSC with 0.1% SDS at either 45° C. (medium stringency) or 68° C. (high stringency). At high stringency, hybridization complexes will remain stable only where the nucleic acid sequences are almost completely complementary. In some membrane-based hybridizations, preferably 35% or most preferably 50%, formamide can be added to the hybridization solution to reduce the temperature at which hybridization is performed, and background signals can be reduced by the use of other detergents such as Sarkosyl or Triton X-100 and a blocking agent such as salmon sperm DNA. Selection of components and conditions for hybridization are well known to those skilled in the art and are reviewed in Ausubel (supra) and Sambrook et al. (1989) Molecular Cloning, A Laboratory Manual, Cold Spring Harbor Press, Plainview N.Y.

Exemplary highly stringent hybridization conditions are as follows: hybridization at 42° C. in a hybridization solution comprising 50% formamide, 1% SDS, 1M NaCl, 10% Dextran sulfate, and washing twice for 30 minutes at 60° C. in a wash solution comprising 0.1×SSC and 1% SDS. It is understood in the art that conditions of equivalent stringency can be achieved through variation of temperature and buffer, or salt concentration as described in Ausubel, et al. (Eds.), Protocols in Molecular Biology, John Wiley & Sons (1994), pp. 6.0.3 to 6.4.10. Modifications in hybridization conditions can be empirically determined or precisely calculated based on the length and the percentage of guanosine/cytosine (GC) base pairing of the probe. The hybridization conditions can be calculated as described in Sambrook, et al., (Eds.), Molecular Cloning: A Laboratory Manual, Cold Spring Harbor Laboratory Press: Cold Spring Harbor, N.Y. (1989), pp. 9.47 to 9.51.

Hybridization specificity can be evaluated by comparing the hybridization of specificity-control nucleic acid molecules to specificity-control sample nucleic acid molecules that are added to a sample in a known amount. The specificity-control arrayed nucleic acid molecules may have one or more sequence mismatches compared with the corresponding arrayed nucleic acid molecules. In this manner, it is possible to determine whether only complementary arrayed nucleic acid molecules are hybridizing to the sample nucleic acid molecules or whether mismatched hybrid duplexes are forming is determined.

Hybridization reactions can be performed in absolute or differential hybridization formats. In the absolute hybridization format, nucleic acid molecules from one sample are hybridized to the molecules in a microarray format and signals detected after hybridization complex formation correlate to nucleic acid molecule levels in a sample. In the differential hybridization format, the differential expression of a set of genes in two biological samples is analyzed. For differential hybridization, nucleic acid molecules from both biological samples are prepared and labeled with different labeling moieties. A mixture of the two labeled nucleic acid molecules is added to a microarray. The microarray is then examined under conditions in which the emissions from the two different labels are individually detectable. Molecules in the microarray that are hybridized to substantially equal numbers of nucleic acid molecules derived from both biological samples give a distinct combined fluorescence (Shalon et al.; PCT publication WO95/35505). In a preferred embodiment, the labels are fluorescent markers with distinguishable emission spectra, such as Cy3 and Cy5 fluorophores.

After hybridization, the microarray is washed to remove nonhybridized nucleic acid molecules and complex formation between the hybridizable array elements and the nucleic acid molecules is detected. Methods for detecting complex formation are well known to those skilled in the art. In a preferred embodiment, the nucleic acid molecules are labeled with a fluorescent label and measurement of levels and patterns of fluorescence indicative of complex formation is accomplished by fluorescence microscopy, preferably confocal fluorescence microscopy.

In a differential hybridization experiment, nucleic acid molecules from two or more different biological samples are labeled with two or more different fluorescent labels with different emission wavelengths. Fluorescent signals are detected separately with different photomultipliers set to detect specific wavelengths. The relative abundances/expression levels of the nucleic acid molecules in two or more samples are obtained.

Typically, microarray fluorescence intensities can be normalized to take into account variations in hybridization intensities when more than one microarray is used under similar test conditions. In a preferred embodiment, individual arrayed-sample nucleic acid molecule complex hybridization intensities are normalized using the intensities derived from internal normalization controls contained on each microarray.

Polypeptide Based Assays

The present invention provides methods and reagents for detecting and quantifying CD163 polypeptides. These methods include analytical biochemical methods such as electrophoresis, mass spectroscopy, chromatographic methods and the like, or various immunological methods such as radioimmunoassay (RIA), enzyme-linked immunosorbent assays (ELISAs), immunofluorescent assays, western blotting, affinity capture mass spectrometry, biological activity, and others described below and apparent to those of skill in the art upon review of this disclosure.

Immunoassays

The present invention also provides methods for detection of CD163 polypeptides employing one or more anti-CD163 antibody reagents (i.e., immunoassays). As used herein, an immunoassay is an assay that utilizes an antibody (as broadly defined herein and specifically includes fragments, chimeras and other binding agents) that specifically binds a CD163 polypeptide or epitope.

A number of well-established immunological binding assay formats suitable for the practice of the invention are known (see, e.g., U.S. Pat. Nos. 4,366,241; 4,376,110; 4,517,288; and 4,837,168). See, e.g., Methods in Cell Biology Volume 37: Antibodies in Cell Biology, Asai, ed. Academic Press, Inc. New York (1993); Basic and Clinical Immunology 7th Edition, Stites & Terr, eds. (1991); Harlow and Lane, supra [e.g., Chapter 14], and Ausubel et al., supra, [e.g., Chapter 11]. Typically, immunological binding assays (or immunoassays) utilize a "capture agent" to specifically bind to and, often, immobilize the analyte to a solid phase. In one embodiment, the capture agent is a moiety that specifically binds to a CD163 polypeptide or subsequence, such as an anti-CD163 antibody.

Usually the CD163 gene product being assayed is detected directly or indirectly using a detectable label. The particular label or detectable group used in the assay is usually not a critical aspect of the invention, so long as it does not significantly interfere with the specific binding of the antibody or antibodies used in the assay. The label may be covalently attached to the capture agent (e.g., an anti-CD163 antibody), or may be attached to a third moiety, such as another antibody, that specifically binds to the CD163 polypeptide.

The present invention provides methods and reagents for competitive and noncompetitive immunoassays for detecting CD163 polypeptides. Noncompetitive immunoassays are assays in which the amount of captured analyte (in this case CD163) is directly measured. One such assay is a two-site, monoclonal-based immunoassay utilizing monoclonal antibodies reactive to two non-interfering epitopes on the CD163 polypeptide. See, e.g., Maddox et al., 1983, J. Exp. Med., 158:1211 for background information. In one "sandwich" assay, the capture agent (e.g., an anti-CD163 antibody) is bound directly to a solid substrate where it is immobilized. These immobilized antibodies then capture any CD163 polypeptide present in the test sample. The CD163 polypeptide thus immobilized can then be labeled, e.g., by binding to a second anti-CD163 antibody bearing a label. Alternatively, the second CD163 antibody may lack a label, but be bound by a labeled third antibody specific to antibodies of the species from which the second antibody is derived. The second antibody alternatively can be modified with a detectable moiety, such as biotin, to which a third labeled molecule can specifically bind, such as enzyme-labeled streptavidin.

In competitive assays, the amount of CD163 polypeptide present in the sample is measured indirectly by measuring the amount of an added (exogenous) CD163 polypeptide displaced (or competed away) from a capture agent (e.g., CD163 antibody) by the CD163 polypeptide present in the sample. A hapten inhibition assay is another example of a competitive assay. In this assay CD163 polypeptide is immobilized on a solid substrate. A known amount of CD163 antibody is added to the sample, and the sample is then contacted with the immobilized CD163 polypeptide. In this case, the amount of anti-CD163 antibody bound to the immobilized CD163 polypeptide is inversely proportional to the amount of CD163 polypeptide present in the sample. The amount of immobilized antibody may be detected by detecting either the immobilized fraction of antibody or the fraction of the antibody that remains in solution. In this aspect, detection may be direct, where the antibody is labeled, or indirect where the label is bound to a molecule that specifically binds to the antibody as described above.

Other Antibody-Based Assay Formats

The invention also provides reagents and methods for detecting and quantifying the presence of CD163 polypeptide in the sample by using an immunoblot (Western blot) format. Another immunoassay is the so-called "lateral flow chromatography." In a non-competitive version of lateral flow chromatography, a sample moves across a substrate by, e.g., capillary action, and encounters a mobile-labeled antibody that binds the analyte forming a conjugate. The conjugate then moves across the substrate and encounters an immobilized second antibody that binds the analyte. Thus, immobilized analyte is detected by detecting the labeled antibody. In a competitive version of lateral flow chromatography a labeled version of the analyte moves across the carrier and competes with unlabeled analyte for binding with the immobilized antibody. The greater the amount of the analyte in the sample, the less the binding by labeled analyte and, therefore, the weaker the signal. See, e.g., May et al., U.S. Pat. No. 5,622,871; and Rosenstein, U.S. Pat. No. 5,591,645.

Depending upon the assay, various components, including the antigen, target antibody, or anti-cathepsin S antibody, may be bound to a solid surface or support (i.e., a substrate, membrane, or filter paper). Many methods for immobilizing biomolecules to a variety of solid surfaces are known in the art. For instance, the solid surface may be a membrane (e.g., nitrocellulose), a microtiter dish (e.g., PVC, polypropylene, or polystyrene), a test tube (glass or plastic), a dipstick (e.g. glass, PVC, polypropylene, polystyrene, latex, and the like), a microcentrifuge tube, or a glass or plastic bead. The desired component may be covalently bound or noncovalently attached through nonspecific bonding.

A wide variety of organic and inorganic polymers, both natural and synthetic may be employed as the material for the solid surface. Illustrative polymers include polyethylene, polypropylene, poly (4-methylbutene), polystyrene, polymethacrylate, poly(ethylene terephthalate), rayon, nylon, poly(vinylbutyrate), polyvinylidene difluoride (PVDF), silicones, polyformaldehyde, cellulose, cellulose acetate, nitrocellulose, and the like. Other materials that may be employed, include paper, glasses, ceramics, metals, metalloids, semiconductive materials, cements or the like. In addition, substances that form gels, such as proteins (e.g., gelatins), lipopolysaccharides, silicates, agarose and polyacrylamides can be used. Polymers that form several aqueous phases, such as dextrans, polyalkylene glycols or surfactants, such as phospholipids, long chain (12-24 carbon atoms) alkyl ammonium salts and the like are also suitable. Where the solid surface is porous, various pore sizes may be employed depending upon the nature of the system.

Mass Spectrometry

The mass of a molecule frequently can be used as an identifier of the molecule. Therefore, methods of mass spectrometry can be used to identify a protein analyte. Mass spectrometers can measure mass by determining the time required for an ionized analyte to travel down a flight tube and to be detected by an ion detector. One method of mass spectrometry for proteins is matrix-assisted laser desorption ionization mass spectrometry ("MALDI"). In MALDI the analyte is mixed with an energy absorbing matrix material that absorbs energy of the wavelength of a laser and placed on the surface of a probe. Upon striking the matrix with the laser, the analyte is desorbed from the probe surface, ionized, and detected by the ion detector. See, for example, Hillenkamp et al., U.S. Pat. No. 5,118,937.

Other methods of mass spectrometry for proteins are described in Hutchens and Yip, U.S. Pat. No. 5,719,060. In one such method referred to as Surfaces Enhanced for Affinity Capture ("SEAC") a solid phase affinity reagent that binds the analyte specifically or non-specifically, such as an antibody or a metal ion, is used to separate the analyte from other materials in a sample. Then the captured analyte is desorbed from the solid phase by, e.g., laser energy, ionized, and detected by the detector.

Nucleic Acids of the Invention

The examples below disclose our discovery of several novel CD163 polynucleotides. The invention includes these novel CD163 polynucleotides. The present invention provides several isolated novel polynucleotides (e.g., DNA sequences and RNA transcripts, both sense and complementary antisense strands, both single and double-stranded, including splice variants thereof, which encode novel CD163 polypeptides. We report herein isolated novel polynucleotides which encode porcine, murine, human, canine, and african green monkey CD163 polypeptides and which comprise the sequences set forth in SEQ ID NOs: 1, 5, 12, 13, 22, 23, 25, 26, 30, 31, 33, 35, 37, 39, 41, 43, 45, and 47.

It should be recognized that by disclosing SEQ ID NOs: 1, 5, 12, 13, 22, 23, 25, 26, 30, 31, 33, 35, 37, 39, 41, 43, 45, and 47 it provides one skilled in the art a multitude of methods of obtaining these sequences. By way of example, it would be possible to generate probes from the sequences disclosed in SEQ ID NOs: 1, 5, 12, 13, 22, 23, 25, 26, 30, 31, 33, 35, 37, 39, 41, 43, 45, and 47 and screen porcine, murine, human, canine, and african green monkey cDNA or genomic libraries and thereby obtain the entire sequence disclosed in SEQ ID NOs: 1, 3, 5, 12, 13, 17, 18, 22, 23, 25, 26, 30, 31, 33, 35, 37, 39, 41, 43, 45 and 47, or its genomic equivalent. Sambrook, et al., (Eds.), *Molecular Cloning: A Laboratory Manual*, Cold Spring Harbor Laboratory Press: Cold Spring Harbor, N.Y. (1989). Also by way of example, one skilled in the art would immediately recognize that given the sequence disclosed in SEQ ID NO: 1, 5, 12, 13, 22, 23, 25, 26, 30, 31, 33, 35, 37, 39, 41, 43, 45, and 47 it is then possible to generate the appropriate primers for PCR amplification to obtain the entire sequence represented by these sequences. (See e.g., PCR Technology, H. A. Erlich, ed., Stockton Press, New York, 1989; PCR Protocols: A Guide to Methods and Applications, M. A. Innis, David H. Gelfand, John J. Sninsky, and Thomas J. White, eds., Academic Press, Inc., New York, 1990.)

DNA polynucleotides of the invention include cDNA, and DNA that has been chemically synthesized in whole or in part and is also intended to include allelic variants thereof. Allelic variants are modified forms of a wild type gene sequence, the modification resulting from recombination during chromosomal segregation, or exposure to conditions which give rise to genetic mutation. Allelic variants, like wild type genes, are naturally occurring sequences (as opposed to non-naturally occurring variants which arise from in vitro manipulation).

DNA sequences encoding the novel CD163 polypeptides are set forth in SEQ ID NOs: 1, 5, 12, 13, 22, 23, 25, 26, 30, 31, 33, 35, 37, 39, 41, 43, 45, and 47. The worker of skill in the art will readily appreciate that the DNA of the invention comprises a double stranded molecule, for example the molecule having the sequence set forth in SEQ ID NO: 1, 5, 12, 13, 22, 23, 25, 26, 30, 31, 33, 35, 37, 39, 41, 43, 45, and 47 along with the complementary molecule (the "non-coding strand" or "complement") having a sequence deducible from the sequences of SEQ ID NOs: 1, 5, 12, 13, 22, 23, 25, 26, 30, 31, 33, 35, 37, 39, 41, 43, 45, and 47 according to Watson-Crick base pairing rules for DNA. Also contemplated by the invention are other polynucleotides encoding for the porcine, murine, and african green monkey CD163 polypeptides of SEQ ID NOS: 2, 14, 24, 27, 32, 34, 36, 38, 40, 42, 44, 46, and 48 which differ in sequence from the polynucleotide of SEQ ID NOs: 1, 3, 5, 12, 13, 17, 18, 22, 23, 25, 26, 30, 31, 33, 35, 37, 39, 41, 43, 45, and 47 by virtue of the well-known degeneracy of the universal genetic code, as is well known in the art. The present invention, therefore, contemplates those other DNA and RNA molecules that, on expression, encode the polypeptides of SEQ ID NO: 2, 14, 24, 27, 32, 34, 36, 38, 40, 42, 44, 46, and 48. Having identified the amino acid residue sequence encoded the porcine CD163 polypeptide, and with the knowledge of all triplet codons for each particular amino acid residue, it is possible to describe all such encoding RNA and DNA sequences. DNA and RNA molecules other than those specifically disclosed herein characterized simply by a change in a codon for a particular amino acid, are, therefore, within the scope of this invention.

A table of amino acids and their representative abbreviations, symbols and codons is set forth below in the following Table 4.

TABLE 4

| Amino acid | Abbrev. | Symbol | Codon(s) | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |

TABLE 4-continued

| Amino acid | Abbrev. | Symbol | Codon(s) | | | | | |
|---|---|---|---|---|---|---|---|---|
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

As is well known in the art, codons constitute triplet sequences of nucleotides in mRNA and their corresponding cDNA molecules. Codons are characterized by the base uracil (U) when present in an mRNA molecule but are characterized by the base thymidine (T) when present in DNA. A simple change in a codon for the same amino acid residue within a polynucleotide will not change the sequence or structure of the encoded polypeptide. It is apparent that when a phrase stating that a particular 3 nucleotide sequence "encode(s)" any particular amino acid, the ordinarily skilled artisan would recognize that the table above provides a means of identifying the particular nucleotides at issue. By way of example, if a particular three-nucleotide sequence encodes theonine the table above discloses that the possible triplet sequences are ACA, ACG, ACC, and ACU (ACT if in DNA).

The invention includes therefore, an isolated polynucleotide comprising:

(a) a susCD163v1 polynucleotide sequence set forth in SEQ ID NOs: 1 and 5;

(b) a polynucleotide that encodes a polypeptide that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity and/or similarity to a polypeptide set forth in SEQ ID NO: 2;

(c) a polynucleotide encoding a polypeptide of SEQ ID NO: 2;

(d) a polynucleotide that is the complement of any of (a), (b), or (c).

The invention also includes an isolated polynucleotide comprising:

(a) a susCD163v2 polynucleotide sequence set forth in SEQ ID NOs: 12 or 13;

(b) a polynucleotide that encodes a polypeptide that has at least 99% identity and/or similarity to a polypeptide set forth in SEQ ID NO: 14;

(c) a polynucleotide encoding a polypeptide of SEQ ID NO: 14;

(d) a polynucleotide that is the complement of any of (a), (b), or (c).

The invention also includes an isolated polynucleotide comprising:

(a) a susCD163v2 polynucleotide sequence set forth in SEQ ID NOs: 17 or 18;

(b) a polynucleotide encoding a polypeptide of SEQ ID NO: 19;

(d) a polynucleotide that is the complement of any of (a) or (b).

The invention also includes an isolated polynucleotide comprising:

(a) a CD63v2 polynucleotide sequence set forth in SEQ ID NOs: 22 or 23;

(b) a polynucleotide encoding a polypeptide of SEQ ID NO: 24;

(c) a polynucleotide that is the complement of (a) or (b).

The invention also includes an isolated polynucleotide comprising:

(a) a CD163v3 polynucleotide sequence set forth in SEQ ID NOs: 25 or 26;

(b) a polynucleotide that encodes a polypeptide that has at least 96%, 97%, 98%, or 99% identity and/or similarity to a polypeptide set forth in SEQ ID NO: 27;

(c) a polynucleotide encoding a polypeptide of SEQ ID NO: 27;

(d) a polynucleotide that is the complement of any of (a), (b), or (c).

The invention also includes an isolated polynucleotide comprising:

(a) a CD163v2 polynucleotide sequence set forth in SEQ ID NOs: 30 or 31;

(b) a polynucleotide that encodes a polypeptide that has at least 98% or 99% identity and/or similarity to a polypeptide set forth in SEQ ID NO: 32;

(c) a polynucleotide encoding a polypeptide of SEQ ID NO: 32;

(d) a polynucleotide that is the complement of any of (a), (b), or (c).

The invention also includes an isolated polynucleotide comprising:

(a) a polynucleotide sequence set forth in SEQ ID NO: 33;

(b) a polynucleotide that encodes a polypeptide that has at least 95%, 96%, 97%, 98%, or 99% identity and/or similarity to a polypeptide set forth in SEQ ID NO: 34;

(c) a polynucleotide encoding a polypeptide of SEQ ID NO: 34;

(d) a polynucleotide that is the complement of any of (a), (b), or (c).

The invention also includes an isolated polynucleotide comprising:

(a) a polynucleotide sequence set forth in SEQ ID NO: 35;

(b) a polynucleotide that encodes a polypeptide that has at least 95%, 96%, 97%, 98%, or 99% identity and/or similarity to a polypeptide set forth in SEQ ID NO: 36;

(c) a polynucleotide encoding a polypeptide of SEQ ID NO: 36;

(d) a polynucleotide that is the complement of any of (a), (b), or (c).

The invention also includes an isolated polynucleotide comprising:

(a) a polynucleotide sequence set forth in SEQ ID NO: 37;

(b) a polynucleotide that encodes a polypeptide that has at least 95%, 96%, 97%, 98%, or 99% identity and/or similarity to a polypeptide set forth in SEQ ID NO: 38

(c) a polynucleotide encoding a polypeptide of SEQ ID NO: 38;

(d) a polynucleotide that is the complement of any of (a), (b), or (c).

The invention also includes an isolated polynucleotide comprising:

(a) a polynucleotide sequence set forth in SEQ ID NO: 39;

(b) a polynucleotide that encodes a polypeptide that has at least 95%, 96%, 97%, 98%, or 99% identity and/or similarity to a polypeptide set forth in SEQ ID NO: 40;

(c) a polynucleotide encoding a polypeptide of SEQ ID NO: 40;

(d) a polynucleotide that is the complement of any of (a), (b), or (c).

The invention also includes an isolated polynucleotide comprising:

(a) a polynucleotide sequence set forth in SEQ ID NO: 41;

(b) a polynucleotide that encodes a polypeptide that has at least 95%, 96%, 97%, 98%, or 99% identity and/or similarity to a polypeptide set forth in SEQ ID NO: 42;

(c) a polynucleotide encoding a polypeptide of SEQ ID NO: 42;

(d) a polynucleotide that is the complement of any of (a), (b), or (c).

The invention also includes an isolated polynucleotide comprising:

(a) a polynucleotide sequence set forth in SEQ ID NO: 43;

(b) a polynucleotide that encodes a polypeptide that has at least 95%, 96%, 97%, 98%, or 99% identity and/or similarity to a polypeptide set forth in SEQ ID NO: 44;

(c) a polynucleotide encoding a polypeptide of SEQ ID NO: 44;

(d) a polynucleotide that is the complement of any of (a), (b), or (c).

The invention also includes an isolated polynucleotide comprising:

(a) a polynucleotide sequence set forth in SEQ ID NO: 45;

(b) a polynucleotide that encodes a polypeptide that has at least 90%, 91%, 92%, 93%, 94%, 95%, 96%, 97%, 98%, or 99% identity and/or similarity to a polypeptide set forth in SEQ ID NO: 46;

(c) a polynucleotide encoding a polypeptide of SEQ ID NO: 46;

(d) a polynucleotide that is the complement of any of (a), (b), or (c).

The invention also includes an isolated polynucleotide comprising:

(a) a polynucleotide sequence set forth in SEQ ID NO: 47;

(b) a polynucleotide that encodes a polypeptide that has at least 90%, 91%, 92%, 93%, 94%, 95%, 96%, 97%, 98%, or 99% identity and/or similarity to a polypeptide set forth in SEQ ID NO: 48;

(c) a polynucleotide encoding a polypeptide of SEQ ID NO: 49;

(d) a polynucleotide that is the complement of any of (a), (b), or (c).

The polynucleotide sequence information provided by the invention makes possible large-scale expression of the encoded polypeptide by techniques well known and routinely practiced in the art. Polynucleotides of the invention also permit identification and isolation of polynucleotides encoding related porcine CD163v1 polypeptides, such as human allelic variants and species homologs, by well-known techniques including Southern and/or Northern hybridization, and the polymerase chain reaction (PCR).

Knowledge of the sequence of any of the CD163 sequences disclosed herein also makes possible through use of Southern hybridization or polymerase chain reaction (PCR), the identification of genomic DNA sequences encoding CD163 regulatory sequences, such as promoters, operators, enhancers, repressors, and the like.

As noted in the section above entitled "Assays of the Invention" polynucleotides of the invention are also useful in hybridization assays to detect the capacity of cells to express CD163, or to measure levels of CD163 expression. Polynucleotides of the invention may also be the basis for diagnostic methods useful for determining the susceptibility of an animal to virus infection as described above.

The disclosure herein of the full-length polynucleotides encoding a CD163 polypeptide makes readily available to the worker of ordinary skill in the art fragments of the full length polynucleotide. The invention therefore provides unique fragments of the CD163 encoding polynucleotides comprising at least 15 through the length of the full-length sequence (including each and every integer value between) consecutive nucleotides of a polynucleotide encoding a CD163 disclosed herein. Because polynucleotides of the invention (including fragments) comprise sequences unique to the particular CD163-encoding polynucleotide sequence, they therefore would hybridize under highly stringent or moderately stringent conditions only (i.e., "specifically") to polynucleotides encoding the various CD163 polypeptides. Sequences unique to polynucleotides of the invention are recognizable through sequence comparison to other known polynucleotides, and can be identified through use of alignment programs routinely utilized in the art, e.g., those made available in public sequence databases. Such sequences also are recognizable from Southern hybridization analyses to determine the number of fragments of genomic DNA to which a polynucleotide will hybridize. Polynucleotides of the invention can be labeled in a manner that permits their detection, including radioactive, fluorescent, and enzymatic labeling.

One or more unique fragment polynucleotides (or other CD163 polynucleotides as discussed above) can be included in kits that are used to detect the presence of a polynucleotide encoding for CD163, or used to detect variations in a polynucleotide sequence encoding for CD163. Also made available by the invention are anti-sense polynucleotides that recognize and hybridize to polynucleotides encoding CD163. Full length and fragment anti-sense polynucleotides are provided. Fragment anti-sense molecules of the invention include (i) those that specifically recognize and hybridize to the CD163 variants disclosed herein (as determined by sequence comparison of DNA encoding CD163s to DNA encoding other known molecules). Identification of sequences unique to the novel CD163-encoding polynucleotides can be deduced through the use of any publicly available sequence database, and/or through the use of commercially available sequence comparison programs. The uniqueness of selected sequences in an entire genome can be further verified by hybridization analyses. After identification of the desired sequences, isolation through restriction digestion or amplification using any of the various polymerase chain reaction techniques well known in the art can be performed. Anti-sense polynucleotides are particularly relevant to regulating expression of CD163 by those cells expressing CD163 mRNA.

Antisense nucleic acids (preferably 10 to 20 base pair oligonucleotides) capable of specifically binding to CD163 expression control sequences or CD163 RNA are introduced into cells (e.g., by a viral vector or colloidal dispersion system such as a liposome). The antisense nucleic acid binds to the porcine CD163 target nucleotide sequence in the cell and prevents transcription or translation of the target sequence. Phosphorothioate and methylphosphonate antisense oligonucleotides are specifically contemplated for therapeutic use by the invention. The antisense oligonucleotides may be further modified by poly-L-lysine, transferrin polylysine, or cholesterol moieties at their 5' end. Suppression of porcine CD163 expression at either the transcriptional or translational level is useful to generate cellular or animal models for diseases characterized by aberrant porcine CD163 expression or as a therapeutic modality.

As noted above in more detail, the nucleic acids of the invention include vectors comprising a polynucleotide of the invention. Such vectors are useful, e.g., for amplifying the polynucleotides in host cells to create useful quantities thereof. In other embodiments, the vector is an expression vector wherein the polynucleotide of the invention is operatively linked to a polynucleotide comprising an expression control sequence. Such vectors are useful for recombinant production of polypeptides of the invention.

Also as noted above the invention provides host cells that are transformed or transfected (stably or transiently) with polynucleotides of the invention or vectors of the invention. As stated above, such host cells are useful for the production of virus and the production of vaccines.

The invention also provides isolated CD163 polypeptides encoded by a novel polynucleotide of the invention.

Polypeptides of the Invention

The examples disclose our discovery of several novel CD163 polypeptides. The invention includes these novel CD163 polypeptide which are set forth in SEQ ID NOs: 2, 14, 19, 24, 27, 32, 34, 36, 38, 40, 42, 44, 46, and 48.

The invention includes therefore, an isolated polynucleotide comprising a susCD163v1 polypeptide with the sequence set forth in SEQ ID NO: 2.

The invention also includes a polypeptide that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity and/or similarity to a polypeptide set forth in SEQ ID NO: 2.

The invention includes therefore, an isolated polynucleotide comprising a susCD163v2 polypeptide with the sequence set forth in SEQ ID NO: 14.

The invention also includes a polypeptide that has at least 99%, identity and/or similarity to a susCD163v2 polypeptide set forth in SEQ ID NO: 14.

The invention also includes a CD163v2 polypeptide having the sequence set forth in SEQ ID NO: 24.

The invention also includes a CD163v3 polypeptide having the sequence set forth in SEQ ID NO: 27.

The invention also includes a polypeptide having at least 96%, 97% 98%, or 99% identity and/or similarity to a polypeptide set forth in SEQ ID NO: 27.

The invention also includes a polypeptide having the sequence set forth in SEQ ID NO: 32.

The invention also includes a polypeptide that has at least 98% or 99% identity and/or similarity to a polypeptide set forth in SEQ ID NO: 32.

The invention also includes a polypeptide having the sequence set forth in SEQ ID NO: 34.

The invention also includes a polypeptide that has at least 95%, 96%, 97%, 98%, or 99% identity and/or similarity to a polypeptide set forth in SEQ ID NO: 34.

The invention also includes a polypeptide having the sequence set forth in SEQ ID NO: 36.

The invention also includes a polypeptide that has at least 95%, 96%, 97%, 98%, or 99% identity and/or similarity to a polypeptide set forth in SEQ ID NO: 36.

The invention also includes a polypeptide having the sequence set forth in SEQ ID NO: 38.

The invention also includes a polypeptide that has at least 95%, 96%, 97%, 98%, or 99% identity and/or similarity to a polypeptide set forth in SEQ ID NO: 39.

The invention also includes a polypeptide having the sequence set forth in SEQ ID NO: 40.

The invention also includes a polypeptide that has at least 95%, 96%, 97%, 98%, or 99% identity and/or similarity to a polypeptide set forth in SEQ ID NO: 40.

The invention also includes a polypeptide having the sequence set forth in SEQ ID NO: 42.

The invention also includes a polypeptide that has at least 90%, 91%, 92%, 93%, 94%, 95%, 96%, 97%, 98%, or 99% identity and/or similarity to a polypeptide set forth in SEQ ID NO: 42.

The invention also includes a polypeptide having the sequence set forth in SEQ ID NO: 44.

The invention also includes a polypeptide that has at least 90%, 91%, 92%, 93%, 94%, 95%, 96%, 97%, 98%, or 99% identity and/or similarity to a polypeptide set forth in SEQ ID NO: 44.

The invention also includes a polypeptide having the sequence set forth in SEQ ID NO: 46.

The invention also includes a polypeptide that has at least 90%, 91%, 92%, 93%, 94%, 95%, 96%, 97%, 98%, or 99% identity and/or similarity to a polypeptide set forth in SEQ ID NO: 46.

The invention also includes a polypeptide having the sequence set forth in SEQ ID NO: 48.

The invention also includes a polypeptide that has at least 90%, 91%, 92%, 93%, 94%, 95%, 96%, 97%, 98%, or 99% identity and/or similarity to a polypeptide set forth in SEQ ID NO: 48.

Polypeptides of the invention may be isolated from natural cell sources or may be chemically synthesized, but are preferably produced by recombinant procedures involving host cells of the invention. Use of mammalian host cells is expected to provide for such post-translational modifications (e.g., glycosylation, truncation, lipidation, and phosphorylation) as may be needed to confer optimal biological activity on recombinant expression products of the invention. Glycosylated and non-glycosylated forms of the novel CD163 polypeptides are embraced.

Overexpression in eukaryotic and prokaryotic hosts as described above facilitates the isolation of CD163 polypeptides. The invention therefore includes isolated CD163 polypeptides as set out in SEQ ID NOs: 2, 14, 19, 24, 27, 32, 34, 36, 38, 40, 42, 44, 46, and 48 and variants and conservative amino acid substitutions therein including labeled and tagged polypeptides.

The invention includes novel CD163 polypeptides that are "labeled". The term "labeled" is used herein to refer to the conjugating or covalent bonding of any suitable detectable group, including enzymes (e.g., horseradish peroxidase, beta-glucuronidase, alkaline phosphatase, and beta-D-galactosidase), fluorescent labels (e.g., fluorescein, luciferase), and radiolabels (e.g., $^{14}C$, $^{125}I$, $^{3}H$, $^{32}P$, and $^{35}S$) to the compound being labeled. Techniques for labeling various compounds, including proteins, peptides, and antibodies, are well known. See, e.g., Morrison, Methods in Enzymology 32b, 103 (1974); Syvanen et al., J. Biol. Chem. 284, 3762 (1973); Bolton and Hunter, Biochem. J. 133, 529 (1973). The termed labeled may also encompass a polypeptide which has covalently attached an amino acid tag as discussed below.

In addition, the novel CD163 polypeptides of the invention may be indirectly labeled. This involves the covalent addition of a moiety to the polypeptide and subsequent coupling of the added moiety to a label or labeled compound that exhibits specific binding to the added moiety. Possibilities for indirect labeling include biotinylation of the peptide followed by binding to avidin coupled to one of the above label groups. Another example would be incubating a radiolabeled antibody specific for a histidine tag with a CD163s polypeptide comprising a polyhistidine tag. The net effect is to bind the radioactive antibody to the polypeptide because of the considerable affinity of the antibody for the tag.

The invention also embraces variants (or analogs) of the novel CD163 protein. In one example, insertion variants are provided wherein one or more amino acid residues supplement a novel CD163 amino acid sequence. Insertions may be located at either or both termini of the protein, or may be positioned within internal regions of the novel CD163 protein amino acid sequence. Insertional variants with additional residues at either or both termini can include for example, fusion proteins and proteins including amino acid tags or labels. Insertion variants include novel CD163 polypeptides wherein one or more amino acid residues are added to a CD163 acid sequence, or to a biologically active fragment thereof.

Insertional variants therefore can also include fusion proteins wherein the amino and/or carboxy termini of the novel CD163 polypeptide is fused to another polypeptide. Various tag polypeptides and their respective antibodies are well known in the art. Examples include poly-histidine (poly-his) or poly-histidine-glycine (poly-his-gly) tags; the influenza HA tag polypeptide and its antibody 12CA5 [Field et al., Mol. Cell. Biol., 8:2159-2165 (1988)]; the c-myc tag and the 8F9, 3C7, 6E10, G4, B7 and 9E10 antibodies thereto [Evan et al., Molecular and Cellular Biology, 5:3610-3616 (1985)], and the Herpes Simplex virus glycoprotein D (gD) tag and its antibody [Paborsky et al., Protein Engineering, 3(6):547-553 (1990)]. Other tag polypeptides include the Flag-peptide [Hopp et al., BioTechnology, 6:1204-1210 (1988)]; the KT3 epitope peptide [Martin et al., Science, 255:192-194 (1992)]; an alpha-tubulin epitope peptide [Skinner et al., J. Biol. Chem., 266:15163-15166 (1991)]; and the T7 gene 10 protein peptide tag [Lutz-Freyermuth et al., Proc. Natl. Acad. Sci. USA, 87:6393-6397 (1990)]. In addition, the CD163 polypeptide can be tagged with enzymatic proteins such as peroxidase and alkaline phosphatase.

In another aspect, the invention provides deletion variants wherein one or more amino acid residues in a novel CD163 polypeptide is removed. Deletions can be effected at one or both termini of the novel CD163 polypeptide, or with removal of one or more residues within the novel CD163 amino acid sequence. Deletion variants, therefore, include all fragments of the novel CD163 polypeptide.

CD163 polypeptides contain a transmembrane or membrane anchor region. It should be recognized that such transmembrane domains are useful when expressed in the context of a heterologous protein to aid in the targeting of the heterologous protein to membranes. It should also be recognized that it may be advantageous to delete some transmembrane domains to enhance the purification or solubility of the protein. Transmembrane deleted variants of CD163 and polynucleotides encoding them are of potential value as antiviral therapeutics. Such variants are specifically disclosed here as SEQ ID NOs: 37-40.

The present invention also includes variants of the aforementioned polypetides, that is, polypeptides that vary from the reference sequence by conservative amino acid substitutions.

Exemplary conservative substitutions are set out in Tables 1, 2 and 3 in the section above entitled "Definitions".

In those situations where it is preferable to partially or completely isolate the novel CD163 polypeptides, purification can be accomplished using standard methods well known to the skilled artisan. Such methods include, without limitation, separation by electrophoresis followed by electroelution, various types of chromatography (immunoaffinity, molecular sieve, and/or ion exchange), and/or high pressure liquid chromatography. In some cases, it may be preferable to use more than one of these methods for complete purification.

Purification of novel CD163 polypeptides can be accomplished using a variety of techniques. If the polypeptide has been synthesized such that it contains a tag such as Hexahistidine (CD163/hexaHis) or other small peptide such as FLAG (Eastman Kodak Co., New Haven, Conn.) or myc (Invitrogen, Carlsbad, Calif.) at either its carboxyl or amino terminus, it may essentially be purified in a one-step process by passing the solution through an affinity column where the column matrix has a high affinity for the tag or for the polypeptide directly (i.e., a monoclonal antibody specifically recognizing CD163). For example, polyhistidine binds with great affinity and specificity to nickel, thus an affinity column of nickel (such as the Qiagen Registered TM nickel columns) can be used for purification of CD163/polyHis. (See for example, Ausubel et al., eds., Current Protocols in Molecular Biology, Section 10.11.8, John Wiley & Sons, New York [1993]).

Even if the novel CD163 polypeptide is prepared without a label or tag to facilitate purification, the novel CD163 of the invention may be purified by immunoaffinity chromatography. To accomplish this, antibodies specific for CD163 polypeptides must be prepared by means well known in the art.

Antibodies generated against the novel CD163 polypeptides of the invention can be obtained by administering the polypeptides or epitope-bearing fragments, analogues, or cells to an animal, preferably a non-human, using routine protocols. For preparation of monoclonal antibodies, any technique known in the art that provides antibodies produced by continuous cell line cultures can be used. Examples include various techniques, such as those in Kohler, G. and Milstein, C., Nature 256: 495-497 (1975); Kozbor et al., Immunology Today 4: 72 (1983); Cole et al., pg. 77-96 in Monoclonal Antibodies and Cancer Therapy, Alan R. Liss, Inc. (1985).

Where the novel CD163 polypeptides are prepared without a tag attached, and no antibodies are available, other well-known procedures for purification can be used. Such procedures include, without limitation, ion exchange chromatography, molecular sieve chromatography, HPLC, native gel electrophoresis in combination with gel elution, and preparative isoelectric focusing ("Isoprime" machine/technique, Hoefer Scientific). In some cases, two or more of these techniques may be combined to achieve increased purity.

It should be understood that the definition of polypeptides of the invention is intended to include polypeptides bearing modifications other than insertion, deletion, or substitution of amino acid residues. By way of example, the modifications may be covalent in nature, and include for example, chemical bonding with polymers, lipids, other organic, and inorganic moieties.

Antibodies

Also comprehended by the present invention are antibodies (e.g., monoclonal and polyclonal antibodies, single chain antibodies, chimeric antibodies, bifunctional/bispecific antibodies, humanized antibodies, human antibodies, and complementary determining region (CDR)-grafted antibodies, including compounds which include CDR sequences which specifically recognize a polypeptide of the invention) specific for novel CD163 or fragments thereof.

The term "specific for," when used to describe antibodies of the invention, indicates that the variable regions of the antibodies of the invention recognize and bind CD163s polypeptides exclusively (i.e., able to distinguish CD163s polypeptides from other known polypeptides by virtue of measurable differences in binding affinity, despite the possible existence of localized sequence identity, homology, or similarity between the novel CD163 and such polypeptides). It will be understood that specific antibodies may also interact with other proteins (for example, *S. aureus* protein A or other antibodies in ELISA techniques) through interactions with sequences outside the variable region of the antibodies, and in particular, in the constant region of the molecule. Screening assays to determine binding specificity of an antibody of the invention are well known and routinely practiced in the art. For a comprehensive discussion of such assays, see Harlow et al. (Eds), Antibodies A Laboratory Manual; Cold Spring Harbor Laboratory; Cold Spring Harbor, N.Y. (1988), Chapter 6. Antibodies that recognize and bind fragments of the CD163s polypeptides of the invention are also contemplated, provided that the antibodies are, first and foremost, specific for novel CD163 polypeptides. Antibodies of the invention can be produced using any method well known and routinely practiced in the art. Non-human antibodies may be humanized by any methods known in the art. In one method, the non-human CDRs are inserted into a human antibody or consensus antibody framework sequence. Further changes can then be introduced into the antibody framework to modulate affinity or immunogenicity.

Antibodies of the invention are useful for, diagnostic purposes to detect or quantitate CD163s, as well as purification of CD163s. Kits comprising an antibody of the invention for any of the purposes described herein are also contemplated. In general, a kit of the invention also includes a control antigen for which the antibody is immunospecific.

The present invention is further illustrated, but not limited, by the following examples.

Example 1

Transient transfection with porcine CD163 confers permissivity to PRRS virus infection to a non-permissive cell line. Total mRNA from primary porcine alveolar macrophage cells was used to construct a cDNA library in the plasmid pCMV-Sport6.1 (Invitrogen), with the cDNA cloned between the EcoRV and NotI sites. A member of this library, when isolated and transiently transfected into the BHK-21 (baby hamster kidney) cell line, conferred a PRRS-permissive phenotype. Cells were grown in Dulbecco's modified Eagle medium (DMEM) supplemented with 5% fetal bovine serum (FBS) in a 5% $CO_2$ atmosphere at 37° C. Cell cultures were transiently transfected using 10.0 uL of Lipofectamine 2000 (Invitrogen) and 2.0 ug of plasmid. A duplicate monolayer was transfected with negative control plasmid pPAMB. This plasmid is pCMV-Sport6.1 lacking an insert. Transfection efficiency was monitored with a plasmid expressing green fluorescent protein (GFP). Approximately 24 hours post-transfection, monolayers were infected with either North American (isolate P129) or European (isolate 96V198) genotypes of PRRS virus. For detection of PRRS replication, the monolayers were fixed using 80% acetone approximately 24 hours post-infection and incubated for approximately 1 hour with FITC-conjugated monoclonal antibody SDOW17 (Rural Technologies Inc.). This monoclonal antibody is specific for PRRS viral nucleocapsid expressed from open reading frame 7. A Nikon TE 300 inverted fluorescent microscope with a 10× objective was used to photograph a monolayer containing FITC positive cells and a negative control monolayer.

It was confirmed that transfected cells became permissive to both the North American (isolate P129) and European (isolate 96V198) genotypes of PRRSV. Expression of viral genes could be detected in many of the transfected BHK cells, and progeny virus was readily detectable in the supernatant. Control transfections using vector without insert or irrelevant plasmids did not confer permissivity.

Sequencing of the insert in the functional plasmid, using the Big Dye Terminator Version 1.0 Sequence Reaction kit (Applied Biosystems, Foster City, Calif.) and the Applied Biosystems 3730 DNA Analyzer (Applied Biosystems), revealed a gene that was highly homologous to the published porcine CD163 gene cDNA (Genbank accession number AJ311716). The cDNA we identified contained additional 5' and 3' untranslated regions relative to AJ311716, and the open reading frame differed in three ways: (1) a 738 by internal deletion near the 5' end, (2) a 15 by extension of the 5' end to an upstream ATG codon, and (3) sixteen nucleotide changes predicted to cause 10 amino acid changes. Nucleotide sequence identity between the sequences was 99.4%. Alignments of the newly discovered porcine CD163 sequence with the previously reported sequence AJ311716 are shown in FIGS. 1 and 2. The novel porcine CD163 variant was designated "susCD163v1".

| SEQUENCE | | ID NO |
|---|---|---|
| gtaataatac aagaagattt aaatgggcat aaaaccttgg aatggacaaa ctcagaatgg | 60 | SEQ ID NO: 5 |
| tgctacatga aaactctgga tctgcagacc tgaaactgag agtggtagat ggagtcactg | 120 | |
| aatgttcagg aagattggaa gtgaaattcc aaggagaatg ggaacaatc tgtgatgatg | 180 | |
| gctgggatag tgatgatgcc gctgtggcat gtaagcaact gggatgtcca actgctgtca | 240 | |
| ctgccattgg tcgagttaac gccagtgagg gaactggaca catttggctt gacagtgttt | 300 | |
| cttgccatgg acacgagtct gctctctggc agtgtagaca ccatgaatgg ggaaagcatt | 360 | |
| attgcaatca taatgaagat gctggtgtga catgttctga tggatcagat ctggaactga | 420 | |
| gacttaaagg tggaggcagc cactgtgctg ggacagtgga ggtggaaatt cagaaactgg | 480 | |
| taggaaaagt gtgtgataga agctggggac tgaaagaagc tgatgtggtt tgcaggcagc | 540 | |

-continued

| SEQUENCE | ID NO |
|---|---|
| tgggatgtgg atctgcactc aaaacatcat atcaagttta ttccaaaacc aaggcaacaa 600 | |
| acacatggct gtttgtaagc agctgtaatg gaaatgaaac ttctctttgg gactgcaaga 660 | |
| attggcagtg gggtggactt agttgtgatc actatgacga agccaaaatt acctgctcag 720 | |
| cccacaggaa acccaggctg gttggagggg acattccctg ctctggtcgt gttgaagtac 780 | |
| aacatggaga cacgtggggc accgtctgtg attctgactt ctctctggag gcggccagcg 840 | |
| tgctgtgcag ggaactacag tgcggcactg tggtttccct cctgggggga gctcactttg 900 | |
| gagaaggaag tggacagatc tgggctgaag aattccagtg tgaggggcac gagtcccacc 960 | |
| tttcactctg cccagtagca ccccgccctg acgggacatg tagccacagc agggacgtcg 1020 | |
| gcgtagtctg ctcaagatac acacaaatcc gcttggtgaa tggcaagacc ccatgtgaag 1080 | |
| gaagagtgga gctcaacatt cttgggtcct gggggtccct ctgcaactct cactgggaca 1140 | |
| tggaagatgc ccatgtttta tgccagcagc ttaaatgtgg agttgccctt tctatcccgg 1200 | |
| gaggagcacc ttttgggaaa ggaagtgagc aggtctggag gcacatgttt cactgcactg 1260 | |
| ggactgagaa gcacatggga gattgttccg tcactgctct gggcgcatca ctctgttctt 1320 | |
| cagggcaagt ggcctctgta atctgctcag ggaaccagag tcagacacta tccccgtgca 1380 | |
| attcatcatc ctcggaccca tcaagctcta ttatttcaga agaaaatggt gttgcctgca 1440 | |
| tagggagtgg tcaacttcgc ctggtcgatg gaggtggtcg ttgtgctggg agagtagagg 1500 | |
| tctatcatga gggctcctgg ggcaccatct gtgatgacag ctgggacctg aatgatgccc 1560 | |
| atgtggtgtg caaacagctg agctgtggat gggccattaa tgccactggt tctgctcatt 1620 | |
| ttggggaagg aacagggccc atttggctgg atgagataaa ctgtaatgga aaagaatctc 1680 | |
| atatttggca atgccactca catggttggg ggcggcacaa ttgcaggcat aaggaggatg 1740 | |
| caggagtcat ctgctcggag ttcatgtctc tcagactgat cagtgaaaac agcagagaga 1800 | |
| cctgtgcagg gcgcctggaa gtttttttaca acggagcttg gggcagcgtt ggcaagaata 1860 | |
| gcatgtctcc agccacagtg gggtggtat gcaggcagct gggctgtgca gacagagggg 1920 | |
| acatcagccc tgcatcttca gacaagacag tgtccaggca catgtgggtg gacaatgttc 1980 | |
| agtgtcctaa aggacctgac accctatggc agtgcccatc atctccatgg aagaagagac 2040 | |
| tggccagccc ctcagaggag acatggatca catgtgccaa caaaataaga cttcaagaag 2100 | |
| gaaacactaa ttgttctgga cgtgtggaga tctggtacgg aggttcctgg ggcactgtgt 2160 | |
| gtgacgactc ctgggacctt gaagatgctc aggtggtgtg ccgacagctg ggctgtggct 2220 | |
| cagctttgga ggcaggaaaa gaggccgcat ttggccaggg gactgggccc atatggctca 2280 | |
| atgaagtgaa gtgcaagggg aatgaaacct ccttgtggga ttgtcctgcc agatcctggg 2340 | |
| gccacagtga ctgtggacac aaggaggatg ctgctgtgac gtgttcagaa attgcaaaga 2400 | |
| gccgagaatc cctacatgcc acaggtcgct catcttttgt tgcacttgca atctttgggg 2460 | |
| tcattctgtt ggcctgtctc atcgcattcc tcatttggac tcagaagcga agacagaggc 2520 | |
| agcggctctc agttttctca ggaggagaga attctgtcca tcaaattcaa taccgggaga 2580 | |
| tgaattcttg cctgaaagca gatgaaacgg atatgctaaa tccctcagga gaccactctg 2640 | |
| aagtacaatg aaaaggaaaa tgggaattat aacctggtga gttcagcctt taagatacct 2700 | |
| tgatgaagac ctggactatt gaatgagcaa gaatctgcct cttacactga agattacaat 2760 | |
| acagtcctct gtctcctggt attccaaaga ctgctgttga atttctaaaa aatagattgg 2820 | |

-continued

```
                         SEQUENCE                                    ID NO

tgaatgtgac tactcaaagt tgtatgtaag actttcaagg gcattaaata aaaaagaata  2880

ttgctgaaaa aaaaaaaaaa aaaaaaaaaa aaaaaaaaaa aaaaaaaaaa            2930

   1  M  D  K  L  R  M  V  L  H  E  N  S  G  S  A  D  L  K  L  R     SEQ ID NO: 1 and 2
   1  atggacaaactcagaatggtgctacatgaaaactctggatctgcagacctgaaactgaga

  21  V  V  D  G  V  T  E  C  S  G  R  L  E  V  K  F  Q  G  E  W
  61  gtggtagatggagtcactgaatgttcaggaagattggaagtgaaattccaaggagaatgg

  41  G  T  I  C  D  D  G  W  D  S  D  D  A  A  V  A  C  K  Q  L
 121  ggaacaatctgtgatgatggctgggatagtgatgatgccgctgtggcatgtaagcaactg

  61  G  C  P  T  A  V  T  A  I  G  R  V  N  A  S  E  G  T  G  H
 181  ggatgtccaactgctgtcactgccattggtcgagttaacgccagtgagggaactggacac

  81  I  W  L  D  S  V  S  C  H  G  H  E  S  A  L  W  Q  C  R  H
 241  atttggcttgacagtgtttcttgccatggacacgagtctgctctctggcagtgtagacac

 101  H  E  W  G  K  H  Y  C  N  H  N  E  D  A  G  V  T  C  S  D
 301  catgaatggggaaagcattattgcaatcataatgaagatgctggtgtgacatgttctgat

 121  G  S  D  L  E  L  R  L  K  G  G  G  S  H  C  A  G  T  V  E
 361  ggatcagatctggaactgagacttaaaggtggaggcagccactgtgctgggacagtggag

 141  V  E  I  Q  K  L  V  G  K  V  C  D  R  S  W  G  L  K  E  A
 421  gtggaaattcagaaactggtaggaaaagtgtgtgatagaagctggggactgaaagaagct

 161  D  V  V  C  R  Q  L  G  C  G  S  A  L  K  T  S  Y  Q  V  Y
 481  gatgtggtttgcaggcagctgggatgtggatctgcactcaaaacatcatatcaagtttat

 181  S  K  T  K  A  T  N  T  W  L  F  V  S  S  C  N  G  N  E  T
 541  tccaaaaccaaggcaacaaacacatggctgtttgtaagcagctgtaatggaaatgaaact

 201  S  L  W  D  C  K  N  W  Q  W  G  G  L  S  C  D  H  Y  D  E
 601  tctctttgggactgcaagaattggcagtggggtggacttagttgtgatcactatgacgaa

 221  A  K  I  T  C  S  A  H  R  K  P  R  L  V  G  G  D  I  P  C
 661  gccaaaattacctgctcagcccacaggaaacccaggctggttggaggggacattccctgc

 241  S  G  R  V  E  V  Q  H  G  D  T  W  G  T  V  C  D  S  D  F
 721  tctggtcgtgttgaagtacaacatggagacacgtggggcaccgtctgtgattctgacttc

 261  S  L  E  A  A  S  V  L  C  R  E  L  Q  C  G  T  V  V  S  L
 781  tctctggaggcggccagcgtgctgtgcagggaactacagtgcggcactgtggtttccctc

 281  L  G  G  A  H  F  G  E  G  S  G  Q  I  W  A  E  E  F  Q  C
 841  ctgggggggagctcactttggagaaggaagtggacagatctgggctgaagaattccagtgt

 301  E  G  H  E  S  H  L  S  L  C  P  V  A  P  R  P  D  G  T  C
 901  gaggggcacgagtcccacctttcactctgcccagtagcaccccgccctgacgggacatgt

 321  S  H  S  R  D  V  G  V  V  C  S  R  Y  T  Q  I  R  L  V  N
 961  agccacagcagggacgtcggcgtagtctgctcaagatacacacaaatccgcttggtgaat

 341  G  K  T  P  C  E  G  R  V  E  L  N  I  L  G  S  W  G  S  L
1021  ggcaagaccccatgtgaaggaagagtggagctcaacattcttgggtcctggggtccctc

 361  C  N  S  H  W  D  M  E  D  A  H  V  L  C  Q  Q  L  K  C  G
1081  tgcaactctcactgggacatggaagatgcccatgttttatgccagcagcttaaatgtgga

 381  V  A  L  S  I  P  G  G  A  P  F  G  K  G  S  E  Q  V  W  R
1141  gttgccctttctatcccgggaggagcaccttttgggaaaggaagtgagcaggtctggagg

 401  H  M  F  H  C  T  G  T  E  K  H  M  G  D  C  S  V  T  A  L
1201  cacatgtttcactgcactgggactgagaagcacatgggagattgttccgtcactgctctg

 421  G  A  S  L  C  S  S  G  Q  V  A  S  V  I  C  S  G  N  Q  S
1261  ggcgcatcactctgttcttcagggcaagtggcctctgtaatctgctcagggaaccagagt

 441  Q  T  L  S  P  C  N  S  S  S  S  D  P  S  S  S  I  I  S  E
1321  cagacactatccccgtgcaattcatcatcctcggacccatcaagctctattatttcagaa

 461  E  N  G  V  A  C  I  G  S  G  Q  L  R  L  V  D  G  G  G  R
1381  gaaaatggtgttgcctgcatagggagtggtcaacttcgcctggtcgatggaggtggtcgt

 481  C  A  G  R  V  E  V  Y  H  E  G  S  W  G  T  I  C  D  D  S
```

-continued

| | SEQUENCE | ID NO |
|---|---|---|
| 1441 | tgtgctgggagagtagaggtctatcatgagggctcctggggcaccatctgtgatgacagc | |
| 501 | W D L N D A H V V C K Q L S C G W A I N | |
| 1501 | tgggacctgaatgatgcccatgtggtgtgcaaacagctgagctgtggatgggccattaat | |
| 521 | A T G S A H F G E G T G P I W L D E I N | |
| 1561 | gccactggttctgctcattttggggaaggaacagggcccatttggctggatgagataaac | |
| 541 | C N G K E S H I W Q C H S H G W G R H N | |
| 1621 | tgtaatggaaaagaatctcatatttggcaatgccactcacatggttgggggcggcacaat | |
| 561 | C R H K E D A G V I C S E F M S L R L I | |
| 1681 | tgcaggcataaggaggatgcaggagtcatctgctcggagttcatgtctctcagactgatc | |
| 581 | S E N S R E T C A G R L E V F Y N G A W | |
| 1741 | agtgaaaacagcagagagacctgtgcagggcgcctggaagtttttttacaacggagcttgg | |
| 601 | G S V G K N S M S P A T V G V V C R Q L | |
| 1801 | ggcagcgttggcaagaatagcatgtctccagccacagtgggggtggtatgcaggcagctg | |
| 621 | G C A D R G D I S P A S S D K T V S R H | |
| 1861 | ggctgtgcagacagaggggacatcagccctgcatcttcagacaagacagtgtccaggcac | |
| 641 | M W V D N V Q C P K G P D T L W Q C P S | |
| 1921 | atgtgggtggacaatgttcagtgtcctaaaggacctgacaccctatggcagtgcccatca | |
| 661 | S P W K K R L A S P S E E T W I T C A N | |
| 1981 | tctccatggaagaagagactggccagcccctcagaggagacatggatcacatgtgccaac | |
| 681 | K I R L Q E G N T N C S G R V E I W Y G | |
| 2041 | aaaataagacttcaagaaggaaacactaattgttctggacgtgtggagatctggtacgga | |
| 701 | G S W G T V C D D S W D L E D A Q V V C | |
| 2101 | ggttcctggggcactgtgtgtgacgactcctgggaccttgaagatgctcaggtggtgtgc | |
| 721 | R Q L G C G S A L E A G K E A A F G Q G | |
| 2161 | cgacagctgggctgtggctcagctttggaggcaggaaaagaggccgcatttggccagggg | |
| 741 | T G P I W L N E V K C K G N E T S L W D | |
| 2221 | actgggcccatatggctcaatgaagtgaagtgcaaggggaatgaaacctccttgtgggat | |
| 761 | C P A R S W G H S D C G H K E D A A V T | |
| 2281 | tgtcctgccagatcctggggccacagtgactgtggacacaaggaggatgctgctgtgacg | |
| 781 | C S E I A K S R E S L H A T G R S S F V | |
| 2341 | tgttcagaaattgcaaagagccgagaatccctacatgccacaggtcgctcatcttttgtt | |
| 801 | A L A I F G V I L L A C L I A F L I W T | |
| 2401 | gcacttgcaatctttggggtcattctgttggcctgtctcatcgcattcctcatttggact | |
| 821 | Q K R R Q R Q R L S V F S G G E N S V H | |
| 2461 | cagaagcgaagacagaggcagcggctctcagttttctcaggaggagagaattctgtccat | |
| 841 | Q I Q Y R E M N S C L K A D E T D M L N | |
| 2521 | caaattcaataccgggagatgaattcttgcctgaaagcagatgaaacggatatgctaaat | |
| 861 | P S G D H S E V Q | |
| 2581 | ccctcaggagaccactctgaagtacaa | |
| 1 | MDKLRMVLHE NSGSADLKLR VVDGVTECSG RLEVKFQGEW GTICDDGWDS | SEQ ID NO: 2 |
| 51 | DDAAVACKQL GCPTAVTAIG RVNASEGTGH IWLDSVSCHG HESALWQCRH | |
| 101 | HEWGKHYCNH NEDAGVTCSD GSDLELRLKG GGSHCAGTVE VEIQKLVGKV | |
| 151 | CDRSWGLKEA DVVCRQLGCG SALKTSYQVY SKTKATNTWL FVSSCNGNET | |
| 201 | SLWDCKNWQW GGLSCDHYDE AKITCSAHRK PRLVGGDIPC SGRVEVQHGD | |
| 251 | TWGTVCDSDF SLEAASVLCR ELQCGTVVSL LGGAHFGEGS GQIWAEEFQC | |
| 301 | EGHESHLSLC PVAPRPDGTC SHSRDVGVVC SRYTQIRLVN GKTPCEGRVE | |
| 351 | LNILGSWGSL CNSHWDMEDA HVLCQQLKCG VALSIPGGAP FGKGSEQVWR | |
| 401 | HMFHCTGTEK HMGDCSVTAL GASLCSSGQV ASVICSGNQS QTLSPCNSSS | |
| 451 | SDPSSSIISE ENGVACIGSG QLRLVDGGGR CAGRVEVYHE GSWGTICDDS | |

-continued

| | SEQUENCE | ID NO |
|---|---|---|
| 501 | WDLNDAHVVC KQLSCGWAIN ATGSAHFGEG TGPIWLDEIN CNGKESHIWQ | |
| 551 | CHSHGWGRHN CRHKEDAGVI CSEFMSLRLI SENSRETCAG RLEVFYNGAW | |
| 601 | GSVGKNSMSP ATVGVVCRQL GCADRGDISP ASSDKTVSRH MWVDNVQCPK | |
| 651 | GPDTLWQCPS SPWKKRLASP SEETWITCAN KIRLQEGNTN CSGRVEIWYG | |
| 701 | GSWGTVCDDS WDLEDAQVVC RQLGCGSALE AGKEAAFGQG TGPIWLNEVK | |
| 751 | CKGNETSLWD CPARSWGHSD CGHKEDAAVT CSEIAKSRES LHATGRSS**FV** | |
| 801 | **ALAIFGVILL ACLIAFLI**WT QKRRQRQRLS VFSGGENSVH QIQYREMNSC | |
| 851 | LKADETDMLN PSGDHSEVQ | |

Example 2

Construction of Plasmid pCMVsusCD163v1

Construction of the plasmid pCMVsusCD163v1 was performed as follows. The functional clone identified in the primary porcine macrophage cDNA library as conferring PRRSV permissivity served as template for PCR amplification of the CD163 insert, including the 5' and 3' untranslated regions, using the primers 5'DS-CD163 (SEQ ID NO:6) (5'-CGGAATTCCGCGGATGTAATAATACAAGAAGA-3') and 3'CD163 (SEQ ID NO:7) (5'CCG CTCGAGTAGTCCAGGTCTTCATCAAGGTATCTT-3'). Primer 5'DS-CD163 incorporates a SacII restriction site at the 5' end of the CD163 insert, while primer 3'CD163 incorporates an XhoI restriction site at the 3' end of the insert (underlined). Reactions containing 190 ng of plasmid template were amplified using Platinum Pfx DNA polymerase (Invitrogen cat # 11708-013) following the manufacture's instructions. Reactions were heated to 94° for 2 minutes then cycled 35 times through 94° for 20 seconds, 55° for 30 seconds, and 68° for 3.5 minutes followed by a terminal extension at 72° for 7 minutes. The resulting PCR products were purified using the Qiaquick PCR purification kit (Qiagen cat # 28104), digested with restriction enzymes SacII and XhoI, and the resulting fragments were gel purified using the Qiaquick Gel Extraction kit (Qiagen cat # 28704). The CD163 PCR fragment was then ligated into the plasmid pCMV-Script (Stratagene cat # 212220) prepared to accept the digested PCR fragment by digestion with SacII and XhoI followed by gel purification as described above. The ligated material was transformed into *E. coli* strain DH5α and recombinants were selected by growth in 50 μg/ml kanamycin and identified by restriction analysis. The resulting plasmid, "pCMVsusCD163v1", contains the internally deleted porcine CD163 insert described in Example 1 under the transcriptional control of the eukaryotic CMV promoter and the neomycin/kanamycin resistance gene under the control of both eukaryotic and prokaryotic promoters.

Example 3

Construction of the pRSV-Script Expression Vector and pRSVsusCD163v1

The plasmid pRc/RSV (Invitrogen) was used as a template for PCR amplification of the RSV promoter. RSV promoter sequence was contained within nucleotides 209 through 604 of pRc/RSV. Forward primer PCIRSVLTR (SEQ ID NO:8) (5'-ACACTCG ACATGTCGATGTACGGGCCAGATATACGCGT-3') and reverse primer VSRRTLSAC (SEQ ID NO: 9) (5'TTCCTTACAGAGCTCGAGGTGCACACCAATGTGGTGAA-3') were synthesized. Restriction endonuclease Pci I and Sac I recognition sites (underlined) were incorporated into the 5' and 3' primers, respectively, for future cloning. PCR was performed using the HotMaster Taq DNA Polymerase kit (Eppendorf) following the manufacturer's instructions. The reactions contained 0.9 ng of pRc/RSV plasmid template and 0.3 μM of each primer described above. The reactions were heated to 94° for 2 minutes then cycled 30 times through 94° for 20 seconds, 52° for 10 seconds, and 65° for 1 minute. The resulting PCR fragment was digested with restriction enzymes Pci I and Sac I, gel purified, and cloned into the plasmid pCMV-Script (Stratagene) that had been similarly digested to remove the CMV promoter sequence. The final construct placed the RSV promoter immediately upstream of the multiple cloning site, and was named "pRSV-Script".

The susCD163v1 insert was cloned behind the RSV promoter as follows. The susCD163v1 sequence was excised from plasmid pCMVsusCD163v1 by restriction digestion (Kpn I and Sac II) and gel purified. This fragment was ligated into pRSV-Script which had also been digested with the same enzymes and gel purified. The ligation mixture was transformed into DH5α *E. coli* and transformants selected using kanamycin at 50 μg/ml. The clone contained the correct insert was designed "pRSVsusCD163v1".

Example 4

Cloning and Characterization of a Longer Variant of Porcine CD163 cDNA

Based on the porcine CD163v1 sequence, a forward primer 5'CD163NotIlong

```
                                            (SEQ ID NO: 10)
(5'CGGTCCGGAGCGGCCGCGATGTAATAATACAAGAAGATTTAAATG
G-3')
```

and a reverse primer 3'CD163 KpnI (SEQ ID NO:11) (5'CG-GTT GGTACCCAGCAATATTCTTTTTTATTTAATGCC-3') were designed using the Lasergene PrimerSelect program (DNASTAR Inc., Madison Wis.) for amplification of a full-length porcine CD163 gene. Restriction endonuclease sites for Not I and Kpn I (underlined) were included in 5' and 3' primers, respectively, to allow for convenient cloning. Total cellular RNA was prepared from primary alveolar macrophages (PAM) harvested from lung lavages of healthy pigs. RNA preparation was done using the RNeasy mini kit (Qiagen, Valencia, Calif.). RT-PCR reactions were prepared using the SuperScript one-step RT-PCR for Long Templates kit (Invitrogen, Carlsbad, Calif.) and RT-PCR parameters were set as follows: 50° C. for 30 min, 94° C. for 55° C. 30 sec and 68° C. 4 min) for 35 cycles, 72° C. for 10 min. PCR products were analyzed on 0.8% SeaKem GTG agarose gels. RT-PCR products of various sizes were cut from agarose gels and DNA was extracted using the GeneClean kit (QBiogene). These RT-PCR products were cloned into the pCR2.1-TOPO cloning vector (Invitrogen). Clones were analyzed by restriction enzyme digestion for the presence of an insert. Colonies containing inserts were sequenced using Big Dye Terminator Version 1.0 Sequence Reaction kit (Applied Biosystems, Foster City, Calif.) and Applied Biosystems 3730 DNA Analyzer (Applied Biosystems) to confirm sequence authenticity. Sequences were edited and assembled using the Lasergene EditSeq and SeqMan programs (DNASTAR Inc., Madison Wis.). One plasmid with a large insert was designated "pCRsusCD163v2" (pCR2.1 containing porcine CD163 variant 2 which we have designated SEQ ID NO:12). The coding sequence contained within SEQ ID NO:12 is reproduced below and is designated SEQ ID NO:13. Sequence analysis showed that this porcine CD163 encodes an amino acid sequence of 1115 amino acids which we have designated SEQ ID NO:14. When compared to the porcine CD163 sequence in GenBank (Accession No. AJ311716), our CD163v2 sequence is 98.9% identical at the amino acid level. CD163v2 also has an additional 5 amino acid residues at the extreme 5' end, extending the open reading frame to an in-frame upstream ATG initiation codon (as in the porcine CD163v1 sequence described in example 1). Porcine CD163 is 84.3% identical to human CD163 (GenBank Accession No. Z22968), and 73.7% identical to mouse CD163 (GenBank Accession No. AF274883) at the amino acid level. The predicted signal sequence and transmembrane region of SEQ ID NO:14 are indicated by underlining and bolding respectively. To determine whether other CD163 sequences contain similar sequence features is easily determined by inspection of the sequence.

| SEQUENCE | | ID NO |
|---|---|---|
| gtaataatac aagaagattt aaatggcata aaaccttgga atggacaaac tcagaatggt | 60 | SEQ ID NO: 12 |
| gctacatgaa aactctggat ctgcagactt tagaagatgt tctgcccatt taagttcctt | 120 | |
| cacttttgct gtagtcgctg ttctcagtgc ctgcttggtc actagttctc ttggaggaaa | 180 | |
| agacaaggag ctgaggctaa cgggtggtga aaacaagtgc tctggaagag tggaggtgaa | 240 | |
| agtgcaggag gagtggggaa ctgtgtgtaa taatggctgg gacatggatg tggtctctgt | 300 | |
| tgtttgtagg cagctgggat gtccaactgc tatcaaagcc actggatggg ctaattttag | 360 | |
| tgcaggttct ggacgcattt ggatggatca tgtttcttgt cgagggaatg agtcagctct | 420 | |
| ctgggactgc aaacatgatg gatggggaaa gcataactgt actcaccaac aggatgctgg | 480 | |
| agtaacctgc tcagatggat ctgatttaga gatggggctg gtgaatggag gaaaccggtg | 540 | |
| cttaggaaga atagaagtca aatttcaagg acggtgggga acagtgtgtg atgataactt | 600 | |
| caacataaat catgcttctg tggtttgtaa acaacttgaa tgtggaagtg ctgtcagttt | 660 | |
| ctctggttca gctaattttg gagaaggttc tggaccaatc tggtttgatg atcttgtatg | 720 | |
| caatggaaat gagtcagctc tctggaactg caaacatgaa ggatggggaa agcacaattg | 780 | |
| cgatcatgct gaggatgctg gagtgatttg cttaaatgga gcagacctga aactgagagt | 840 | |
| ggtagatgga gtcactgaat gttcaggaag attggaagtg aaattccaag gagaatgggg | 900 | |
| aacaatctgt gatgatggct gggatagtga tgatgccgct gtggcatgta agcaactggg | 960 | |
| atgtccaact gctgtcactg ccattggtcg agttaacgcc agtgagggaa ctggacacat | 1020 | |
| ttggcttgac agtgtttctt gccatggaca cgagtctgct ctctggcagt gtagacacca | 1080 | |
| tgaatgggga aagcattatt gcaatcatga tgaagatgct ggtgtgacat gttctgatgg | 1140 | |
| atcagatctg gaactgagac ttaaaggtgg aggcagccac tgtgctggga cagtggaggt | 1200 | |
| ggaaattcag aaactggtag gaaaagtgtg tgatagaagc tggggactga aagaagctga | 1260 | |
| tgtggtttgc aggcagctgg gatgtggatc tgcactcaaa acatcatatc aagtttattc | 1320 | |
| caaaaccaag gcaacaaaca catggctgtt tgtaagcagc tgtaatggaa atgaaacttc | 1380 | |
| tctttgggac tgcaagaatt ggcagtgggg tggacttagt tgtgatcact atgacgaagc | 1440 | |
| caaaattacc tgctcagccc acaggaaacc caggctggtt ggaggggaca ttccctgctc | 1500 | |

-continued

| SEQUENCE | ID NO |
|---|---|
| tggtcgtgtt gaagtacaac atggagacac gtggggcacc gtctgtgatt ctgacttctc 1560 | |
| tctggaggcg gccagcgtgc tgtgcaggga actacagtgc ggcactgtgg tttccctcct 1620 | |
| ggggggagct cactttggag aaggaagtgg acagatctgg gctgaagaat tccagtgtga 1680 | |
| ggggcacgag tcccaccttt cactctgccc agtagcaccc cgccctgacg ggacatgtag 1740 | |
| ccacagcagg gacgtcggcg tagtctgctc aagatacaca caaatccgct tggtgaatgg 1800 | |
| caagacccca tgtgaaggaa gagtggagct caacattctt gggtcctggg ggtccctctg 1860 | |
| caactctcac tgggacatgg aagatgccca tgttttatgc cagcagctta aatgtggagt 1920 | |
| tgccctttct atcccgggag gagcaccttt tgggaaagga agtgagcagg tctggaggca 1980 | |
| catgtttcac tgcactggga ctgagaagca catgggagat tgttccgtca ctgctctggg 2040 | |
| cgcatcactc tgttcttcag ggcaagtggc ctctgtaatc tgctcaggga accagagtca 2100 | |
| gacactatct ccgtgcaatt catcatcctc ggacccatca agctctatta tttcagaaga 2160 | |
| aaatggtgtt gcctgcatag ggagtggtca acttcgcctg gtcgatggag gtggtcgttg 2220 | |
| tgctgggaga gtagaggtct atcatgaggg ctcctggggc accatctgtg atgacagctg 2280 | |
| ggacctgaat gatgcccatg tggtgtgcaa acagctgagc tgtggatggg ccattaatgc 2340 | |
| cactggttct gctcattttg gggaaggaac agggcccatt tggctggatg agataaactg 2400 | |
| taatggaaaa gaatctcata tttggcaatg ccactcacat ggttgggggc ggcacaattg 2460 | |
| caggcataag gaggatgcag gagtcatctg ctcagagttc atgtctctga gactgatcag 2520 | |
| tgaaaacagc agagagacct gtgcagggcg cctggaagtt ttttacaacg gagcttgggg 2580 | |
| cagcgttggc aggaatagca tgtctccagc cacagtgggg gtggtatgca ggcagctggg 2640 | |
| ctgtgcagac agaggggaca tcagccctgc atcttcagac aagacagtgt ccaggcacat 2700 | |
| gtgggtggac aatgttcagt gtcctaaagg acctgacaca ctatggcagt gcccatcatc 2760 | |
| tccatggaag aagagactgg ccagcccctc agaggagaca tggatcacat gtgccaacaa 2820 | |
| aataagactt caagaaggaa acactaattg ttctggacgt gtggagatct ggtacggagg 2880 | |
| ttcctggggc actgtgtgtg acgactcctg ggaccttgaa gatgctcagg tggtgtgccg 2940 | |
| acagctgggc tgtggctcag ctttggaggc aggaaaagag gccgcatttg gccaggggac 3000 | |
| tgggcccata tggctcaatg aagtgaagtg caaggggaat gaaacctcct tgtgggattg 3060 | |
| tcctgccaga tcctggggcc acagtgactg tggacacaag gaggatgctg ctgtgacgtg 3120 | |
| ctcagaaatt gcaaagagcc gagaatccct acatgccaca ggtcgctcat cttttgttgc 3180 | |
| acttgcaatc tttggggtca ttctgttggc ctgtctcatc gcattcctca tttggactca 3240 | |
| gaagcgaaga cagaggcagc ggctctcagt tttctcagga ggagagaatt ctgtccatca 3300 | |
| aattcaatac cgggagatga attcttgcct gaaagcagat gaaacggata tgctaaatcc 3360 | |
| ctcaggagac cactctgaag tacaatgaaa aggaaaatgg gaattataac ctggtgagtt 3420 | |
| cagcctttaa gataccttga tgaagacctg gactattgaa tgagcaagaa tctgcctctt 3480 | |
| acactgaaga ttacaataca gtcctctgtc tcctggtatt ccaaagactg ctgctgaatt 3540 | |
| tctaaagaat agattggtga atgtgactac tcaaagttgt atgtaagact ttcaagggca 3600 | |
| ttaaataaaa aagaatattg ctg 3623 | |

```
 1   M  D  K  L  R  M  V  L  H  E  N  S  G  S  A  D  F  R  R  C      SEQ ID NO: 13 and 14
 1   atggacaaactcagaatggtgctacatgaaaactctggatctgcagactttagaagatgt

21   S  A  H  L  S  S  F  T  F  A  V  V  A  V  L  S  A  C  L  V
61   tctgcccatttaagttccttcacttttgctgtagtcgctgttctcagtgcctgcttggtc
```

-continued

| SEQUENCE | ID NO |
|---|---|
| 41 T S S L G G K D K E L R L T G G E N K C<br>121 actagttctcttggaggaaaagacaaggagctgaggctaacgggtggtgaaaacaagtgc | |
| 61 S G R V E V K V Q E E W G T V C N N G W<br>181 tctggaagagtggaggtgaaagtgcaggaggagtggggaactgtgtgtaataatggctgg | |
| 81 D M D V V S V V C R Q L G C P T A I K A<br>241 gacatggatgtggtctctgttgtttgtaggcagctgggatgtccaactgctatcaaagcc | |
| 101 T G W A N F S A G S G R I W M D H V S C<br>301 actggatgggctaattttagtgcaggttctggacgcatttggatggatcatgtttcttgt | |
| 121 R G N E S A L W D C K H D G W G K H N C<br>361 cgagggaatgagtcagctctctgggactgcaaacatgatggatggggaaagcataactgt | |
| 141 T H Q Q D A G V T C S D G S D L E M G L<br>421 actcaccaacaggatgctggagtaacctgctcagatggatctgatttagagatggggctg | |
| 161 V N G G N R C L G R I E V K F Q G R W G<br>481 gtgaatggaggaaaccggtgcttaggaagaatagaagtcaaatttcaaggacggtgggga | |
| 181 T V C D D N F N I N H A S V V C K Q L E<br>541 acagtgtgtgatgataacttcaacataaatcatgcttctgtggtttgtaaacaacttgaa | |
| 201 C G S A V S F S G S A N F G E G S G P I<br>601 tgtggaagtgctgtcagtttctctggttcagctaattttggagaaggttctggaccaatc | |
| 221 W F D D L V C N G N E S A L W E C K H E<br>661 tggtttgatgatcttgtatgcaatggaaatgagtcagctctctggaactgcaaacatgaa | |
| 241 G W G K H N C D H A E D A G V I C L N G<br>721 ggatggggaaagcacaattgcgatcatgctgaggatgctggagtgatttgcttaaatgga | |
| 261 A D L K L R V V D G V T E C S G R L E V<br>781 gcagacctgaaactgagagtggtagatggagtcactgaatgttcaggaagattggaagtg | |
| 281 K F Q G E W G T I C D D G W D S D D A A<br>841 aaattccaaggagaatggggaacaatctgtgatgatggctgggatagtgatgatgccgct | |
| 301 V A C K Q L G C P T A V T A I G R V N A<br>901 gtggcatgtaagcaactgggatgtccaactgctgtcactgccattggtcgagttaacgcc | |
| 321 S E G T G H I W L D S V S C H G H E S A<br>961 agtgagggaactggacacatttggcttgacagtgtttcttgccatggacacgagtctgct | |
| 341 L W Q C R H H E W G K H Y C N H D E D A<br>1021 ctctggcagtgtagacaccatgaatggggaaagcattattgcaatcatgatgaagatgct | |
| 361 G V T C S D G S D L E L R L K G G G S H<br>1081 ggtgtgacatgttctgatggatcagatctggaactgagacttaaaggtggaggcagccac | |
| 381 C A G T V E V E I Q K L V G K V C D R S<br>1141 tgtgctgggacagtggaggtggaaattcagaaactggtaggaaaagtgtgtgatagaagc | |
| 401 W G L K E A D V V C R Q L G C G S A L K<br>1201 tggggactgaaagaagctgatgtggtttgcaggcagctgggatgtggatctgcactcaaa | |
| 421 T S Y Q V Y S K T K A T N T W L F V S S<br>1261 acatcatatcaagtttattccaaaaccaaggcaacaaacacatggctgtttgtaagcagc | |
| 441 C N G N E T S L W D C K N W Q W G G L S<br>1321 tgtaatggaaatgaaacttctctttgggactgcaagaattggcagtggggtggacttagt | |
| 461 C D H Y D E A K I T C S A H R K P R L V<br>1381 tgtgatcactatgacgaagccaaaattacctgctcagcccacaggaaacccaggctggtt | |
| 481 G G D I P C S G R V E V Q H G D T W G T<br>1441 ggaggggacattccctgctctggtcgtgttgaagtacaacatggagacacgtggggcacc | |
| 501 V C D S D F S L E A A S V L C R E L Q C<br>1501 gtctgtgattctgacttctctctggaggcggccagcgtgctgtgcagggaactacagtgc | |
| 521 G T V V S L L G G A H F G E G S G Q I W<br>1561 ggcactgtggtttccctcctgggggagctcactttggagaaggaagtggacagatctgg | |
| 541 A E E F Q C E G H E S H L S L C P V A P<br>1621 gctgaagaattccagtgtgaggggcacgagtcccacctttcactctgcccagtagcaccc | |

-continued

| | SEQUENCE | ID NO |
|---|---|---|
| 561 | R P D G T C S H S R D V G V V C S R Y T | |
| 1681 | cgccctgacgggacatgtagccacagcagggacgtcggcgtagtctgctcaagatacaca | |
| 581 | Q I R L V N G K T P C E G R V E L N I L | |
| 1741 | caaatccgcttggtgaatggcaagaccccatgtgaaggaagagtggagctcaacattctt | |
| 601 | G S W G S L C N S H W D M E D A H V L C | |
| 1801 | gggtcctgggggtccctctgcaactctcactgggacatggaagatgcccatgttttatgc | |
| 621 | Q Q L K C G V A L S I P G G A P F G K G | |
| 1861 | cagcagcttaaatgtggagttgccctttctatcccgggaggagcaccttttgggaaagga | |
| 641 | S E Q V W R H M F H C T G T E K H M G D | |
| 1921 | agtgagcaggtctggaggcacatgtttcactgcactgggactgagaagcacatgggagat | |
| 661 | C S V T A L G A S L C S S G Q V A S V I | |
| 1981 | tgttccgtcactgctctgggcgcatcactctgttcttcagggcaagtggcctctgtaatc | |
| 681 | C S G N Q S Q T L S P C N S S S S D P S | |
| 2041 | tgctcagggaaccagagtcagacactatctccgtgcaattcatcatcctcggacccatca | |
| 701 | S S I I S E E N G V A C I G S G Q L R L | |
| 2101 | agctctattatttcagaagaaaatggtgttgcctgcatagggagtggtcaacttcgcctg | |
| 721 | V D G G G R C A G R V E V Y H E G S W G | |
| 2161 | gtcgatggaggtggtcgttgtgctgggagagtagaggtctatcatgagggctcctggggc | |
| 741 | T I C D D S W D L N D A H V V C K Q L S | |
| 2221 | accatctgtgatgacagctgggacctgaatgatgcccatgtggtgtgcaaacagctgagc | |
| 761 | C G W A I N A T G S A H F G E G T G P I | |
| 2281 | tgtggatgggccattaatgccactggttctgctcattttggggaaggaacagggcccatt | |
| 781 | W L D E I N C E G K E S H I W Q C H S H | |
| 2341 | tggctggatgagataaactgtaatggaaaagaatctcatatttggcaatgccactcacat | |
| 801 | G W G R H N C R H K E D A G V I C S E F | |
| 2401 | ggttgggggcggcacaattgcaggcataaggaggatgcaggagtcatctgctcagagttc | |
| 821 | M S L R L I S E N S R E T C A G R L E V | |
| 2461 | atgtctctgagactgatcagtgaaaacagcagagagacctgtgcagggcgcctggaagtt | |
| 841 | F Y N G A W G S V G R N S M S P A T V G | |
| 2521 | ttttacaacggagcttggggcagcgttggcaggaatagcatgtctccagccacagtgggg | |
| 861 | V V C R Q L G C A D R G D I S P A S S D | |
| 2581 | gtggtatgcaggcagctgggctgtgcagacagaggggacatcagccctgcatcttcagac | |
| 881 | K T V S R H M W V D N V Q C P K G P D T | |
| 2641 | aagacagtgtccaggcacatgtgggtggacaatgttcagtgtcctaaaggacctgacaca | |
| 901 | L W Q C P S S P W K K R L A S P S E E T | |
| 2701 | ctatggcagtgcccatcatctccatggaagaagagactggccagcccctcagaggagaca | |
| 921 | W I T C A N K I R L Q E G N I N C S G R | |
| 2761 | tggatcacatgtgccaacaaaataagacttcaagaaggaaacactaattgttctggacgt | |
| 941 | V E I W Y G G S W G T V C D D S W D L E | |
| 2821 | gtggagatctggtacggaggttcctggggcactgtgtgtgacgactcctgggaccttgaa | |
| 961 | D A Q V V C R Q L G C G S A L E A G K E | |
| 2881 | gatgctcaggtggtgtgccgacagctgggctgtggctcagctttggaggcaggaaaagag | |
| 981 | A A F G Q G T G P I W L N E V K C K G N | |
| 2941 | gccgcatttggccaggggactgggcccatatggctcaatgaagtgaagtgcaaggggaat | |
| 1001 | E T S L W D C P A R S W G H S D C G H K | |
| 3001 | gaaacctccttgtgggattgtcctgccagatcctggggccacagtgactgtggacacaag | |
| 1021 | E D A A V T C S E I A K S R E S L H A T | |
| 3061 | gaggatgctgctgtgacgtgctcagaaattgcaaagagccgagaatccctacatgccaca | |
| 1041 | G R S S F V A L A I F G V I L L A C L I | |
| 3121 | ggtcgctcatcttttgttgcacttgcaatctttggggtcattctgttggcctgtctcatc | |
| 1061 | A F L I W T Q K R R Q R Q R L S V F S G | |
| 3181 | gcattcctcatttggactcagaagcgaagacagaggcagcggctctcagttttctcagga | |

-continued

| | SEQUENCE | ID NO |
|---|---|---|
| 1081<br>3241 | G E N S V H Q I Q Y R E M N S C L K A D<br>ggagagaattctgtccatcaaattcaataccgggagatgaattcttgcctgaaagcagat | |
| 1101<br>3301 | E T D M L N P S G D H S E V Q<br>gaaacggatatgctaaatccctcaggagaccactctgaagtacaa | |
| 1 | MDKLRMVLHE NSGSADFRRC SAHLSSFTFA VVAVLSACLV TSSLGGKDKE | SEQ ID NO: 14 |
| 51 | LRLTGGENKC SGRVEVKVQE EWGTVCNNGW DMDVVSVVCR QLGCPTAIKA | |
| 101 | TGWANFSAGS GRIWMDHVSC RGNESALWDC KHDGWGKHNC THQQDAGVTC | |
| 151 | SDGSDLEMGL VNGGNRCLGR IEVKFQGRWG TVCDDNFNIN HASVVCKQLE | |
| 201 | CGSAVSFSGS ANFGEGSGPI WFDDLVCNGN ESALWNCKHE GWGKHNCDHA | |
| 251 | EDAGVICLNG ADLKLRVVDG VTECSGRLEV KFQGEWGTIC DDGWDSDDAA | |
| 301 | VACKQLGCPT AVTAIGRVNA SEGTGHIWLD SVSCHGHESA LWQCRHHEWG | |
| 351 | KHYCNHDEDA GVTCSDGSDL ELRLKGGGSH CAGTVEVEIQ KLVGKVCDRS | |
| 401 | WGLKEADVVC RQLGCGSALK TSYQVYSKTK ATNTWLFVSS CNGNETSLWD | |
| 451 | CKNWQWGGLS CDHYDEAKIT CSAHRKPRLV GGDIPCSGRV EVQHGDTWGT | |
| 501 | VCDSDFSLEA ASVLCRELQC GTVVSLLGGA HFGEGSGQIW AEEFQCEGHE | |
| 551 | SHLSLCPVAP RPDGTCSHSR DVGVVCSRYT QIRLVNGKTP CEGRVELNIL | |
| 601 | GSWGSLCNSH WDMEDAHVLC QQLKCGVALS IPGGAPFGKG SEQVWRHMFH | |
| 651 | CTGTEKHMGD CSVTALGASL CSSGQVASVI CSGNQSQTLS PCNSSSSDPS | |
| 701 | SSIISEENGV ACIGSGQLRL VDGGGRCAGR VEVYHEGSWG TICDDSWDLN | |
| 751 | DAHVVCKQLS CGWAINATGS AHFGEGTGPI WLDEINCNGK ESHIWQCHSH | |
| 801 | GWGRHNCRHK EDAGVICSEF MSLRLISENS RETCAGRLEV FYNGAWGSVG | |
| 851 | RNSMSPATVG VVCRQLGCAD RGDISPASSD KTVSRHMWVD NVQCPKGPDT | |
| 901 | LWQCPSSPWK KRLASPSEET WITCANKIRL QEGNTNCSGR VEIWYGGSWG | |
| 951 | TVCDDSWDLE DAQVVCRQLG CGSALEAGKE AAFGQGTGPI WLNEVKCKGN | |
| 1001 | ETSLWDCPAR SWGHSDCGHK EDAAVTCSEI AKSRESLHAT CRSS**FVALAI** | |
| 1051 | **FGVILLACLI AFLI**WTQKRR QRQRLSVFSG GENSVHQIQY REMNSCLKAD | |
| 1101 | ETDMLNPSGD HSEVQ | |

Sus CD163 v2 in pCRsusCD163v2 was liberated from pCR2.1 vector after restriction enzymes Kpn I and Not I digestion and gel purification. Recipient vector pCMV-script was also cut with the same restriction enzyme pair and allowed for directional cloning of susCD163v2 into the pCMV-script. After ligation of susCD163 v2 with pCMV-script, the ligated mixture was used to transform STBL 2 *E. coli* cells (Invitrogen). One transformant was found to contain the CD163 gene by restriction enzyme digestion analysis and was designed pCMV-script susCD163v2 clone#3.

Example 5

Figure 4:
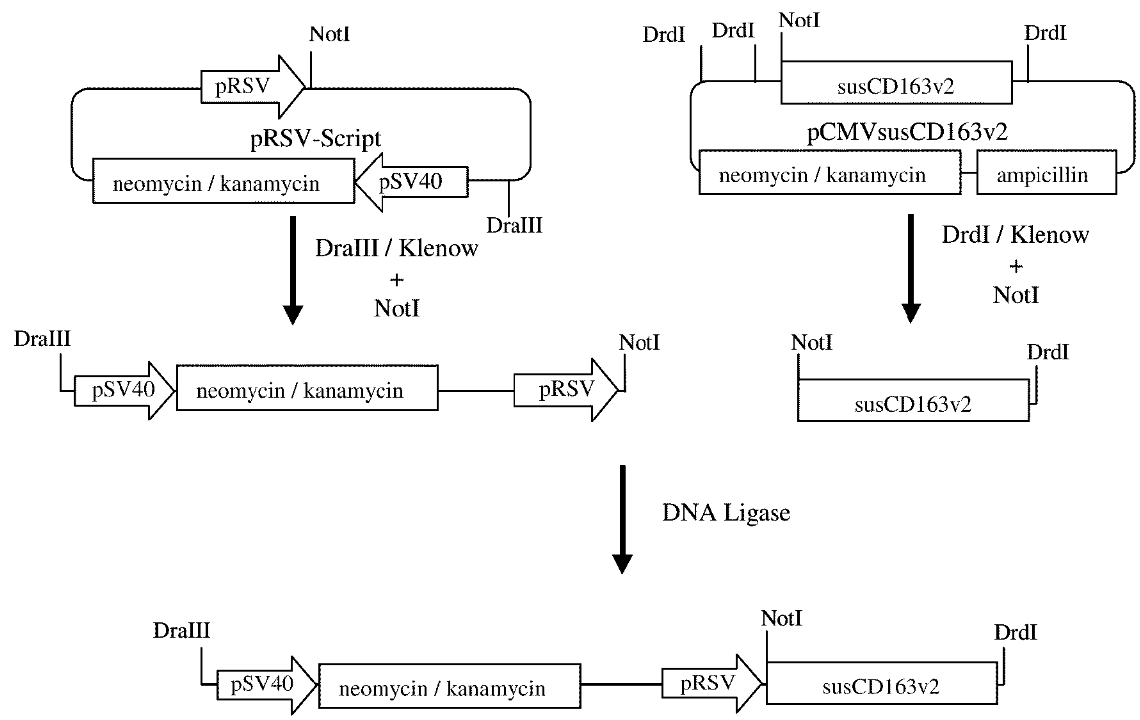
FIG. 4 Generation of DNA fragments and ligation to place CD163 directly behind the RSV promoter. Plasmids were digested with either DraIII or DrdI, followed by a blunting reaction with Klenow enzyme. After clean up, the plasmids were digested with NotI. Gel purification yielded DNA fragments that were subsequently ligated utilizing the cohesive NotI termini. Promoters from RSV (pRSV) and SV40 (pSV40) are indicated with arrows.
Figure 5:
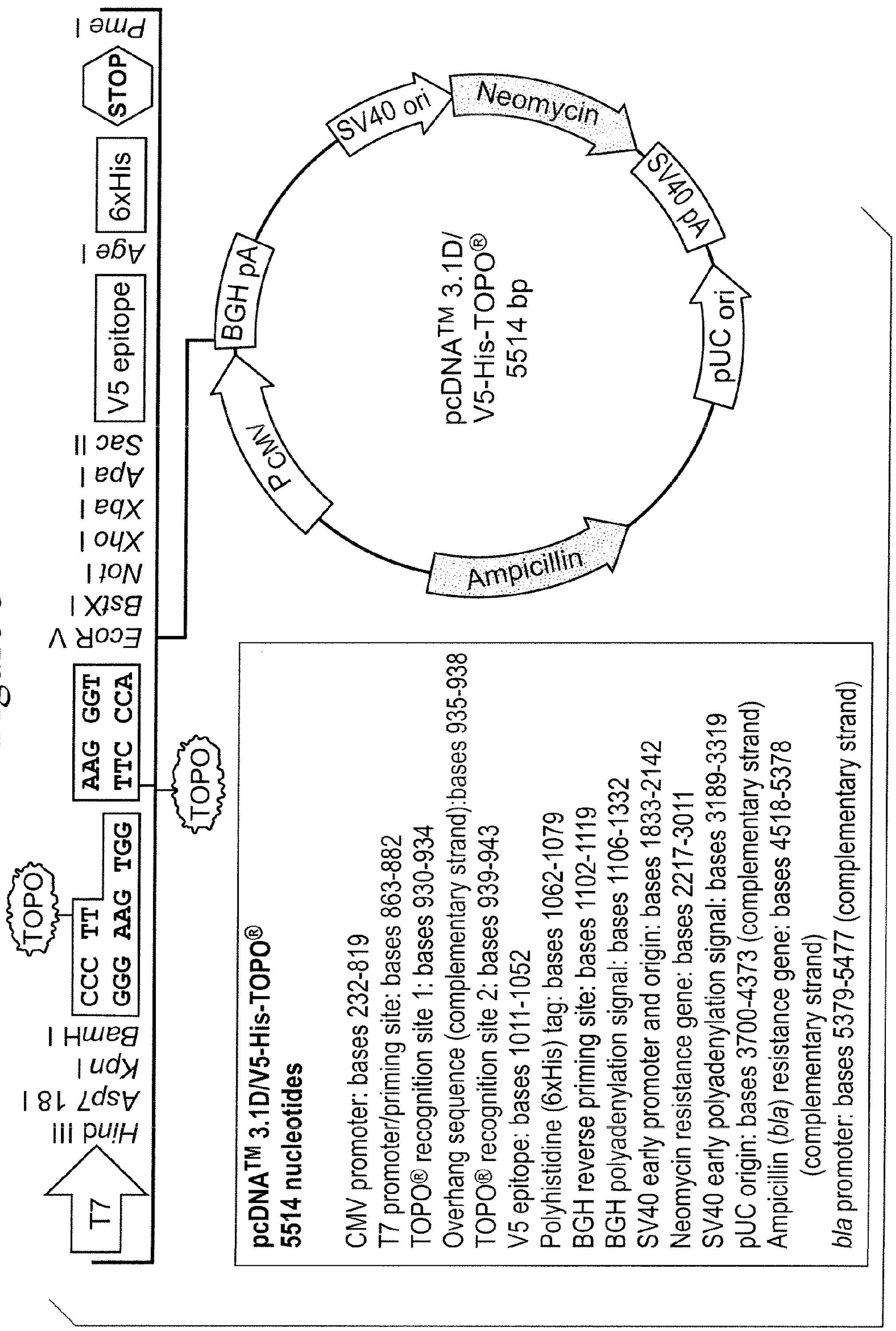
FIG. 5 Map of pcDNA3.1 Directional V5/His/TOPO cloning vector

Preparation of a RSV Promoter Based Expression System by Direct Ligation and Transfection Method A non-cloning based procedure to generate microgram quantities of linear DNA suitable for use in generating stable cell lines expressing CD163 from an RSV promoter was developed (FIG. 4). The procedure involves the isolation and ligation of two pieces of DNA, one containing the neomycin gene and RSV promoter cassette derived from pRSV-script, and the other containing the susCD163v2 coding sequence from pCMVsusCD163v2. Vector plasmid pRSV-Script was linearized with Drain upstream of the neomycin gene, and bunted with the Klenow fragment of *E. coli* DNA polymerase. This plasmid was then digested with NotI immediately downstream of the RSV promoter. The pCMVsusCD163v2 clone was digested in the vector sequence downstream of the CD163 insert with DrdI, and blunted with Klenow fragment of DNA polymerase. The CD163 coding sequence was liberated from the vector with a NotI located immediately upstream of the CD163 coding sequence. For each plasmid digestion the appropriate fragments were purified from agarose gels. A large-scale ligation reaction was performed as follows. Approximately 20 μg of each DNA fragment was incubated in a volume of 600 μL with 15 units of T4 DNA ligase. The reaction was incubated at room temperature for 20 minutes, at which time an aliquot was removed and the reaction frozen on dry ice. Agarose gel analysis of the aliquot revealed that a significant amount of non-ligated DNA remained, so another 15 units of ligase was added and incubated for another 10 minutes at room temperature. Following ligation, a linear piece of DNA containing all of the appropriate elements was purified by agarose gel electrophoresis. Ligation of the two DNA fragments via the cohesive Not I termini resulted in the placement of the 5' sequences of the CD163 gene downstream of the RSV promoter, allowing for directed expression of CD163 in mammalian cells. Once isolated, the purified DNA was used to transfect various mammalian cell lines.

Example 6

Cloning and Characterization of Human CD163 cDNA

Figure 6:
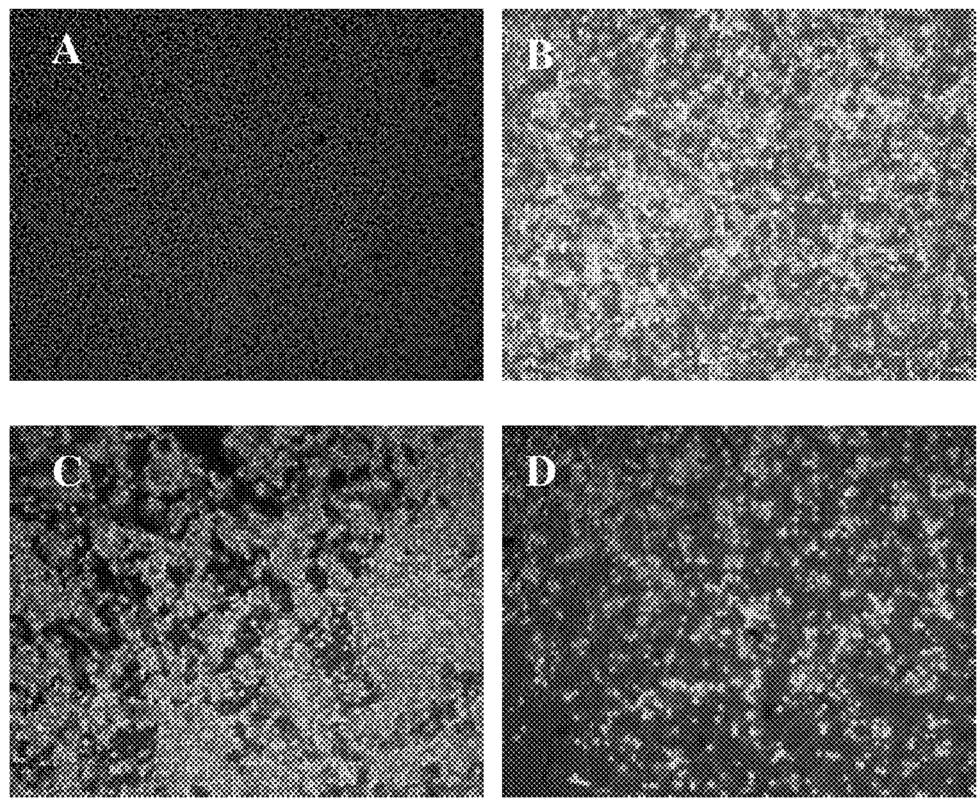
FIG. 6 Three BHK/CMV/v1 cell lines, #3, #5, and #12 and a non-permissive BHK cell line were infected with PRRSV isolate P129 and stained with SDOW17-FITC. Panel A shows a non-permissive BHK21 cell clone. Panel B shows BHK/CMV/v1 clone #3. Panel C shows BHK/CMV/v1 clone #5. Panel D shows BHK/CMV/v1 clone #12.

Based on a known human CD163 cDNA sequence (GenBank Accession No. BC051281), a forward primer Hu5'Not (SEQ ID NO: 15) (5'CACCGCGGCCGC GAAGTTATAAATCGCCACCATGAGCAAACTCAGAATGG-3') and a reverse primer Hu3'Kpn (SEQ ID NO: 16) (5'-TGCTCC GGTACCTAGTCCAGGTCTTCATCAAGGTATCTTA-3') were designed using the PrimerSelect program. Restriction sites for NotI and KpnI (underlined) were incorporated into the 5' and 3' primers, respectively, to facilitate cloning into expression vectors. The sequence CACC was added to the 5' end of the 5' primer to allow directional cloning into the pcDNA3.1D/V5/H is/TOPO vector (Cat. No. K49001, Invitrogen, see FIG. 6). Human CD163 cDNAs were amplified from RNA extracted from the U937 cell line after stimulated with phorbol 12-myristate 13-acetate (100 ng/ml) for 3 days. Total cellular RNA was prepared using the RNeasy kit (Qiagen). RT-PCR reactions and sequencing methods were the same as described in Example 4. PCR products were separated on 0.8% SeaKem agarose gel and extracted from the gel using the GeneClean kit. PCR products were cloned directionally into the pcDNA3.1D/V5/His/TOPO vector following the manufacturer's instructions. Two clones with large inserts were sequenced. Sequencing and sequence analysis methods were described in Example 4. A clone with a correct insert was designed "pcDNA3.1D-humCD163v2" and we have designated the sequence of the insert SEQ ID NO: 17

The CD163 open reading frame in pcDNA3.1D-humCD163v2 is 1121 residues in length (designated SEQ ID NO: 18 which encodes SEQ ID NO:19 disclosed below), and is 100% identical to Genbank Z22968 (a human CD163 cDNA of the same length). Our human CD163v2 sequence is also 100% identical to Genbank BC051281 and Z22969 (splice variants of human CD163) except that 42 nonhomologous residues in the two Genbank sequences replace the seven carboxy-terminal residues of our sequence. This difference is due to the presence of an 83-nucleotide exon in BC051281 and Z22969, and the resulting frame shift at the 3' end of the exon. (Law, S. K., Micklem, K. J., Shaw, J. M., Zhang, X. P., Dong, Y., Willis, A. C. and Mason, D. Y. (1993) A new macrophage differentiation antigen which is a member of the scavenger receptor superfamily. European Journal of Immunology 23 (9), 2320-2325).

| SEQUENCE | ID NO |
|---|---|
| atgagcaaac tcagaatggt gctacttgaa gactctggat ctgctgactt cagaagacat 60 | SEQ ID NO: 17 |
| tttgtcaacc tgagtccctt caccattact gtggtcttac ttctcagtgc ctgttttgtc 120 | |
| accagttctc ttggaggaac agacaaggag ctgaggctag tggatggtga aaacaagtgt 180 | |
| agcgggagag tggaagtgaa agtccaggag gagtggggaa cggtgtgtaa taatggctgg 240 | |
| agcatggaag cggtctctgt gatttgtaac cagctgggat gtccaactgc tatcaaagcc 300 | |
| cctggatggg ctaattccag tgcaggttct ggacgcattt ggatggatca tgtttcttgt 360 | |
| cgtgggaatg agtcagctct ttgggattgc aaacatgatg gatggggaaa gcatagtaac 420 | |
| tgtactcacc aacaagatgc tggagtgacc tgctcagatg gatccaattt ggaaatgagg 480 | |
| ctgacgcgtg gagggaatat gtgttctgga agaatagaga tcaaattcca aggacggtgg 540 | |
| ggaacagtgt gtgatgataa cttcaacata gatcatgcat ctgtcatttg tagacaactt 600 | |
| gaatgtggaa gtgctgtcag tttctctggt tcatctaatt ttggagaagg ctctggacca 660 | |
| atctggtttg atgatcttat atgcaacgga aatgagtcag ctctctggaa ctgcaaacat 720 | |
| caaggatggg gaaagcataa ctgtgaccat gctgaggatg ctggagtgat ttgctcaaag 780 | |
| ggagcagatc tgagcctgag actggtagat ggagtcactg aatgttcagg aagattagaa 840 | |
| gtgagattcc aaggggaatg gggacaata tgtgatgacg gctgggacag ttacgatgct 900 | |
| gctgtggcat gcaagcaact gggatgtcca actgccgtca cagccattgg tcgagttaac 960 | |
| gccagtaagg gatttggaca catctggctt gacagcgttt cttgccaggg acatgaacct 1020 | |
| gctgtctggc aatgtaaaca ccatgaatgg ggaaagcatt attgcaatca caatgaagat 1080 | |
| gctggcgtga catgttctga tggatcagat ctggagctaa gacttagagg tggaggcagc 1140 | |
| cgctgtgctg ggacagttga ggtggagatt cagagactgt tagggaaggt gtgtgacaga 1200 | |

-continued

| SEQUENCE | ID NO |
|---|---|
| ggctggggac tgaaagaagc tgatgtggtt tgcaggcagc tgggatgtgg atctgcactc 1260 | |
| aaaacatctt atcaagtgta ctccaaaatc caggcaacaa acacatggct gtttctaagt 1320 | |
| agctgtaacg gaaatgaaac ttctctttgg gactgcaaga actggcaatg gggtggactt 1380 | |
| acctgtgatc actatgaaga agccaaaatt acctgctcag cccacaggga acccagactg 1440 | |
| gttggagggg acattccctg ttctggacgt gttgaagtga agcatggtga cacgtggggc 1500 | |
| tccatctgtg attcggactt ctctctggaa gctgccagcg ttctatgcag ggaattacag 1560 | |
| tgtggcacag ttgtctctat cctgggggga gctcactttg gagagggaaa tggacagatc 1620 | |
| tgggctgaag aattccagtg tgagggacat gagtcccatc tttcactctg cccagtagca 1680 | |
| ccccgcccag aaggaacttg tagccacagc agggatgttg gagtagtctg ctcaagatac 1740 | |
| acagaaattc gcttggtgaa tggcaagacc ccgtgtgagg gcagagtgga gctcaaaacg 1800 | |
| cttggtgcct ggggatccct ctgtaactct cactgggaca tagaagatgc ccatgttctt 1860 | |
| tgccagcagc ttaaatgtgg agttgccctt tctaccccag gaggagcacg ttttggaaaa 1920 | |
| ggaaatggtc agatctggag gcatatgttt cactgcactg ggactgagca gcacatggga 1980 | |
| gattgtcctg taactgctct aggtgcttca ttatgtcctt cagagcaagt ggcctctgta 2040 | |
| atctgctcag gaaaccagtc ccaaacactg tcctcgtgca attcatcgtc tttgggccca 2100 | |
| acaaggccta ccattccaga agaaagtgct gtggcctgca tagagagtgg tcaacttcgc 2160 | |
| ctggtaaatg gaggaggtcg ctgtgctggg agagtagaga tctatcatga gggctcctgg 2220 | |
| ggcaccatct gtgatgacag ctgggacctg agtgatgccc acgtggtttg cagacagctg 2280 | |
| ggctgtggag aggccattaa tgccactggt tctgctcatt ttggggaagg aacagggccc 2340 | |
| atctggctgg atgagatgaa atgcaatgga aaagaatccc gcatttggca gtgccattca 2400 | |
| cacggctggg ggcagcaaaa ttgcaggcac aaggaggatg cgggagttat ctgctcagaa 2460 | |
| ttcatgtctc tgagactgac cagtgaagcc agcagagagg cctgtgcagg gcgtctggaa 2520 | |
| gtttttttaca atggagcttg gggcactgtt ggcaagagta gcatgtctga aaccactgtg 2580 | |
| ggtgtggtgt gcaggcagct gggctgtgca gacaaaggga aaatcaaccc tgcatcttta 2640 | |
| gacaaggcca tgtccattcc catgtgggtg gacaatgttc agtgtccaaa aggacctgac 2700 | |
| acgctgtggc agtgcccatc atctccatgg gagaagagac tggccagccc ctcggaggag 2760 | |
| acctggatca catgtgacaa caagataaga cttcaggaag gacccacttc ctgttctgga 2820 | |
| cgtgtggaga tctggcatgg aggttcctgg gggacagtgt gtgatgactc ttgggacttg 2880 | |
| gacgatgctc aggtggtgtg tcaacaactt ggctgtggtc cagctttgaa agcattcaaa 2940 | |
| gaagcagagt ttggtcaggg gactggaccg atatggctca atgaagtgaa gtgcaaaggg 3000 | |
| aatgagtctt ccttgtggga ttgtcctgcc agacgctggg gccatagtga gtgtgggcac 3060 | |
| aaggaagacg ctgcagtgaa ttgcacagat atttcagtgc agaaaacccc acaaaaagcc 3120 | |
| acaacaggtc gctcatcccg tcagtcatcc tttattgcag tcgggatcct tggggttgtt 3180 | |
| ctgttggcca ttttcgtcgc attattcttc ttgactaaaa agcgaagaca gagacagcgg 3240 | |
| cttgcagttt cctcaagagg agagaactta gtccaccaaa ttcaataccg ggagatgaat 3300 | |
| tcttgcctga atgcagatga tctggaccta atgaattcct caggaggcca ttctgagcca 3360 | |
| cactgaaaag gaaaatggga atttataacc cagtgagttc agcctttaag ataccttgat 3420 | |
| gaagacctgg acta 3434 | |

1 M S K L R M V L L E D S G S A D F R R H SEQ ID NO: 18 and 19
1 atgagcaaactcagaatggtgctacttgaagactctggatctgctgacttcagaagacat -continued

| SEQUENCE | ID NO |
|---|---|

```
 21 F   V   N   L   S   P   F   T   I   T   V   V   L   L   L   S   A   C   F   V
 61 tttgtcaacctgagtcccttcaccattactgtggtcttacttctcagtgcctgttttgtc

 41 T   S   S   L   G   G   T   D   K   E   L   R   L   V   D   G   E   N   K   C
121 accagttctcttggaggaacagacaaggagctgaggctagtggatggtgaaaacaagtgt

 61 S   G   R   V   E   V   K   V   Q   E   E   W   G   T   V   C   N   N   G   W
181 agcgggagagtggaagtgaaagtccaggaggagtggggaacggtgtgtaataatggctgg

 81 S   M   E   A   V   S   V   I   C   N   Q   L   G   C   P   T   A   I   K   A
241 agcatggaagcggtctctgtgatttgtaaccagctgggatgtccaactgctatcaaagcc

101 P   G   W   A   N   S   S   A   G   S   G   R   I   W   M   D   H   V   S   C
301 cctggatgggctaattccagtgcaggttctggacgcatttggatggatcatgtttcttgt

121 R   G   N   E   S   A   L   W   D   C   K   H   D   G   W   G   K   H   S   N
361 cgtgggaatgagtcagctctttgggattgcaaacatgatggatggggaaagcatagtaac

141 C   T   H   Q   Q   D   A   G   V   T   C   S   D   G   S   N   L   E   M   R
421 tgtactcaccaacaagatgctggagtgacctgctcagatggatccaatttggaaatgagg

161 L   T   R   G   G   N   M   C   S   G   R   I   E   I   K   F   Q   G   R   W
481 ctgacgcgtggagggaatatgtgttctggaagaatagagatcaaattccaaggacggtgg

181 G   T   V   C   D   D   N   F   N   I   D   H   A   S   V   I   C   R   Q   L
541 ggaacagtgtgtgatgataacttcaacatagatcatgcatctgtcatttgtagacaactt

201 E   C   G   S   A   V   S   F   S   G   S   S   N   F   G   E   G   S   G   P
601 gaatgtggaagtgctgtcagtttctctggttcatctaattttggagaaggctctggacca

221 I   W   F   D   D   L   I   C   N   G   N   E   S   A   L   W   N   C   K   H
661 atctggtttgatgatcttatatgcaacggaaatgagtcagctctctggaactgcaaacat

241 Q   G   W   G   K   H   N   C   D   H   A   E   D   A   G   V   I   C   S   K
721 caaggatggggaaagcataactgtgaccatgctgaggatgctggagtgatttgctcaaag

261 G   A   D   L   S   L   R   L   V   D   G   V   T   E   C   S   G   R   L   E
781 ggagcagatctgagcctgagactggtagatggagtcactgaatgttcaggaagattagaa

281 V   R   F   Q   G   E   W   G   T   I   C   D   D   G   W   D   S   Y   D   A
841 gtgagattccaaggggaatgggggacaatatgtgatgacggctgggacagttacgatgct

301 A   V   A   C   K   Q   L   G   C   P   T   A   V   T   A   I   G   R   V   N
901 gctgtggcatgcaagcaactgggatgtccaactgccgtcacagccattggtcgagttaac

321 A   S   K   G   F   G   H   I   W   L   D   S   V   S   C   Q   G   H   E   P
961 gccagtaagggatttggacacatctggcttgacagcgtttcttgccagggacatgaacct

 341 A   V   W   Q   C   K   H   H   E   W   G   K   H   Y   C   N   H   N   E   D
1021 gctgtctggcaatgtaaacaccatgaatggggaaagcattattgcaatcacaatgaagat

 361 A   G   V   T   C   S   D   G   S   D   L   E   L   R   L   R   G   G   G   S
1081 gctggcgtgacatgttctgatggatcagatctggagctaagacttagaggtggaggcagc

 381 R   C   A   G   T   V   E   V   E   I   Q   R   L   L   G   K   V   C   D   R
1141 cgctgtgctgggacagttgaggtggagattcagagactgttagggaaggtgtgtgacaga

 401 G   W   G   L   K   E   A   D   V   V   C   R   Q   L   G   C   G   S   A   L
1201 ggctggggactgaaagaagctgatgtggtttgcaggcagctgggatgtggatctgcactc

 421 K   T   S   Y   Q   V   Y   S   K   I   Q   A   T   N   T   W   L   F   L   S
1261 aaaacatcttatcaagtgtactccaaaatccaggcaacaaacacatggctgtttctaagt

 441 S   C   N   G   N   E   T   S   L   W   D   C   K   N   W   Q   W   G   G   L
1321 agctgtaacggaaatgaaacttctctttgggactgcaagaactggcaatggggtggactt

 461 T   C   D   H   Y   E   E   A   K   I   T   C   S   A   H   R   E   P   R   L
1381 acctgtgatcactatgaagaagccaaaattacctgctcagcccacagggaacccagactg

 481 V   G   G   D   I   P   C   S   G   R   V   E   V   K   H   G   D   T   W   G
1441 gttggaggggacattccctgttctggacgtgttgaagtgaagcatggtgacacgtggggc

 501 S   I   C   D   S   D   F   S   L   E   A   A   S   V   L   C   R   E   L   Q
1501 tccatctgtgattcggacttctctctggaagctgccagcgttctatgcagggaattacag

 521 C   G   T   V   V   S   I   L   G   G   A   H   F   G   E   G   N   G   Q   I
1561 tgtggcacagttgtctctatcctgggggagctcactttggagagggaaatggacagatc
```

-continued

| SEQUENCE | ID NO |
|---|---|

```
 541 W A E E F Q C E G H E S H L S L C P V A
1621 tgggctgaagaattccagtgtgagggacatgagtcccatctttcactctgcccagtagca

 561 P R P E G T C S H S R D V G V V C S R Y
1681 ccccgcccagaaggaacttgtagccacagcagggatgttggagtagtctgctcaagatac

 581 T E I R L V N G K T P C E G R V E L K T
1741 acagaaattcgcttggtgaatggcaagaccccgtgtgagggcagagtggagctcaaaacg

 601 L G A W G S L C N S H W D I E D A H V L
1801 cttggtgcctggggatccctctgtaactctcactgggacatagaagatgcccatgttctt

 621 C Q Q L K C G V A L S T P G G A R F G K
1861 tgccagcagcttaaatgtggagttgccctttctaccccaggaggagcacgttttggaaaa

 641 G N G Q I W R H M F H C T G T E Q H M G
1921 ggaaatggtcagatctggaggcatatgtttcactgcactgggactgagcagcacatggga

 661 D C P V T A L G A S L C P S E Q V A S V
1981 gattgtcctgtaactgctctaggtgcttcattatgtccttcagagcaagtggcctctgta

 681 I C S G N Q S Q T L S S C N S S S L G P
2041 atctgctcaggaaaccagtcccaaacactgtcctcgtgcaattcatcgtctttgggccca

 701 T R P T I P E E S A V A C I E S G Q L R
2101 acaaggcctaccattccagaagaaagtgctgtggcctgcatagagagtggtcaacttcgc

 721 L V N G G G R C A G R V E I Y H E G S W
2161 ctggtaaatggaggaggtcgctgtgctgggagagtagagatctatcatgagggctcctgg

 741 G T I C D D S W D L S D A H V V C R Q L
2221 ggcaccatctgtgatgacagctgggacctgagtgatgcccacgtggtttgcagacagctg

 761 G C G E A I N A T G S A H F G E G T G P
2281 ggctgtggagaggccattaatgccactggttctgctcattttggggaaggaacagggccc

 781 I W L D E M K C N G K E S R I W Q C H S
2341 atctggctggatgagatgaaatgcaatggaaaagaatcccgcatttggcagtgccattca

 801 H G W G Q Q N C R H K E D A G V I C S E
2401 cacggctgggggcagcaaaattgcaggcacaaggaggatgcgggagttatctgctcagaa

 821 F M S L R L T S E A S R E A C A G R L E
2461 ttcatgtctctgagactgaccagtgaagccagcagagaggcctgtgcagggcgtctggaa

 841 V F Y N G A W G T V G K S S M S E T T V
2521 gtttttacaatggagcttggggcactgttggcaagagtagcatgtctgaaaccactgtg

 861 G V V C R Q L G C A D K G K I N P A S L
2581 ggtgtggtgtgcaggcagctgggctgtgcagacaaagggaaaatcaaccctgcatcttta

 881 D K A M S I P M W V D N V Q C P K G P D
2641 gacaaggccatgtccattcccatgtgggtggacaatgttcagtgtccaaaaggacctgac

 901 T L W Q C P S S P W E K R L A S P S E E
2701 acgctgtggcagtgcccatcatctccatgggagaagagactggccagcccctcggaggag

 921 T W I T C D N K I R L Q E G P T S C S G
2761 acctggatcacatgtgacaacaagataagacttcaggaaggacccacttcctgttctgga

 941 R V E I W H G G S W G T V C D D S W D L
2821 cgtgtggagatctggcatggaggttcctggggacagtgtgtgatgactcttgggacttg

 961 D D A Q V V C Q Q L G C G P A L K A F K
2881 gacgatgctcaggtggtgtgtcaacaacttggctgtggtccagctttgaaagcattcaaa

 981 E A E F G Q G T G P I W L N E V K C K G
2941 gaagcagagtttggtcaggggactggaccgatatggctcaatgaagtgaagtgcaaaggg

1001 N E S S L W D C P A R R W G H S E C G H
3001 aatgagtcttccttgtgggattgtcctgccagacgctggggccatagtgagtgtgggcac

1021 K E D A A V N C T D I S V Q K T P Q K A
3061 aaggaagacgctgcagtgaattgcacagatatttcagtgcagaaaaccccacaaaaagcc

1041 T T G R S S R Q S S F I A V G I L G V V
3121 acaacaggtcgctcatcccgtcagtcatcctttattgcagtcgggatccttggggttgtt
```

-continued

| SEQUENCE | ID NO |
|---|---|
| 1061 L L A I F V A L F F L T K K R R Q R Q R<br>3181 ctgttggccattttcgtcgcattattcttcttgactaaaaagcgaagacagagacagcgg | |
| 1081 L A V S S R G E N L V H Q I Q Y R E M N<br>3241 cttgcagtttcctcaagaggagagaacttagtccaccaaattcaataccgggagatgaat | |
| 1101 S C L N A D D L D L M N S S G G H S E P<br>3301 tcttgcctgaatgcagatgatctggacctaatgaattcctcaggaggccattctgagcca | |
| 1121 H<br>3361 cac | |
| 1 MSKLRMVLLE DSGSADFRRH FVNLSPFTIT VVLLLSACFV TSSLGGTDKE | SEQ ID NO: 19 |
| 51 LRLVDGENKC SGRVEVKVQE EWGTVCNNGW SMEAVSVICN QLGCPTAIKA | |
| 101 PGWANSSAGS GRIWMDHVSC RGNESALWDC KHDGWGKHSN CTHQQDAGVT | |
| 151 CSDGSNLEMR LTRGGNMCSG RIEIKFQGRW GTVCDDNFNI DHASVICRQL | |
| 201 ECGSAVSFSG SSNFGEGSGP IWFDDLICNG NESALWNCKH QGWGKHNCDH | |
| 251 AEDAGVICSK GADLSLRLVD GVTECSGRLE VRFQGEWGTI CDDGWDSYDA | |
| 301 AVACKQLGCP TAVTAIGRVN ASKGFGHIWL DSVSCQGHEP AVWQCKHHEW | |
| 351 GKHYCNHNED AGVTCSDGSD LELRLRGGGS RCAGTVEVEI QRLLGKVCDR | |
| 401 GWGLKEADVV CRQLGCGSAL KTSYQVYSKI QATNTWLFLS SCNGNETSLW | |
| 451 DCKNWQWGGL TCDHYEEAKI TCSAHREPRL VGGDIPCSGR VEVKHGDTWG | |
| 501 SICDSDFSLE AASVLCRELQ CGTVVSILGG AHFGEGNGQI WAEEFQCEGH | |
| 551 ESHLSLCPVA PRPEGTCSHS RDVGVVCSRY TEIRLVNGKT PCEGRVELKT | |
| 601 LGAWGSLCNS HWDIEDAHVL CQQLKCGVAL STPGGARFGK GNGQIWRHMF | |
| 651 HCTGTEQHMG DCPVTALGAS LCPSEQVASV ICSGNQSQTL SSCNSSSLGP | |
| 701 TRPTIPEESA VACIESGQLR LVNGGGRCAG RVEIYHEGSW GTICDDSWDL | |
| 751 SDAHVVCRQL GCGEAINATG SAHFGEGTGP IWLDEMKCNG KESRIWQCHS | |
| 801 HGWGQQNCRH KEDAGVICSE FMSLRLTSEA SREACAGRLE VFYNGAWGTV | |
| 851 GKSSMSETTV GVVCRQLGCA DKGKINPASL DKAMSIPMWV DNVQCPKGPD | |
| 901 TLWQCPSSPW EKRLASPSEE TWITCDNKIR LQEGPTSCSG RVEIWHGGSW | |
| 951 GTVCDDSWDL DDAQVVCQQL GCGPALKAFK EAEFGQGTGP IWLNEVKCKG | |
| 1001 NESSLWDCPA RRWGHSECGH KEDAAVNCTD ISVQKTPQKA TTGRSSRQSS | |
| 1051 FIAVGILGVV LLAIFVALFF LTKKRRQRQR LAVSSRGENL VHQIQYREMN | |
| 1101 SCLNADDLDL MNSSGGHSEP H | |

Example 7

Cloning and Characterization of Murine CD163

Based on the murine CD163 sequence in GenBank (AF274883), a forward primer Mus-new5' (SEQ ID NO: 20) (5'-CACCGCGGCCGCCACACGGAGCCAT-CAAAATCATCAA-3') and a reverse primer Mus-new3' (SEQ ID NO:21) (5'-GGTACCGCGAACAAGCAAAC-CAATAGCAATATTGTTTAATTCCCTC-3') were designed using the PrimerSelect program. Restriction endonucleases sites for NotI and KpnI were included in 5' and 3' primers, respectively, to allow future cloning into other expression vectors. Mouse peritoneal macrophages were harvested from mice 2 days after injecting thioglycollate medium into the peritoneal cavity. Total cellular RNA was prepared from peritoneal macrophages using the RNeasy kit. RT-PCR reactions and RT-PCR parameters were the same as described in Example 4, except the annealing temperature was increased to 60° C. and extension temperature increased to 72° C. The PCR product was purified on a 0.8% SeaKem agarose gel and directionally cloned into pcDNA3.1D/V5/His/TOPO according to the manufacturer's instructions. Several clones with large inserts were identified for further analysis. A plasmid containing an insert (SEQ ID NO: 22) with a murine CD163 that encodes a protein of the same length as (1121 amino acids SEQ ID NO:24) and differs from Genbank AF274883 by only two amino acids (99.8% identity) was designated "pcDNA3.1D-murCD163v2".

Another plasmid, "pcDNA3.1D-murCD163v3 was generated which contained an insert (SEQ ID NO: 25) containing a murine CD163 coding sequence (SEQ ID NO: 26) which encodes a protein of 1159 amino acids in length (SEQ ID NO: 27). It differs from AF274883 by only 3 amino acids within the first 1107 residues (99.7% identity), but the sequences diverge completely beginning at residue 1108. This is due to an insertion of 82 nucleotides in the cDNA, and a concomitant shift in reading frame downstream of the insertion. As a result, murine CD163v3 contains 52 amino acids at its carboxy-terminus that are not homologous to the 14 carboxy-terminal residues of murine CD163v2. These two alternative versions of "full length" murine CD163 are most likely splice variant of the same gene, as has been described for human CD163 (Law, S. K., Micklem, K. J., Shaw, J. M., Zhang, X. P., Dong, Y., Willis, A. C. and Mason, D. Y. (1993) A new macrophage differentiation antigen which is a member of the scavenger receptor superfamily. European Journal of Immunology 23 (9), 2320-2325).

| SEQUENCE | | ID NO |
|---|---|---|
| gctttggaat gggtggacac agaatggttc ttcttggagg tgctggatct cctggttgta | 60 | SEQ ID NO: 22 |
| aaaggtttgt ccatctaggt ttctttgttg tggctgtgag ctcacttctc agtgcctctg | 120 | |
| ctgtcactaa cgctcctgga gaaatgaaga aggaactgag actggcgggt ggtgaaaaca | 180 | |
| actgtagtgg gagagtggaa cttaagatcc atgacaagtg gggcacagtg tgcagtaacg | 240 | |
| gctggagcat gaatgaagtg tccgtggttt gccagcagct gggatgccca acttctatta | 300 | |
| aagcccttgg atgggctaac tccagcgccg gctctggata tatctggatg gacaaagttt | 360 | |
| cttgtacagg gaatgagtca gctctttggg actgcaaaca tgatgggtgg ggaaagcata | 420 | |
| actgtaccca tgaaaaagat gctggagtga cctgctcaga tggatctaat ttggagatga | 480 | |
| gactggtgaa cagtgcgggc caccgatgct taggaagagt agaaataaag ttccagggaa | 540 | |
| agtgggggac ggtgtgtgac gacaacttca gcaaagatca cgcttctgtg atttgtaaac | 600 | |
| agcttggatg tggaagtgcc attagtttct ctggctcagc taaattggga gctggttctg | 660 | |
| gaccaatctg gctcgatgac ctggcatgca atggaaatga gtcagctctc tgggactgca | 720 | |
| aacaccgggg atggggcaag cataactgtg accatgctga ggatgtcggt gtgatttgct | 780 | |
| tagagggagc agatctgagc ctgagactag tggatggagt gtccagatgt tcaggaagat | 840 | |
| tggaagtgag attccaagga gaatggggga ccgtgtgtga tgataactgg gatctccggg | 900 | |
| atgcttctgt ggtgtgcaag caactgggat gtccaactgc catcagtgcc attggtcgag | 960 | |
| ttaatgccag tgagggatct ggacagattt ggcttgacaa catttcatgc gaaggacatg | 1020 | |
| aggcaactct ttgggagtgt aaacaccaag agtggggaaa gcattactgt catcatagag | 1080 | |
| aagacgctgg cgtgacatgt tctgatggag cagatctgga acttagactt gtaggtggag | 1140 | |
| gcagtcgctg tgctggcatt gtggaggtgg agattcagaa gctgactggg aagatgtgta | 1200 | |
| gccgaggctg gacactggca gatgcggatg tggtttgcag acagcttgga tgtggatctg | 1260 | |
| cgcttcaaac ccaggctaag atctactcta aaactggggc aacaaatacg tggctctttc | 1320 | |
| ctggatcttg taatggaaat gaaactactt tttggcaatg caaaaactgg cagtggggcg | 1380 | |
| gcctttcctg tgataatttc gaagaagcca aagttacctg ctcaggccac agggaaccca | 1440 | |
| gactggttgg aggagaaatc ccatgctctg gtcgtgtgga agtgaaacac ggagacgtgt | 1500 | |
| ggggctccgt ctgtgatttt gacttgtctc tggaagctgc cagtgtggtg tgcagggaat | 1560 | |
| tacaatgtgg aacagtcgtc tctatcctag ggggagcaca ttttggagaa ggaagtggac | 1620 | |
| agatctgggg tgaagaattc cagtgtagtg gggatgagtc ccatctttca ctatgctcag | 1680 | |
| tggcgccccc gctagacaga acttgtaccc acagcaggga tgtcagcgta gtctgctcac | 1740 | |
| gatacataga tattcgtctg gcaggcggcg agtcctcctg tgagggaaga gtggagctca | 1800 | |
| agacactcgg agcctggggt cccctctgca gttctcattg ggacatggaa gatgctcatg | 1860 | |
| tcttatgtca gcagctgaag tgtggggttg cccaatctat tccagaagga gcacattttg | 1920 | |
| ggaaaggagc tggtcaggtc tggagtcaca tgttccactg cactggaact gaggaacata | 1980 | |

| SEQUENCE | ID NO |
|---|---|
| taggagattg cctcatgact gctctgggtg cgccgacgtg ttccgaagga caggtggcct 2040 | |
| ctgtcatctg ctcaggaaac caatcccaga cactattgcc atgtagttca ttgtctccag 2100 | |
| tccaaacaac aagctctaca attccaaagg agagtgaagt tccctgcata gcaagtggcc 2160 | |
| agcttcgctt ggtaggtgga ggtggtcgct gcgctggaag agtggaggtc taccacgagg 2220 | |
| gctcttgggg caccgtctgt gatgacaatt gggatatgac tgatgccaat gtggtgtgca 2280 | |
| agcagctgga ctgtggcgtg gcaattaacg ccactggctc tgcttacttc ggggaaggag 2340 | |
| caggagctat ctggctagac gaagtcatct gcactgggaa agagtctcat atttggcagt 2400 | |
| gccattcaca tggctgggga cgccataact gcaggcacaa agaagatgca ggtgttatct 2460 | |
| gctccgagtt catgtctctg aggctgacca acgaagccca caaagaaaac tgcacaggtc 2520 | |
| gccttgaagt gttttacaat ggtacatggg gcagtattgg cagtagcaat atgtctccaa 2580 | |
| ccactgtggg ggtggtgtgc cgtcagctgg gctgtgcaga caacgggact gtgaaaccca 2640 | |
| taccttcaga caagacacca tccaggccca tgtgggtaga tcgtgtgcag tgtccaaaag 2700 | |
| gagttgacac tttgtggcag tgcccctcgt caccttggaa acagagacag gccagcccct 2760 | |
| cctcccagga gtcctggatc atctgtgaca acaaaataag actccaggaa gggcatacag 2820 | |
| actgttctgg acgtgtggag atctggcaca aaggttcctg ggaacagtg tgtgatgact 2880 | |
| cctgggatct taatgatgct aaggttgtat gtaagcagtt gggctgtggc caagctgtga 2940 | |
| aggcactaaa agaagcagca tttggtccag gaactgggcc catatggctc aatgaaatta 3000 | |
| agtgtagagg gaatgagtct tccctgtggg attgtcctgc caaaccgtgg agtcacagcg 3060 | |
| actgtgggca caaagaagat gcttccatcc agtgcctccc aaaaatgact tcagaatcac 3120 | |
| atcatggcac aggtcacccc accctcacgg cactcttggt ttgtggagcc attctattgg 3180 | |
| tcctcctcat tgtcttcctc ctgtggactc tgaagcgacg acagattcag cgacttacag 3240 | |
| tttcctcaag aggagaggtc ttgatacatc aagttcagta ccaagagatg gattcaaagg 3300 | |
| cggatgatct ggacttgctg aaatcctcgg gggtcattca gaggcacact gagaaggaaa 3360 | |
| atgataattt ataatccact gaggttggag tttaagaagc cttgacagga cagccagcta 3420 | |
| aatggaacaa gagcccaggc aacgcacgga tgaccacagc tgcatcttca tgcagtcctt 3480 | |
| tgtttcctgg aactctgctg aacctgcaaa aaccatattt gtgaatgtga ccacttaata 3540 | |
| gagatgggag actttt 3556 | |

```
  1  M  G  G  H  R  M  V  L  L  G  G  A  G  S  P  G  C  K  R  F     SEQ ID NO: 23 and 24
  1  atgggtggacacagaatggttcttcttggaggtgctggatctcctggttgtaaaaggttt

 21  V  H  L  G  F  F  V  V  A  V  S  S  L  L  S  A  S  A  V  T
 61  gtccatctaggtttctttgttgtggctgtgagctcacttctcagtgcctctgctgtcact

 41  N  A  P  G  E  M  K  K  E  L  R  L  A  G  G  E  N  N  C  S
121  aacgctcctggagaaatgaagaaggaactgagactggcgggtggtgaaaacaactgtagt

 61  G  R  V  E  L  K  I  H  D  K  W  G  T  V  C  S  N  G  W  S
181  gggagagtggaacttaagatccatgacaagtggggcacagtgtgcagtaacggctggagc

 81  M  N  E  V  S  V  V  C  Q  Q  L  G  C  P  T  S  I  K  A  L
241  atgaatgaagtgtccgtggtttgccagcagctgggatgcccaacttctattaaagccctt

101  G  W  A  N  S  S  A  G  S  G  Y  I  W  M  D  K  V  S  C  T
301  ggatgggctaactccagcgccggctctggatatatctggatggacaaagtttcttgtaca

121  G  N  E  S  A  L  W  D  C  K  H  D  G  W  G  K  H  N  C  T
361  gggaatgagtcagctctttgggactgcaaacatgatgggtggggaaagcataactgtacc

141  H  E  K  D  A  G  V  T  C  S  D  G  S  N  L  E  M  R  L  V
421  catgaaaaagatgctggagtgacctgctcagatggatctaatttggagatgagactggtg
```

-continued

| SEQUENCE | ID NO |
| --- | --- |

```
 161  N  S  A  G  H  R  C  L  G  R  V  E  I  K  F  Q  G  K  W  G
 481  aacagtgcgggccaccgatgcttaggaagagtagaaataaagttccagggaaagtggggg

 181  T  V  C  D  D  N  F  S  K  D  H  A  S  V  I  C  K  Q  L  G
 541  acggtgtgtgacgacaacttcagcaaagatcacgcttctgtgatttgtaaacagcttgga

 201  C  G  S  A  I  S  F  S  G  S  A  K  L  G  A  G  S  G  P  I
 601  tgtggaagtgccattagtttctctggctcagctaaattgggagctggttctggaccaatc

 221  W  L  D  D  L  A  C  N  G  N  E  S  A  L  W  D  C  K  H  R
 661  tggctcgatgacctggcatgcaatggaaatgagtcagctctctgggactgcaaacaccgg

 241  G  W  G  K  H  N  C  D  H  A  E  D  V  G  V  I  C  L  E  G
 721  ggatggggcaagcataactgtgaccatgctgaggatgtcggtgtgatttgcttagaggga

 261  A  D  L  S  L  R  L  V  D  G  V  S  R  C  S  G  R  L  E  V
 781  gcagatctgagcctgagactagtggatggagtgtccagatgttcaggaagattggaagtg

 281  R  F  Q  G  E  W  G  T  V  C  D  D  N  W  D  L  R  D  A  S
 841  agattccaaggagaatggggggaccgtgtgtgatgataactgggatctccgggatgcttct

 301  V  V  C  K  Q  L  G  C  P  T  A  I  S  A  I  G  R  V  N  A
 901  gtggtgtgcaagcaactgggatgtccaactgccatcagtgccattggtcgagttaatgcc

 321  S  E  G  S  G  Q  I  W  L  D  N  I  S  C  E  G  H  E  A  T
 961  agtgagggatctggacagatttggcttgacaacatttcatgcgaaggacatgaggcaact

 341  L  W  E  C  K  H  Q  E  W  G  K  H  Y  C  H  H  R  E  D  A
1021  ctttgggagtgtaaacaccaagagtggggaaagcattactgtcatcatagagaagacgct

 361  G  V  T  C  S  D  G  A  D  L  E  L  R  L  V  G  G  G  S  R
1081  ggcgtgacatgttctgatggagcagatctggaacttagacttgtaggtggaggcagtcgc

 381  C  A  G  I  V  E  V  E  I  Q  K  L  T  G  K  M  C  S  R  G
1141  tgtgctggcattgtggaggtggagattcagaagctgactgggaagatgtgtagccgaggc

 401  W  T  L  A  D  A  D  V  V  C  R  Q  L  G  C  G  S  A  L  Q
1201  tggacactggcagatgcggatgtggtttgcagacagcttggatgtggatctgcgcttcaa

 421  T  Q  A  K  I  Y  S  K  T  G  A  T  N  T  W  L  F  P  G  S
1261  acccaggctaagatctactctaaaactggggcaacaaatacgtggctctttcctggatct

 441  C  N  G  N  E  T  T  F  W  Q  C  K  N  W  Q  W  G  G  L  S
1321  tgtaatggaaatgaaactactttttggcaatgcaaaaactggcagtggggcggcctttcc

 461  C  D  N  F  E  E  A  K  V  T  C  S  G  H  R  E  P  R  L  V
1381  tgtgataatttcgaagaagccaaagttacctgctcaggccacagggaacccagactggtt

 481  G  G  E  I  P  C  S  G  R  V  E  V  K  H  G  D  V  W  G  S
1441  ggaggagaaatcccatgctctggtcgtgtggaagtgaaacacggagacgtgtggggctcc

 501  V  C  D  F  D  L  S  L  E  A  A  S  V  V  C  R  E  L  Q  C
1501  gtctgtgattttgacttgtctctggaagctgccagtgtggtgtgcagggaattacaatgt

 521  G  T  V  V  S  I  L  G  G  A  H  F  G  E  G  S  G  Q  I  W
1561  ggaacagtcgtctctatcctaggggggagcacattttggagaaggaagtggacagatctgg

 541  G  E  E  F  Q  C  S  G  D  E  S  H  L  S  L  C  S  V  A  P
1621  ggtgaagaattccagtgtagtggggatgagtcccatctttcactatgctcagtggcgccc

 561  P  L  D  R  T  C  T  H  S  R  D  V  S  V  V  C  S  R  Y  I
1681  ccgctagacagaacttgtacccacagcagggatgtcagcgtagtctgctcacgatacata

 581  D  I  R  L  A  G  G  E  S  S  C  E  G  R  V  E  L  K  T  L
1741  gatattcgtctggcaggcggcgagtcctcctgtgagggaagagtggagctcaagacactc

 601  G  A  W  G  P  L  C  S  S  H  W  D  M  E  D  A  H  V  L  C
1801  ggagcctggggtcccctctgcagttctcattgggacatggaagatgctcatgtcttatgt

 621  Q  Q  L  K  C  G  V  A  Q  S  I  P  E  G  A  H  F  G  K  G
1861  cagcagctgaagtgtggggttgcccaatctattccagaaggagcacattttggaaagga

 641  A  G  Q  V  W  S  H  M  F  H  C  T  G  T  E  E  H  I  G  D
1921  gctggtcaggtctggagtcacatgttccactgcactggaactgaggaacatataggagat

 661  C  L  M  T  A  L  G  A  P  T  C  S  E  G  Q  V  A  S  V  I
1981  tgcctcatgactgctctgggtgcgccgacgtgttccgaaggacaggtggcctctgtcatc
```

-continued

| SEQUENCE | ID NO |
|---|---|
| 681 C S G N Q S Q I L L P C S S L S P V Q T<br>2041 tgctcaggaaaccaatcccagacactattgccatgtagttcattgtctccagtccaaaca | |
| 701 T S S T I P K E S E V P C I A S G Q L R<br>2101 acaagctctacaattccaaaggagagtgaagttccctgcatagcaagtggccagcttcgc | |
| 721 L V G G G G R C A G R V E V Y H E G S W<br>2161 ttggtaggtggaggtggtcgctgcgctggaagagtggaggtctaccacgagggctcttgg | |
| 741 G T V C D D N W D M T D A N V V C K Q L<br>2221 ggcaccgtctgtgatgacaattgggatatgactgatgccaatgtggtgtgcaagcagctg | |
| 761 D C G V A I N A T G S A Y F G E G A G A<br>2281 gactgtggcgtggcaattaacgccactggctctgcttacttcggggaaggagcaggagct | |
| 781 I W L D E V I C T G K E S H I W Q C H S<br>2341 atctggctagacgaagtcatctgcactgggaaagagtctcatatttggcagtgccattca | |
| 801 H G W G R H N C R H K E D A G V I C S E<br>2401 catggctggggacgccataactgcaggcacaaagaagatgcaggtgttatctgctccgag | |
| 821 F M S L R L I N E A H K E N C T G R L E<br>2461 ttcatgtctctgaggctgaccaacgaagcccacaaagaaaactgcacaggtcgccttgaa | |
| 841 V E Y N G T W G S I G S S N M S P T T V<br>2521 gtgttttacaatggtacatggggcagtattggcagtagcaatatgtctccaaccactgtg | |
| 861 G V V C R Q L G C A D N G T V K P I P S<br>2581 ggggtggtgtgccgtcagctgggctgtgcagacaacgggactgtgaaacccataccttca | |
| 881 D K T P S R P M W V D R V Q C P K G V D<br>2641 gacaagacaccatccaggcccatgtgggtagatcgtgtgcagtgtccaaaaggagttgac | |
| 901 T L W Q C P S S P W K Q R Q A S P S S Q<br>2701 actttgtggcagtgcccctcgtcaccttggaaacagagacaggccagcccctcctcccag | |
| 921 E S W I I C D N K I R L Q E G H T D C S<br>2761 gagtcctggatcatctgtgacaacaaaataagactccaggaagggcatacagactgttct | |
| 941 G R V E I W H K G S W G T V C D D S W D<br>2821 ggacgtgtggagatctggcacaaaggttcctggggaacagtgtgtgatgactcctgggat | |
| 961 L N D A K V V C K Q L G C G Q A V K A L<br>2881 cttaatgatgctaaggttgtatgtaagcagttgggctgtggccaagctgtgaaggcacta | |
| 981 K E A A F G P G T G P I W L N E I K C R<br>2941 aaagaagcagcatttggtccaggaactgggcccatatggctcaatgaaattaagtgtaga | |
| 1001 G N E S S L W D C P A K P W S H S D C G<br>3001 gggaatgagtcitccctgtgggattgtcctgccaaaccgtggagtcacagcgactgtggg | |
| 1021 H K E D A S I Q C L P K M T S E S H H G<br>3061 cacaaagaagatgcttccatccagtgcctcccaaaaatgacttcagaatcacatcatggc | |
| 1041 T G H P T L T A L L V C G A I L L V L L<br>3121 acaggtcaccccaccctcacggcactcttggtttgtggagccattctattggtcctcctc | |
| 1061 I V F L L W T L K R R Q I Q R L T V S S<br>3181 attgtcttcctcctgtggactctgaagcgacgacagattcagcgacttacagtttcctca | |
| 1081 R G E V L I H Q V Q Y Q E M D S K A D D<br>3241 agaggagaggtcttgatacatcaagttcagtaccaagagatggattcaaaggcggatgat | |
| 1101 L D L L K S S G V I Q R H T E K E N D N<br>3301 ctggacttgctgaaatcctcgggggtcattcagaggcacactgagaaggaaaatgataat | |
| 1121 L<br>3361 tta | |
| 1 MGGHRMVLLG GAGSPGCKRF VHLGFFVVAV SSLLSASAVT NAPGEMKKEL | SEQ ID NO: 24 |
| 51 RLAGGENNCS GRVELKIHDK WGTVCSNGWS MNEVSVVCQQ LGCPTSIKAL | |
| 101 GWANSSAGSG YIWMDKVSCT GNESALWDCK HDGWGKHNCT HEKDAGVTCS | |
| 151 DGSNLEMRLV NSAGHRCLGR VEIKFQGKWG TVCDDNFSKD HASVICKQLG | |

-continued

| SEQUENCE | ID NO |
|---|---|
| 201 CGSAISFSGS AKLGAGSGPI WLDDLACNGN ESALWDCKHR GWGKHNCDHA | |
| 251 EDVGVICLEG ADLSLRLVDG VSRCSGRLEV RFQGEWGTVC DDNWDLRDAS | |
| 301 VVCKQLGCPT AISAIGRVNA SEGSGQIWLD NISCEGHEAT LWECKHQEWG | |
| 351 KHYCHHREDA GVTCSDGADL ELRLVGGGSR CAGIVEVEIQ KLTGKMCSRG | |
| 401 WTLADADVVC RQLGCGSALQ TQAKIYSKTG ATNTWLFPGS CNGNETTFWQ | |
| 451 CKNWQWGGLS CDNFEEAKVT CSGHREPRLV GGEIPCSGRV EVKHGDVWGS | |
| 501 VCDFDLSLEA ASVVCRELQC GTVVSILGGA HFGEGSGQIW GEEFQCSGDE | |
| 551 SHLSLCSVAP PLDRTCTHSR DVSVVCSRYI DIRLAGGESS CEGRVELKTL | |
| 601 GAWGPLCSSH WDMEDAHVLC QQLKCGVAQS IPEGAHFGKG AGQVWSHMFH | |
| 651 CTGTEEHIGD CLMTALGAPT CSEGQVASVI CSGNQSQTLL PCSSLSPVQT | |
| 701 TSSTIPKESE VPCIASGQLR LVGGGGRCAG RVEVYHEGSW GTVCDDNWDM | |
| 751 TDANVVCKQL DCGVAINATG SAYFGEGAGA IWLDEVICTG KESHIWQCHS | |
| 801 HGWGRHNCRH KEDAGVICSE FMSLRLTNEA HKENCTGRLE VFYNGTWGSI | |
| 851 GSSNMSPTTV GVVCRQLGCA DNGTVKPIPS DKTPSRPMWV DRVQCPKGVD | |
| 901 TLWQCPSSPW KQRQASPSSQ ESWIICDNKI RLQEGHTDCS GRVEIWHKGS | |
| 951 WGTVCDDSWD LNDAKVVCKQ LGCGQAVKAL KEAAFGPGTG PIWLNEIKCR | |
| 1001 GNESSLWDCP AKPWSHSDCG HKEDASIQCL PKMTSESHHG TGHPTLTALL | |
| 1051 VCGAILLVLL IVFLLWTLKR RQIQRLTVSS RGEVLIHQVQ YQEMDSKADD | |
| 1101 LDLLKSSGVI QRHTEKENDN L | |
| gctttggaat gggtggacac agaatggttc ttcttggagg tgctggatct cctggttgta 60 | ID NO: 25 |
| aaaggtttgt ccatctaggt ttctttgttg tggctgtgag ctcacttctc agtgcctctg 120 | |
| ctgtcactaa cgctcctgga gaaatgaaga aggaactgag actggcgggt ggtgaaaaca 180 | |
| actgtagtgg gagagtggaa cttaagatcc atgacaagtg ggcacagtg tgcagtaacg 240 | |
| gctggagcat gaatgaagtg tccgtggttt gccagcagct gggatgccca acttctatta 300 | |
| aagcccttgg atgggctaac tccagcgccg gctctggata tatctggatg gacaaagttt 360 | |
| cttgtacagg gaatgagtca gctctttggg actgcaaaca tgatgggtgg ggaaagcata 420 | |
| actgtaccca tgaaaaagat gctggagtga cctgctcaga tggatctaat ttggagatga 480 | |
| gactggtgaa cagtgcgggc caccgatgct taggaagagt agaaataaag ttccagggaa 540 | |
| agtgggggac ggtgtgtgac gacaacttca gcaaagatca cgcttctgtg atttgtaaac 600 | |
| agcttggatg tggaagtgcc attagtttct ctggctcagc taaattggga gctggttctg 660 | |
| gaccaatctg gctcgatgac ctggcatgca atggaaatga gtcagctctc tgggactgca 720 | |
| aacaccgggg atggggcaag cataactgtg accatgctga ggatgtcggt gtgatttgct 780 | |
| tagagggagc agatctgagc ctgagactag tggatggagt gtccagatgt tcaggaagat 840 | |
| tggaagtgag attccaagga gaatggggga ccgtgtgtga tgataactgg gatctccggg 900 | |
| atgcttctgt ggtgtgcaag caactgggat gtccaactgc catcagtgcc attggtcgag 960 | |
| ttaatgccag tgagggatct ggacagattt ggcttgacaa catttcatgc gaaggacatg 1020 | |
| aggcaactct ttgggagtgt aaacaccaag agtggggaaa gcattactgt catcatagag 1080 | |
| aagacgctgg cgtgacatgt tctgatggag cagatctgga acttagactt gtaggtggag 1140 | |
| gcagtcgctg tgctggcatt gtggaggtgg agattcagaa gctgactggg aagatgtgta 1200 | |

-continued

| SEQUENCE | ID NO |
|---|---|
| gccgaggctg gacactggca gatgcggatg tggtttgcag acagcttgga tgtggatctg | 1260 |
| cgcttcaaac ccaggctaag atctactcta aaactggggc aacaaatacg tggctctttc | 1320 |
| ctggatcttg taatggaaat gaaactactt tttggcaatg caaaaactgg cagtggggcg | 1380 |
| gcctttcctg tgataatttc gaagaagcca aagttacctg ctcaggccac agggaaccca | 1440 |
| gactggttgg aggagaaatc ccatgctctg gtcgtgtgga aatgaaacac ggagacgtgt | 1500 |
| ggggctccgt ctgtgatttt gacttgtctc tggaagctgc cagtgtggtg tgcagggaat | 1560 |
| tacaatgtgg aacagtcgtc tctatcctag ggggagcaca ttttggagaa ggaagtggac | 1620 |
| agatctgggg tgaagaattc cagtgtagtg gggatgagtc ccatctttca ctatgctcag | 1680 |
| tggcgccccc gctagacaga acttgtaccc acagcaggga tgtcagcgta gtctgctcac | 1740 |
| gatacataga tattcgtctg gcaggcggcg agtcctcctg tgagggaaga gtggagctca | 1800 |
| agacactcgg agcctggggt cccctctgca gttctcattg ggacatggaa gatgctcatg | 1860 |
| tcttatgtca gcagctgaag tgtggggttg cccaatctat tccagaagga gcacattttg | 1920 |
| ggaaaggagc tggtcaggtc tggagtcaca tgttccactg cactggaact gaggaacata | 1980 |
| taggagattg cctcatgact gctctgggtg cgccgacgtg ttccgaagga caggtggcct | 2040 |
| ctgtcatctg ctcaggaaac caatcccaga cactattgcc atgtagttca ttgtctccag | 2100 |
| tccaaacaac aagctctaca attccaaagg agagtgaagt tccctgcata gcaagtggcc | 2160 |
| agcttcgctt ggtaggtgga ggtggtcgct gcgctggaag agtggaggtc taccacgagg | 2220 |
| gctcttgggg caccgtctgt gatgacaatt gggatatgac tgatgccaat gtggtgtgca | 2280 |
| agcagctgga ctgtggcgtg gcaattaacg ccactggctc tgcttacttc ggggaaggag | 2340 |
| caggagctat ctggctagac gaagtcatct gcactgggaa agagtctcat atttggcagt | 2400 |
| gccattcaca tggctgggga cgccataact gcaggcacaa agaagatgca ggtgttatct | 2460 |
| gctccgagtt catgtctctg aggctgacca acgaagccca caaagaaaac tgcacaggtc | 2520 |
| gccttgaagt gttttacaat ggtacatggg gcagtattgg cagtagcaat atgtctccaa | 2580 |
| ccactgtggg ggtggtgtgc cgtcagctgg gctgtgcaga caacgggact gtgaaaccca | 2640 |
| taccttcaga caagacacca tccaggccca tgtgggtaga tcgtgtgcag tgtccaaaag | 2700 |
| gagttgacac tttgtggcag tgcccctcgt caccttggaa acagagacag gccagcccct | 2760 |
| cctcccagga gtcctggatc atctgtgaca acaaaataag actccaggaa gggcatacag | 2820 |
| actgttctgg acgtgtggag atctggcaca aaggttcctg ggaacagtg tgtgatgact | 2880 |
| cctgggatct taatgatgct aaggttgtat gtaagcagtt gggctgtggc caagctgtga | 2940 |
| aggcactaaa agaagcagca tttggtccag gaactgggcc catatggctc aatgaaatta | 3000 |
| agtgtagagg gaatgagtct tccctgtggg attgtcctgc caaaccgtgg agtcacagcg | 3060 |
| actgtgggca caaagaagat gcttccatcc agtgcctccc caaaatgact tcagaatcac | 3120 |
| atcatggcac aggtcacccc accctcacgg cactcttggt ttgtggagcc attctattgg | 3180 |
| tcctcctcat tgtcttcctc ctgtggactc tgaagcgacg acagattcag cgacttacag | 3240 |
| tttcctcaag aggagaggtc ttgatacatc aagttcagta ccaagagatg gattcaaagg | 3300 |
| cggatgatct ggacttgctg aaatcctcgg aaaattccaa caattcatat gattttaatg | 3360 |
| atgatggact gacatctttg tctaaatatc ttcctatttc tggaattaaa aaggggtcat | 3420 |
| tcagaggcac actgagaagg aaaatgataa tttataatcc actgaggttg gagtttaaga | 3480 |
| agccttgaca ggacagccag ctaaatggaa caagagccca ggcaacgcac ggatgaccac | 3540 |

-continued

```
                          SEQUENCE                                 ID NO

agctgcatct tcatgcagtc ctttgtttcc tggaactctg ctgaacctgc aaaaaccata  3600

tttgtgaatg tgaccactta atagagatgg gagactttt                         3639

   1  M  G  G  H  R  M  V  L  L  G  G  A  G  S  P  G  C  K  R  F    ID NO: 26 and 27
   1  atgggtggacacagaatggttcttcttggaggtgctggatctcctggttgtaaaaggttt

  21  V  H  L  G  F  F  V  V  A  V  S  S  L  L  S  A  S  A  V  T
  61  gtccatctaggtttctttgttgtggctgtgagctcacttctcagtgcctctgctgtcact

  41  N  A  P  G  E  M  K  K  E  L  R  L  A  G  G  E  N  N  C  S
 121  aacgctcctggagaaatgaagaaggaactgagactggcgggtggtgaaaacaactgtagt

  61  G  R  V  E  L  K  I  H  D  K  W  G  T  V  C  S  N  G  W  S
 181  gggagagtggaacttaagatccatgacaagtggggcacagtgtgcagtaacggctggagc

  81  M  N  E  V  S  V  V  C  Q  Q  L  G  C  P  T  S  I  K  A  L
 241  atgaatgaagtgtccgtggtttgccagcagctgggatgcccaacttctattaaagccctt

 101  G  W  A  N  S  S  A  G  S  G  Y  I  W  M  D  K  V  S  C  T
 301  ggatgggctaactccagcgccggctctggatatatctggatggacaaagtttcttgtaca

 121  G  N  E  S  A  L  W  D  C  K  H  D  G  W  G  K  H  N  C  T
 361  gggaatgagtcagctctttgggactgcaaacatgatgggtggggaaagcataactgtacc

 141  H  E  K  D  A  G  V  T  C  S  D  G  S  N  L  E  M  R  L  V
 421  catgaaaaagatgctggagtgacctgctcagatggatctaatttggagatgagactggtg

 161  N  S  A  G  H  R  C  L  G  R  V  E  I  K  F  Q  G  K  W  G
 481  aacagtgcgggccaccgatgcttaggaagagtagaaataaagttccagggaaagtggggg

 181  T  V  C  D  D  N  F  S  K  D  H  A  S  V  I  C  K  Q  L  G
 541  acggtgtgtgacgacaacttcagcaaagatcacgcttctgtgatttgtaaacagcttgga

 201  C  G  S  A  I  S  F  S  G  S  A  K  L  G  A  G  S  G  P  I
 601  tgtggaagtgccattagtttctctggctcagctaaattgggagctggttctggaccaatc

 221  W  L  D  D  L  A  C  N  G  N  E  S  A  L  W  D  C  K  H  R
 661  tggctcgatgacctggcatgcaatggaaatgagtcagctctctgggactgcaaacaccgg

 241  G  W  G  K  H  N  C  D  H  A  E  D  V  G  V  I  C  L  E  G
 721  ggatggggcaagcataactgtgaccatgctgaggatgtcggtgtgatttgcttagaggga

 261  A  D  L  S  L  R  L  V  D  G  V  S  R  C  S  G  R  L  E  V
 781  gcagatctgagcctgagactagtggatggagtgtccagatgttcaggaagattggaagtg

 281  R  F  Q  G  E  W  G  T  V  C  D  D  N  W  D  L  R  D  A  S
 841  agattccaaggagaatggggggaccgtgtgtgatgataactgggatctccgggatgcttct

 301  V  V  C  K  Q  L  G  C  P  T  A  I  S  A  I  G  R  V  N  A
 901  gtggtgtgcaagcaactgggatgtccaactgccatcagtgccattggtcgagttaatgcc

 321  S  E  G  S  G  Q  I  W  L  D  N  I  S  C  E  G  H  E  A  T
 961  agtgagggatctggacagatttggcttgacaacatttcatgcgaaggacatgaggcaact

 341  L  W  E  C  K  H  Q  E  W  G  K  H  Y  C  H  H  R  E  D  A
1021  ctttgggagtgtaaacaccaagagtggggaaagcattactgtcatcatagagaagacgct

 361  G  V  T  C  S  D  G  A  D  L  E  L  R  L  V  G  G  G  S  R
1081  ggcgtgacatgttctgatggagcagatctggaacttagacttgtaggtggaggcagtcgc

 381  C  A  G  I  V  E  V  E  I  Q  K  L  T  G  K  M  C  S  R  G
1141  tgtgctggcattgtggaggtggagattcagaagctgactgggaagatgtgtagccgaggc

 401  W  T  L  A  D  A  D  V  V  C  R  Q  L  G  C  G  S  A  L  Q
1201  tggacactggcagatgcggatgtggtttgcagacagcttggatgtggatctgcgcttcaa

 421  T  Q  A  K  I  Y  S  K  T  G  A  T  N  T  W  L  F  P  G  S
1261  acccaggctaagatctactctaaaactggggcaacaaatacgtggctctttcctggatct

 441  C  N  G  N  E  T  T  F  W  Q  C  K  N  W  Q  W  G  G  L  S
1321  tgtaatggaaatgaaactacttttggcaatgcaaaaactggcagtggggcggcctttcc

 461  C  D  N  F  E  E  A  K  V  T  C  S  G  H  R  E  P  R  L  V
1381  tgtgataatttcgaagaagccaaagttacctgctcaggccacagggaacccagactggtt

 481  G  G  E  I  P  C  S  G  R  V  E  M  K  H  G  D  V  W  G  S
1441  ggaggagaaatcccatgctctggtcgtgtggaaatgaaacacggagacgtgtggggctcc
```

-continued

| SEQUENCE | ID NO |
|---|---|

```
 501  V  C  D  F  D  L  S  L  E  A  A  S  V  V  C  R  E  L  Q  C
1501  gtctgtgattttgacttgtctctggaagctgccagtgtggtgtgcagggaattacaatgt

 521  G  T  V  V  S  I  L  G  G  A  H  F  G  E  G  S  G  Q  I  W
1561  ggaacagtcgtctctatcctaggggagcacatttggagaaggaagtggacagatctgg

 541  G  E  E  F  Q  C  S  G  D  E  S  H  L  S  L  C  S  V  A  P
1621  ggtgaagaattccagtgtagtggggatgagtcccatctttcactatgctcagtggcgccc

 561  P  L  D  R  T  C  T  H  S  R  D  V  S  V  V  C  S  R  Y  I
1681  ccgctagacagaacttgtacccacagcagggatgtcagcgtagtctgctcacgatacata

 581  D  I  R  L  A  G  G  E  S  S  C  E  G  R  V  E  L  K  T  L
1741  gatattcgtctggcaggcggcgagtcctcctgtgagggaagagtggagctcaagacactc

 601  G  A  W  G  P  L  C  S  S  H  W  D  M  E  D  A  H  V  L  C
1801  ggagcctggggtcccctctgcagttctcattgggacatggaagatgctcatgtcttatgt

 621  Q  Q  L  K  C  G  V  A  Q  S  I  P  E  G  A  H  F  G  K  G
1861  cagcagctgaagtgtggggttgcccaatctattccagaaggagcacatttgggaaagga

 641  A  G  Q  V  W  S  H  M  F  H  C  T  G  T  E  E  H  I  G  D
1921  gctggtcaggtctggagtcacatgttccactgcactggaactgaggaacatataggagat

 661  C  L  M  T  A  L  G  A  P  T  C  S  E  G  Q  V  A  S  V  I
1981  tgcctcatgactgctctgggtgcgccgacgtgttccgaaggacaggtggcctctgtcatc

 681  C  S  G  N  Q  S  Q  T  L  L  P  C  S  S  L  S  P  V  Q  T
2041  tgctcaggaaaccaatcccagacactattgccatgtagttcattgtctccagtccaaaca

 701  T  S  S  T  I  P  K  E  S  E  V  P  C  I  A  S  G  Q  L  R
2101  acaagctctacaattccaaaggagagtgaagttccctgcatagcaagtggccagcttcgc

 721  L  V  G  G  G  G  R  C  A  G  R  V  E  V  Y  H  E  G  S  W
2161  ttggtaggtggaggtggtcgctgcgctggaagagtggaggtctaccacgagggctcttgg

 741  G  T  V  C  D  D  N  W  D  M  T  D  A  N  V  V  C  K  Q  L
2221  ggcaccgtctgtgatgacaattgggatatgactgatgccaatgtggtgtgcaagcagctg

 761  D  C  G  V  A  I  N  A  T  G  S  A  Y  F  G  E  G  A  G  A
2281  gactgtggcgtggcaattaacgccactggctctgcttacttcggggaaggagcaggagct

 781  I  W  L  D  E  V  I  C  T  G  K  E  S  H  I  W  Q  C  H  S
2341  atctggctagacgaagtcatctgcactgggaaagagtctcatatttggcagtgccattca

 801  H  G  W  G  R  H  N  C  R  H  K  E  D  A  G  V  I  C  S  E
2401  catggctggggacgccataactgcaggcacaaagaagatgcaggtgttatctgctccgag

 821  F  M  S  L  R  L  T  N  E  A  H  K  E  N  C  T  G  R  L  E
2461  ttcatgtctctgaggctgaccaacgaagcccacaaagaaaactgcacaggtcgccttgaa

 841  V  F  Y  N  G  T  W  G  S  I  G  S  S  N  M  S  P  T  T  V
2521  gtgttttacaatggtacatggggcagtattggcagtagcaatatgtctccaaccactgtg

 861  G  V  V  C  R  Q  L  G  C  A  D  N  G  T  V  K  P  I  P  S
2581  ggggtggtgtgccgtcagctgggctgtgcagacaacgggactgtgaaacccataccttca

 881  D  K  T  P  S  R  P  M  W  V  D  R  V  Q  C  P  K  G  V  D
2641  gacaagacaccatccaggcccatgtgggtagatcgtgtgcagtgtccaaaaggagttgac

 901  T  L  W  Q  C  P  S  S  P  W  K  Q  R  Q  A  S  P  S  S  Q
2701  actttgtggcagtgcccctcgtcaccttggaaacagagacaggccagcccctcctcccag

 921  E  S  W  I  I  C  D  N  K  I  R  L  Q  E  G  H  T  D  C  S
2761  gagtcctggatcatctgtgacaacaaaataagactccaggaagggcatacagactgttct

 941  G  R  V  E  I  W  H  K  G  S  W  G  T  V  C  D  D  S  W  D
2821  ggacgtgtggagatctggcacaaaggttcctggggaacagtgtgtgatgactcctgggat

 961  L  N  D  A  K  V  V  C  K  Q  L  G  C  G  Q  A  V  K  A  L
2881  cttaatgatgctaaggttgtatgtaagcagttgggctgtggccaagctgtgaaggcacta

 981  K  E  A  A  F  G  P  G  T  G  P  I  W  L  N  E  I  K  C  R
2941  aaagaagcagcatttggtccaggaactgggcccatatggctcaatgaaattaagtgtaga

1001  G  N  E  S  S  L  W  D  C  P  A  K  P  W  S  H  S  D  C  G
3001  gggaatgagtcttccctgtgggattgtcctgccaaaccgtggagtcacagcgactgtggg
```

-continued

| | SEQUENCE | ID NO |
|---|---|---|
| 1021 | H K E D A S I Q C L P K M T S E S H H G | |
| 3061 | cacaaagaagatgcttccatccagtgcctccccaaaatgacttcagaatcacatcatggc | |
| 1041 | T G H P T L T A L L V C G A I L L V L L | |
| 3121 | acaggtcaccccaccctcacggcactcttggtttgtggagccattctattggtcctcctc | |
| 1061 | I V F L L W T L K R R Q I Q R L T V S S | |
| 3181 | attgtcttcctcctgtggactctgaagcgacgacagattcagcgacttacagtttcctca | |
| 1081 | R G E V L I H Q V Q Y Q E M D S K A D D | |
| 3241 | agaggagaggtcttgatacatcaagttcagtaccaagagatggattcaaaggcggatgat | |
| 1101 | L D L L K S S E N S N N S Y D F N D D G | |
| 3301 | ctggacttgctgaaatcctcggaaaattccaacaattcatatgattttaatgatgatgga | |
| 1121 | L T S L S K Y L P I S G I K K G S F R G | |
| 3361 | ctgacatctttgtctaaatatcttcctatttctggaattaaaaaggggtcattcagaggc | |
| 1141 | T L R R K M I I Y N P L R L E F K K P | |
| 3421 | acactgagaaggaaaatgataatttataatccactgaggttggagtttaagaagcct | |
| 1 | MGGHRMVLLG GGAGSPGCKRF VHLGEFVVAV SSLLSASAVT NAPGEMKKEL | ID NO: 27 |
| 51 | RLAGGENNCS GRVELKIHDK WGTVCSNGWS MNEVSVVCQQ LGCPTSIKAL | |
| 101 | GWANSSAGSG YIWMDKVSCT GNESALWDCK HDGWGKHNCT HEKDAGVTCS | |
| 151 | DGSNLEMRLV NSAGHRCLGR VEIKFQGKWG TVCDDNFSKD HASVICKQLG | |
| 201 | CGSAISFSGS AKLGAGSGPI WLDDLACNGN ESALWDCKHR GWGKHNCDHA | |
| 251 | EDVGVICLEG ADLSLRLVDG VSRCSGRLEV RFQGEWGTVC DDNWDLRDAS | |
| 301 | VVCKQLGCPT AISAIGRVNA SEGSGQIWLD NISCEGHEAT LWECKHQEWG | |
| 351 | KHYCHHREDA GVTCSDGADL ELRLVGGGSR CAGIVEVEIQ KLTGKMCSRG | |
| 401 | WTLADADVVC RQLGCGSALQ TQAKIYSKTG ATNTWLFPGS CNGNETTFWQ | |
| 451 | CKNWQWGGLS CDNFEEAKVT CSGHREPRLV GGEIPCSGRV EMKHGDVWGS | |
| 501 | VCDFDLSLEA ASVVCRELQC GTVVSILGGA HFGEGSGQIW GEEFQCSGDE | |
| 551 | SHLSLCSVAP PLDRTCTHSR DVSVVCSRYI DIRLAGGESS CEGRVELKTL | |
| 601 | GAWGPLCSSH WDMEDAHVLC QQLKCGVAQS IPEGAHFGKG AGQVWSHMFH | |
| 651 | CTGTEEHIGD CLMTALGAPT CSEGQVASVI CSGNQSQTLL PCSSLSPVQT | |
| 701 | TSSTIPKESE VPCIASGQLR LVGGGGRCAG RVEVYHEGSW GTVCDDNWDM | |
| 751 | TDANVVCKQL DCGVAINATG SAYFGEGAGA IWLDEVICTG KESHIWQCHS | |
| 801 | HGWGRHNCRH KEDAGVICSE FMSLRLTNEA HKENCTGRLE VFYNGTWGSI | |
| 851 | GSSNMSPTTV GVVCRQLGCA DNGTVKPIPS DKTPSRPMWV DRVQCPKGVD | |
| 901 | TLWQCPSSPW KQRQASPSSQ ESWIICDNKI RLQEGHTDCS GRVEIWHKGS | |
| 951 | WGTVCDDSWD LNDAKVVCKQ LGCGQAVKAL KEAAFGPGTG PIWLNEIKCR | |
| 1001 | GNESSLWDCP AKPWSHSDCG HKEDASIQCL PKMTSESHHG TGHPTLTALL | |
| 1051 | VCGAILLVLL IVFLLWTLKR RQIQRLTVSS RGEVLIHQVQ YQEMDSKADD | |
| 1101 | LDLLKSSENS NNSYDFNDDG LTSLSKYLPI SGIKKGSFRG TLRRKMIIYN | |
| 1151 | PLRLEFKKP | |

Example 8

Cloning and Characterization of MARC-145 CD163

A forward primer 5' simianCD163 (SEQ ID NO: 28) (5'-CACCGGAATGAGCAAACTCAGAATGG-3' based on human CD163) and a reverse primer HuCD163-3'Kpn (SEQ ID NO:29) (5'-TGCTCCGGTACCTAGTCCAGGTCT-TCATCAAGGTATCTTA-3') were used to amplify CD163 cDNA from MARC-145 African Green Monkey kidney cells. Total cellular RNA was prepared from MARC-145 cells using the RNeasy kit. RT-PCR parameters were the same as described in Example 4. RT-PCR products were cloned directionally into the pcDNA3.1D/V5/His/TOPO vector according to the manufacturer's instruction. Several clones containing large inserts were analyzed. Clone #25 was designated "pcDNA3.1D-MARC-CD163v2". This novel CD163 cDNA from MARC-145 cells is 1116 amino acids in length. When compared to the sequences in GenBank database, the MARC-145 CD163 amino acid sequence is 96.3% identical to human CD163 (Genbank Z22968), 84.7% identical to pig CD163 (Genbank AJ311716), and 73.9% identical to mouse CD163 (Genbank AF274883).

| SEQUENCE | | ID NO |
|---|---|---|
| atgagcaaac tcagaatggt gctacttgaa gactctggat ctgctgacgt cagaagacat | 60 | SEQ ID NO: 30 |
| tttgtcaact tgagtccctt cactattgct gtggtcttac ttctccgtgc ctgttttgtc | 120 | |
| accagttctc ttggaggaac aaccaaggag ctgaggctag tggatggtga aaacaagtgt | 180 | |
| agtgggagag tggaagtgaa aatccaggag gagtggggaa cggtgtgtaa taatggctgg | 240 | |
| agcatggaag cagtctctgt gatttgtaac cagctgggat gtccaactgc tatcaaagcc | 300 | |
| actggatggg ctaattccag tgcaggttct ggacgcattt ggatggatca tgtttcttgt | 360 | |
| cgtgggaatg agtcagctct ttgggactgc aaacatgatg gatggggaaa gcatagtaac | 420 | |
| tgtactcacc aacaagatgc tggagtgact tgctcagatg gatccgattt ggaaatgagg | 480 | |
| ctgacgaatg gagggaatat gtgttctgga agaatagaga tcaaattcca aggacagtgg | 540 | |
| ggaacagtgt gtgatgataa cttcaacatc aatcatgcat ctgtggtttg taaacaactt | 600 | |
| gaatgtggaa gtgctgtcag tttctctggt tcagctaatt ttggagaagg ctctggacca | 660 | |
| atctggtttg atgatcttat atgcaacgga aatgagtcag ctctctggaa ctgcaaacat | 720 | |
| caaggatggg gaaagcataa ctgtgatcat gctgaggatg ctggagtgat ttgctcaaag | 780 | |
| ggagcagatc tgagcctgag actggtagat ggagtcactg aatgttcagg aagattagaa | 840 | |
| gtgagattcc aaggagaatg gggacaata tgtgatgacg gctgggacag tcatgatgct | 900 | |
| gctgtggcat gcaagcaact gggatgtcca actgctatca ccgccattgg tcgagttaac | 960 | |
| gccagtgagg gatttggaca catctggctt gacagtgttt cttgccaggg acatgaacct | 1020 | |
| gcggtctggc aatgtaaaca ccatgaatgg ggaaagcatt attgcaatca caatgaagat | 1080 | |
| gctggcgtaa catgttctga tggatcagat ctggagctaa gacttagagg tggaggcagc | 1140 | |
| cgctgtgctg ggacagttga ggtggagatt cagagactgt tagggaaggt gtgtgacaga | 1200 | |
| ggctggggac tgaaagaagc tgatgtggtt tgcaggcagc tgggatgtgg atctgcactc | 1260 | |
| aaaacatcct atcaagtata ctccaaaatc caggcaacaa acatgtggct gtttctaagt | 1320 | |
| agctgtaacg gaaatgaaac ttctctttgg gactgcaaga actggcaatg gggtggactt | 1380 | |
| acctgtgatc actatgaaga agccaaaatt acctgctcag cccacaggga acccagactg | 1440 | |
| gttggaggag acattccctg ttctggacgc gttgaagtga agcatggtga cacatggggc | 1500 | |
| tccgtctgtg attcggattt ctctctggaa gctgccagcg ttctatgcag ggaattacag | 1560 | |
| tgtggcacag tcgtctctat cctgggggga gctcactttg gagagggaaa tggacagatc | 1620 | |
| tgggctgaag aattccagtg tgagggacat gagtcccatc tttcactctg cccagtagca | 1680 | |
| ccccgcccag aaggaacttg tagccacagc agggatgttg gagtagtctg ctcaagatac | 1740 | |
| acagaaattc gcttggtgaa tggcaagacc ccatgtgagg gcagagtgga gctcaaaacg | 1800 | |
| cttaatgcct ggggatccct ctgcaactct cactgggaca tagaagatgc ccacgttctt | 1860 | |
| tgccaacaac ttaaatgtgg agttgccctt tctaccccag gaggagcaca ttttggaaaa | 1920 | |
| ggaaatggtc aggtctggag gcatatgttt cactgcactg ggactgagca gcacatggga | 1980 | |
| gattgtcctg taactgctct gggtgcttca ctatgtcctt cagggcaagt ggcctctgta | 2040 | |
| atttgctcag gaaaccagtc ccaaacactg tcctcgtgca attcatcatc tctgggccca | 2100 | |

-continued

| SEQUENCE | ID NO |
|---|---|
| acaaggccta ccattccaga agaaagtgct gtggcctgca tagagagtgg tcaacttcgc 2160 | |
| ttggtaaatg gaggaggtcg ctgtgctggg agagtagaga tttatcatga gggctcctgg 2220 | |
| ggcaccatct gtgatgacag ctgggacctg agcgatgccc acgtggtgtg cagacagctg 2280 | |
| ggctgtggag aggccattaa tgccactggt tctgctcatt ttggagaagg aacagggccc 2340 | |
| atctggctgg atgagatgaa atgcaatgga aaagaatccc gcatttggca gtgccattca 2400 | |
| catggctggg ggcagcaaaa ctgcaggcac aaggaggatg caggagttat ctgctcagag 2460 | |
| ttcatgtctc tgagactgac cagtgaagcc agcagagagg cctgtgcagg gcgtctagaa 2520 | |
| gtttttttaca acggagcttg gggcagtgtt ggcaggagta acatgtctga aaccactgtg 2580 | |
| ggtgtggtgt gcaggcagct gggctgtgca gacaaaggga aaatcaaccc tgcatcttta 2640 | |
| gacaaggcca tgtccattcc catgtgggtg gacaatgttc agtgtccaaa aggacctgac 2700 | |
| acgctgtggc agtgcccatc atctccatgg gagaagagac tggccaggcc ctcggaggag 2760 | |
| acctggatca catgtgacaa caagatgaga ctacaagaag gacccacttc ctgttctgga 2820 | |
| cgtgtggaga tctggcacgg aggttcctgg gggacagtgt gtgatgactc ctgggacttg 2880 | |
| aacgatgctc aggtggtgtg tcaacaactt ggctgtggtc cagctttgaa agcattcaaa 2940 | |
| gaagcagagt ttggtcaggg gactggaccc atatggctca atgaagtgaa gtgcaaaggg 3000 | |
| aatgagtctt ccttgtggga ttgtcctgcc agacgctggg gccacagtga gtgtggacac 3060 | |
| aaggaagacg ctgcagtgaa ttgcacagat atttcaacga acaaaacccc acaaaaagcc 3120 | |
| acaacaggtc agtcatccct tattgcagtc ggaatccttg gagttgttct cttggtcatt 3180 | |
| ttcgtcgcat tattcttgac tcaaaagcga agacagagac agcggcttac agtttcctca 3240 | |
| agaggagaga acttagtcca ccaaattcaa taccgggaga tgaattcttg cctgaatgca 3300 | |
| gatgatctgg acctaatgaa ttcctcagga ggccattctg aggcacactg aaaaggaaaa 3360 | |
| tgggaattta taacccagtg agccttgaag ataccttgat gaagacctgg acta 3414 | |
| 1 M S K L R M V L L E D S G S A D V R R H<br>1 atgagcaaactcagaatggtgctacttgaagactctggatctgctgacgtcagaagacat | SEQ ID NO: 31 and 32 |
| 21 F V N L S P F T I A V V L L L R A C F V<br>61 tttgtcaacttgagtcccttcactattgctgtggtcttacttctccgtgcctgttttgtc | |
| 41 T S S L G G T T K E L R L V D G E N K C<br>121 accagttctcttggaggaacaaccaaggagctgaggctagtggatggtgaaaacaagtgt | |
| 61 S G R V E V K I Q E E W G T V C N N G W<br>181 agtgggagagtggaagtgaaaatccaggaggagtggggaacggtgtgtaataatggctgg | |
| 81 S M E A V S V I C N Q L G C P T A I K A<br>241 agcatggaagcagtctctgtgatttgtaaccagctgggatgtccaactgctatcaaagcc | |
| 101 T G W A N S S A G S G R I W M D H V S C<br>301 actggatgggctaattccagtgcaggttctggacgcatttggatggatcatgtttcttgt | |
| 121 R G N E S A L W D C K H D G W G K H S N<br>361 cgtgggaatgagtcagctctttgggactgcaaacatgatggatggggaaagcatagtaac | |
| 141 C T H Q Q D A G V T C S D G S D L E M R<br>421 tgtactcaccaacaagatgctggagtgacttgctcagatggatccgatttggaaatgagg | |
| 161 L T N G G N M C S G R I E I K F Q G Q W<br>481 ctgacgaatggagggaatatgtgttctggaagaatagagatcaaattccaaggacagtgg | |
| 181 G T V C D D N F N I N H A S V V C K Q L<br>541 ggaacagtgtgtgatgataacttcaacatcaatcatgcatctgtggtttgtaaacaactt | |
| 201 E C G S A V S F S G S A N F G E G S G P<br>601 gaatgtggaagtgctgtcagtttctctggttcagctaattttggagaaggctctggacca | |
| 221 I W F D D L I C N G N E S A L W N C K H | |

-continued

| SEQUENCE | ID NO |
|---|---|
| 661 atctggtttgatgatcttatatgcaacggaaatgagtcagctctctggaactgcaaacat | |
| 241 Q G W G K H N C D H A E D A G V I C S K | |
| 721 caaggatggggaaagcataactgtgatcatgctgaggatgctggagtgatttgctcaaag | |
| 261 G A D L S L R L V D G V T E C S G R L E | |
| 781 ggagcagatctgagcctgagactggtagatggagtcactgaatgttcaggaagattagaa | |
| 281 V R F Q G E W G T I C D D G W D S H D A | |
| 841 gtgagattccaaggagaatggggacaatatgtgatgacggctgggacagtcatgatgct | |
| 301 A V A C K Q L G C P T A I T A I G R V N | |
| 901 gctgtggcatgcaagcaactgggatgtccaactgctatcaccgccattggtcgagttaac | |
| 321 A S E G F G H I W L D S V S C Q G H E P | |
| 961 gccagtgagggatttggacacatctggcttgacagtgtttcttgccagggacatgaacct | |
| 341 A V W Q C K H H E W G K H Y C N H N E D | |
| 1021 gcggtctggcaatgtaaacaccatgaatggggaaagcattattgcaatcacaatgaagat | |
| 361 A G V T C S D G S D L E L R L R G G G S | |
| 1081 gctggcgtaacatgttctgatggatcagatctggagctaagacttagaggtggaggcagc | |
| 381 R C A G T V E V E I Q R L L G K V C D R | |
| 1141 cgctgtgctgggacagttgaggtggagattcagagactgttagggaaggtgtgtgacaga | |
| 401 G W G L K E A D V V C R Q L G C G S A L | |
| 1201 ggctggggactgaaagaagctgatgtggtttgcaggcagctgggatgtggatctgcactc | |
| 421 K T S Y Q V Y S K I Q A T N M W L F L S | |
| 1261 aaaacatcctatcaagtatactccaaaatccaggcaacaaacatgtggctgtttctaagt | |
| 441 S C N G N E T S L W D C K N W Q W G G L | |
| 1321 agctgtaacggaaatgaaacttctctttgggactgcaagaactggcaatggggtggactt | |
| 461 T C D H Y E E A K I T C S A H R E P R L | |
| 1381 acctgtgatcactatgaagaagccaaaattacctgctcagcccacagggaacccagactg | |
| 481 V G G D I P C S G R V E V K H G D T W G | |
| 1441 gttggaggagacattccctgttctggacgcgttgaagtgaagcatggtgacacatggggc | |
| 501 S V C D S D F S L E A A S V L C R E L Q | |
| 1501 tccgtctgtgattcggatttctctctggaagctgccagcgttctatgcagggaattacag | |
| 521 C G T V V S I L G G A H F G E G N G Q I | |
| 1561 tgtggcacagtcgtctctatcctgggggggagctcactttggagagggaaatggacagatc | |
| 541 W A E E F Q C E G H E S H L S L C P V A | |
| 1621 tgggctgaagaattccagtgtgagggacatgagtcccatctttcactctgcccagtagca | |
| 561 P R P E G T C S H S R D V G V V C S R Y | |
| 1681 ccccgcccagaaggaacttgtagccacagcagggatgttggagtagtctgctcaagatac | |
| 581 T E I R L V N G K T P C E G R V E L K T | |
| 1741 acagaaattcgcttggtgaatggcaagaccccatgtgagggcagagtggagctcaaaacg | |
| 601 L N A W G S L C N S H W D I E D A H V L | |
| 1801 cttaatgcctggggatccctctgcaactctcactgggacatagaagatgcccacgttctt | |
| 621 C Q Q L K C G V A L S T P G G A H F G K | |
| 1861 tgccaacaacttaaatgtggagttgccctttctaccccaggaggagcacattttggaaaa | |
| 641 G N G Q V W R H M F H C T G T E Q H M G | |
| 1921 ggaaatggtcaggtctggaggcatatgtttcactgcactgggactgagcagcacatggga | |
| 661 D C P V T A L G A S L C P S G Q V A S V | |
| 1981 gattgtcctgtaactgctctgggtgcttcactatgtccttcagggcaagtggcctctgta | |
| 681 I C S G N Q S Q T L S S C N S S S L G P | |
| 2041 atttgctcaggaaaccagtcccaaacactgtcctcgtgcaattcatcatctctgggccca | |
| 701 T R P T I P E E S A V A C I E S G Q L R | |
| 2101 acaaggcctaccattccagaagaaagtgctgtggcctgcatagagagtggtcaacttcgc | |
| 721 L V N G G G R C A G R V E I Y H E G S W | |
| 2161 ttggtaaatggaggaggtcgctgtgctgggagagtagagatttatcatgagggctcctgg | |
| 741 G T I C D D S W D L S D A H V V C R Q L | |

-continued

| SEQUENCE | ID NO |
|---|---|
| 2221 ggcaccatctgtgatgacagctgggacctgagcgatgcccacgtggtgtgcagacagctg | |
| 761 G C G E A I N A T G S A H F G E G T G P<br>2281 ggctgtggagaggccattaatgccactggttctgctcattttggagaaggaacagggccc | |
| 781 I W L D E M K C N G K E S R I W Q C H S<br>2341 atctggctggatgagatgaaatgcaatggaaaagaatcccgcatttggcagtgccattca | |
| 801 H G W G Q Q N C R H K E D A G V I C S E<br>2401 catggctgggggcagcaaaactgcaggcacaaggaggatgcaggagttatctgctcagag | |
| 821 F M S L R L T S E A S R E A C A G R L E<br>2461 ttcatgtctctgagactgaccagtgaagccagcagagaggcctgtgcagggcgtctagaa | |
| 841 V F Y N G A W G S V G R S N M S E T T V<br>2521 gtttttttacaacggagcttggggcagtgttggcaggagtaacatgtctgaaaccactgtg | |
| 861 G V V C R Q L G C A D K G K I N P A S L<br>2581 ggtgtggtgtgcaggcagctgggctgtgcagacaaagggaaaatcaaccctgcatcttta | |
| 881 D K A M S I P M W V D N V Q C P K G P D<br>2641 gacaaggccatgtccattcccatgtgggtggacaatgttcagtgtccaaaaggacctgac | |
| 901 T L W Q C P S S P W E K R L A R P S E E<br>2701 acgctgtggcagtgcccatcatctccatgggagaagagactggccaggccctcggaggag | |
| 921 T W I T C D N K M R L Q E G P T S C S G<br>2761 acctggatcacatgtgacaacaagatgagactacaagaaggacccacttcctgttctgga | |
| 941 R V E I W H G G S W G T V C D D S W D L<br>2821 cgtgtggagatctggcacggaggttcctggggggacagtgtgtgatgactcctgggacttg | |
| 961 N D A Q V V C Q Q L G C G P A L K A F K<br>2881 aacgatgctcaggtggtgtgtcaacaacttggctgtggtccagctttgaaagcattcaaa | |
| 981 E A E F G Q G T G P I W L N E V K C K G<br>2941 gaagcagagtttggtcaggggactggacccatatggctcaatgaagtgaagtgcaaaggg | |
| 1001 N E S S L W D C P A R R W G H S E C G H<br>3001 aatgagtcttccttgtgggattgtcctgccagacgctggggccacagtgagtgtggacac | |
| 1021 K E D A A V N C T D I S T N K T P Q K A<br>3061 aaggaagacgctgcagtgaattgcacagatatttcaacgaacaaaaccccacaaaaagcc | |
| 1041 T T G Q S S L I A V G I L G V V L L V I<br>3121 acaacaggtcagtcatcccttattgcagtcggaatccttggagttgttctcttggtcatt | |
| 1061 F V A L F L T Q K R R Q R Q R L T V S S<br>3181 ttcgtcgcattattcttgactcaaaagcgaagacagagacagcggcttacagtttcctca | |
| 1081 R G E N L V H Q I Q Y R E M N S C L N A<br>3241 agaggagagaacttagtccaccaaattcaataccgggagatgaattcttgcctgaatgca | |
| 1101 D D L D L M N S S G G H S E A H<br>3301 gatgatctggacctaatgaattcctcaggaggccattctgaggcacac | |
| 1 MSKLRMVLLE DSGSADVRRH FVNLSPFTIA VVLLLRACFV TSSLGGTTKE | SEQ ID NO: 32 |
| 51 LRLVDGENKC SGRVEVKIQE EWGTVCNNGW SMEAVSVICN QLGCPTAIKA | |
| 101 TGWANSSAGS GRIWMDHVSC RGNESALWDC KHDGWGKHSN CTHQQDAGVT | |
| 151 CSDGSDLEMR LTNGGNMCSG RIEIKFQGQW GTVCDDNFNI NHASVVCKQL | |
| 201 ECGSAVSFSG SANFGEGSGP IWFDDLICNG NESALWNCKH QGWGKHNCDH | |
| 251 AEDAGVICSK GADLSLRLVD GVTECSGRLE VRFQGEWGTI CDDGWDSHDA | |
| 301 AVACKQLGCP TAITAIGRVN ASEGFGHIWL DSVSCQGHEP AVWQCKHHEW | |
| 351 GKHYCNHNED AGVTCSDGSD LELRLRGGGS RCAGTVEVEI QRLLGKVCDR | |
| 401 GWGLKEADVV CRQLGCGSAL KTSYQVYSKI QATNMWLFLS SCNGNETSLW | |
| 451 DCKNWQWGGL TCDHYEEAKI TCSAHREPRL VGGDIPCSGR VEVKHGDTWG | |
| 501 SVCDSDFSLE AASVLCRELQ CGTVVSILGG AHFGEGNGQI WAEEFQCEGH | |

-continued

| SEQUENCE | ID NO |
|---|---|
| 551 ESHLSLCPVA PRPEGTCSHS RDVGVVCSRY TEIRLVNGKT PCEGRVELKT | |
| 601 LNAWGSLCNS HWDIEDAHVL CQQLKCGVAL STPGGAHFGK GNGQVWRHMF | |
| 651 HCTGTEQHMG DCPVTALGAS LCPSGQVASV ICSGNQSQTL SSCNSSSLGP | |
| 701 TRPTIPEESA VACIESGQLR LVNGGGRCAG RVEIYHEGSW GTICDDSWDL | |
| 751 SDAHVVCRQL GCGEAINATG SAHFGEGTGP IWLDEMKCNG KESRIWQCHS | |
| 801 HGWGQQNCRH KEDAGVICSE FMSLRLTSEA SREACAGRLE VFYNGAWGSV | |
| 851 GRSNMSETTV GVVCRQLGCA DKGKINPASL DKAMSIPMWV DNVQCPKGPD | |
| 901 TLWQCPSSPW EKRLARPSEE TWITCDNKMR LQEGPTSCSG RVEIWHGGSW | |
| 951 GTVCDDSWDL NDAQVVCQQL GCGPALKAFK EAEFGQGTGP IWLNEVKCKG | |
| 1001 NESSLWDCPA RRWGHSECGH KEDAAVNCTD ISTNKTPQKA TTGQSSLIAV | |
| 1051 GILGVVLLVI FVALFLTQKR RQRQRLTVSS RGENLVHQIQ YREMNSCLNA | |
| 1101 DDLDLMNSSG GHSEAH | |

Example 9

Cloning and Characterization of Simian CD163 from Vero Cells

Figure 17:
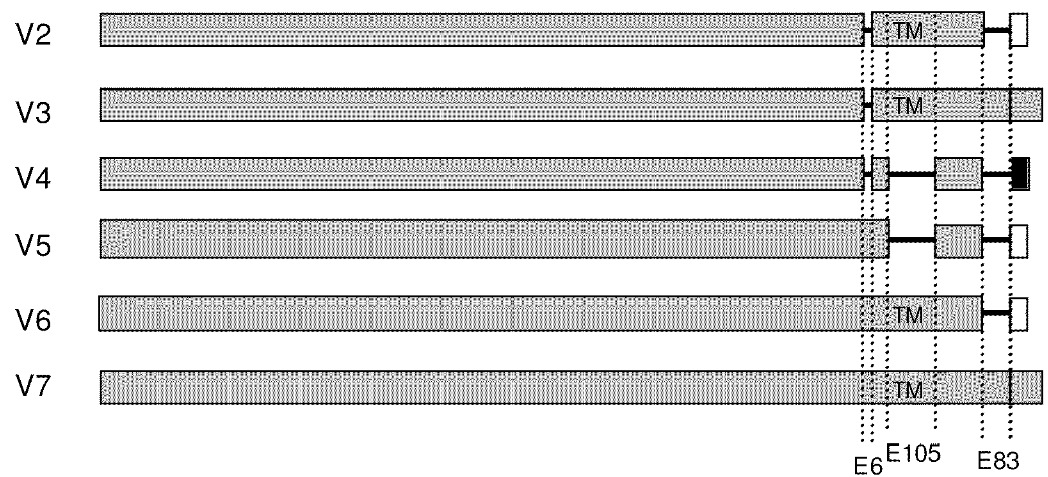

A forward primer 5' simianCD163 (SEQ ID NO: 28) (5'-CACCGGAATGAGCAAACTCAGAATGG-3' based on human CD163) and a reverse primer HuCD163-3'Kpn (SEQ ID NO:29) (5'-TGCTCCGGTACCTAGTCCAGGTCT-TCATCAAGGTATCTTA-3') were used to amplify CD163 cDNA from Vero cells. Total cellular RNA was prepared from Vero cells using the RNeasy kit. RT-PCR parameters were the same as described in Example 4. RT-PCR products were cloned directionally into the pcDNA3.1DN5/His/TOPO vector according to the manufacturer's instruction. Eight clones containing large inserts were sequenced, and six discreet splicing patterns were found. These patterns are depicted graphically in FIG. 17.

The six splicing variants differ in the presence or absence of three exons, designated E6, E105, and E83. Omissions of E6 or E105 do not change the reading frame, whereas omission of E83 does. Patterns similar to v2 and/or v3 were also seen in porcine, murine, human, and MARC-145 monkey cells. Patterns v4 and v5 lack the 105-nucleotide exon that encodes the hydrophobic transmembrane region. These cDNAs were unable to render BHK cells permissive to PRRSV infection in a transient transfection assay, probably because the CD163 is secreted rather than remaining membrane bound. Although CD163 molecules lacking a transmembrane region appear to be non-functional as cellular permissivity factors, it is possible that they may have utility either in direct virus neutralization (similar to neutralizing antibodies), or as an immunogen for the induction of anti-CD163 antibodies which would block viral infection in the host animal.

The longest splice variant, v7, contains all three of the exons E6, E105, and E83. This novel CD163 cDNA from Vero cells encodes a polypeptide that is 1153 amino acids in length. When compared to the sequences in Genbank database, the Vero CD163v7 amino acid sequence is 95.4% identical to human CD163 (Genbank Z22968), 83.7% identical to pig CD163 (Genbank AJ311716), and 72.1% identical to mouse CD163 (Genbank AF274883). The nucleotide and amino acid sequences of the six splice variants found in Vero cells are provided below (SEQ ID NOS:33-44).

| SEQUENCE | ID NO |
|---|---|
| 1 M S K L R M V L L E D S G S A D V R R H<br>1 ATGAGCAAACTCAGAATGGTGCTACTTGAAGACTCTGGATCTGCTGACGTCAGAAGACAT | SEQ ID NO: 33 and 34 |
| 21 F V N L S P F T I A V V L L L R A C F V<br>61 TTTGTCAACTTGAGTCCCTTCACTATTGCTGTGGTCTTACTTCTCCGTGCCTGTTTTGTC | |
| 41 T S S L G G T T K E L R L V D G E N K C<br>121 ACCAGTTCTCTTGGAGGAACAACCAAGGAGCTGAGGCTAGTGGATGGTGAAAACAAGTGT | |
| 61 S G R V E V K I Q E E W G T V C N N G W<br>181 AGTGGGAGAGTGGAAGTGAAAATCCAGGAGGAGTGGGGAACGGTGTGTAATAATGGCTGG | |
| 81 S M E A V S V I C N Q L G C P T A I K A<br>241 AGCATGGAAGCAGTCTCTGTGATTTGTAACCAGCTGGGATGTCCAACTGCTATCAAAGCC | |
| 101 T G W A N S S A G S G R I W M D H V S C<br>301 ACTGGATGGGCTAATTCCAGTGCAGGTTCTGGACGCATTTGGATGGATCATGTTTCTTGT | |
| 121 R G N E S A L W D C K H D G W G K H S N | |

-continued

| SEQUENCE | ID NO |
|---|---|
| 361 CGTGGGAATGAGTCAGCTCTTTGGGACTGCAAACATGATGGATGGGGAAAGCATAGTAAC | |
| 141 C T H Q Q D A G V T C S D G S D L E M R | |
| 421 TGTACTCACCAACAAGATGCTGGAGTAACTTGCTCAGATGGATCCGATTTGGAAATGAGG | |
| 161 L T N G G N M C S G R I E I K F Q G Q W | |
| 481 CTGACGAATGGAGGGAATATGTGTTCTGGAAGAATAGAGATCAAATTCCAAGGACAGTGG | |
| 181 G T V C D D N F N I N H A S V V C K Q L | |
| 541 GGAACAGTGTGTGATGATAACTTCAACATCAATCATGCATCTGTGGTTTGTAAACAACTT | |
| 201 E C G S A V S F S G S A N F G E G S G P | |
| 601 GAATGTGGAAGTGCTGTCAGTTTCTCTGGTTCAGCTAATTTTGGAGAAGGCTCTGGACCA | |
| 221 I W F D D L I C N G N E S A L W N C K H | |
| 661 ATCTGGTTTGATGATCTTATATGCAACGGAAATGAGTCAGCTCTCTGGAACTGCAAACAT | |
| 241 Q G W G K H N C D H A E D A G V I C S K | |
| 721 CAAGGATGGGGAAAGCATAACTGTGATCATGCTGAGGATGCTGGAGTGATTTGCTCAAAG | |
| 261 G A D L S L R L V D G V T E C S G R L E | |
| 781 GGAGCAGATCTGAGCCTGAGACTGGTAGATGGAGTCACTGAATGTTCAGGAAGATTAGAA | |
| 281 V R F Q G E W G T I C D D G W D S H D A | |
| 841 GTGAGATTCCAAGGAGAATGGGGGACAATATGTGATGACGGCTGGGACAGTCATGATGCT | |
| 301 A V A C K Q L G C P T A I T A I G R V N | |
| 901 GCTGTGGCATGCAAGCAACTGGGATGTCCAACTGCTATCACCGCCATTGGTCGAGTTAAC | |
| 321 A S E G F G H I W L D S V S C Q G H E P | |
| 961 GCCAGTGAGGGATTTGGACACATCTGGCTTGACAGTGTTTCTTGCCAGGGACATGAACCT | |
| 341 A V W Q C K H H E W G K H Y C N H N E D | |
| 1021 GCGGTCTGGCAATGTAAACACCATGAATGGGGAAAGCATTATTGCAATCACAATGAAGAT | |
| 361 A G V T C S D G S G L E L R L R G G G S | |
| 1081 GCTGGCGTAACATGTTCTGATGGATCAGGTCTGGAGCTAAGACTTAGAGGTGGAGGCAGC | |
| 381 R C A G T V E V E I Q R L L G K V C D R | |
| 1141 CGCTGTGCTGGGACAGTTGAGGTGGAGATTCAGAGACTGTTAGGGAAGGTGTGTGACAGA | |
| 401 G W G L K E A D V V C R Q L G C G S A L | |
| 1201 GGCTGGGGACTGAAAGAAGCTGATGTGGTTTGCAGGCAGCTGGGATGTGGATCTGCACTC | |
| 421 K T S Y Q V Y S K I Q A T N M W L F L S | |
| 1261 AAAACATCCTATCAAGTATACTCCAAAATCCAGGCAACAAACATGTGGCTGTTTCTAAGT | |
| 441 S C N G N E T S L W D C K N W Q W G G L | |
| 1321 AGCTGTAACGGAAATGAAACTTCTCTTTGGGACTGCAAGAACTGGCAATGGGGTGGACTT | |
| 461 T C D H Y E E A K I T C S A H R E P R L | |
| 1381 ACCTGTGATCACTATGAAGAAGCCAAAATTACCTGCTCAGCCCACAGGGAACCCAGACTG | |
| 481 V G G D I P C S G R V E V K H G D T W G | |
| 1441 GTTGGAGGAGACATTCCCTGTTCTGGACGCGTTGAAGTGAAGCATGGTGACACATGGGGC | |
| 501 S V C D S D F S L E A A S V L C R E L Q | |
| 1501 TCCGTCTGTGATTCGGATTTCTCTCTGGAAGCTGCCAGCGTTCTATGCAGGGAATTACAG | |
| 521 C G T V V S I L G G A H F G E G N G Q I | |
| 1561 TGTGGCACAGTCGTCTCTATCCTGGGGGGAGCTCACTTTGGAGAGGGAAATGGACAGATC | |
| 541 W T E E F Q C E G H E S H L S L C P V A | |
| 1621 TGGACTGAAGAATTCCAGTGTGAGGGACATGAGTCCCATCTTTCACTCTGCCCAGTAGCA | |
| 561 P R P E G T C S H S R D V G V V C S R Y | |
| 1681 CCCCGCCCAGAAGGAACTTGTAGCCACAGCAGGGATGTTGGAGTAGTCTGCTCAAGATAC | |
| 581 T E I R L V N G K T P C E G R V E L K T | |
| 1741 ACAGAAATTCGCTTGGTGAATGGCAAGACCCCATGTGAGGGCAGAGTGGAGCTCAAAACG | |
| 601 L N A W G S L C N S H W D I E D A H V L | |
| 1801 CTTAATGCCTGGGGATCCCTCTGCAACTCTCACTGGGACATAGAAGATGCCCACGTTCTT | |
| 621 C Q Q L K C G V A L S T P G G A H F G K | |
| 1861 TGCCAACAACTTAAATGTGGAGTTGCCCTTTCTACCCCAGGAGGAGCACATTTTGGAAAA | |
| 641 G N G Q V W R H M F H C T G T E Q H M G | |

-continued

| SEQUENCE | ID NO |
|---|---|
| 1921 GGAAATGGTCAGGTCTGGAGGCATATGTTTCACTGCACTGGGACTGAGCAGCACATGGGA | |
| 661 D C P V T A L G A S L C P S G Q V A S V<br>1981 GATTGTCCTGTAACTGCTCTGGGTGCTTCACTATGTCCTTCAGGGCAAGTGGCCTCTGTA | |
| 681 I C S G N Q S Q T L S S R N S S S L G P<br>2041 ATTTGCTCAGGAAACCAGTCCCAAACACTGTCCTCGCGCAATTCATCATCTCTGGGCCCA | |
| 701 T R P T I P E E S A V A C I E S G Q L R<br>2101 ACAAGGCCTACCATTCCAGAAGAAAGTGCTGTGGCCTGCATAGAGAGTGGTCAACTTCGC | |
| 721 L V N G G G R C A G R V E I Y H E G S W<br>2161 TTGGTAAATGGAGGAGGTCGCTGTGCTGGGAGAGTAGAGATTTATCATGAGGGCTCCTGG | |
| 741 G T I C D D S W D L S D A H V V C R Q L<br>2221 GGCACCATCTGTGATGACAGCTGGGACCTGAGCGATGCCCACGTGGTGTGCAGACAGCTG | |
| 761 G C G E A I N A T G S A H F G E G T G P<br>2281 GGCTGTGGAGAGGCCATTAATGCCACTGGTTCTGCTCATTTTGGAGAAGGAACAGGGCCC | |
| 781 I W L D E M K C N G K E S R I W Q C H S<br>2341 ATCTGGCTGGATGAGATGAAATGCAATGGAAAAGAATCCCGCATTTGGCAGTGCCATTCA | |
| 801 H G W G Q Q N C R H K E D A G V I C S E<br>2401 CATGGCTGGGGGCAGCAAAACTGCAGGCACAAGGAGGATGCAGGAGTTATCTGCTCAGAG | |
| 821 F M S L R L T S E A S R E A C A G R L E<br>2461 TTCATGTCTCTGAGACTGACCAGTGAAGCCAGCAGAGAGGCCTGTGCAGGGCGTCTAGAA | |
| 841 V F Y N G A W G S V G R S N M S E T T V<br>2521 GTTTTTTACAACGGAGCTTGGGGCAGTGTTGGCAGGAGTAACATGTCTGAAACCACTGTG | |
| 861 G V V C R Q L G C A D K G K I N S A S L<br>2581 GGTGTAGTGTGCAGGCAGCTGGGCTGTGCAGACAAAGGGAAAATCAACTCTGCATCTTTA | |
| 881 D K A M S I P M W V D N V Q C P K G P D<br>2641 GACAAGGCCATGTCCATTCCCATGTGGGTGGACAATGTTCAGTGTCCAAAAGGACCTGAC | |
| 901 T L W Q C P S S P W E K R L A R P S E E<br>2701 ACGCTGTGGCAGTGCCCATCATCTCCATGGGAGAAGAGACTGGCCAGGCCCTCGGAGGAG | |
| 921 T W I T C D N K M R L Q E G P T S C S G<br>2761 ACCTGGATCACATGTGACAACAAGATGAGACTACAAGAAGGACCCACTTCCTGTTCTGGA | |
| 941 R V E I W H G G S W G T V C D D S W D L<br>2821 CGTGTGGAGATCTGGCACGGAGGTTCCTGGGGGACAGTGTGTGATGACTCCTGGGACTTG | |
| 961 N D A Q V V C Q Q L G C G P A L K A F K<br>2881 AACGATGCTCAGGTGGTGTGTCAACAACTTGGCTGTGGTCCAGCTTTGAAAGCATTCAAA | |
| 981 E A E F G Q G T G P I W L N E V K C E G<br>2941 GAAGCAGAGTTTGGTCAGGGGACTGGACCCATATGGCTCAATGAAGTGAAGTGCGAAGGG | |
| 1001 N E S S L W D C P A R R W G H S E C G H<br>3001 AATGAGTCTTCCTTGTGGGATTGTCCTGCCAGACGCTGGGGCCACAGTGAGTGTGGACAC | |
| 1021 K E D A A V N C T D I S T R K T P Q K A<br>3061 AAGGAAGACGCTGCAGTGAATTGCACAGATATTTCAACGCGCAAAACCCCACAAAAAGCC | |
| 1041 T T G Q S S L I A V G I L G V V L L A I<br>3121 ACAACAGGTCAGTCATCCCTTATTGCAGTCGGAATCCTTGGAGTTGTTCTCTTGGCCATT | |
| 1061 F V A L F L T Q K R R Q R Q R L T V S S<br>3181 TTCGTCGCATTATTCTTGACTCAAAAGCGAAGACAGAGACAGCGGCTTACAGTTTCCTCA | |
| 1081 R G E N L V H Q I Q Y R E M N S C L N A<br>3241 AGAGGAGAGAACTTAGTCCACCAAATTCAATACCGGGAGATGAATTCTTGCCTGAATGCA | |
| 1101 D D L D L M N S S G G H S E A H<br>3301 GATGATCTGGACCTAATGAATTCCTCAGGAGGCCATTCTGAGGCACAC | |
| 1 MSKLRMVLLE DSGSADVRRH FVNLSPFTIA VVLLLRACFV TSSLGGTTKE LRLVDGENKC | SEQ ID NO: 34 |
| 61 SGRVEVKIQE EWGTVCNNGW SMEAVSVICN QLGCPTAIKA TGWANSSAGS GRIWMDHVSC | |
| 121 RGNESALWDC KHDGWGKHSN CTHQQDAGVT CSDGSDLEMR LTNGGNMCSG RIEIKFQGQW | |
| 181 GTVCDDNFNI NHASVVCKQL ECGSAVSFSG SANFGEGSGP IWFDDLICNG NESALWNCKH | |

-continued

| SEQUENCE | ID NO |
|---|---|
| 241 QGWGKHNCDH AEDAGVICSK GADLSLRLVD GVTECSGRLE VRFQGEWGTI CDDGWDSHDA | |
| 301 AVACKQLGCP TAITAIGRVN ASEGFGHIWL DSVSCQGHEP AVWQCKHHEW GKHYCNHNED | |
| 361 AGVTCSDGSG LELRLRGGGS RCAGTVEVEI QRLLGKVCDR GWGLKEADVV CRQLGCGSAL | |
| 421 KTSYQVYSKI QATNMWLFLS SCNGNETSLW DCKNWQWGGL TCDHYEEAKI TCSAHREPRL | |
| 481 VGGDIPCSGR VEVKHGDTWG SVCDSDFSLE AASVLCRELQ CGTVVSILGG AHFGEGNGQI | |
| 541 WTEEFQCEGH ESHLSLCPVA PRPEGTCSHS RDVGVVCSRY TEIRLVNGKT PCEGRVELKT | |
| 601 LNAWGSLCNS HWDIEDAHVL CQQLKCGVAL STPGGAHFGK GNGQVWRHMF HCTGTEQHMG | |
| 661 DCPVTALGAS LCPSGQVASV ICSGNQSQTL SSRNSSSLGP TRPTIPEESA VACIESGQLR | |
| 721 LVNGGGRCAG RVEIYHEGSW GTICDDSWDL SDAHVVCRQL GCGEAINATG SAHFGEGTGP | |
| 781 IWLDEMKCNG KESRIWQCHS HGWGQQNCRH KEDAGVICSE FMSLRLTSEA SREACAGRLE | |
| 841 VFYNGAWGSV GRSNMSETTV GVVCRQLGCA DKGKINSASL DKAMSIPMWV DNVQCPKGPD | |
| 901 TLWQCPSSPW EKRLARPSEE TWITCDNKMR LQEGPTSCSG RVEIWHGGSW GTVCDDSWDL | |
| 961 NDAQVVCQQL GCGPALKAFK EAEFGQGTGP IWLNEVKCEG NESSLWDCPA RRWGHSECGH | |
| 1021 KEDAAVNCTD ISTRKTPQKA TTGQSSLIAV GILGVVLLAI FVALFLTQKR RQRQRLTVSS | |
| 1081 RGENLVHQIQ YREMNSCLNA DDLDLMNSSG GHSEAH | |
| 1 M S K L R M V L L E D S G S A D V R R H<br>1 ATGAGCAAACTCAGAATGGTGCTACTTGAAGACTCTGGATCTGCTGACGTCAGAAGACAT | SEQ ID NO: 35 and 36 |
| 21 F V N L S P F T I A V V L L L R A C F V<br>61 TTTGTCAACTTGAGTCCCTTCACTATTGCTGTGGTCTTACTTCTCCGTGCCTGTTTTGTC | |
| 41 T S S L G G T T K E L R L V D G E N K C<br>121 ACCAGTTCTCTTGGAGGAACAACCAAGGAGCTGAGGCTAGTGGATGGTGAAAACAAGTGT | |
| 61 S G R V E V K I Q E E W G T V C N N G W<br>181 AGTGGGAGAGTGGAAGTGAAAATCCAGGAGGAGTGGGGAACGGTGTGTAATAATGGCTGG | |
| 81 S M E A V S V I C N Q L G C P T A I K A<br>241 AGCATGGAAGCAGTCTCTGTGATTTGTAACCAGCTGGGATGTCCAACTGCTATCAAAGCC | |
| 101 T G W A N S S A G S G R I W M D H V S C<br>301 ACTGGATGGGCTAATTCCAGTGCAGGTTCTGGACGCATTTGGATGGATCATGTTTCTTGT | |
| 121 R G N E S A L W D C K H D G W G K H S N<br>361 CGTGGGAATGAGTCAGCTCTTTGGGACTGCAAACATGATGGATGGGGAAAGCATAGTAAC | |
| 141 C T H Q Q D A G V T C S D G S D L E M R<br>421 TGTACTCACCAACAAGATGCTGGAGTAACTTGCTCAGATGGATCCGATTTGGAAATGAGG | |
| 161 L T N G G N M C S G R I E I K F Q G Q W<br>481 CTGACGAATGGAGGGAATATGTGTTCTGGAAGAATAGAGATCAAATTCCAAGGACAGTGG | |
| 181 G T V C D D N F N I N H A S V V C K Q L<br>541 GGAACAGTGTGTGATGATAACTTCAACATCAATCATGCATCTGTGGTTTGTAAACAACTT | |
| 201 E C G S A V S F S G S A N F G E G S G P<br>601 GAATGTGGAAGTGCTGTCAGTTTCTCTGGTTCAGCTAATTTTGGAGAAGGCTCTGGACCA | |
| 221 I W F D D L I C N G N E S A L W N C K H<br>661 ATCTGGTTTGATGATCTTATATGCAACGGAAATGAGTCAGCTCTCTGGAACTGCAAACAT | |
| 241 Q G W G K H N C D H A E D A G V I C S K<br>721 CAAGGATGGGGAAAGCATAACTGTGATCATGCTGAGGATGCTGGAGTGATTTGCTCAAAG | |
| 261 G A D L S L R L V D G V T E C S G R L E<br>781 GGAGCAGATCTGAGCCTGAGACTGGTAGATGGAGTCACTGAATGTTCAGGAAGATTAGAA | |
| 281 V R F Q G E W G T I C D D G W D S H D A<br>841 GTGAGATTCCAAGGAGAATGGGGGACAATATGTGATGACGGCTGGGACAGTCATGATGCT | |
| 301 A V A C K Q L G C P T A I T A I G R V N<br>901 GCTGTGGCATGCAAGCAACTGGGATGTCCAACTGCTATCACCGCCATTGGTCGAGTTAAC | |

-continued

| SEQUENCE | ID NO |
|---|---|

321 A S E G F G H I W L D S V S C Q G H E P
961 GCCAGTGAGGGATTTGGACACATCTGGCTTGACAGTGTTTCTTGCCAGGGACATGAACCT

341 A V W Q C K H H E W G K H Y C N H N E D
1021 GCGGTCTGGCAATGTAAACACCATGAATGGGGAAAGCATTATTGCAATCACAATGAAGAT

361 A G V T C S D G S D L E L R L R G G G S
1081 GCTGGCGTAACATGTTCTGATGGATCAGATCTGGAGCTAAGACTTAGAGGTGGAGGCAGC

381 R C A G T V E V E I Q R L L G K V C D R
1141 CGCTGTGCTGGgACAGTTGAGGTgGAGATTCAGAGACTGTTAGGGAAGGTGTGTGACAGA

401 G W G L K E A D V V C R Q L G C G S A L
1201 GGCTGGGGACTGAAAGAAGCTGATGTGGTTTGCAGGCAGCTGGGATGTGGATCTGCACTC

421 K T S Y Q V Y S K I Q A T N M W L F L S
1261 AAAACATCCTATCAAGTATACTCCAAAATCCAGGCAACAAACATGTGGCTGTTTCTAAGT

441 S C N G N E T S L W D C K N W Q W G G L
1321 AGCTGTAACGGAAATGAAACTTCTCTTTGGGACTGCAAGAACTGGCAATGGGGTGGACTT

461 T C D H Y E E A K I T C S A H R E P R L
1381 ACCTGTGATCACTATGAAGAAGCCAAAATTACCTGCTCAGCCCACAGGGAACCCAGACTG

481 V G G D I P C S G R V E V K H G D T W G
1441 GTTGGAGGAGACATTCCCTGTTCTGGACGCGTTGAAGTGAAGCATGGTGACACATGGGGC

501 S V C D S D F S L E A A S V L C R E L Q
1501 TCCGTCTGTGATTCGGATTTCTCTCTGGAAGCTGCCAGCGTTCTATGCAGGGAATTACAG

521 C G T V V S I L G G A H F G E G N G Q I
1561 TGTGGCACAGTCGTCTCTATCCTGGGGGGAGCTCACTTTGGAGAGGGAAATGGACAGATC

541 W T E E F Q C E G H E S H L S L C P V A
1621 TGGACTGAAGAATTCCAGTGTGAGGGACATGAGTCCCATCTTTCACTCTGCCCAGTAGCA

561 P R P E G T C S H S R D V G V V C S R Y
1681 CCCCGCCCAGAAGGAACTTGTAGCCACAGCAGGGATGTTGGAGTAGTCTGCTCAAGATAC

581 T E I R L V N G K T P C E G R V E L K T
1741 ACAGAAATTCGCTTGGTGAATGGCAAGACCCCATGTGAGGGCAGAGTGGAGCTCAAAACG

601 L N A W G S L C N S H W D I E D A H V L
1801 CTTAATGCCTGGGGATCCCTCTGCAACTCTCACTGGGACATAGAAGATGCCCACGTTCTT

621 C Q Q L K C G V A L S T P G G A H F G K
1861 TGCCAACAACTTAAATGTGGAGTTGCCCTTTCTACCCCAGGAGGAGCACATTTTGGAAAA

641 G N G Q V W R H M F H C T G T E Q H M G
1921 GGAAATGGTCAGGTCTGGAGGCATATGTTTCACTGCACTGGGACTGAGCAGCACATGGGA

661 D C P V T A L G A S L C P S G Q V A S V
1981 GATTGTCCTGTAACTGCTCTGGGTGCTTCACTATGTCCTTCAGGGCAAGTGGCCTCTGTA

681 I C S G N Q S Q T L S S C N S S S L G P
2041 ATTTGCTCAGGAAACCAGTCCCAAACACTGTCCTCGTGCAATTCATCATCTCTGGGCCCA

701 T R P T I P E E S A V A C I E S G Q L R
2101 ACAAGGCCTACCATTCCAGAAGAAAGTGCTGTGGCCTGCATAGAGAGTGGTCAACTTCGC

721 L V N G G G R C A G R V E I Y H E G S W
2161 TTGGTAAATGGAGGAGGTCGCTGTGCTGGGAGAGTAGAGATTTATCATGAGGGCTCCTGG

741 G T I C D D S W D L S D A H V V C R Q L
2221 GGCACCATCTGTGATGACAGCTGGGACCTGAGCGATGCCCACGTGGTGTGCAGACAGCTG

761 G C G E A I N A T G S A H F G E G T G P
2281 GGCTGTGGAGAGGCCATTAATGCCACTGGTTCTGCTCATTTTGGAGAAGGAACAGGGCCC

781 I W L D E M K C N G K E S R I W Q C H S
2341 ATCTGGCTGGATGAGATGAAATGCAATGGAAAAGAATCCCGCATTTGGCAGTGCCATTCA

801 H G W G Q Q N C R H K E D A G V I C S E
2401 CATGGCTGGGGGCAGCAAAACTGCAGGCACAAGGAGGATGCAGGAGTTATCTGCTCAGAG

821 F M S L R L T S E A S R E A C A G R L E
2461 TTCATGTCTCTGAGACTGACCAGTGAAGCCAGCAGAGAGGCCTGTGCAGGGCGTCTAGAA

-continued

| SEQUENCE | ID NO |
|---|---|
| 841 V F Y N G A W G S V G R S N M S E T T V<br>2521 GTTTTTTACAACGGAGCTTGGGGCAGTGTTGGCAGGAGTAACATGTCTGAAACCACTGTG | |
| 861 G V V C R Q L G C A D K G K I N S A S L<br>2581 GGTGTAGTGTGCAGGCAGCTGGGCTGTGCAGACAAAGGGAAAATCAACTCTGCATCTTTA | |
| 881 D K A M S I P M W V D N V Q C P K G P D<br>2641 GACAAGGCCATGTCCATTCCCATGTGGGTGGACAATGTTCAGTGTCCAAAAGGACCTGAC | |
| 901 T L W Q C P S S P W E K R L A R P S E E<br>2701 ACGCTGTGGCAGTGCCCATCATCTCCATGGGAGAAGAGACTGGCCAGGCCCTCGGAGGAG | |
| 921 T W I T C D N K M R L Q E G P T S C S G<br>2761 ACCTGGATCACATGTGACAACAAGATGAGACTACAAGAAGGACCCACTTCCTGTTCTGGA | |
| 941 R V E I W H G G S W G T V C D D S W D L<br>2821 CGTGTGGAGATCTGGCACGGAGGTTCCTGGGGGACAGTGTGTGATGACTCCTGGGACTTG | |
| 961 N D A Q V V C Q Q L G C G P A L K A F K<br>2881 AACGATGCTCAGGTGGTGTGTCAACAACTTGGCTGTGGTCCAGCTTTGAAAGCATTCAAA | |
| 981 E A E F G Q G T G P I W L N E V K C K G<br>2941 GAAGCAGAGTTTGGTCAGGGGACTGGACCCATATGGCTCAATGAAGTGAAGTGCAAAGGG | |
| 1001 N E S S L W D C P A R R W G H S E C G H<br>3001 AATGAGTCTTCCTTGTGGGATTGTCCTGCCAGACGCTGGGGCCACAGTGAGTGTGGACAC | |
| 1021 K E D A A V N C T D I S T R K T P Q K A<br>3061 AAGGAAGACGCTGCAGTGAATTGCACAGATATTTCAACGCGCAAAACCCCACAAAAAGCC | |
| 1041 T T G Q S S L I A V G I L G V V L L A I<br>3121 ACAACAGGTCAGTCATCCCTTATTGCAGTCGGAATCCTTGGAGTTGTTCTCTTGGCCATT | |
| 1061 F V A L F L T Q K R R Q R Q R L T V S S<br>3181 TTCGTCGCATTATTCTTGACTCAAAAGCGAAGACAGAGACAGCGGCTTACAGTTTCCTCA | |
| 1081 R G E N L V H Q I Q Y R E M N S C L N A<br>3241 AGAGGAGAGAACTTAGTCCACCAAATTCAATACCGGGAGATGAATTCTTGCCTGAATGCA | |
| 1101 D D L D L M N S S E N S N E S A D F N A<br>3301 GATGATCTGGACCTAATGAATTCCTCAGAAAATTCCAATGAGTCAGCTGATTTCAATGCT | |
| 1121 A E L I S V S K F L P I S G M E K E A I<br>3361 GCTGAACTAATTTCTGTGTCTAAATTTCTTCCTATTTCTGGAATGGAAAAGGAGGCCATT | |
| 1141 L R H T E K E N G N L<br>3421 CTGAGGCACACTGAAAAGGAAAATGGGAATTTA | |
| 1 MSKLRMVLLE DSGSADVRRH FVNLSPFTIA VVLLLRACFV TSSLGGTTKE LRLVDGENKC | SEQ ID NO: 36 |
| 61 SGRVEVKIQE EWGTVCNNGW SMEAVSVICN QLGCPTAIKA TGWANSSAGS GRIWMDHVSC | |
| 121 RGNESALWDC KHDGWGKHSN CTHQQDAGVT CSDGSDLEMR LTNGGNMCSG RIEIKFQGQW | |
| 181 GTVCDDNFNI NHASVVCKQL ECGSAVSFSG SANFGEGSGP IWFDDLICNG NESALWNCKH | |
| 241 QGWGKHNCDH AEDAGVICSK GADLSLRLVD GVTECSGRLE VRFQGEWGTI CDDGWDSHDA | |
| 301 AVACKQLGCP TAITAIGRVN ASEGFGHIWL DSVSCQGHEP AVWQCKHHEW GKHYCNHNED | |
| 361 AGVTCSDGSD LELRLRGGGS RCAGTVEVEI QRLLGKVCDR GWGLKEADVV CRQLGCGSAL | |
| 421 KTSYQVYSKI QATNMWLFLS SCNGNETSLW DCKNWQWGGL TCDHYEEAKI TCSAHREPRL | |
| 481 VGGDIPCSGR VEVKHGDTWG SVCDSDFSLE AASVLCRELQ CGTVVSILGG AHFGEGNGQI | |
| 541 WTEEFQCEGH ESHLSLCPVA PRPEGTCSHS RDVGVVCSRY TEIRLVNGKT PCEGRVELKT | |
| 601 LNAWGSLCNS HWDIEDAHVL CQQLKCGVAL STPGGAHFGK GNGQVWRHMF HCTGTEQHMG | |
| 661 DCPVTALGAS LCPSGQVASV ICSGNQSQTL SSCNSSSLGP TRPTIPEESA VACIESGQLR | |
| 721 LVNGGGRCAG RVEIYHEGSW GTICDDSWDL SDAHVVCRQL GCGEAINATG SAHFGEGTGP | |
| 781 IWLDEMKCNG KESRIWQCHS HGWGQQNCRH KEDAGVICSE FMSLRLTSEA SREACAGRLE | |
| 841 VFYNGAWGSV GRSNMSETTV GVVCRQLGCA DKGKINSASL DKAMSIPMWV DNVQCPKGPD | |

-continued

| SEQUENCE | ID NO |
|---|---|
| 901 TLWQCPSSPW EKRLARPSEE TWITCDNKMR LQEGPTSCSG RVEIWHGGSW GTVCDDSWDL | |
| 961 NDAQVVCQQL GCGPALKAFK EAEFGQGTGP IWLNEVKCKG NESSLWDCPA RRWGHSECGH | |
| 1021 KEDAAVNCTD ISTRKTPQKA TTGQSSLIAV GILGVVLLAI FVALFLTQKR RQRQRLTVSS | |
| 1081 RGENLVHQIQ YREMNSCLNA DDLDLMNSSE NSNESADFNA AELISVSKFL PISGMEKEAI | |
| 1141 LRHTEKENGN L | |
| 1 M S K L R M V L L E D S G S A D V R R H<br>1 ATGAGCAAACTCAGAATGGTGCTACTTGAAGACTCTGGATCTGCTGACGTCAGAAGACAT | SEQ ID NO: 37 and 38 |
| 21 F V N L S P F T I A V V L L L R A C F V<br>61 TTTGTCAACTTGAGTCCCTTCACTATTGCTGTGGTCTTACTTCTCCGTGCCTGTTTTGTC | |
| 41 T S S L G G T T K E L R L V D G E N K C<br>121 ACCAGTTCTCTTGGAGGAACAACCAAGGAGCTGAGGCTAGTGGATGGTGAAAACAAGTGT | |
| 61 S G R V E V K I Q E E W G T V C N N G W<br>181 AGTGGGAGAGTGGAAGTGAAAATCCAGGAGGAGTGGGGAACGGTGTGTAATAATGGCTGG | |
| 81 S M E A V S V I C N Q L G C P T A I K A<br>241 AGCATGGAAGCAGTCTCTGTGATTTGTAACCAGCTGGGATGTCCAACTGCTATCAAAGCC | |
| 101 T G W A N S S A G S G R I W M D H V S C<br>301 ACTGGATGGGCTAATTCCAGTGCAGGTTCTGGACGCATTTGGATGGATCATGTTTCTTGT | |
| 121 R G N E S A L W D C K H D G W G K H S N<br>361 CGTGGGAATGAGTCAGCTCTTTGGGACTGCAAACATGATGGATGGGGAAAGCATAGTAAC | |
| 141 C T H Q Q D A G V T C S D G S D L E M R<br>421 TGTACTCACCAACAAGATGCTGGAGTAACTTGCTCAGATGGATCCGATTTGGAAATGAGG | |
| 161 L T N G G N M C S G R I E I K F Q G Q W<br>481 CTGACGAATGGAGGGAATATGTGTTCTGGAAGAATAGAGATCAAATTCCAAGGACAGTGG | |
| 181 G T V C D D N F N I N H A S V V C K Q L<br>541 GGAACAGTGTGTGATGATAACTTCAACATCAATCATGCATCTGTGGTTTGTAAACAACTT | |
| 201 E C G S A V S F S G S A N F G E G S G P<br>601 GAATGTGGAAGTGCTGTCAGTTTCTCTGGTTCAGCTAATTTTGGAGAAGGCTCTGGACCA | |
| 221 I W F D D L I C N G N E S A L W N C K H<br>661 ATCTGGTTTGATGATCTTATATGCAACGGAAATGAGICAGCTCTCTGGAACTGCAAACAT | |
| 241 Q G W G K H N C D H A E D A G V I C S K<br>721 CAAGGATGGGGAAAGCATAACTGTGATCATGCTGAGGATGCTGGAGTGATTTGCTCAAAG | |
| 261 G A D L S L R L V D G V T E C S G R L E<br>781 GGAGCAGATCTGAGCCTGAGACTGGTAGATGGAGTCACTGAATGTTCAGGAAGATTAGAA | |
| 281 V R F Q G E W G T I C D D G W D S H D A<br>841 GTGAGATTCCAAGGAGAATGGGGGACAATATGTGATGACGGCTGGGACAGTCATGATGCT | |
| 301 A V A Q L G C P T A I T A I G R V N<br>901 GCTGTGGCATGCAAGCAACTGGGATGTCCAACTGCTATCACCGCCATTGGTCGAGTTAAC | |
| 321 A S E G F G H I W L D S V S C Q G H E P<br>961 GCCAGTGAGGGATTTGGACACATCTGGCTTGACAGTGTTTCTTGCCAGGGACATGAACCT | |
| 341 A V W Q C K H H E W G K H Y C N H N E D<br>1021 GCGGTCTGGCAATGTAAACACCATGAATGGGGAAAGCATTATTGCAATCACAATGAAGAT | |
| 361 A G V T C S D G S D L E L R L R G G G S<br>1081 GCTGGCGTAACATGTTCTGATGGATCAGATCTGGAGCTAAGACTTAGAGGTGGAGGCAGC | |
| 381 R C A G T V E V E I Q R L L G K V C D R<br>1141 CGCTGTGCTGGGACAGTTGAGGTGGAGATTCAGAGACTGTTAGGGAAGGTGTGTGACAGA | |
| 401 G W G L K E A D V V C R Q L G C G S A L<br>1201 GGCTGGGGACTGAAAGAAGCTGATGTGGTTTGCAGGCAGCTGGGATGTGGATCTGCACTC | |
| 421 K T S Y Q V Y S K I Q A T N M W L F L S<br>1261 AAAACATCCTATCAAGTATACTCCAAAATCCAGGCAACAAACATGTGGCTGTTTCTAAGT | |
| 441 S C N G N E T S L W D C K N W Q W G G L | |

-continued

| SEQUENCE | ID NO |
|---|---|
| 1321 AGCTGTAACGGAAATGAAACTTCTCTTTGGGACTGCAAGAACTGGCAATGGGGTGGACTT | |
| 461 T C D H Y E E A K I T C S A H R E P R L<br>1381 ACCTGTGATCACTATGAAGAAGCCAAAATTACCTGCTCAGCCCACAGGGAACCCAGACTG | |
| 481 V G G D I P C S G R V E V K H G D T W G<br>1441 GTTGGAGGAGACATTCCCTGTTCTGGACGCGTTGAAGTGAAGCATGGTGACACATGGGGC | |
| 501 S V C D S D F S L E A A S V L C R E L Q<br>1501 TCCGTCTGTGATTCGGATTTCTCTCTGGAAGCTGCCAGCGTTCTATGCAGGGAATTACAG | |
| 521 C G T V V S I L G G A H F G E G N G Q I<br>1561 TGTGGCACAGTCGTCTCTATCCTGGGGGGAGCTCACTTTGGAGAGGGAAATGGACAGATC | |
| 541 W T E E F Q C E G H E S H L S L C P V A<br>1621 TGGACTGAAGAATTCCAGTGTGAGGGACATGAGTCCCATCTTTCACTCTGCCCAGTAGCA | |
| 561 P R P E G T C S H S R D V G V V C S R Y<br>1681 CCCCGCCCAGAAGGAACTTGTAGCCACAGCAGGGATGTTGGAGTAGTCTGCTCAAGATAC | |
| 581 T E I R L V N G K T P C E G R V E L K T<br>1741 ACAGAAATTCGCTTGGTGAATGGCAAGACCCCATGTGAGGGCAGAGTGGAGCTCAAAACG | |
| 601 L N A W G S L C N S H W D I E D A H V L<br>1801 CTTAATGCCTGGGGATCCCTCTGCAACTCTCACTGGGACATAGAAGATGCCCACGTTCTT | |
| 621 C Q Q L K C G V A L S T P G G A H F G K<br>1861 TGCCAACAACTTAAATGTGGAGTTGCCCTTTCTACCCCAGGAGGAGCACATTTTGGAAAA | |
| 641 G N G Q V W R H M F H C T G T E Q H M G<br>1921 GGAAATGGTCAGGTCTGGAGGCATATGTTTCACTGCACTGGGACTGAGCAGCACATGGGA | |
| 661 D C P V T A L G A S L C P S G Q V A S V<br>1981 GATTGTCCTGTAACTGCTCTGGGTGCTTCACTATGTCCTTCAGGGCAAGTGGCCTCTGTA | |
| 681 I C S G N Q S Q T L S S C N S S S L G P<br>2041 ATTTGCTCAGGAAACCAGTCCCAAACACTGTCCTCGTGCAATTCATCATCTCTGGGCCCA | |
| 701 T R P T I P E E S A V A C I E S G Q L R<br>2101 ACAAGGCCTACCATTCCAGAAGAAAGTGCTGTGGCCTGCATAGAGAGTGGTCAACTTCGC | |
| 721 L V N G G G R C A G R V E I Y H E G S W<br>2161 TTGGTAAATGGAGGAGGTCGCTGTGCTGGGAGAGTAGAGATTTATCATGAGGGCTCCTGG | |
| 741 G T I C D D S W D L S D A H V V C R Q L<br>2221 GGCACCATCTGTGATGACAGCTGGGACCTGAGCGATGCCCACGTGGTGTGCAGACAGCTG | |
| 761 G C G E A I N A T G S A H F G E G T G P<br>2281 GGCTGTGGAGAGGCCATTAATGCCACTGGTTCTGCTCATTTTGGAGAAGGAACAGGGCCC | |
| 781 I W L D E M K C N G K E S R I W Q C H S<br>2341 ATCTGGCTGGATGAGATGAAATGCAATGGAAAAGAATCCCGCATTTGGCAGTGCCATTCA | |
| 801 H G W G Q Q N C R H K E D A G V I C S E<br>2401 CATGGCTGGGGGCAGCAAAACTGCAGGCACAAGGAGGATGCAGGAGTTATCTGCTCAGAG | |
| 821 F M S L R L T S E A S R E A C A G R L E<br>2461 TTCATGTCTCTGAGACTGACCAGTGAAGCCAGCAGAGAGGCCTGTGCAGGGCGTCTAGAA | |
| 841 V F Y N G A W G S V G R S N M S E T T V<br>2521 GTTTTTTACAACGGAGCTTGGGGCAGTGTTGGCAGGAGTAACATGTCTGAAACCACTGTG | |
| 861 G V V C R Q L G C A D K G K I N S A S L<br>2581 GGTGTAGTGTGCAGGCAGCTGGGCTGTGCAGACAAAGGGAAAATCAACTCTGCATCTTTA | |
| 881 D K A M S I P M W V D N V Q C P K G P D<br>2641 GACAAGGCCATGTCCATTCCCATGTGGGTGGACAATGTTCAGTGTCCAAAAGGACCTGAC | |
| 901 T L W Q C P S S P W E K R L A R P S E E<br>2701 ACGCTGTGGCAGTGCCCATCATCTCCATGGGAGAAGAGACTGGCCAGGCCCTCGGAGGAG | |
| 921 T W I T C D N K M R L Q E G P T S C S G<br>2761 ACCTGGATCACATGTGACAACAAGATGAGACTACAAGAAGGACCCACTTCCTGTTCTGGA | |
| 941 R V E I W H G G S W G T V C D D S W D L<br>2821 CGTGTGGAGATCTGGCACGGAGGTTCCTGGGGGACAGTGTGTGATGACTCCTGGGACTTG | |
| 961 N D A Q V V C Q Q L G C G P A L K A F K | |

-continued

| SEQUENCE | ID NO |
|---|---|
| 2881 AACGATGCTCAGGTGGTGTGTCAACAACTTGGCTGTGGTCCAGCTTTGAAAGCATTCAAA | |
| 981 E A E F G Q G T G P I W L N E V K C K G<br>2941 GAAGCAGAGTTTGGTCAGGGGACTGGACCCATATGGCTCAATGAAGTGAAGTGCAAAGGG | |
| 1001 N E S S L W D C P A R R W G H S E C G H<br>3001 AATGAGTCTTCCTTGTGGGATTGTCCTGCCAGACGCTGGGGCCACAGTGAGTGTGGACAC | |
| 1021 K E D A A V N C T D I S T R K T P Q K A<br>3061 AAGGAAGACGCTGCAGTGAATTGCACAGATATTTCAACGCGCAAAACCCCACAAAAAGCC | |
| 1041 T T V S S R G E N L V H Q I Q Y R E M N<br>3121 ACAACGGTTTCCTCAAGAGGAGAGAACTTAGTCCACCAAATTCAATACCGGGAGATGAAT | |
| 1061 S C L N A D D L N L M N S S G G H S E A<br>3181 TCTTGCCTGAATGCAGATGATCTGAACCTAATGAATTCCTCAGGAGGCCATTCTGAGGCA | |
| 1081 H * K G K W E F I T Q<br>3241 CACTGAAAAGGAAAATGGGAATTTATAACCCAG | |
| 1 MSKLRMVLLE DSGSADVRRH FVNLSPFTIA VVLLLRACFV TSSLGGTTKE LRLVDGENKC | SEQ ID NO: 38 |
| 61 SGRVEVKIQE EWGTVCNNGW SMEAVSVICN QLGCPTAIKA TGWANSSAGS GRIWMDHVSC | |
| 121 RGNESALWDC KHDGWGKHSN CTHQQDAGVT CSDGSDLEMR LTNGGNMCSG RIEIKFQGQW | |
| 181 GTVCDDNFNI NHASVVCKQL ECGSAVSFSG SANFGEGSGP IWFDDLICNG NESALWNCKH | |
| 241 QGWGKHNCDH AEDAGVICSK GADLSLRLVD GVTECSGRLE VRFQGEWGTI CDDGWDSHDA | |
| 301 AVACKQLGCP TAITAIGRVN ASEGFGHIWL DSVSCQGHEP AVWQCKHHEW GKHYCNHNED | |
| 361 AGVTCSDGSD LELRLRGGGS RCAGTVEVEI QRLLGKVCDR GWGLKEADVV CRQLGCGSAL | |
| 421 KTSYQVYSKI QATNMWLFLS SCNGNETSLW DCKNWQWGGL TCDHYEEAKI TCSAHREPRL | |
| 481 VGGDIPCSGR VEVKHGDTWG SVCDSDFSLE AASVLCRELQ CGTVVSILGG AHFGEGNGQI | |
| 541 WTEEFQCEGH ESHLSLCPVA PRPEGTCSHS RDVGVVCSRY TEIRLVNGKT PCEGRVELKT | |
| 601 LNAWGSLCNS HWDIEDAHVL CQQLKCGVAL STPGGAHFGK GNGQVWRHMF HCTGTEQHMG | |
| 661 DCPVTALGAS LCPSGQVASV ICSGNQSQTL SSCNSSSLGP TRPTIPEESA VACIESGQLR | |
| 721 LVNGGGRCAG RVEIYHEGSW GTICDDSWDL SDAHVVCRQL GCGEAINATG SAHFGEGTGP | |
| 781 IWLDEMKCNG KESRIWQCHS HGWGQQNCRH KEDAGVICSE FMSLRLTSEA SREACAGRLE | |
| 841 VFYNGAWGSV GRSNMSETTV GVVCRQLGCA DKGKINSASL DKAMSIPMWV DNVQCPKGPD | |
| 901 TLWQCPSSPW EKRLARPSEE TWITCDNKMR LQEGPTSCSG RVEIWHGGSW GTVCDDSWDL | |
| 961 NDAQVVCQQL GCGPALKAFK EAEFGQGTGP IWLNEVKCKG NESSLWDCPA RRWGHSECGH | |
| 1021 KEDAAVNCTD ISTRKTPQKA TTVSSRGENL VHQIQYREMN SCLNADDLNL MNSSGGHSEA | |
| 1081 H | |
| 1 M S K L R M V L L E D S G S A D V R R H<br>1 ATGAGCAAACTCaGAATGGTGCTACTTGAAGACTCTGGATCTGCTGACGTCAGAAGACAT | SEQ ID NO: 39 and 40 |
| 21 F V N L S P F T I A V V L L L R A C F V<br>61 TTTGTCAACTTGAGTCCCTTCACTATTGCTGTGGTCTTACTTCTCCGTGCCTGTTTTGTC | |
| 41 T S S L G G T T K E L R L V D G E N K C<br>121 ACCAGTTCTCTTGGAGGAACAACCAAGGAGCTGAGGCTAGTGGATGGTGAAAACAAGTGT | |
| 61 S G R V E V K I Q E E W G T V C N N G W<br>181 AGTGGGAGAGTGGAAGTGAAAATCCAGGAGGAGTGGGGAACGGTGTGTAATAATGGCTGG | |
| 81 S M E A V S V I C N Q L G C P T A I K A<br>241 AGCATGGAAGCAGTCTCTGTGATTTGTAACCAGCTGGGATGTCCAACTGCTATCAAAGCC | |
| 101 T G W A N S S A G S G R I W M D H V S C<br>301 ACTGGATGGGCTAATTCCAGTGCAGGTTCTGGACGCATTTGGATGGATCATGTTTCTTGT | |
| 121 R G N E S A L W D C K H D G W G K H S N<br>361 CGTGGGAATGAGTCAGCTCTTTGGGACTGCAAACATGATGGATGGGGAAAGCATAGTAAC | |

-continued

| SEQUENCE | ID NO |
|---|---|

141 C T H Q Q D A G V T C S D G S D L E M R
421 TGTACTCACCAACAAGATGCTGGAGTGACTTGCTCAGATGGATCCGATTTGGAAATGAGG

161 L T N G G N M C S G R I E I K F Q G Q W
481 CTGACGAATGGAGGGAATATGTGTTCTGGAAGAATAGAGATCAAATTCCAAGGACAGTGG

181 G T V C D D N F N V N H A S V V C K Q L
541 GGAACAGTGTGTGATGATAACTTCAACGTCAATCATGCATCTGTGGTTTGTAAACAACTT

201 E C G S A V S F S G S A N F G E G S G P
601 GAATGTGGAAGTGCTGTCAGTTTCTCTGGTTCAGCTAATTTTGGAGAAGGCTCTGGACCA

221 I W F D D L I C N G N E S A L W N C K H
661 ATCTGGTTTGATGATCTTATATGCAACGGAAATGAGTCAGCTCTCTGGAACTGCAAACAT

241 Q G W G K H N C D H A E D A G V I C S K
721 CAAGGATGGGGAAAGCATAACTGTGATCATGCTGAGGATGCTGGAGTGATTTGCTCAAAG

261 G A D L S L R L V D G V T E C S G R L E
781 GGAGCAGATCTGAGCCTGAGACTGGTAGATGGAGTCACTGAATGTTCAGGAAGATTAGAA

281 V R F Q G E W G T I C D D G W D S H D A
841 GTGAGATTCCAAGGAGAATGGGGGACAATATGTGATGACGGCTGGGACAGTCATGATGCT

301 A V A C K Q L G C P T A I T A I G R V N
901 GCTGTGGCATGCAAGCAACTGGGATGTCCAACTGCTATCACCGCCATTGGTCGAGTTAAC

321 A S E G F G H I W L D S V S C Q G H E P
961 GCCAGTGAGGGATTTGGACACATCTGGCTTGACAGTGTTTCTTGCCAGGGACATGAACCT

341 A V W Q C K H H E W G K H Y C N H N E D
1021 GCGGTCTGGCAATGTAAACACCATGAATGGGGAAAGCATTATTGCAATCACAATGAAGaT

361 A G V T C S D G S D L E L R L R G G G S
1081 GCTGGCGTAACATGTTCTGATGGATCAGATCTGGAGCTAAGACTTAGAGGTGGAGGCAGC

381 R C A G T V E V E I Q R L L G K V C D R
1141 CGCTGTGCTGGGACAGTTGAGGTGGAGATtCAGAGACTGTTAGGGAAGGTGTGTGACAGA

401 G W G L K E A D V V C R Q L G C G S A L
1201 GGCTGGGGACTGAAAGAAGCTGATGTGGTTTGCAGGCAGCTGGGATGTGGATCTGCACTC

421 K T S Y Q V Y S K I Q A T N M W L F L S
1261 AAAACATCCTATCAAGTATACTCCAAAATCCAGGCAACAAACATGTGGCTGTTTCTAAGT

441 S C N G N E T S L W D C K N W Q W G G L
1321 AGCTGTAACGGAAATGAAACTTCTCTTTGGGACTGCAAGAACTGGCAATGGGGTGGACTT

461 T C D H Y E E A K I T C S A H R E P R L
1381 ACCTGTGATCACTATGAAGAAGCCAAAATTACCTGCTCAGCCCACAGGGAACCCAGACTG

481 V G G D I P C S G R V E V K H G D T W G
1441 GTTGGAGGAGACATTCCCTGTTCTGGACGCGTTGAAGTGAAGCATGGTGACACATGGGGC

501 S V C D S D F S L E A A S V L C R E L Q
1501 TCCGTCTGTGATTCGGATTTCTCTCTGGAAGCTGCCAGCGTTCTATGCAGGGAATTACAG

521 C G T V V S I L G G A H F G E G N G Q I
1561 TGTGGCACAGTCGTCTCTATCCTGGGGGGAGCTCACTTTGGAGAGGGAAATGGACAGATC

541 W A E E F Q C E G H E S H L S L C P V A
1621 TGGGCTGAAGAATTCCAGTGTGAGGGACATGAGTCCCATCTTTCACTCTGCCCAGTAGCA

561 P R P E G T C S H S R D V G V V C S R Y
1681 CCCCGCCCAGAAGGAACTTGTAGCCACAGCAGGGATGTTGGAGTAGTCTGCTCAAGATAC

581 T E I R L V N G K T P C E G R V E L K T
1741 ACAGAAATTCGCTTGGTGAATGGCAAGACCCCATGTGAGGGCAGAGTGGAGCTCAAAACG

601 L N A W G S L C N S H W D I E D A H V L
1801 CTTAATGCCTGGGGATCCCTCTGCAACTCTCACTGGGACATAGAAGATGCCCACGTTCTT

621 C Q Q L K C G V A L S T P G G A H F G K
1861 TGCCAACAACTTAAATGTGGAGTTGCCCTTTCTACCCCAGGAGGAGCACATTTTGGAAAA

641 G N G Q V W R H M F H C T G T E Q H M G
1921 GGAAATGGTCAGGTCTGGAGGCATATGTTTCACTGCACTGGGACTGAGCAGCACATGGGA

-continued

| SEQUENCE | ID NO |
|---|---|
| 661 D C P V T A L G A S L C P S G Q V A S V<br>1981 GATTGTCCTGTAACTGCTCTGGGTGCTTCACTATGTCCTTCAGGGCAAGTGGCCTCTGTA | |
| 681 I C S G N Q S Q T L S S C N S S S L G P<br>2041 ATTTGCTCAGGAAACCAGTCCCAAACACTGTCCTCGTGCAATTCATCATCTCTGGGCCCA | |
| 701 T R P T I P E E S A V A C I E S G Q L R<br>2101 ACAAGGCCTACCATTCCAGAAGAAAGTGCTGTGGCCTGCATAGAGAGTGGTCAACTTCGC | |
| 721 L V N G G G R C A G R V E I Y H E G S W<br>2161 TTGGTAAATGGAGGAGGTCGCTGTGCTGGGAGAGTAGAGATTTATCATGAGGGCTCCTGG | |
| 741 G T I C D D S W D L S D A H V V C R Q L<br>2221 GGCACCATCTGTGATGACAGCTGGGACCTGAGCGATGCCCACGTGGTGTGCAGACAGCTG | |
| 761 G C G E A I N A T G S A H F G E G T G P<br>2281 GGCTGTGGAGAGGCCATTAATGCCACTGGTTCTGCTCATTTTGGAGAAGGAACAGGGCCC | |
| 781 I W L D E M K C N G K E S R I W Q C H S<br>2341 ATCTGGCTGGATGAGATGAAATGCAATGGAAAAGAATCCCGTATTTGGCAGTGCCATTCA | |
| 801 H G W G Q Q N C R H K E D A G V I C S E<br>2401 CATGGCTGGGGGCAGCAAAACTGCAGGCACAAGGAGGATGCAGGAGTTATCTGCTCAGAG | |
| 821 F M S L R L T S E A S R E A C A G R L E<br>2461 TTCATGTCTCTGAGACTGACCAGTGAAGCCAGCAGAGAGGCCTGTGCAGGGCGTCTAGAA | |
| 841 V F Y N G A W G S V G R S N M S E T T V<br>2521 GTTTTTTACAACGGAGCTTGGGGCAGTGTTGGCAGGAGTAACATGTCTGAAACCACTGTG | |
| 861 G V V C R Q L G C A D K G K I N S A S L<br>2581 GGTGTGGTGTGCAGGCAGCTGGGCTGTGCAGACAAAGGGAAAATCAACTCTGCATCTTTA | |
| 881 D K A M S I P M W V D N V Q C P K G P D<br>2641 GACAAGGCCATGTCCATTCCCATGTGGGTGGACAATGTTCAGTGTCCAAAAGGACCTGAC | |
| 901 T L W Q C P S S P W E K R L A R P S E E<br>2701 ACGCTGTGGCAGTGCCCATCATCTCCATGGGAGAAGAGACTGGCCAGGCCCTCGGAGGAG | |
| 921 T W I T C D N K M R L Q E G P T S C S G<br>2761 ACCTGGATCACATGTGACAACAAGATGAGACTACAAGAAGGACCCACTTCCTGTTCTGGA | |
| 941 R V E I W H G G S W G T V C D D S W D L<br>2821 CGTGTGGAGATCTGGCACGGAGGTTCCTGGGGGACAGTGTGTGATGACTCCTGGGACTTG | |
| 961 N D A Q V V C Q Q L G C G P A L K A F K<br>2881 AACGATGCTCAGGTGGTGTGTCAACAACTTGGCTGTGGTCCAGCTTTGAAAGCATTCAAA | |
| 981 E A E F G Q G T G P I W L N E V K C K G<br>2941 GAAGCAGAGTTTGGTCAGGGGACTGGACCCATATGGCTCAATGAAGTGAAGTGCAAAGGG | |
| 1001 N E S S L W D C P A R R W G H S E C G H<br>3001 AATGAGTCTTCCTTGTGGGATTGTCCTGCCAGACGCTGGGGCCACAGTGAGTGTGGACAC | |
| 1021 K E D A A V N C T A Q K I S T H K T P Q<br>3061 AAGGAAGACGCTGCAGTGAATTGCACAGCACAAAAAATTTCAACGCACAAAACCCCACAA | |
| 1041 K A T T V S S R G E N L V H Q I Q Y R E<br>3121 AAAGCCACAACAGTTTCCTCAAGAGGAGAGAACTTAGTCCACCAAATTCAATACCGGGAG | |
| 1061 M N S C L N A D D L D L M N S S G G H S<br>3181 ATGAATTCTTGCCTGAATGCAGATGATCTGGACCTAATGAATTCCTCAGGAGGCCATTCT | |
| 1081 E A H * K G K W E F I T Q<br>3241 GAGGCACACTGAAAAGGAAAATGGGAATTTATAACCCAG | |
| 1 MSKLRMVLLE DSGSADVRRH FVNLSPFTIA VVLLLRACFV TSSLGGTTKE LRLVDGENKC | SEQ ID NO: 40 |
| 61 SGRVEVKIQE EWGTVCNNGW SMEAVSVICN QLGCPTAIKA TGWANSSAGS GRIWMDHVSC | |
| 121 RGNESALWDC KHDGWGKHSN CTHQQDAGVT CSDGSDLEMR LTNGGNMCSG RIEIKFQGQW | |
| 181 GTVCDDNFNV NHASVVCKQL ECGSAVSFSG SANFGEGSGP IWFDDLICNG NESALWNCKH | |
| 241 QGWGKHNCDH AEDAGVICSK GADLSLRLVD GVTECSGRLE VRFQGEWGTI CDDGWDSHDA | |
| 301 AVACKQLGCP TAITAIGRVN ASEGFGHIWL DSVSCQGHEP AVWQCKHHEW GKHYCNHNED | |

-continued

| SEQUENCE | ID NO |
|---|---|
| 361 AGVTCSDGSD LELRLRGGGS RCAGTVEVEI QRLLGKVCDR GWGLKEADVV CRQLGCGSAL | |
| 421 KTSYQVYSKI QATNMWLFLS SCNGNETSLW DCKNWQWGGL TCDHYEEAKI TCSAHREPRL | |
| 481 VGGDIPCSGR VEVKHGDTWG SVCDSDFSLE AASVLCRELQ CGTVVSILGG AHFGEGNGQI | |
| 541 WAEEFQCEGH ESHLSLCPVA PRPEGTCSHS RDVGVVCSRY TEIRLVNGKT PCEGRVELKT | |
| 601 LNAWGSLCNS HWDIEDAHVL CQQLKCGVAL STPGGAHFGK GNGQVWRHMF HCTGTEQHMG | |
| 661 DCPVTALGAS LCPSGQVASV ICSGNQSQTL SSCNSSSLGP TRPTIPEESA VACIESGQLR | |
| 721 LVNGGGRCAG RVEIYHEGSW GTICDDSWDL SDAHVVCRQL GCGEAINATG SAHFGEGTGP | |
| 781 IWLDEMKCNG KESRIWQCHS HGWGQQNCRH KEDAGVICSE FMSLRLTSEA SREACAGRLE | |
| 841 VFYNGAWGSV GRSNMSETTV GVVCRQLGCA DKGKINSASL DKAMSIPMWV DNVQCPKGPD | |
| 901 TLWQCPSSPW EKRLARPSEE TWITCDNKMR LQEGPTSCSG RVEIWHGGSW GTVCDDSWDL | |
| 961 NDAQVVCQQL GCGPALKAFK EAEFGQGTGP IWLNEVKCKG NESSLWDCPA RRWGHSECGH | |
| 1021 KEDAAVNCTA QKISTHKTPQ KATTVSSRGE NLVHQIQYRE MNSCLNADDL DLMNSSGGHS | |
| 1081 EAH | |
| 1 M S K L R M V L L E D S G S A D V R R H<br>1 ATGAGCAAACTCAGAATGGTGCTACTTGAAGACTCTGGATCTGCTGACGTCAGAAGACAT | SEQ ID NO: 41 and 42 |
| 21 F V N L S P F T I A V V L L L R A C F V<br>61 TTTGTCAACTTGAGTCCCTTCACTATTGCTGTGGTCTTACTTCTCCGTGCCTGTTTTGTC | |
| 41 T S S L G G T T K E L R L V D G E N K C<br>121 ACCAGTTCTCTTGGAGGAACAACCAAGGAGCTGAGGCTAGTGGATGGTGAAAACAAGTGT | |
| 61 S G R V E V K I Q E E W G T V C N N G W<br>181 AGTGGGAGAGTGGAAGTGAAAATCCAGGAGGAGTGGGGAACGGTGTGTAATAATGGCTGG | |
| 81 S M E A V S V I C N Q L G C P T A I K A<br>241 AGCATGGAAGCAGTCTCTGTGATTTGTAACCAGCTGGGATGTCCAACTGCTATCAAAGCC | |
| 101 T G W A N S S A G S G R I W M D H V S C<br>301 ACTGGATGGGCTAATTCCAGTGCAGGTTCTGGACGCATTTGGATGGATCATGTTTCTTGT | |
| 121 R G N E S A L W D C K H D G W G K H S N<br>361 CGTGGGAATGAGTCAGCTCTTTGGGACTGCAAACATGATGGATGGGGAAAGCATAGTAAC | |
| 141 C T H Q Q D A G V T C S D G S D L E M R<br>421 TGTACTCACCAACAAGATGCTGGAGTGACTTGCTCAGATGGATCCGATTTGGAAATGAGG | |
| 161 L T N G G N M C S G R I E I K F Q G Q W<br>481 CTGACGAATGGAGGGAATATGTGTTCTGGAAGAATAGAGATCAAATTCCAAGGACAGTGG | |
| 181 G T V C D D N F N I N H A S V V C K Q L<br>541 GGAACAGTGTGTGATGATAACTTCAACATCAATCATGCATCTGTGGTTTGTAAACAACTT | |
| 201 E C G S A V S F S G S A N F G E G S G P<br>601 GAATGTGGAAGTGCTGTCAGTTTCTCTGGTTCAGCTAATTTTGGAGAAGGCTCTGGACCA | |
| 221 I W F D D L I C N G N E S A L W N C K H<br>661 ATCTGGTTTGATGATCTTATATGCAACGGAAATGAGTCAGCTCTCTGGAACTGCAAACAT | |
| 241 Q G W G K H N C D H A E D A G V I C S K<br>721 CAAGGATGGGGAAAGCATAACTGTGATCATGCTGAGGATGCTGGAGTGATTTGCTCAAAG | |
| 261 G A D L S L R L V D G V T E C S G R L E<br>781 GGAGCAGATCTGAGCCTGAGACTGGTAGATGGAGTCACTGAATGTTCAGGAAGATTAGAA | |
| 281 V R F Q G E W G T I C D D G W D S H D A<br>841 GTGAGATTCCAAGGAGAATGGGGGACAATATGTGATGACGGCTGGGACAGTCATGATGCT | |
| 301 A V A C K Q L G C P T A I T A I G R V N<br>901 GCTGTGGCATGCAAGCAACTGGGATGTCCAACTGCTATCACCGCCATTGGTCGAGTTAAC | |
| 321 A S E G F G H I W L D S V S C Q G H E P<br>961 GCCAGTGAGGGATTTGGACACATCTGGCTTGACAGTGTTTCTTGCCAGGGACATGAACCT | |

-continued

| SEQUENCE | ID NO |
|---|---|
| 341 A V W Q C K H H E W G K H Y C N H N E D<br>1021 GCGGTCTGGCAATGTAAACACCATGAATGGGGAAAGCATTATTGCAATCACAATGAAGAT<br><br>361 A G V T C S D G S D L E L R L R G G G S<br>1081 GCTGGCGTAACATGTTCTGATGGATCAGATCTGGAGCTAAGACTTAGAGGTGGAGGCAGC<br><br>381 R C A G T V E V E I Q R L L G K V C D R<br>1141 CGCTGTGCTGGGACAGTTGAGGTGGAGATTCAGAGACTGTTAGGGAAGGTGTGtGACAGA<br><br>401 G W G L K E A D V V C R Q L G C G S A L<br>1201 GGCTGGGGACTGAAAGAAGCTGATGTGGTTTGCAGGCAGCTGGGATGTGGATCTGCACTC<br><br>421 K T S Y Q V Y S K I Q A T N M W L F L S<br>1261 AAAACATCCTATCAAGTATACTCCAAAATCCAGGCAACAAACATGTGGCTGTTTCTAAGT<br><br>441 S C N G N E T S L W D C K N W Q W G G L<br>1321 AGCTGTAACGGAAATGAAACTTCTCTTTGGGACTGCAAGAACTGGCAATGGGGTGGACTT<br><br>461 T C D H Y E E A K I T C S A H R E P R L<br>1381 ACCTGTGATCACTATGAAGAAGCCAAAATTACCTGCTCAGCCCACAGGGAACCCAGACTG<br><br>481 V G G D I P C S G R V E V K H G D T W G<br>1441 GTTGGAGGAGACATTCCCTGTTCTGGACGCGTTGAAGTGAAGCATGGTGACACATGGGGC<br><br>501 S V C D S D F S L E A A S V L C R E L Q<br>1501 TCCGTCTGTGATTCGGATTTCTCTCTGGAAGCTGCCAGCGTTCTATGCAGGGAATTACAG<br><br>521 C G T V V S I L G G A H F G E G N G Q I<br>1561 TGTGGCACAGTCGTCTCTATCCTGGGGGGAGCTCACTTTGGAGAGGGAAATGGACAGATC<br><br>541 W A E E F Q C E G H E S H L S L C P V A<br>1621 TGGGCTGAAGAATTCCAGTGTGAGGGACATGAGTCCCATCTTTCACTCTGCCCAGTAGCA<br><br>561 P R P E G T C S H S R D V G V V C S R Y<br>1681 CCCCGCCCAGAAGGAACTTGTAGCCACAGCAGGGATGTTGGAGTAGTCTGCTCAAGATAC<br><br>581 T E I R L V N G K T P C E G R V E L K T<br>1741 ACAGAAATTCGCTTGGTGAATGGCAAGACCCCATGTGAGGGCAGAGTGGAGCTCAAAACG<br><br>601 L N A W G S L C N S H W D I E D A H V L<br>1801 CTTAATGCCTGGGGATCCCTCTGCAACTCTCACTGGGACATAGAAGATGCCCACGTTCTT<br><br>621 C Q Q L K C G V A L S T P G G A H F G K<br>1861 TGCCAACAACTTAAATGTGGAGTTGCCCTTTCTACCCCAGGAGGAGCACATTTTGGAAAA<br><br>641 G N G Q V W R H M F H C T G T E Q H M G<br>1921 GGAAATGGTCAGGTCTGGAGGCATATGTTTCACTGCACTGGGACTGAGCAGCACATGGGA<br><br>661 D C P V T A L G A S L C P S G Q V A S V<br>1981 GATTGTCCTGTAACTGCTCTGGGTGCTTCACTATGTCCTTCAGGGCAAGTGGCCTCTGTA<br><br>681 I C S G N Q S Q T L S S C N S S S L G P<br>2041 ATTTGCTCAGGAAACCAGTCCCAAACACTGTCCTCGTGCAATTCATCATCTCTGGGCCCA<br><br>701 T R P T I P E E S A V A C I E S G Q L R<br>2101 ACAAGGCCTACCATTCCAGAAGAAAGTGCTGTGGCCTGCATAGAGAGTGGTCAACTTCGC<br><br>721 L V N G G G R C A G R V E I Y H E G S W<br>2161 TTGGTAAATGGAGGAGGTCGCTGTGCTGGGAGAGTAGAGATTTATCATGAGGGCTCCTGG<br><br>741 G T I C D D S W D L S D A H V V C R Q L<br>2221 GGCACCATCTGTGATGACAGCTGGGACCTGAGCGATGCCCACGTGGTGTGCAGACAGCTG<br><br>761 G C G E A I N A T G S A H F G E G T G P<br>2281 GGCTGTGGAGAGGCCATTAATGCCACTGGTTCTGCTCATTTTGGAGAAGGAACAGGGCCC<br><br>781 I W L D E M K C N G K E S R I W Q C H S<br>2341 ATCTGGCTGGATGAGATGAAATGCAATGGAAAAGAATCCCGTATTTGGCAGTGCCATTCA<br><br>801 H G W G Q Q N C R H K E D A G V I C S E<br>2401 CATGGCTGGGGGCAGCAAAACTGCAGGCACAAGGAGGATGCAGGAGTTATCTGCTCAGAG<br><br>821 F M S L R L T S E A S R E A C A G R L E<br>2461 TTCATGTCTCTGAGACTGACCAGTGAAGCCAGCAGAGAGGCCTGTGCAGGGCGTCTAGAA<br><br>841 V F Y N G A W G S V G R S N M S E T T V<br>2521 GTTTTTTACAACGGAGCTTGGGGCAGTGTTGGCAGGAGTAACATGTCTGAAACCACTGTG | |

-continued

| SEQUENCE | ID NO |
|---|---|
| 861 G V V C R Q L G C A D K G K I N S A S L<br>2581 GGTGTGGTGTGCAGGCAGCTGGGCTGTGCAGACAAAGGGAAAATCAACTCTGCATCTTTA | |
| 881 D K A M S I P M W V D N V Q C P K G P D<br>2641 GACAAGGCCATGTCCATTCCCATGTGGGTGGACAATGTTCAGTGTCCAAAAGGACCTGAC | |
| 901 T L W Q C P S S P W E K R L A R P S E E<br>2701 ACGCTGTGGCAGTGCCCATCATCTCCATGGGAGAAGAGACTGGCCAGGCCCTCGGAGGAG | |
| 921 T W I T C D N K M R L Q E G P T S C S G<br>2761 ACCTGGATCACATGTGACAACAAGATGAGACTACAAGAAGGACCCACTTCCTGTTCTGGA | |
| 941 R V E I W H G G S W G T V C D D S W D L<br>2821 CGTGTGGAGATCTGGCACGGAGGTTCCTGGGGGACAGTGTGTGATGACTCCTGGGACTTG | |
| 961 N D A Q V V C Q Q L G C G P A L K A F K<br>2881 AACGATGCTCAGGTGGTGTGTCAACAACTTGGCTGTGGTCCAGCTTTGAAAGCATTCAAA | |
| 981 E A E F G Q G T G P I W L N E V K C K G<br>2941 GAAGCAGAGTTTGGTCAGGGGACTGGACCCATATGGCTCAATGAAGTGAAGTGCAAAGGG | |
| 1001 N E S S L W D C P A R R W G H S E C G H<br>3001 AATGAGTCTTCCTTGTGGGATTGTCCTGCCAGACGCTGGGGCCACAGTGAGTGTGGACAC | |
| 1021 K E D A A V N C T A Q K I S T H K T P Q<br>3061 AAGGAAGACGCTGCAGTGAATTGCACAGCACAAAAAATTTCAACGCACAAAACCCCACAA | |
| 1041 K A T T G R S F L I A F G I L G V V L L<br>3121 AAAGCCACAACAGGTCGGTCATTCCTTATTGCATTCGGAATCCTTGGAGTTGTTCTCTTG | |
| 1061 A I F V A L F L T Q K R R Q R Q R L T V<br>3181 GCCATTTTCGTCGCATTATTCTTGACTCAAAAGCGAAGACAGAGACAGCGGCTTACAGTT | |
| 1081 S S R G E N L V H Q I Q Y R E M N S C L<br>3241 TCCTCAAGAGGAGAGAACTTAGTCCACCAAATTCAATACCGGGAGATGAATTCTTGCCTG | |
| 1101 N A D D L D L M N S S G G H S E A H<br>3301 AATGCAGATGATCTGGACCTAATGAATTCCTCAGGAGGCCATTCTGAGGCACAC | |
| 1 MSKLRMVLLE DSGSADVRRH FVNLSPFTIA VVLLLRACFV TSSLGGTTKE LRLVDGENKC | SEQ ID NO: 42 |
| 61 SGRVEVKIQE EWGTVCNNGW SMEAVSVICN QLGCPTAIKA TGWANSSAGS GRIWMDHVSC | |
| 121 RGNESALWDC KHDGWGKHSN CTHQQDAGVT CSDGSDLEMR LTNGGNMCSG RIEIKFQGQW | |
| 181 GTVCDDNFNI NHASVVCKQL ECGSAVSFSG SANFGEGSGP IWFDDLICNG NESALWNCKH | |
| 241 QGWGKHNCDH AEDAGVICSK GADLSLRLVD GVTECSGRLE VRFQGEWGTI CDDGWDSHDA | |
| 301 AVACKQLGCP TAITAIGRVN ASEGFGHIWL DSVSCQGHEP AVWQCKHHEW GKHYCNHNED | |
| 361 AGVTCSDGSD LELRLRGGGS RCAGTVEVEI QRLLGKVCDR GWGLKEADVV CRQLGCGSAL | |
| 421 KTSYQVYSKI QATNMWLFLS SCNGNETSLW DCKNWQWGGL TCDHYEEAKI TCSAHREPRL | |
| 481 VGGDIPCSGR VEVKHGDTWG SVCDSDFSLE AASVLCRELQ CGTVVSILGG AHFGEGNGQI | |
| 541 WAEEFQCEGH ESHLSLCPVA PRPEGTCSHS RDVGVVCSRY TEIRLVNGKT PCEGRVELKT | |
| 601 LNAWGSLCNS HWDIEDAHVL CQQLKCGVAL STPGGAHFGK GNGQVWRHMF HCTGTEQHMG | |
| 661 DCPVTALGAS LCPSGQVASV ICSGNQSQTL SSCNSSSLGP TRPTIPEESA VACIESGQLR | |
| 721 LVNGGGRCAG RVEIYHEGSW GTICDDSWDL SDAHVVCRQL GCGEAINATG SAHFGEGTGP | |
| 781 IWLDEMKCNG KESRIWQCHS HGWGQQNCRH KEDAGVICSE FMSLRLTSEA SREACAGRLE | |
| 841 VFYNGAWGSV GRSNMSETTV GVVCRQLGCA DKGKINSASL DKAMSIPMWV DNVQCPKGPD | |
| 901 TLWQCPSSPW EKRLARPSEE TWITCDNKMR LQEGPTSCSG RVEIWHGGSW GTVCDDSWDL | |
| 961 NDAQVVCQQL GCGPALKAFK EAEFGQGTGP IWLNEVKCKG NESSLWDCPA RRWGHSECGH | |
| 1021 KEDAAVNCTA QKISTHKTPQ KATTGRSFLI AFGILGVVLL AIFVALFLTQ KRRQRQRLTV | |
| 1081 SSRGENLVHQ IQYREMNSCL NADDLDLMNS SGGHSEAH | |
| 1 M S K L R M V L L E D S G S A D V R R H | SEQ ID NO: 43 and 44 |

-continued

| SEQUENCE | ID NO |
|---|---|

```
   1 ATGAGCAAACTCAGAATGGTGCTACTTGAAGACTCTGGATCTGCTGACGTCAGAAGACAT

  21 F  V  N  L  S  P  F  T  I  A  V  V  L  L  L  R  A  C  F  V
  61 TTTGTCAACTTGAGTCCCTTCACTATTGCTGTGGTCTTACTTCTCCGTGCCTGTTTTGTC

  41 T  S  S  L  G  G  T  T  K  E  L  R  L  V  D  G  E  N  K  C
 121 ACCAGTTCTCTTGGAGGAACAACCAAGGAGCTGAGGCTAGTGGATGGTGAAAACAAGTGT

  61 S  G  R  V  E  V  K  I  Q  E  E  W  G  T  V  C  N  N  G  W
 181 AGTGGGAGAGTGGAAGTGAAAATCCAGGAGGAGTGGGGAACGGTGTGTAATAATGGCTGG

  81 S  M  E  A  V  S  V  I  C  N  Q  L  G  C  P  T  A  I  K  A
 241 AGCATGGAAGCAGTCTCTGTGATTTGTAACCAGCTGGGATGTCCAACTGCTATCAAAGCC

 101 T  G  W  A  N  S  S  A  G  S  G  R  I  W  M  D  H  V  S  C
 301 ACTGGATGGGCTAATTCCAGTGCAGGTTCTGGACGCATTTGGATGGATCATGTTTCTTGT

 121 R  G  N  E  S  A  L  W  D  C  K  H  D  G  W  G  K  H  S  N
 361 CGTGGGAATGAGTCAGCTCTTTGGGACTGCAAACATGATGGATGGGGAAAGCATAGTAAC

 141 C  T  H  Q  Q  D  A  G  V  T  C  S  D  G  S  D  L  E  M  R
 421 TGTACTCACCAACAAGATGCTGGAGTGACTTGCTCAGATGGATCCGATTTGGAAATGAGG

 161 L  T  N  G  G  N  M  C  S  G  R  I  E  I  K  F  Q  G  Q  W
 481 CTGACGAATGGAGGGAATATGTGTTCTGGAAGAATAGAGATCAAATTCCAAGGACAGTGG

 181 G  T  V  C  D  D  N  F  N  I  N  H  A  S  V  V  C  K  Q  L
 541 GGAACAGTGTGTGATGATAACTTCAACATCAATCATGCATCTGTGGTTTGTAAACAACTT

 201 E  C  G  S  A  V  S  F  S  G  S  A  N  F  G  E  G  S  G  P
 601 GAATGTGGAAGTGCTGTCAGTTTCTCTGGTTCAGCTAATTTTGGAGAAGGCTCTGGACCA

 221 I  W  F  D  D  L  I  C  N  G  N  E  S  A  L  W  N  C  K  H
 661 ATCTGGTTTGATGATCTTATATGCAACGGAAATGAGTCAGCTCTCTGGAACTGCAAACAT

 241 Q  G  W  G  K  H  N  C  D  H  A  E  D  A  G  V  I  C  S  K
 721 CAAGGATGGGGAAAGCATAACTGTGATCATGCTGAGGATGCTGGAGTGATTTGCTCAAAG

 261 G  A  D  L  S  L  R  L  V  D  G  V  T  E  C  S  G  R  L  E
 781 GGAGCAGATCTGAGCCTGAGACTGGTAGATGGAGTCACTGAATGTTCAGGAAGATTAGAA

 281 V  R  F  Q  G  E  W  G  T  I  C  D  D  G  W  D  S  H  D  A
 841 GTGAGATTCCAAGGAGAATGGGGGACAATATGTGATGACGGCTGGGACAGTCATGATGCT

 301 A  V  A  C  K  Q  L  G  C  P  T  A  I  T  A  I  G  R  V  N
 901 GCTGTGGCATGCAAGCAACTGGGATGTCCAACTGCTATCACCGCCATTGGTCGAGTTAAC

 321 A  S  E  G  F  G  H  I  W  L  D  S  V  S  C  Q  G  H  E  P
 961 GCCAGTGAGGGATTTGGACACATCTGGCTTGACAGTGTTTCTTGCCAGGGACATGAACCT

 341 A  V  W  Q  C  K  H  H  E  W  G  K  H  Y  C  N  H  N  E  D
1021 GCGGTCTGGCAATGTAAACACCATGAATGGGGAAAGCATTATTGCAATCACAATGAAGAT

 361 A  G  V  T  C  S  D  G  S  D  L  E  L  R  L  R  G  G  G  S
1081 GCTGGCGTAACATGTTCTGATGGATCAGATCTGGAGCTAAGACTTAGAGGTGGAGGCAGC

 381 R  C  A  G  T  V  E  V  E  I  Q  R  L  L  G  K  V  C  D  R
1141 CGCTGTGCTGGGACAGTTGAGGTGGAGATTCAGAGACTGTTAGGGAAGGTGTGTGACAGA

 401 G  W  G  L  K  E  A  D  V  V  C  R  Q  L  G  C  G  S  A  L
1201 GGCTGGGGACTGAAAGAAGCTGATGTGGTTTGCAGGCAGCTGGGATGTGGATCTGCACTC

 421 K  T  S  Y  Q  V  Y  S  K  I  Q  A  T  N  M  W  L  F  L  S
1261 AAAACATCCTATCAAGTATACTCCAAAATCCAGGCAACAAACATGTGGCTGTTTCTAAGT

 441 S  C  N  G  N  E  T  S  L  W  D  C  K  N  W  Q  W  G  G  L
1321 AGCTGTAACGGAAATGAAACTTCTCTTTGGGACTGCAAGAACTGGCAATGGGGTGGACTT

 461 T  C  D  H  Y  E  E  A  K  I  T  C  S  A  H  R  E  P  R  L
1381 ACCTGTGATCACTATGAAGAAGCCAAAATTACCTGCTCAGCCCACAGGGAACCCAGACTG

 481 V  G  G  D  I  P  C  S  G  R  V  E  V  K  H  G  D  T  W  G
1441 GTTGGAGGAGACATTCCCTGTTCTGGACGCGTTGAAGTGAAGCATGGTGACACATGGGGC

 501 S  V  C  D  S  D  F  S  L  E  A  A  S  V  L  C  R  E  L  Q
1501 TCCGTCTGTGATTCGGATTTCTCTCTGGAAGCTGCCAGCGTTCTATGCAGGGAATTACAG

 521 C  G  T  V  V  S  I  L  G  G  A  H  F  G  E  G  N  G  Q  I
```

-continued

| SEQUENCE | ID NO |
|---|---|
| 1561 TGTGGCACAGTCGTCTCTATCCTGGGGGGAGCTCACTTTGGAGAGGGAAATGGACAGATC<br><br>541 W A E E F Q C E G H E S H L S L C P V A<br>1621 TGGGCTGAAGAATTCCAGTGTGAGGGACATGAGTCCCATCTTTCACTCTGCCCAGTAGCA<br><br>561 P R P E G T C S H S R D V G V V C S R Y<br>1681 CCCCGCCCAGAAGGAACTTGTAGCCACAGCAGGGATGTTGGAGTAGTCTGCTCAAGATAC<br><br>581 T E I R L V N G K T P C E G R V E L K T<br>1741 ACAGAAATTCGCTTGGTGAATGGCAAGACCCCATGTGAGGGCAGAGTGGAGCTCAAAACG<br><br>601 L N A W G S L C N S H W D I E D A H V L<br>1801 CTTAATGCCTGGGGATCCCTCTGCAACTCTCACTGGGACATAGAAGATGCCCACGTTCTT<br><br>621 C Q Q L K C G V A L S T P G G A H F G K<br>1861 TGCCAACAACTTAAATGTGGAGTTGCCCTTTCTACCCCAGGAGGAGCACATTTTGGAAAA<br><br>641 G N G Q V W R H M F H C T G T E Q H M G<br>1921 GGAAATGGTCAGGTCTGGAGGCATATGTTTCACTGCACTGGGACTGAGCAGCACATGGGA<br><br>661 D C P V T A L G A S L C P S G Q V A S V<br>1981 GATTGTCCTGTAACTGCTCTGGGTGCTTCACTATGTCCTTCAGGGCAAGTGGCCTCTGTA<br><br>681 I C S G N Q S Q T L S S C N S S S L G P<br>2041 ATTTGCTCAGGAAACCAGTCCCAAACACTGTCCTCGTGCAATTCATCATCTCTGGGCCCA<br><br>701 T R P T I P E E S A V A C I E S G Q L R<br>2101 ACAAGGCCTACCATTCCAGAAGAAAGTGCTGTGGCCTGCATAGAGAGTGGTCAACTTCGC<br><br>721 L V N G G G R C A G R V E I Y H E G S W<br>2161 TTGGTAAATGGAGGAGGTCGCTGTGCTGGGAGAGTAGAGATTTATCATGAGGGCTCCTGG<br><br>741 G T I C D D S W D L S D A H V V C R Q L<br>2221 GGCACCATCTGTGATGACAGCTGGGACCTGAGCGATGCCCACGTGGTGTGCAGACAGCTG<br><br>761 G C G E A I N A T G S A H F G E G T G P<br>2281 GGCTGTGGAGAGGCCATTAATGCCACTGGTTCTGCTCATTTTGGAGAAGGAACAGGGCCC<br><br>781 I W L D E M K C N G K E S R I W Q C H S<br>2341 ATCTGGCTGGATGAGATGAAATGCAATGGAAAAGAATCCCGTATTTGGCAGTGCCATTCA<br><br>801 H G W G Q Q N C R H K E D A G V I C S E<br>2401 CATGGCTGGGGGCAGCAAAACTGCAGGCACAAGGAGGATGCAGGAGTTATCTGCTCAGAG<br><br>821 F M S L R L T S E A S R E A C A G R L E<br>2461 TTCATGTCTCTGAGACTGACCAGTGAAGCCAGCAGAGAGGCCTGTGCAGGGCGTCTAGAA<br><br>841 V F Y N G A W G S V G R S N M S E T T V<br>2521 GTTTTTTACAACGGAGCTTGGGGCAGTGTTGGCAGGAGTAACATGTCTGAAACCACTGTG<br><br>861 G V V C R Q L G C A D K G K I N S A S L<br>2581 GGTGTGGTGTGCAGGCAGCTGGGCTGTGCAGACAAAGGGAAAATCAACTCTGCATCTTTA<br><br>881 D K A M S I P M W V D N V Q C P K G P D<br>2641 GACAAGGCCATGTCCATTCCCATGTGGGTGGACAATGTTCAGTGTCCAAAAGGACCTGAC<br><br>901 T L W Q C P S S P W E K R L A R P S E E<br>2701 ACGCTGTGGCAGTGCCCATCATCTCCATGGGAGAAGAGACTGGCCAGGCCCTCGGAGGAG<br><br>921 T W I T C D N K M R L Q E G P T S C S G<br>2761 ACCTGGATCACATGTGACAACAAGATGAGACTACAAGAAGGACCCACTTCCTGTTCTGGA<br><br>941 R V E I W H G G S W G T V C D D S W D L<br>2821 CGTGTGGAGATCTGGCACGGAGGTTCCTGGGGGACAGTGTGTGATGACTCCTGGGACTTG<br><br>961 N D A Q V V C Q Q L G C G P A L K A F K<br>2881 AACGATGCTCAGGTGGTGTGTCAACAACTTGGCTGTGGTCCAGCTTTGAAAGCATTCAAA<br><br>981 E A E F G Q G T G P I W L N E V K C K G<br>2941 GAAGCAGAGTTTGGTCAGGGGACTGGACCCATATGGCTCAATGAAGTGAAGTGCAAAGGG<br><br>1001 N E S S L W D C P A R R W G H S E C G H<br>3001 AATGAGTCTTCCTTGTGGGATTGTCCTGCCAGACGCTGGGGCCACAGTGAGTGTGGACAC<br><br>1021 K E D A A V N C T A Q K I S T H K T P Q<br>3061 AAGGAAGACGCTGCAGTGAATTGCACAGCACAAAAAATTTCAACGCACAAAACCCCACAA<br><br>1041 K A T T G Q S F L I A F G I L G V V L L | |

-continued

| SEQUENCE | ID NO |
|---|---|
| 3121 AAAGCCACAACAGGTCAGTCATTCCTTATTGCATTCGGAATCCTTGGAGTTGTTCTCTTG | |
| 1061 A I F V A L F L T Q K R R Q R Q R L T V<br>3181 GCCATTTTCGTCGCATTATTCTTGACTCAAAAGCGAAGACAGAGACAGCGGCTTACAGTT | |
| 1081 S S R G E N L V H Q I Q Y R E M N S C L<br>3241 TCCTCAAGAGGAGAGAACTTAGTCCACCAAATTCAATACCGGGAGATGAATTCTTGCCTG | |
| 1101 N A D D L D L M N S S E N S N E S A D F<br>3301 AATGCAGATGATCTGGACCTAATGAATTCCTCAGAAAATTCCAATGAGTCAGCTGATTTC | |
| 1121 N A A E L I S V S K F L P I S G M E K E<br>3361 AATGCTGCTGAACTAATTTCTGTGTCTAAATTTCTTCCTATTTCTGGAATGGAAAAGGAG | |
| 1141 A I L R H T E K E N G N L<br>3421 GCCATTCTGAGGCACACTGAAAAGGAAAATGGGAATTTA | |
| 1 MSKLRMVLLE DSGSADVRRH FVNLSPFTIA VVLLLRACFV TSSLGGTTKE LRLVDGENKC | SEQ ID NO: 44 |
| 61 SGRVEVKIQE EWGTVCNNGW SMEAVSVICN QLGCPTAIKA TGWANSSAGS GRIWMDHVSC | |
| 121 RGNESALWDC KHDGWGKHSN CTHQQDAGVT CSDGSDLEMR LTNGGNMCSG RIEIKFQGQW | |
| 181 GTVCDDNFNI NHASVVCKQL ECGSAVSFSG SANFGEGSGP IWFDDLICNG NESALWNCKH | |
| 241 QGWGKHNCDH AEDAGVICSK GADLSLRLVD GVTECSGRLE VRFQGEWGTI CDDGWDSHDA | |
| 301 AVACKQLGCP TAITAIGRVN ASEGFGHIWL DSVSCQGHEP AVWQCKHHEW GKHYCNHNED | |
| 361 AGVTCSDGSD LELRLRGGGS RCAGTVEVEI QRLLGKVCDR GWGLKEADVV CRQLGCGSAL | |
| 421 KTSYQVYSKI QATNMWLFLS SCNGNETSLW DCKNWQWGGL TCDHYEEAKI TCSAHREPRL | |
| 481 VGGDIPCSGR VEVKHGDTWG SVCDSDFSLE AASVLCRELQ CGTVVSILGG AHFGEGNGQI | |
| 541 WAEEFQCEGH ESHLSLCPVA PRPEGTCSHS RDVGVVCSRY TEIRLVNGKT PCEGRVELKT | |
| 601 LNAWGSLCNS HWDIEDAHVL CQQLKCGVAL STPGGAHFGK GNGQVWRHMF HCTGTEQHMG | |
| 661 DCPVTALGAS LCPSGQVASV ICSGNQSQTL SSCNSSSLGP TRPTIPEESA VACIESGQLR | |
| 721 LVNGGGRCAG RVEIYHEGSW GTICDDSWDL SDAHVVCRQL GCGEAINATG SAHFGEGTGP | |
| 781 IWLDEMKCNG KESRIWQCHS HGWGQQNCRH KEDAGVICSE FMSLRLTSEA SREACAGRLE | |
| 841 VFYNGAWGSV GRSNMSETTV GVVCRQLGCA DKGKINSASL DKAMSIPMWV DNVQCPKGPD | |
| 901 TLWQCPSSPW EKRLARPSEE TWITCDNKMR LQEGPTSCSG RVEIWHGGSW GTVCDDSWDL | |
| 961 NDAQVVCQQL GCGPALKAFK EAEFGQGTGP IWLNEVKCKG NESSLWDCPA RRWGHSECGH | |
| 1021 KEDAAVNCTA QKISTHKTPQ KATTGQSFLI AFGILGVVLL AIFVALFLTQ KRRQRQRLTV | |
| 1081 SSRGENLVHQ IQYREMNSCL NADDLDLMNS SENSNESADF NAAELISVSK FLPISGMEKE | |
| 1141 AILRHTEKEN GNL | |

Example 10

Cloning and Characterization of Canine CD163 from DH82 Cells

A forward primer 5' simianCD163 (SEQ ID NO: 28) (5'-CACCGGAATGAGCAAACTCAGAATGG-3' based on human CD163) and a reverse primer HuCD163-3'Kpn (SEQ ID NO: 29) (5'-GCTCCGGTACCTAGTCCAGGTCTTCAT-CAAGGTATCTTA-3') were used to amplify CD163 cDNA from DH82 cells. Total cellular RNA was prepared from DH82 cells using the RNeasy kit. RT-PCR parameters were the same as described in Example 4. RT-PCR products were cloned directionally into the pcDNA3.1D/V5/His/TOPO vector according to the manufacturer's instruction. Several clones containing large inserts were analyzed. Several clones with large inserts were analyzed, and these fell into either the v2 or v3 splicing patterns seen in other species. The v2 variant is missing an 81-nucleotide exon (E81) relative to the v3 variant, which results in a reading frame shift and alternative carboxy terminal amino acid sequences. The canine CD163v2 cDNA from DH82 cells encodes a peptide of 1115 amino acids. When compared to the sequences in Genbank database, it is 83.9% identical to human CD163 (Genbank Z22968), 85.1% identical to pig CD163 (Genbank AJ311716), and 74.3% identical to mouse CD163 (Genbank AF274883). The nucleotide and amino acid sequences of the two splice variants found in DH82 cells are provided below (SEQ ID NOS: 45-48).

| SEQUENCE | ID NO |
|---|---|
| 1 M S K L R M V P H G N S G S A D F R R C | SEQ ID NO: 45 and 46 |
| 1 ATGAGCAAACTCAGAATGGTCCCACATGGAAACTCTGGATCTGCTGACTTTAGAAGATGT | |
| 21 F A L L C P S A V A V V S I L S T C L M | |
| 61 TTTGCCCTCTTGTGTCCCTCTGCTGTGGCTGTGGTCTCCATTCTCAGTACCTGTTTGATG | |
| 41 T N S L G R A D K E M R L T D G E D N C | |
| 121 ACCAATTCTCTTGGGAGAGCAGATAAAGAGATGAGGCTAACGGATGGTGAAGACAATTGC | |
| 61 S G R V E V K V Q E E W G T V C N N G W | |
| 181 TCCGGGAGAGTGGAAGTGAAAGTCCAGGAGGAGTGGGGAACGGTGTGTAATAATGGCTGG | |
| 81 G M D E V S V I C R Q L G C P T A I K A | |
| 241 GGCATGGATGAAGTCTCTGTGATTTGCAGGCAGCTGGGATGTCCCACTGCTATCAAAGCC | |
| 101 A G W A N S R A G S G R I W M D H V S C | |
| 301 GCTGGATGGGCCAATTCCAGGGCAGGCTCTGGACGAATCTGGATGGATCATGTTTCTTGT | |
| 121 R G N E S A L W D C K H D G W G K H N C | |
| 361 CGAGGGAATGAATCTGCTCTCTGGGACTGCAAACATGATGGATGGGGAAAGCACAACTGC | |
| 141 S H Q Q D A G V T C S D G S S L E M R L | |
| 421 AGTCATCAACAGGATGCTGGAGTAACCTGTTCAGATGGATCCAGTTTGGAGATGAGGTTG | |
| 161 M N G G N Q C S G R I E V K F Q G Q W G | |
| 481 ATGAACGGCGGAAACCAGTGTTCTGGCAGAATAGAAGTCAAGTTCCAGGGACAGTGGGGA | |
| 181 T V C D D N F N I D H A S V V C K Q L E | |
| 541 ACAGTGTGTGATGACAACTTCAACATAGATCATGCTTCTGTGGTTTGTAAACAGCTCGAA | |
| 201 C G S A V S F S G S A N F G E G S G P I | |
| 601 TGTGGAAGTGCTGTCAGTTTCTCTGGTTCAGCTAATTTTGGAGAAGGTTCTGGGCCAATC | |
| 221 W F D D L V C S G N E S A L W N C K H E | |
| 661 TGGTTTGATGATCTTGTGTGCAGTGGAAATGAGTCAGCTCTCTGGAACTGCAAGCATGAA | |
| 241 G W G K H N C D H A E D V G V I C L D G | |
| 721 GGATGGGGAAAGCATAACTGTGATCACGCTGAGGATGTTGGAGTGATTTGCTTGGATGGA | |
| 261 A D L S L R L V D G V T E C S G R L E V | |
| 781 GCAGATCTGAGCCTGAGACTGGTAGATGGAGTCACTGAATGTTCAGGAAGATTAGAAGTA | |
| 281 K F Q G E W G T V C D D G W D S N D A A | |
| 841 AAATTCCAAGGGGAATGGGGGACAGTGTGTGATGATGGCTGGGATAGTAATGATGCTGCT | |
| 301 V V C K Q L G C P T A V T A I G R V N A | |
| 901 GTGGTATGTAAACAACTGGGATGCCCAACTGCTGTCACCGCCATTGGTCGAGTTAACGCC | |
| 321 S E G S G H I W L D N L S C Q G D E S A | |
| 961 AGTGAGGGAAGTGGACACATTTGGCTTGACAATCTTTCCTGCCAAGGAGACGAATCTGCT | |
| 341 L W Q C R H H E W G K H Y C N H N E D A | |
| 1021 CTCTGGCAGTGTAGACACCATGAATGGGGAAAGCATTATTGCAATCATAATGAAGATGCT | |
| 361 G V T C S D G S D L E L R L V G G G S R | |
| 1081 GGTGTGACATGTTCTGATGGATCAGACCTGGAGCTGAGACTTGTCGGTGGAGGCAGCCGC | |
| 381 C A G T V E V E I Q K L L G K V C D R G | |
| 1141 TGTGCTGGGACAGTGGAGGTTGAAATTCAGAAACTGCTAGGGAAAGTATGTGATAGAGGC | |
| 401 W G L K E A D V V C K Q L G C G S A L K | |
| 1201 TGGGGACTGAAAGAAGCCGATGTGGTTTGCAAGCAGTTGGGATGTGGATCTGCTCTCAAA | |
| 421 T S Y Q R Y S K V K A T N T W L F L S R | |
| 1261 ACGTCCTATCAGCGTTATTCCAAAGTTAAGGCAACAAACACATGGCTGTTTTTAAGCCGC | |
| 441 C S G N E T S L W D C K N W Q W G G L S | |
| 1321 TGTAGTGGCAATGAAACTTCCCTTTGGGACTGCAAGAACTGGCAGTGGGGTGGACTGAGC | |
| 461 C D H Y E E A K V T C S A H R E P R L V | |
| 1381 TGTGATCACTATGAAGAAGCTAAAGTTACCTGCTCAGCCCACAGGGAACCCAGACTAGTT | |
| 481 G G D I P C S G R V E V K H G D T W G T | |
| 1441 GGAGGAGATATTCCCTGCTCTGGTCGTGTTGAAGTGAAACATGGTGACACATGGGGCACC | |
| 501 V C D S D F S L E A A S V L C R E L Q C | |
| 1501 GTCTGTGATTCCGACTTCTCTTTGGAAGCTGCCAGTGTGCTGTGCAGAGAGTTACAGTGT | |
| 521 G T V I S I L G G A H F G E G N G Q I W | |

-continued

| SEQUENCE | ID NO |
|---|---|
| 1561 GGCACAGTCATCTCCATCCTAGGGGGAGCTCACTTTGGAGAAGGAAATGGACAGATCTGG | |
| 541 A E E F Q C E G Q E S H L S L C S V A S<br>1621 GCTGAAGAATTCCAGTGTGAGGGGCAGGAGTCCCATCTTTCACTCTGTTCAGTAGCCTCT | |
| 561 R P D G T C S H S R D V G V V C S R Y T<br>1681 CGCCCAGATGGGACCTGTAGCCACAGCAGGGATGTTGGAGTCGTCTGCTCAAGATACACG | |
| 581 E I R L V N G Q S P C E G R V E L K I L<br>1741 GAAATCCGCTTGGTGAATGGCCAGTCCCCGTGTGAAGGAAGAGTGGAGCTCAAGATACTT | |
| 601 G N W G S L C N S H W D I E D A H V F C<br>1801 GGGAACTGGGGATCCCTCTGCAACTCTCACTGGGACATAGAAGATGCCCATGTTTTCTGT | |
| 621 Q Q L K C G V A L S I P G G A H F G K G<br>1861 CAGCAGCTCAAATGTGGAGTTGCCCTTTCTATTCCGGGAGGAGCACATTTTGGGAAAGGA | |
| 641 S G Q I W R H M F H C T G T E Q H M G D<br>1921 AGTGGTCAGATCTGGAGGCACATGTTTCACTGCACTGGGACTGAGCAGCACATGGGAGAT | |
| 661 C P V T A L G A T L C S A G Q V A S V I<br>1981 TGCCCTGTAACTGCTCTGGGCGCGACGCTGTGTTCTGCTGGGCAAGTGGCCTCTGTAATC | |
| 681 C S G N Q S Q T L S P C N S T S L D P T<br>2041 TGCTCAGGAAATCAGAGCCAGACGCTATCCCCATGCAATTCAACATCTCTGGACCCAACA | |
| 701 R S T T S E E S A V A C I A S G Q L R L<br>2101 AGATCTACCACTTCGGAAGAAAGTGCTGTTGCTTGTATTGCGAGTGGGCAACTTCGCCTG | |
| 721 V N G G G R C A G R I E V Y H E G S W G<br>2161 GTAAATGGAGGCGGTCGCTGTGCTGGGAGAATAGAGGTCTACCATGAGGGCTCCTGGGGC | |
| 741 T I C D D S W D L S D A H V V C R Q L G<br>2221 ACCATCTGTGATGACAGCTGGGACCTGAGTGATGCCCATGTGGTGTGCAGACAGCTGGGC | |
| 761 C G V A I N A T G S A H F G E G T G P I<br>2281 TGTGGAGTGGCCATTAATGCCACTGGCTCTGCTCATTTTGGGGAAGGAACAGGGCCCATC | |
| 781 W L D E V N C N G K E S H I W Q C R S H<br>2341 TGGCTGGACGAGGTGAACTGTAATGGAAAGGAATCTCATATCTGGCAATGCCGCTCACAC | |
| 801 G W G Q H N C R H K E D A G V I C S E F<br>2401 GGCTGGGGGCAACACAACTGCAGACATAAGGAGGATGCAGGAGTTATCTGCTCAGAGTTC | |
| 821 M S L R L I D E T S R D I C A G R L E V<br>2461 ATGTCTCTCAGACTGATTGATGAAACCAGCAGAGACATCTGTGCAGGGCGTCTTGAAGTT | |
| 841 F Y N G A W G S V G K S N M S A T T V E<br>2521 TTTTACAATGGAGCTTGGGGCAGCGTTGGCAAGAGTAATATGTCTGCAACCACTGTGGAG | |
| 861 V V C R Q L G C A D K G S I N P A S S D<br>2581 GTGGTATGCAGGCAACTGGGTTGTGCAGACAAGGGGAGCATCAACCCTGCATCTTCAGAC | |
| 881 K P M S R H M W V D N V Q C P K G P D T<br>2641 AAGCCCATGTCCAGGCACATGTGGGTGGACAATGTCCAGTGTCCAAAAGGACCTGACACC | |
| 901 L W Q C P S S P W K Q R V A S S S E E T<br>2701 TTATGGCAGTGCCCATCTTCTCCATGGAAACAGAGAGTGGCCAGTTCTTCAGAGGAGACC | |
| 921 W I T C A N K I R L Q E G T S N C S G R<br>2761 TGGATCACATGTGCCAACAAGATAAGACTTCAAGAAGGAACCTCTAATTGTTCTGGACGT | |
| 941 V E L W H G G S W G T V C D D S W D L E<br>2821 GTGGAGCTCTGGCACGGAGGTTCCTGGGGGACAGTGTGCGATGACTCCTGGGACCTTGAA | |
| 961 D A Q V V C R Q L G C G P A L E A L K E<br>2881 GATGCACAAGTGGTGTGTCGACAGCTGGGCTGTGGCCCAGCATTAGAAGCACTAAAAGAG | |
| 981 A A F G Q G T G P I W L N D V K C K G N<br>2941 GCAGCATTTGGTCAGGGGACTGGGCCTATATGGCTCAATGACGTGAAGTGCAAAGGGAAT | |
| 1001 E S S L W D C P A R P W G H S D C G H K<br>3001 GAGTCTTCCTTGTGGGATTGTCCTGCTAGACCCTGGGGGCACAGTGACTGTGGCCACAAG | |
| 1021 E D A A V R C S E I A M A Q R S S N P R<br>3061 GAAGATGCTGCTGTGAGGTGCTCAGAAATTGCAATGGCCCAAAGATCATCAAATCCTAGA | |
| 1041 G H S S L V A L G I F G V I L L A F L I | |

-continued

| SEQUENCE | ID NO |
|---|---|
| 3121 GGTCACTCATCCCTTGTTGCATTGGGGATCTTTGGTGTCATTCTTCTGGCCTTTCTCATC | |
| 1061 A L L L W T Q R R R Q Q Q R L T V S L R<br>3181 GCTCTCCTCTTGTGGACTCAAAGGCGAAGACAGCAACAGCGGCTTACAGTTTCCTTGAGA | |
| 1081 G E N S V H Q I Q Y R E M N S S L K A D<br>3241 GGAGAGAATTCTGTCCACCAAATTCAATACCGGGAAATGAATTCTTCCCTGAAAGCAGAT | |
| 1101 D L D V L T S S E D H F E V H<br>3301 GATCTGGACGTGCTGACTTCCTCAGAAGACCATTTTGAGGTACAC | |
| 1 MSKLRMVPHG NSGSADFRRC FALLCPSAVA VVSILSTCLM TNSLGRADKE MRLTDGEDNC | SEQ ID NO: 46 |
| 61 SGRVEVKVQE EWGTVCNNGW GMDEVSVICR QLGCPTAIKA AGWANSRAGS GRIWMDHVSC | |
| 121 RGNESALWDC KHDGWGKHNC SHQQDAGVTC SDGSSLEMRL MNGGNQCSGR IEVKFQGQWG | |
| 181 TVCDDNFNID HASVVCKQLE CGSAVSFSGS ANFGEGSGPI WFDDLVCSGN ESALWNCKHE | |
| 241 GWGKHNCDHA EDVGVICLDG ADLSLRLVDG VTECSGRLEV KFQGEWGTVC DDGWDSNDAA | |
| 301 VVCKQLGCPT AVTAIGRVNA SEGSGHIWLD NLSCQGDESA LWQCRHHEWG KHYCNHNEDA | |
| 361 GVTCSDGSDL ELRLVGGGSR CAGTVEVEIQ KLLGKVCDRG WGLKEADVVC KQLGCGSALK | |
| 421 TSYQRYSKVK ATNTWLFLSR CSGNETSLWD CKNWQWGGLS CDHYEEAKVT CSAHREPRLV | |
| 481 GGDIPCSGRV EVKHGDTWGT VCDSDFSLEA ASVLCRELQC GTVISILGGA HFGEGNGQIW | |
| 541 AEEFQCEGQE SHLSLCSVAS RPDGTCSHSR DVGVVCSRYT EIRLVNGQSP CEGRVELKIL | |
| 601 GNWGSLCNSH WDIEDAHVFC QQLKCGVALS IPGGAHFGKG SGQIWRHMFH CTGTEQHMGD | |
| 661 CPVTALGATL CSAGQVASVI CSGNQSQTLS PCNSTSLDPT RSTTSEESAV ACIASGQLRL | |
| 721 VNGGGRCAGR IEVYHEGSWG TICDDSWDLS DAHVVCRQLG CGVAINATGS AHFGEGTGPI | |
| 781 WLDEVNCNGK ESHIWQCRSH GWGQHNCRHK EDAGVICSEF MSLRLIDETS RDICAGRLEV | |
| 841 FYNGAWGSVG KSNMSATTVE VVCRQLGCAD KGSINPASSD KPMSRHMWVD NVQCPKGPDT | |
| 901 LWQCPSSPWK QRVASSSEET WITCANKIRL QEGTSNCSGR VELWHGGSWG TVCDDSWDLE | |
| 961 DAQVVCRQLG CGPALEALKE AAFGQGTGPI WLNDVKCKGN ESSLWDCPAR PWGHSDCGHK | |
| 1021 EDAAVRCSEI AMAQRSSNPR GHSSLVALGI FGVILLAFLI ALLLWTQRRR QQQRLTVSLR | |
| 1081 GENSVHQIQY REMNSSLKAD DLDVLTSSED HFEVH | |
| 1 M S K L R M V P H G N S G S A D F R R C<br>1 ATGAGCAAACTCAGAATGGTCCCACATGGAAACTCTGGATCTGCTGACTTTAGAAGATGT | SEQ ID NO: 47 |
| 21 F A L L C P S A V A V V S I L S T C L M<br>61 TTTGCCCTCTTGTGTCCCTCTGCTGTGGCTGTGGTCTCCATTCTCAGTACCTGTTTGATG | |
| 41 T N S L G R A D K E M R L T D G E D N C<br>121 ACCAATTCTCTTGGGAGAGCAGATAAAGAGATGAGGCTAACGGATGGTGAAGACAATTGC | |
| 61 S G R V E V K V Q E E W G T V C N N G W<br>181 TCCGGGAGAGTGGAAGTGAAAGTCCAGGAGGAGTGGGGAACGGTGTGTAATAATGGCTGG | |
| 81 G M D E V S V I C R Q L G C P T A I K A<br>241 GGCATGGATGAAGTCTCTGTGATTTGCAGGCAGCTGGGATGTCCCACTGCTATCAAAGCC | |
| 101 A G W A N S R A G S G R I W M D H V S C<br>301 GCTGGATGGGCCAATTCCAGGGCAGGCTCTGGACGAATCTGGATGGATCATGTTTCTTGT | |
| 121 R G N E S A L W D C K H D G W G K H N C<br>361 CGAGGGAATGAATCTGCTCTCTGGGACTGCAAACATGATGGATGGGGAAAGCACAACTGC | |
| 141 S H Q Q D A G V T C S D G S S L E M R L<br>421 AGTCATCAACAGGATGCTGGAGTAACCTGTTCAGATGGATCCAGTTTGGAGATGAGGTTG | |
| 161 M N G G N Q C S G R I E V K F Q G Q W G<br>481 ATGAACGGCGGAAACCAGTGTTCTGGCAGAATAGAAGTCAAGTTCCAGGGACAGTGGGGA | |
| 181 T V C D D N F N I D H A S V V C K Q L E<br>541 ACAGTGTGTGATGACAACTTCAACATAGATCATGCTTCTGTGGTTTGTAAACAGCTCGAA | |

-continued

| SEQUENCE | ID NO |
|---|---|
| 201 C G S A V S F S G S A N F G E G S G P I<br>601 TGTGGAAGTGCTGTCAGTTTCTCTGGTTCAGCTAATTTTGGAGAAGGTTCTGGGCCAATC<br><br>221 W F D D L V C S G N E S A L W N C K H E<br>661 TGGTTTGATGATCTTGTGTGCAGTGGAAATGAGTCAGCTCTCTGGAACTGCAAGCATGAA<br><br>241 G W G K H N C D H A E D V G V I C L D G<br>721 GGATGGGGAAAGCATAACTGTGATCACGCTGAGGATGTTGGAGTGATTTGCTTGGATGGA<br><br>261 A D L S L R L V D G V T E C S G R L E V<br>781 GCAGATCTGAGCCTGAGACTGGTAGATGGAGTCACTGAATGTTCAGGAAGATTAGAAGTA<br><br>281 K F Q G E W G T V C D D G W D S N D A A<br>841 AAATTCCAAGGGGAATGGGGGACAGTGTGTGATGATGGCTGGGATAGTAATGATGCTGCT<br><br>301 V V C K Q L G C P T A V T A I G R V N A<br>901 GTGGTATGTAAACAACTGGGATGCCCAACTGCTGTCACCGCCATTGGTCGAGTTAACGCC<br><br>321 S E G S G H I W L D N L S C Q G D E S A<br>961 AGTGAGGGAAGTGGACACATTTGGCTTGACAATCTTTCCTGCCAAGGAGACGAATCTGCT<br><br>341 L W Q C R H H E W G K H Y C N H N E D A<br>1021 CTCTGGCAGTGTAGACACCATGAATGGGGAAAGCATTATTGCAATCATAATGAAGATGCT<br><br>361 G V T C S D G S D L E L R L V G G G S R<br>1081 GGTGTGACATGTTCTGATGGATCAGACCTGGAGCTGAGACTTGTCGGTGGAGGCAGCCGC<br><br>381 C A G T V E V E I Q K L L G K V C D R G<br>1141 TGTGCTGGGACAGTGGAGGTTGAAATTCAGAAACTGCTAGGGAAAGTATGTGATAGAGGC<br><br>401 W G L K E A D V V C K Q L G C G S A L K<br>1201 TGGGGACTGAAAGAAGCCGATGTGGTTTGCAAGCAGTTGGGATGTGGATCTGCTCTCAAA<br><br>421 T S Y Q R Y S K V K A T N T W L F L S R<br>1261 ACGTCCTATCAGCGTTATTCCAAAGTTAAGGCAACAAACACATGGCTGTTTTTAAGCCGC<br><br>441 C S G N E T S L W D C K N W Q W G G L S<br>1321 TGTAGTGGCAATGAAACTTCCCTTTGGGACTGCAAGAACTGGCAGTGGGGTGGACTGAGC<br><br>461 C D H Y E E A K V T C S A H R E P R L V<br>1381 TGTGATCACTATGAAGAAGCTAAAGTTACCTGCTCAGCCCACAGGGAACCCAGACTAGTT<br><br>481 G G D I P C S G R V E V K H G D T W G T<br>1441 GGAGGAGATATTCCCTGCTCTGGTCGTGTTGAAGTGAAACATGGTGACACATGGGGCACC<br><br>501 V C D S D F S L E A A S V L C R E L Q C<br>1501 GTCTGTGATTCCGACTTCTCTTTGGAAGCTGCCAGTGTGCTGTGCAGAGAGTTACAGTGT<br><br>521 G T V I S I L G G A H F G E G N G Q I W<br>1561 GGCACAGTCATCTCCATCCTAGGGGGAGCTCACTTTGGAGAAGGAAATGGACAGATCTGG<br><br>541 A E E F Q C E G Q E S H L S L C S V A S<br>1621 GCTGAAGAATTCCAGTGTGAGGGGCAGGAGTCCCATCTTTCACTCTGTTCAGTAGCCTCT<br><br>561 R P D G T C S H S R D V G V V C S R Y T<br>1681 CGCCCAGATGGGACCTGTAGCCACAGCAGGGATGTTGGAGTCGTCTGCTCAAGATACACG<br><br>581 E I R L V N G Q S P C E G R V E L K I L<br>1741 GAAATCCGCTTGGTGAATGGCCAGTCCCCGTGTGAAGGAAGAGTGGAGCTCAAGATACTT<br><br>601 G N W G S L C N S H W D I E D A H V F C<br>1801 GGGAACTGGGGATCCCTCTGCAACTCTCACTGGGACATAGAAGATGCCCATGTTTTCTGT<br><br>621 Q Q L K C G V A L S I P G G A H F G K G<br>1861 CAGCAGCTCAAATGTGGAGTTGCCCTTTCTATTCCGGGAGGAGCACATTTTGGGAAAGGA<br><br>641 S G Q I W R H M F H C T G T E Q H M G D<br>1921 AGTGGTCAGATCTGGAGGCACATGTTTCACTGCACTGGGACTGAGCAGCACATGGGAGAT<br><br>661 C P V T A L G A T L C S A G Q V A S V I<br>1981 TGCCCTGTAACTGCTCTGGGCGCGACGCTGTGTTCTGCTGGGCAAGTGGCCTCTGTAATC<br><br>681 C S G N Q S Q T L S P C N S T S L D P T<br>2041 TGCTCAGGAAATCAGAGCCAGACGCTATCCCCATGCAATTCAACATCTCTGGACCCAACA<br><br>701 R S T T S E E S A V A C I A S G Q L R L<br>2101 AGATCTACCACTTCGGAAGAAAGTGCTGTTGCTTGTATTGCGAGTGGGCAACTTCGCCTG | |

-continued

| SEQUENCE | ID NO |
|---|---|
| 721 V N G G G R C A G R I E V Y H E G S W G<br>2161 GTAAATGGAGGCGGTCGCTGTGCTGGGAGAATAGAGGTCTACCATGAGGGCTCCTGGGGC | |
| 741 T I C D D S W D L S D A H V V C R Q L G<br>2221 ACCATCTGTGATGACAGCTGGGACCTGAGTGATGCCCATGTGGTGTGCAGACAGCTGGGC | |
| 761 C G V A I N A T G S A H F G E G T G P I<br>2281 TGTGGAGTGGCCATTAATGCCACTGGCTCTGCTCATTTTGGGGAAGGAACAGGGCCCATC | |
| 781 W L D E V E C N G K E S H I W Q C R S H<br>2341 TGGCTGGACGAGGTGAACTGTAATGGAAAGGAATCTCATATCTGGCAATGCCGCTCACAC | |
| 801 G W G Q H N C R H K E D A G V I C S E F<br>2401 GGCTGGGGGCAACACAACTGCAGACATAAGGAGGATGCAGGAGTTATCTGCTCAGAGTTC | |
| 821 M S L R L I D E T S R D I C A G R L E V<br>2461 ATGTCTCTCAGACTGATTGATGAAACCAGCAGAGACATCTGTGCAGGGCGTCTTGAAGTT | |
| 841 F Y N G A W G S V G K S N M S A T T V E<br>2521 TTTTACAATGGAGCTTGGGGCAGCGTTGGCAAGAGTAATATGTCTGCAACCACTGTGGAG | |
| 861 V V C R Q L G C A D K G S I N P A S S D<br>2581 GTGGTATGCAGGCAACTGGGTTGTGCAGACAAGGGGAGCATCAACCCTGCATCTTCAGAC | |
| 881 K P M S R H M W V D N V Q C P K G P D T<br>2641 AAGCCCATGTCCAGGCACATGTGGGTGGACAATGTCCAGTGTCCAAAAGGACCTGACACC | |
| 901 L W Q C P S S P W K Q R V A S S S E E T<br>2701 TTATGGCAGTGCCCATCTTCTCCATGGAAACAGAGAGTGGCCAGTTCTTCAGAGGAGACC | |
| 921 W I T C A N K I R L Q E G T S N C S G R<br>2761 TGGATCACATGTGCCAACAAGATAAGACTTCAAGAAGGAACCTCTAATTGTTCTGGACGT | |
| 941 V E L W H G G S W G T V C D D S W D L E<br>2821 GTGGAGCTCTGGCACGGAGGTTCCTGGGGGACAGTGTGCGATGACTCCTGGGACCTTGAA | |
| 961 D A Q V V C R Q L G C G P A L E A L K E<br>2881 GATGCACAAGTGGTGTGTCGACAGCTGGGCTGTGGCCCAGCATTAGAAGCACTAAAAGAG | |
| 981 A A F G Q G T G P I W L N D V K C K G N<br>2941 GCAGCATTTGGTCAGGGGACTGGGCCTATATGGCTCAATGACGTGAAGTGCAAAGGGAAT | |
| 1001 E S S L W D C P A R P W G H S D C G H K<br>3001 GAGTCTTCCTTGTGGGATTGTCCTGCTAGACCCTGGGGGCACAGTGACTGTGGCCACAAG | |
| 1021 E D A A V R C S E I A M A Q R S S N P R<br>3061 GAAGATGCTGCTGTGAGGTGCTCAGAAATTGCAATGGCCCAAAGATCATCAAATCCTAGA | |
| 1041 G H S S L V A L G I F G V I L L A F L I<br>3121 GGTCACTCATCCCTTGTTGCATTGGGGATCTTTGGTGTCATTCTTCTGGCCTTTCTCATC | |
| 1061 A L L L W T Q R R R Q Q Q R L T V S L R<br>3181 GCTCTCCTCTTGTGGACTCAAAGGCGAAGACAGCAACAGCGGCTTACAGTTTCCTTGAGA | |
| 1081 G E N S V H Q I Q Y R E M N S S L K A D<br>3241 GGAGAGAATTCTGTCCACCAAATTCAATACCGGGAAATGAATTCTTCCCTGAAAGCAGAT | |
| 1101 D L D V L T S S E Y P N E S D D F N D A<br>3301 GATCTGGACGTGCTGACTTCCTCAGAATATCCCAATGAGTCAGATGATTTTAATGATGCT | |
| 1121 G L I S V S K S L P I S G<br>3361 GGGCTAATTTCTGTGTCTAAATCTCTTCCTATTTCTGGA | |
| 1 MSKLRMVPHG NSGSADFRRC FALLCPSAVA VVSILSTCLM TNSLGRADKE MRLTDGEDNC | SEQ ID NO: 48 |
| 61 SGRVEVKVQE EWGTVCNNGW GMDEVSVICR QLGCPTAIKA AGWANSRAGS GRIWMDHVSC | |
| 121 RGNESALWDC KHDGWGKHNC SHQQDAGVTC SDGSSLEMRL MNGGNQCSGR IEVKFQGQWG | |
| 181 TVCDDNFNID HASVVCKQLE CGSAVSFSGS ANFGEGSGPI WFDDLVCSGN ESALWNCKHE | |
| 241 GWGKHNCDHA EDVGVICLDG ADLSLRLVDG VTECSGRLEV KFQGEWGTVC DDGWDSNDAA | |
| 301 VVCKQLGCPT AVTAIGRVNA SEGSGHIWLD NLSCQGDESA LWQCRHHEWG KHYCNHNEDA | |
| 361 GVTCSDGSDL ELRLVGGGSR CAGTVEVEIQ KLLGKVCDRG WGLKEADVVC KQLGCGSALK | |

-continued

| SEQUENCE | ID NO |
|---|---|
| 421 TSYQRYSKVK ATNTWLFLSR CSGNETSLWD CKNWQWGGLS CDHYEEAKVT CSAHREPRLV | |
| 481 GGDIPCSGRV EVKHGDTWGT VCDSDFSLEA ASVLCRELQC GTVISILGGA HFGEGNGQIW | |
| 541 AEEFQCEGQE SHLSLCSVAS RPDGTCSHSR DVGVVCSRYT EIRLVNGQSP CEGRVELKIL | |
| 601 GNWGSLCNSH WDIEDAHVFC QQLKCGVALS IPGGAHFGKG SGQIWRHMFH CTGTEQHMGD | |
| 661 CPVTALGATL CSAGQVASVI CSGNQSQTLS PCNSTSLDPT RSTTSEESAV ACIASGQLRL | |
| 721 VNGGGRCAGR IEVYHEGSWG TICDDSWDLS DAHVVCRQLG CGVAINATGS AHFGEGTGPI | |
| 781 WLDEVNCNGK ESHIWQCRSH GWGQHNCRHK EDAGVICSEF MSLRLIDETS RDICAGRLEV | |
| 841 FYNGAWGSVG KSNMSATTVE VVCRQLGCAD KGSINPASSD KPMSRHMWVD NVQCPKGPDT | |
| 901 LWQCPSSPWK QRVASSSEET WITCANKIRL QEGTSNCSGR VELWHGGSWG TVCDDSWDLE | |
| 961 DAQVVCRQLG CGPALEALKE AAFGQGTGPI WLNDVKCKGN ESSLWDCPAR PWGHSDCGHK | |
| 1021 EDAAVRCSEI AMAQRSSNPR GHSSLVALGI FGVILLAFLI ALLLWTQRRR QQQRLTVSLR | |
| 1081 GENSVHQIQY REMNSSLKAD DLDVLTSSEY PNESDDFNDA GLISVSKSLP ISG | |

Example 11

Various Cell Lines are Rendered Permissive to North American PRRSV Infection Following Transient Transfection with pCMV-susCD163v1

Porcine Kidney (PK032495), Norden Labs Swine Testicular (NLST-1), Norden Labs Dog Kidney (NLDK-1) were obtained from Pfizer Inc. and were grown at 37° C. and 5% $CO_2$ in growth media consisting of Dulbecco's Modified Eagle Medium (DMEM, Invitrogen catalog number 11965) supplemented with 5% fetal bovine serum (FBS), 1 mM sodium pyruvate, 2 mM L-glutamine and antibiotics. Cell lines Baby Hamster Kidney (BHK21), Norden Labs Feline Kidney (NLFK-1), and Rabbit Lung (RL) were obtained from Pfizer Inc. and were grown at 37° C. and 5% $CO_2$ in growth media consisting of Dulbecco's Modified Eagle Medium (DMEM, Invitrogen catalog number 11965) supplemented with 10% fetal bovine serum (FBS), 1 mM sodium pyruvate, 2 mM L-glutamine and antibiotics. Vero cells were obtained from Pfizer Inc. and were grown at 37° C. and 5% $CO_2$ in growth media consisting of Minimum Essential Medium Alpha (MEM, Pfizer Inc. formulation) supplemented with 10% fetal bovine serum (FBS), 2 mM L-glutamine and Gentamicin at 20 micrograms per mL. Cell culture wells (35 mm) containing approximately $1\times10^6$ cells were transfected with 2 micrograms per well of plasmid pCMV-susCD163v1, in DMEM without FBS or antibiotics, using Lipofectamine 2000 (Invitrogen catalog number 11668-027) according to the manufacturer's instructions. Cell line RL was transfected with 1.0 micrograms per well of plasmid pCMV-susCD163v1. A member of the PAM cell cDNA library without an insert, designated pPAMB (essentially and empty pSport plasmid vector), was used as a negative control plasmid. At 24 hours post transfection wells were aspirated and washed twice with DMEM/5% FBS followed by infection with North American PRRSV isolate P129. Virus was allowed to adsorb in 0.5 ml growth media for a minimum of two hours, after which additional media was added to a final volume of 2.0 ml and incubated overnight. The virus was then removed, wells washed twice with growth media, and fresh growth media added (2.0 ml per well). A time zero sample of culture fluid was immediately taken in order to determine the background level of infectious virus from the inoculum. At a minimum of 48 hours post infection cultures were screened for permissivity by removing culture fluids in order to assay viable virus, and permissive cells in the monolayer were detected by fluorescent antibody assay (FA). The FA was completed by fixing the monolayer with 80% acetone and stained with FITC-conjugated monoclonal antibody SDOW17 (Rural Technologies Inc), which is specific for the PRRSV nucleocapsid protein. Viable virus was titrated by inoculating dilutions of culture fluids onto MARC-145 cells. Table 5 shows the results of virus infection by FA and the presence of progeny virus for each cell line tested.

Failure to detect progeny virus from some cell lines may be the result of low virus titer in the cell culture fluids, below the assay's limit of detection. Permissivity of Vero cells to PRRSV infection was augmented by the expression of susCD163v1. Compared to the time zero measurement of background virus, there was nearly a two-log increase in virus titers in Vero cells transfected with pCMV-susCD163v1, whereas there was less than a one-log in titer increase in cells transfected with negative control plasmid pPAMB. All cell lines except NLDK-1 were positive by FA for permissivity to North American PRRSV isolate P129 infection after transfection with pCMV-susCD163v1.

TABLE 5

Screening of various cell lines for permissivity to NA PRRSV isolate P129 following transient transfection with pCMV-susCD163v1 or pPAMB

| | Fluorescent Antibody assay | | Progeny virus produced | |
|---|---|---|---|---|
| Transfected cell line | pCMV-susCD163v1 | pPAMB | pCMV-susCD163v1 | pPAMB |
| BHK21 | +++ | − | +++ | − |
| PK032495 | + | − | + | − |
| NKFK-1 | + | − | + | − |
| NLST-1 | + | − | − | − |
| NLDK-1 | − | − | NT | NT |

TABLE 5-continued

Screening of various cell lines for permissivity to NA PRRSV isolate P129 following transient transfection with pCMV-susCD163v1 or pPAMB

| Transfected cell line | Fluorescent Antibody assay | | Progeny virus produced | |
|---|---|---|---|---|
| | pCMV-susCD163v1 | pPAMB | pCMV-susCD163v1 | pPAMB |
| RL | + | − | − | − |
| Vero | ++ | + | ++ | + |

+++ = Highly positive
++ = Moderately positive
+ = Slightly positive
− = Not detectible
NT = Not tested

Example 12

BHK21 Cells are Rendered Permissive to European PRRSV Infection Following Transient Transfection with pCMV-susCD163v1

Cell line Baby Hamster Kidney (BHK21) was obtained from Pfizer Inc. and grown at 37° C. and 5% $CO_2$ in growth media consisting of Dulbecco's Modified Eagle Medium (DMEM, Invitrogen catalog number 11965) supplemented with 10% fetal bovine serum (FBS), 1 mM sodium pyruvate, 2 mM L-glutamine and antibiotics. Cell culture wells (35 mm) containing approximately $1\times10^6$ cells were transfected with 2 micrograms per well of plasmid pCMV-susCD163v1, in DMEM without FBS or antibiotics, using Lipofectamine 2000 (Invitrogen catalog number 11668-027) according to the manufacturer's instructions. At 24 hours post transfection wells were aspirated and washed twice with DMEM/5% FBS followed by infection with European PRRSV isolate 96V198. Virus was allowed to adsorb for a minimum of 2 hours. The virus was then removed, wells washed twice with growth media, and fresh growth media added (2.0 ml per well). A time zero sample of culture fluid was immediately taken in order to determine the background level of infectious virus from the inoculum. At a minimum of 48 hours post infection cultures were screened for permissivity by removing culture fluids in order to assay viable virus, and permissive cells in the monolayer were detected by fluorescent antibody assay (FA). The FA was completed by fixing the monolayer with 80% acetone and stained with FITC-conjugated monoclonal antibody SDOW17 (Rural Technologies Inc), which is specific for the PRRSV nucleocapsid protein. Viable virus was titrated by inoculating dilutions of culture fluids onto MARC-145 cells. As a result of the transient transfection of BKH21 with pCMV-susCD163v1, cells were rendered permissive to European PRRSV isolate 96V198 infection and yielded progeny virus.

Example 13

CD163 Genes from Multiple Animal Species Render BHK21 Cells Permissive to PRRS Virus Infection BHK21 cells grown in DMEM (Invitrogen catalog number 11965) supplemented with 10% fetal bovine serum, 1 mM sodium pyruvate, and antibiotics, were used in transient transfection experiments. Before transfection cells were washed once with OptiMEM (Invitrogen) without serum or other additives. Lipofectamine 2000 (Invitrogen) was used in all transfection experiments according to the protocol provided by the manufacturer. The transfection mixture consisted of 10 microliters of Lipofectamine 2000 and 2-3 micrograms of DNA per 35 mm well. After overnight incubation, transfection medium was removed and cells were infected with PRRSV isolate P129. Infection was allowed to progress for 24-48 hours, when cells were fixed with 80% acetone and stained with monoclonal antibody SDOW17 conjugated with FITC (Rural Technology Inc., Brookings, S. Dak.). Staining of the nucleocapsid protein was visualized under a fluorescence microscope. Table 6. Transient transfection of BHK21 cells with various CD163 genes renders them permissive to PRRS virus infection

TABLE 6

| Plasmid backbone | CD163 gene | PRRSV infection (FA) |
|---|---|---|
| pCMV-Script | Swine CD163v1 | +++ |
| pRSV-Script | Swine CD163v1 | +++ |
| pcDNA3.1D | Swine CD163v2 | ++ |
| pcDNA3.1D | Human CD163v2 | ++ |
| pcDNA3.1D | Mouse CD163v3 | + |
| pcDNA3.1D | African green monkey (MARC-145 cell) CD163v2 | +++ |
| pcDNA3.1D | Vero cells CD163v7 | +++ |
| pcDNA3.1D | DH82 cell CD163v2 | +++ |

+++ = Highly positive
++ = Moderately positive
+ = Slightly positive

Example 14

Generation of PRRSV-Permissive BHK21 Stable Cell Lines Using pCMV-susCD163v1

BHK-21 cells were grown in Dulbecco's Modified Eagle Media (DMEM) supplemented with 10% fetal bovine serum, 1 mM sodium pyruvate, and antibiotics. For transfection, cells were seeded at approximately 90% confluency in 6 well plates and incubated over night at 37° C. in 5% $CO_2$. Cells were transfected with pCMV-susCD163v1 DNA using Lipofectamine 2000 (Invitrogen) according to the manufacturer's instructions. One day after transfection the cells were trypsinized and re-seeded in 96 well plates in a dilution series. To select for stable transfectants, the media was supplemented with 1 mg/ml Geneticin (G418 sulfate, Invitrogen catalog number 10131-027) from this point forward. Medium was changed every 3-5 days. Plates were cultured until those wells with colonies derived from single cells reached confluency, at which point the plates were trypsinized and seeded into duplicate 96 well plates. One of the duplicate 96 well plates was infected with PRRSV isolate P129 and clones permissive to infection were identified by staining with FITC conjugated monoclonal antibody SDOW17. Positive clones were then expanded from the second duplicate plate. To ensure homogeneity the positive cultures were single-cell cloned by limiting dilution. At each cloning the subclones that displayed robust growth and high PRRSV permissivity were chosen for expansion. Three clones designated BHK/CMV/v1 #3, BHK/CMV/v1 #5, and BHK/CMV/v1 #12 (FIG. 6) were selected. These cell lines have maintained the permissive phenotype through 20 passages.

Example 15

Generation of PRRSV-Permissive BHK21 Stable Cell Lines Using pRSV-susCD163v1

Figure 7:
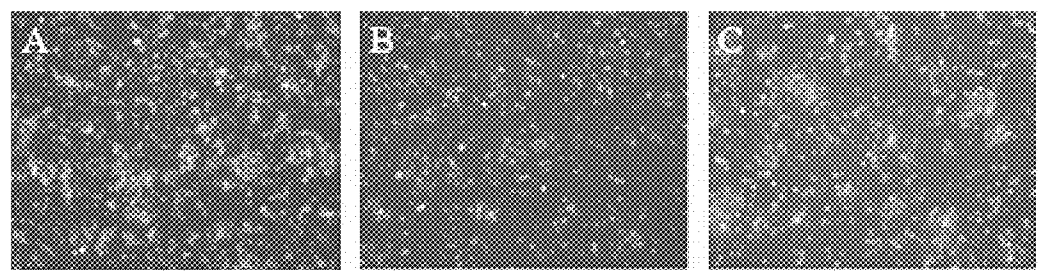
FIG. 7 Three BHK/RSV/v1 cell lines, #2, #3, and #4 were infected with PRRSV isolate P129 and stained with SDOW17-FITC. Panel A shows BHK/RSV/v1 clone #2. Panel B shows BHK/RSV/v1 clone #3. Panel C shows BHK/RSV/v1 clone #4.

BHK-21 cells were cultured as described in Example 14. BHK-21 cells were transfected with pRSVsusCD163v1 using Lipofectamine 2000 as described in Example 14. Cloning of transfected cells and screening for permissive clones was performed essentially as described in Example 14. From the original cloning 3 single cell clones were identified as permissive and were subsequently recloned two more times to ensure homogeneity and to attempt to isolate subclones of higher permissivity (see FIG. 7). The resulting cell lines were named BHK/RSV/v1, #2, #3, and #4. All of these clones have maintained the permissive phenotype through the highest passage tested (passage 11 for clone #2, passage 7 for clone #3, and passage 5 for clone #4).

Example 16

Generation of PRRSV-Permissive Feline Kidney Stable Cell Lines Using pCMV-susCD163v1

Parental Norden Labs Feline Kidney (NLFK) cells were grown at 37 degrees C. and 5% $CO_2$ in Dulbecco's Modified Eagle Medium (Invitrogen catalog number 11965-092) supplemented with 10% fetal bovine serum, 1 mM sodium pyruvate, and antibiotics. Several 35 mm wells containing approximately $2\times10^6$ cells each were transfected with 4 micrograms per well of pCMV-susCD163v1, in OptiMEM, using Lipofectamine 2000 (Invitrogen catalog number 11668-027) according to the manufacturer's instructions. After overnight incubation, cells were removed from the substrate using Accutase (Innovative Cell Technologies, catalog number AT104) diluted in medium, and seeded into three 96-well plates at three densities (approximately $2\times10^2$, $2\times10^3$, and $2\times10^4$ cells per well). The cells were allowed to settle overnight at 37 degrees C. before beginning selection of stable transformants. The next morning medium was replaced with 100 microliters/well fresh medium containing 500 micrograms/ml Geneticin (G418 sulfate, Invitrogen catalog number 10131-027) to select for cells expressing the neomycin resistance gene. Medium was changed every 2 or 3 days to maintain Geneticin potency. After 19 days of selection, the 96-well plate with the lowest initial cell density (approximately 200 cells/well) yielded 70 empty wells and 26 wells with one or more colonies of G418-resistant cells (calculated number of resistant cells/well is 0.3, using the Poisson distribution). These 26 wells were split into duplicate wells and allowed to settle overnight. One set of wells was infected with PRRSV isolate P129, incubated for 24 hours, then fixed with 80% acetone and stained with FITC-conjugated monoclonal antibody SDOW17 (Rural Technologies Inc), which is specific for PRRSV nucleocapsid. Of the 26 clones, 8 contained some cells that were infected by PRRSV. One of these, designated "NLFK-CMV-susCD163v1-G4", was clearly more permissive than the others with nearly 100% of the cells staining positive for viral antigen.

Figure 8:
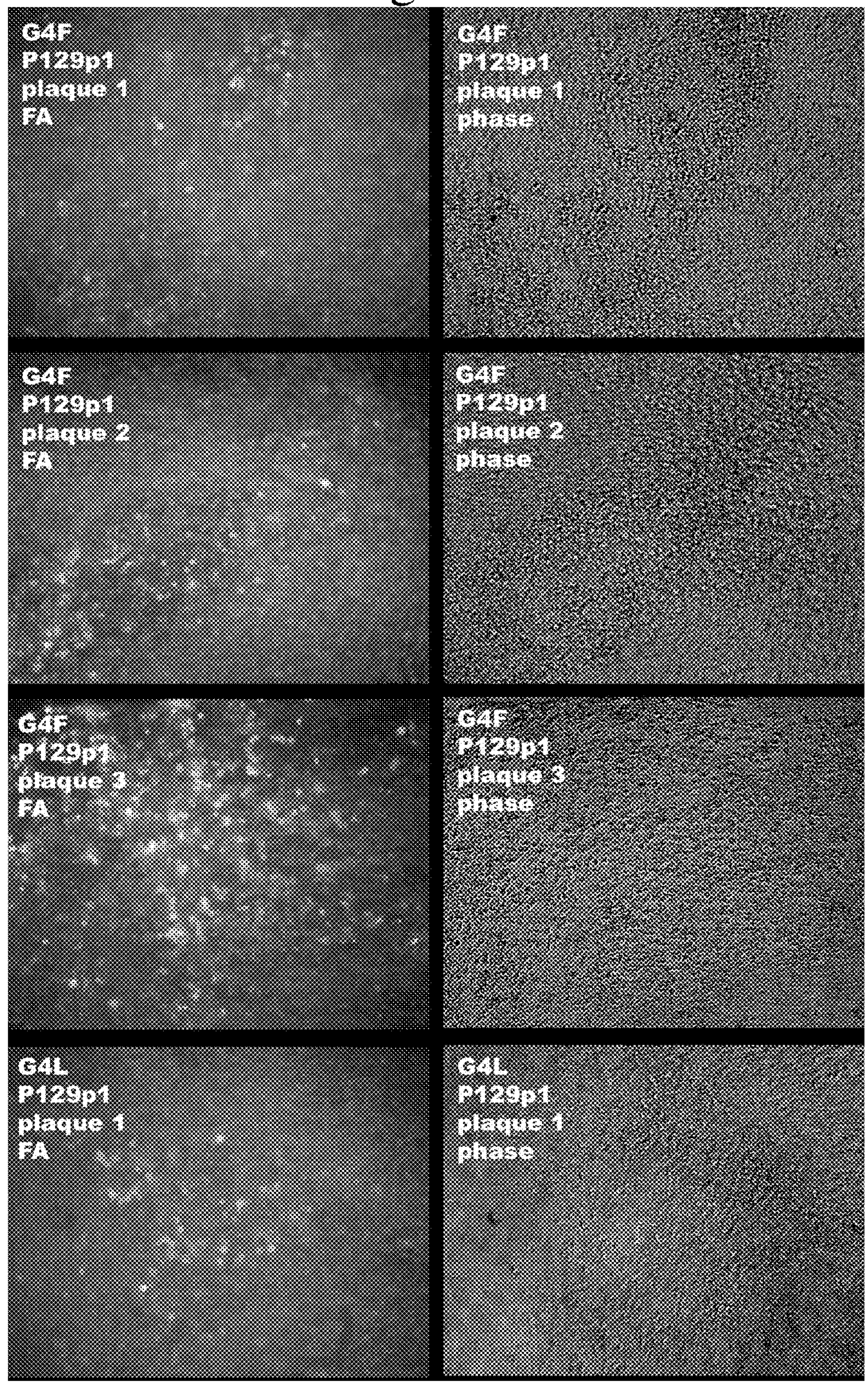
FIG. 8 Feline kidney cell lines stably expressing porcine CD163v1, showing PRRSV plaques. Cell lines NLFK-CMV-susCD163v1-G4F and NLFK-CMV-susCD163v1-G4L, both at passage 4, were infected with the P129 isolate of North American PRRSV and incubated for 6 days. Monolayers were fixed with 80% acetone and stained with monoclonal antibody SDOW17-FITC. Phase contrast microscopy (right) shows localized regions of viral CPE (plaques), while FA detection (left) shows co-localized viral nucleocapsid antigen.

By cell passage number 5, there was some evidence of phenotypic heterogeneity in the NLFK-CMV-susCD163v1-G4 cell line. Therefore, the cells were single-cell cloned by limiting dilution in G418-containing medium, starting with frozen stocks of NLFK-CMV-susCD163v1-G4 passage 4. Twelve such clones ("A"-"L") were expanded for study. Of these, clones NLFK-CMV-susCD163v1-G4F and NLFK-CMV-susCD163v1-G4L were notable for their ability to form discrete plaques (localized areas of CPE) when infected with PRRSV isolate P129 (see FIG. 8).

Example 17

Generation of PRRSV-Permissive Feline Kidney Stable Cell Lines Using pRSV-susCD163v1

Figure 9:
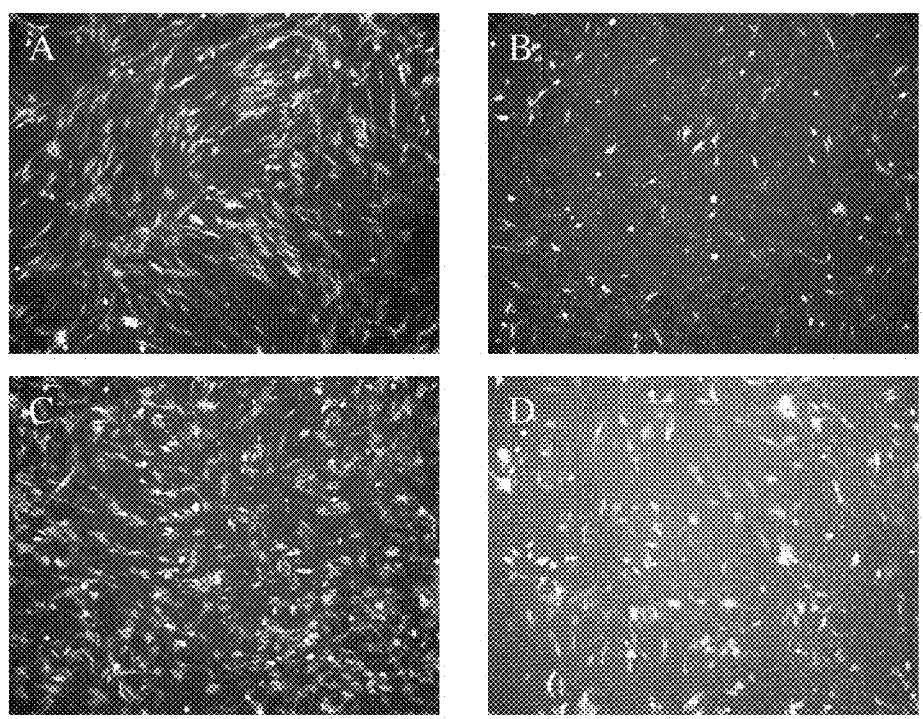
FIG. 9 Four FK/RSV/v1 cell lines, #1, #2, #3, and #4 were infected with PRRSV isolate P129 and stained with monoclonal antibody SDOW17-FITC. Panel A shows FK/RSVv1 #1 cell clone. Panel B shows FK/RSV/v1 clone #2. Panel C shows FK/RSV/v1 clone #3. Panel D shows FK/RSV/v1 #4.

Norden Labs Feline Kidney (NLFK) cells were grown at 37° C. and 5% $CO_2$ in Minimal Essential Medium Alpha Medium (Invitrogen catalog number 12571-071) supplemented with 10% fetal bovine serum and antibiotics. NLFK cells were seeded in 6 well plates at approximately 90% confluency and allowed to attach overnight. The cells were then transfected with plasmid pRSV-susCD163v1 using Lipofectamine 2000 (Invitrogen) following the manufacturer's instructions. After 24 hours the cells were cloned as described in Example 14. Screening for PRRSV permissive cell clones was performed as described in Example 14. Four clones were selected from the screening and were single cell cloned by limiting dilution two more times. Four clones named FK/RSV/v1 #1, FK/RSV/v1 #2, FK/RSV/v1 #3, and FK/RSV/v1 #4 were selected. These cell lines have maintained the PRRSV permissive phenotype through at least 8 passages (see FIG. 9).

Example 18

Generation of PRRSV-Permissive Porcine Kidney Stable Cell Lines Using pCMV-susCD163v1

Figure 10:
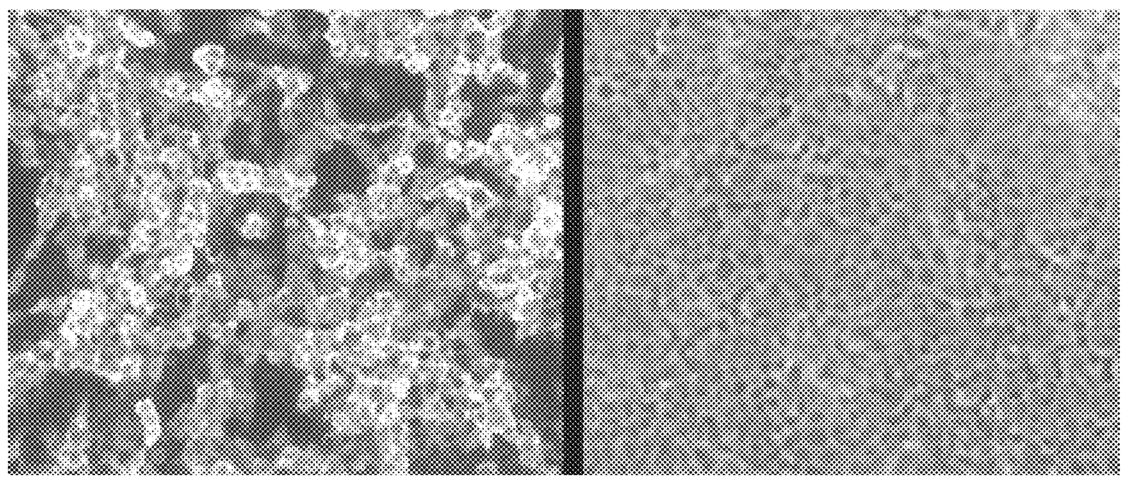
FIG. 10 PK-CMV-susCD163v1-A10 cells at passage 19, infected with PRRSV isolate P129. Left: The monolayer was fixed with 80% acetone and stained with FITC-conjugated monoclonal antibody SDOW17 (Rural Technologies Inc), which is specific for PRRSV nucleocapsid. Right: The same well under bright field illumination, showing cell distribution.

Parental Porcine Kidney (PK032495) cells were obtained from Pfizer Inc. and were grown at 37 degrees C. and 5% $CO_2$ in growth media consisting of Dulbecco's Modified Eagle Medium (DMEM, Invitrogen catalog number 11965) supplemented with 5% fetal bovine serum (FBS), 1 mM sodium pyruvate, 2 mM L-glutamine and antibiotics. Tissue culture wells (35 mm) containing approximately $1\times10^6$ cells each were transfected with 2 micrograms per well of plasmid pCMV-susCD163v1, in DMEM without FBS or antibiotics, using Lipofectamine 2000 (Invitrogen catalog number 11668-027) according to the manufacturer's instructions. After overnight incubation, cells were washed with PBS and removed from the substrate using Accutase (Innovative Cells Technologies, catalog number AT104) and diluted in growth medium containing Geneticin (G418 sulfate, Invitrogen catalog number 10131-027) at 1.0 milligram per ml and seeded into 96-well plates at various densities to ensure recovery of single cell clones after Geneticin selection. Throughout Geneticin selection, media was changed approximately every 3 to 5 days. After selection, wells containing single cell clones were expanded into duplicate 96-well plates and allowed to incubate until 100% confluency was achieved. One set of wells was screened for PRRSV-permissivity by infecting with PRRSV isolate P129 for a minimum of 48 hours. Eleven clones were found to be permissive for PRRSV. One of these, designated "PK-CMV-susCD163v1-A10", clearly retained the permissive phenotype after numerous passages (see FIG. 10).

Example 19

Generation of PRRSV-Permissive BHK21 Stable Cell Lines Using pCMVScript-susCD163v2

Figure 11:
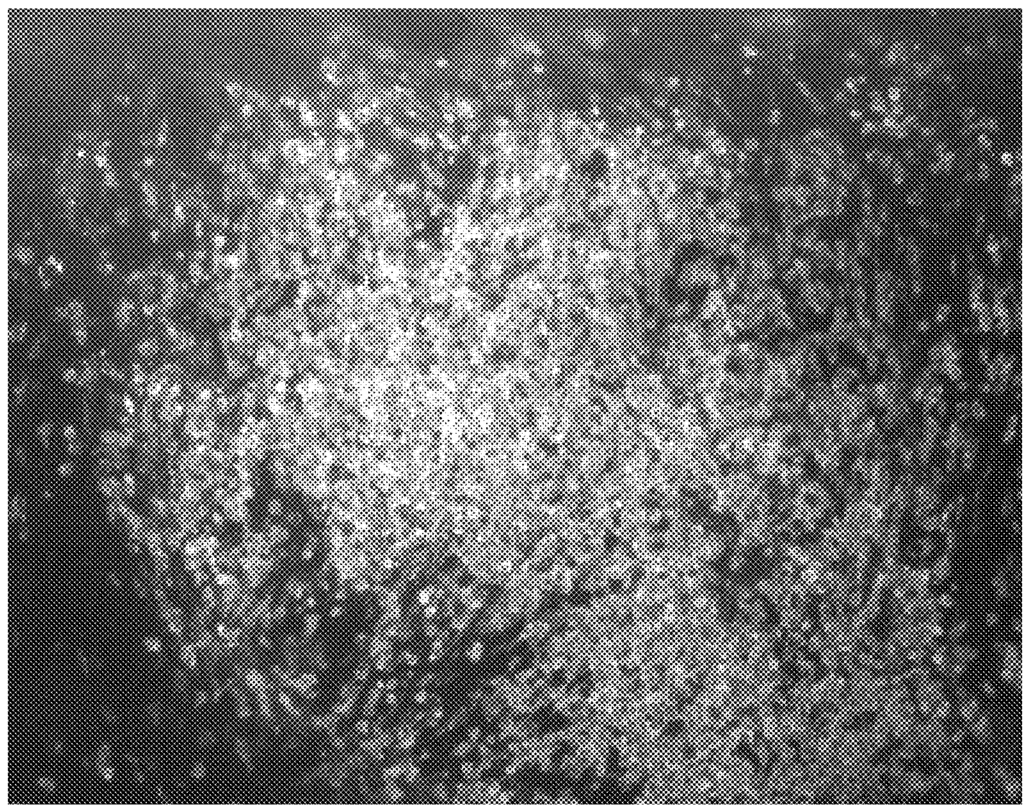
FIG. 11 BHK-CMVScript-susCD163v2-A9 at passage 17 infected with PRRSV isolate P129. The monolayer was fixed with 80% acetone and stained with FITC-conjugated monoclonal antibody SDOW17 (Rural Technologies Inc), which is specific for PRRSV nucleocapsid.

Parental Baby Hamster Kidney (BHK21) cells were obtained from Pfizer Inc. and were grown at 37 degrees C. and 5% $CO_2$ in growth media consisting of Dulbecco's Modified Eagle Medium (DMEM, Invitrogen catalog number 11965) supplemented with 10% fetal bovine serum (FBS), 1 mM sodium pyruvate, 2 mM L-glutamine and antibiotics. Tissue culture wells (35 mm) containing approximately $1\times10^6$ cells each were transfected with 2 micrograms per well of pCMVScript-susCD163v2, in DMEM without FBS or antibiotics, using Lipofectamine 2000 (Invitrogen catalog number 11668-027) according to the manufacturer's instructions. After overnight incubation, cells were washed with PBS and removed from the substrate using Accutase (Innovative Cells Technologies, catalog number AT104) and diluted in growth medium containing Geneticin (G418 sulfate, Invitrogen catalog number 10131-027) at 1.0 milligram per ml and seeded into 96-well plates at various densities to ensure recovery of single cell clones after Geneticin selection. Throughout Geneticin selection, media was changed approximately every 3 to 5 days. After selection, wells containing single cell clones were expanded into duplicate 96-well plates and incubated until 100% confluency was achieved. One set of wells was screened for permissivity by infecting with PRRSV isolate P129 and incubating for a minimum of 48 hours. Three clones were found to be PRRSV-permissive, and one of these, designated "BHK-CMVScript-susCD163v2-A9", was chosen for further study (see FIG. 11).

Example 20

Generation of PRRSV-Permissive BHK-21 Stable Cell Lines Using pRSV-susCD163v2

Figure 12:
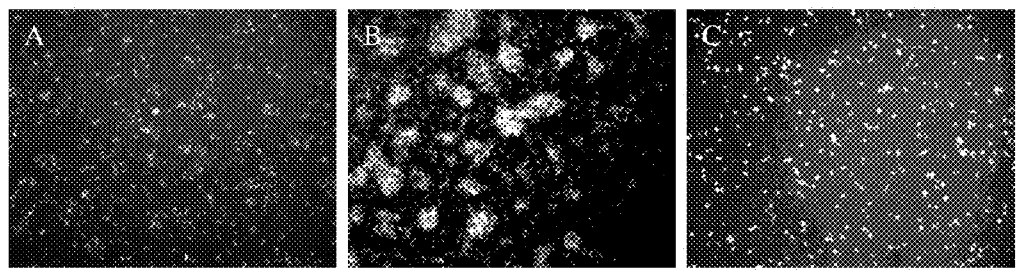
FIG. 12 Three representative examples of the BHK/RSV/v2 cell lines. The cells were infected with PRRSV isolate P129 and subsequently stained with SDOW17-FITC. Panel A shows cell line BHK/RSV/v2 #1, panel B shows cell line BHK/RSV/v2 #34, and panel C shows cell line BHK/RSV/v2 #47.

BHK-21 cells were cultured as described in Example 14. BHK-21 cells were transfected with the ligated pRSV-susCD163v2 DNA construct described in Example 5 using Lipofectamine 2000 (Invitrogen) following manufacture's instructions. Subsequent cloning and selection of PRRSV permissive cell lines was performed as described in Example 14. Of 336 single cell clones screened, 129 were positive. Several of these cell clones have been passed up to 7 times and they have maintained the PRRSV permissive phenotype (see FIG. 12). These cell lines have been named BHK/RSV/v2, followed by a numerical clone number.

Example 21

Generation of PRRSV-Permissive Porcine Kidney Stable Cell Lines Using pCMVScript-susCD163v2

Parental Porcine Kidney (PK032495) cells were obtained from Pfizer Inc. and were grown at 37 degrees C. and 5% $CO_2$ in growth media consisting of Dulbecco's Modified Eagle Medium (DMEM, Invitrogen catalog number 11965) supplemented with 5% fetal bovine serum (FBS), 1 mM sodium pyruvate, 2 mM L-glutamine and antibiotics. Tissue culture wells (35 mm) containing approximately $1\times10^6$ cells each were transfected with 2 micrograms per well of pCMVScript-susCD163v2 in DMEM without FBS or antibiotics, using Lipofectamine 2000 (Invitrogen catalog number 11668-027) according to the manufacturer's instructions. After overnight incubation, cells were washed with PBS and removed from the substrate using Accutase (Innovative Cells Technologies, catalog number AT104) and diluted in growth medium containing Geneticin (G418 sulfate, Invitrogen catalog number 10131-027) at 1.0 milligram per ml and seeded into 96-well plates at various densities to ensure recovery of single cell clones after Geneticin selection. Throughout Geneticin selection, media was changed approximately every 3 to 5 days. After selection, wells containing single cell clones were expanded into duplicate 96-well plates and incubated until 100% confluency was achieved. One set of wells was screened for permissivity by infecting with PRRSV isolate P129 and incubating for a minimum 48 hours. One clone designated "PK-CMVScript-susCD163v2-D1" showed the PRRSV-permissive phenotype.

Example 22

Generation of PRRSV-Permissive BHK21 Stable Cell Lines Using pcDNA3.1D-humCD163v2

Parental Baby Hamster Kidney (BHK21) cells were obtained from Pfizer Inc. and were grown at 37 degrees C. and 5% $CO_2$ in growth media consisting of Dulbecco's Modified Eagle Medium (DMEM, Invitrogen catalog number 11965) supplemented with 10% fetal bovine serum (FBS), 1 mM sodium pyruvate, 2 mM L-glutamine and antibiotics. Tissue culture wells (35 mm) containing approximately $1\times10^6$ cells each were transfected with 2 micrograms per well of pcDNA3.1D-humCD163v2, in DMEM without FBS or antibiotics, using Lipofectamine 2000 (Invitrogen catalog number 11668-027) according to the manufacturer's instructions. After overnight incubation, cells were washed with PBS and removed from the substrate using Accutase (Innovative Cells Technologies, catalog number AT104) and diluted in growth medium containing Geneticin (G418 sulfate, Invitrogen catalog number 10131-027) at 1.0 milligram per ml and seeded into 96-well plates at various densities to ensure recovery of single cell clones after Geneticin selection. Throughout Geneticin selection, media was changed approximately every 3 to 5 days. After selection, wells containing single cell clones were expanded into duplicate 96-well plates and incubated until 100% confluency was achieved. One set of wells was screened for permissivity by infecting with PRRSV isolate P129, incubated for a minimum 48 hours. Seven candidate clones were found to be PRRSV-permissive. There was some evidence of phenotypic heterogeneity in each of the seven candidate clones, likely because they were not clonal. Therefore, the candidate clones were single-cell cloned by limiting dilution in G418 containing medium. One single cell clone with clear PRRS-permissivity was obtained and designated BHK-cDNA3.1D-humCD163v2-H9.

Example 23

Generation of PRRSV-Permissive Feline Kidney Stable Cell Lines Using pcDNA3.1D-humCD163v2

Figure 13:
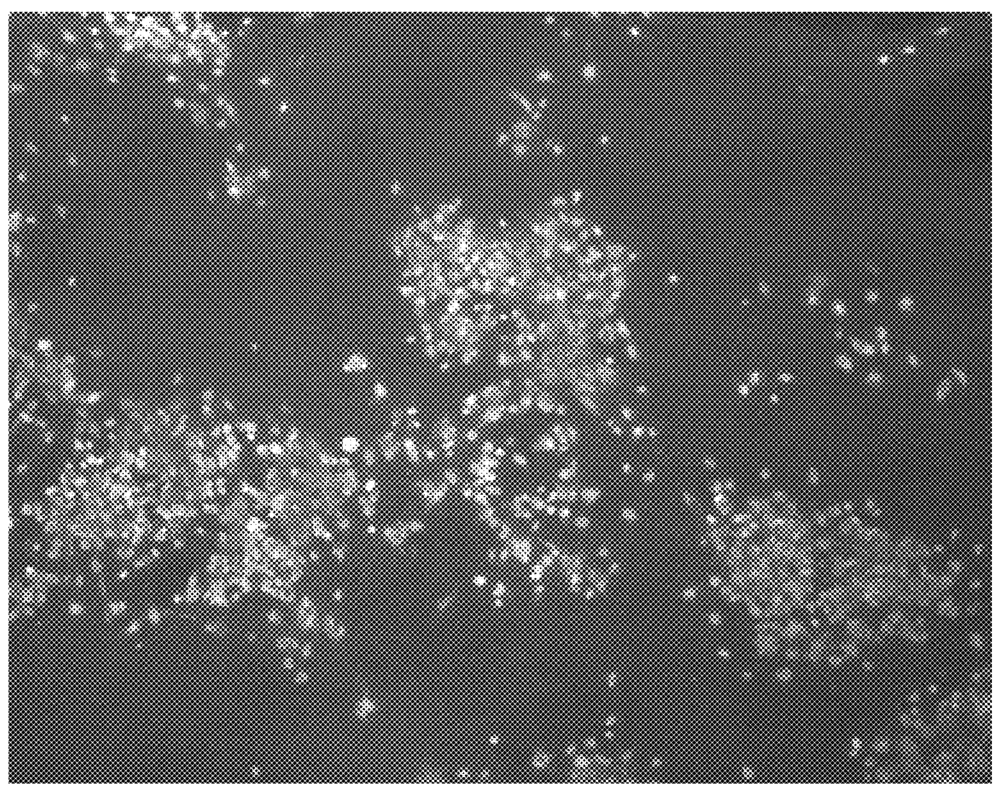
FIG. 13 FK-cDNA3.1D-humCD163v2-A6 at passage 15 infected with PRRSV isolate P129. The monolayer was then fixed with 80% acetone and stained with FITC-conjugated monoclonal antibody SDOW17 (Rural Technologies Inc), which is specific for PRRSV nucleocapsid.
Figure 21A:
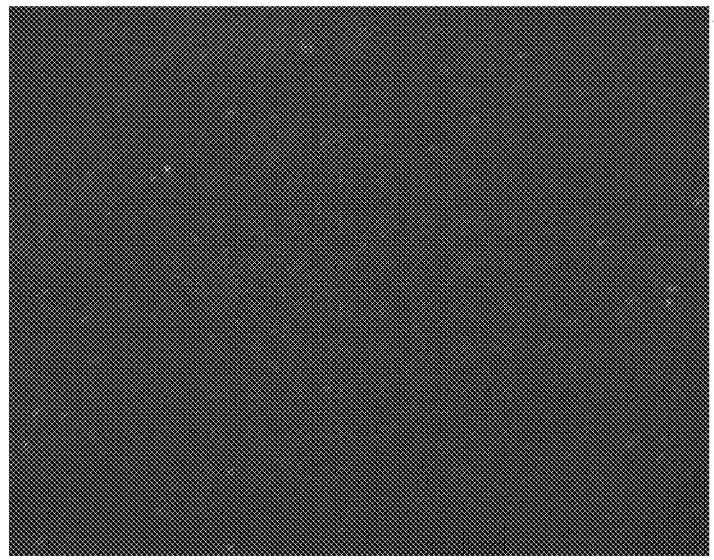
FIG. 21. NLFK parent cells and one subclone of FK-cDNA3.1D-humCD163v2-A6 were examined for the CD163 expression. Cells were fixed in 80% acetone and reacted with Goat anti-human CD163 (R&D System at 1:200) for one hour following by washing with PBS. For visualization, donkey anti-Goat IgG conjugated with FITC (Biodesign Inc at 1:100) were used. No specific fluorescence was detected in the NLFK parent cells as shown in FIG. 21A. The majority of the FK.A6.A2 subclone showed good fluorescent staining indicating the presence of CD163 (FIG. 21B).
Figure 21B:
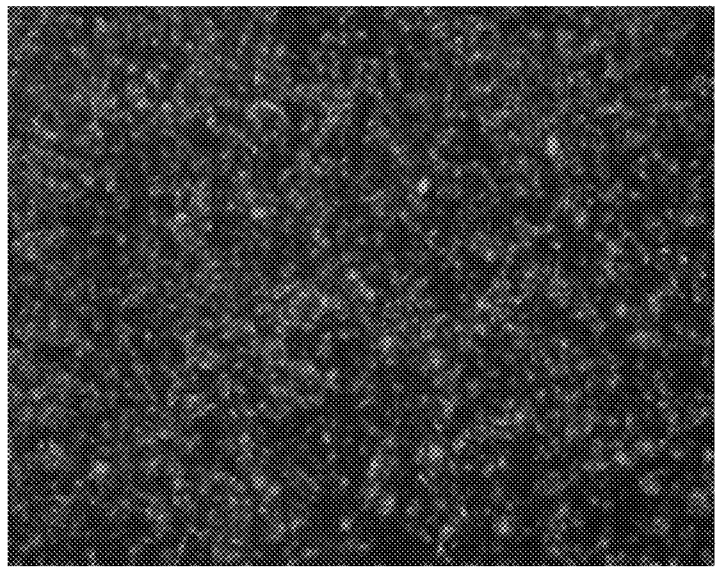

Parental Norden Labs Feline Kidney (NLFK) cells were grown at 37 degrees C. and 5% $CO_2$ in growth media consisting of Dulbecco's Modified Eagle Medium (DMEM, Invitrogen catalog number 11965) supplemented with 10% fetal bovine serum (FBS), 1 mM sodium pyruvate, 2 mM L-glutamine and antibiotics. Tissue culture wells (35 mm) containing approximately $1\times10^6$ cells each were transfected with 2 micrograms per well of pcDNA3.1D-humCD163v2 in DMEM without FBS or antibiotics, using Lipofectamine 2000 (Invitrogen catalog number 11668-027) according to the manufacturer's instructions. After overnight incubation, cells were washed with PBS, removed from the substrate using Accutase (Innovative Cells Technologies, catalog number AT104), diluted in growth medium containing Geneticin (G418 sulfate, Invitrogen catalog number 10131-027) at 500 micrograms per ml, and seeded into 96-well plates at various densities to ensure recovery of single cell clones after Geneticin selection. Throughout Geneticin selection, media was changed approximately every 3 to 5 days. After selection, wells containing single cell clones were expanded into duplicate 96-well plates and incubated until 100% confluency was achieved. One set of wells was screened for PRRSV-permissivity by infecting with PRRSV isolate P129 for a minimum 48 hours. Five clones were found to be permissive. One of these, designated "FK-cDNA3.1D-humCD163v2-A6", clearly displayed the permissive phenotype (see FIG. 13). NLFK parent cells and one subclone of FK-cDNA3.1D-humCD163v2-A6 were examined for the CD163 expression. Cells were fixed in 80% acetone and reacted with Goat anti-human CD163 (R&D System at 1:200) for one hour following by washing with PBS. For visualization, donkey anti-Goat IgG conjugated with FITC (Biodesign Inc at 1:100) were used. No specific fluorescence was detected in the NLFK parent cells as shown in FIG. 21A. The majority of the FK.A6.A2 subclone showed good fluorescent staining indicating the presence of CD163 (FIG. 21B).

Example 24

Generation of PRRSV-Permissive Porcine Kidney Stable Cell Lines Using pcDNA3.1D-humCD163v2

Parental Porcine Kidney (PK032495) cells were obtained from Pfizer Inc. and were grown at 37 degrees C. and 5% $CO_2$ in growth media consisting of Dulbecco's Modified Eagle Medium (DMEM, Invitrogen catalog number 11965) supplemented with 5% fetal bovine serum (FBS), 1 mM sodium pyruvate, 2 mM L-glutamine and antibiotics. Tissue culture wells (35 mm) containing approximately $1\times10^6$ cells each were transfected with 2 micrograms per well of pcDNA3.1D-humCD163v2, in DMEM without FBS or antibiotics, using Lipofectamine 2000 (Invitrogen catalog number 11668-027) according to the manufacturer's instructions. After overnight incubation, cells were washed with PBS, removed from the substrate using Accutase (Innovative Cells Technologies, catalog number AT104), diluted in growth medium containing Geneticin (G418 sulfate, Invitrogen catalog number 10131-027) at 1.0 milligram per ml, and seeded into 96-well plates at various densities to ensure recovery of single cell clones after Geneticin selection. Throughout Geneticin selection, media was changed approximately every 3 to 5 days. After selection, wells containing single cell clones were expanded into duplicate 96-well plates and incubated until 100% confluency was achieved. One set of wells was screened for PRRSV-permissivity by infecting with PRRSV isolate P129 for a minimum 48 hours. Two clones were found to be permissive. One of these, designated "PK-cDNA3.1D-humCD163v2-B11" clearly showed the PRRSV-permissive phenotype.

Example 25

Generation of PRRSV-Permissive Feline Kidney Stable Cell Line Using Ligated pRSV-Script MARC CD163v2

A non-cloning based procedure to generate microgram quantities of linear DNA suitable for use in generating stable cell lines expressing CD163 from an RSV promoter was developed (FIG. 4). A similar process was adapted to place simian CD163v2 from MARC-145 cells behind the RSV promoter. The procedure involves the isolation and ligation of two pieces of DNA, one containing the neomycin gene and RSV promoter cassette derived from pRSV-script, and the other containing the MARC CD163v2 coding sequence from pcDNA3.1D MARC CD163v2. Vector plasmid pRSV-Script was linearized with Hind III and Kpn I. Plasmid was first digested with Kpn I and was bunted with the Klenow fragment of *E. coli* DNA polymerase. This plasmid was then digested with Hind III immediately downstream of the RSV promoter. The pcDNA3.1D MARC CD163v2 clone was digested in the vector sequence downstream of the CD163 insert with EcoRV, and Hind III upstream of CD163. The CD163 coding sequence was liberated from the vector. For each plasmid digestion the appropriate fragments were purified from agarose gels. A large-scale ligation reaction was performed as follows. Approximately 20 μg of each DNA fragment was incubated in a volume of 600 μL with 15 units of T4 DNA ligase. The reaction was incubated at room temperature for 1 hour. Following ligation, a linear piece of DNA containing all of the appropriate elements was purified by agarose gel electrophoresis. Restriction enzyme digestion analysis was performed to confirm the authenticity of each ligated fragment. Ligation of the two DNA fragments via the cohesive Hind III termini resulted in the placement of the 5' sequences of the MARC CD163 gene downstream of the RSV promoter, allowing for directed expression of CD163 in mammalian cells. Once isolated, the purified DNA was used to transfect selected mammalian cell lines.

Norden Labs Feline Kidney (NLFK) cells were grown at 37° C. and 5% $CO_2$ in DMEM supplemented with 5% fetal bovine serum and antibiotics. NLFK cells were seeded in 6 well plates at approximately 90% confluency and allowed to attach overnight. The cells were then transfected with ligated plasmid pRSV-MARC CD163v2 using Lipofectamine 2000 following the manufacturer's instructions. After 24 hours the cells were cloned as described in Example 12. Screening for PRRSV permissive cell clones was performed as described in Example 12. One clone was positive for PRRSV infection and designated NLFK-MARC CD163 D4. This D4 clone has maintained the PRRSV permissive phenotype through 9 passages.

Example 26

Growth Kinetics of PRRSV Isolate NVSL 94-3 in Recombinant BHK-21 and NLFK Cells Stably Expressing susCD163v1 from the CMV Promoter The amounts of progeny virus produced by PRRSV-infected BHK-21 or NLFK cells stably engineered to express susCD163v1 were quantitated. Four cell lines expressing susCD163v1, BHK/CMV/susv1 #3, BHK/CMV/susv1 #5, BHK/CMV/susv1 #12, and FK/CMV/susv1 G4 were seeded at sub confluency in 6 well plates and, after overnight incubation, were infected with the NVSL 94-3 isolate of PRRSV. MARC-145 cells were included in the experiment for comparison. The cells were infected with virus at an m.o.i. of approximately 0.1. Virus was adsorbed for 60-90 minutes and was removed. Cells were washed three times with PBS to remove residual virus. One-milliliter aliquots were harvested from the cultures at 12-hour intervals starting immediately after infection and continued through 96 hrs. Fresh culture media was added to the cells at various time points to maintain a culture volume sufficient to prevent the cell monolayer from drying out. Culture supernatants were stored at −80° until all samples were collected. The amount of PRRSV present in the culture supernatants was determined by plaque assay on MARC-145 cells. FIG. 14 shows that all CD163 expressing recombinant cell lines tested were able to produce progeny PRRSV.

Example 27

Figure 15:
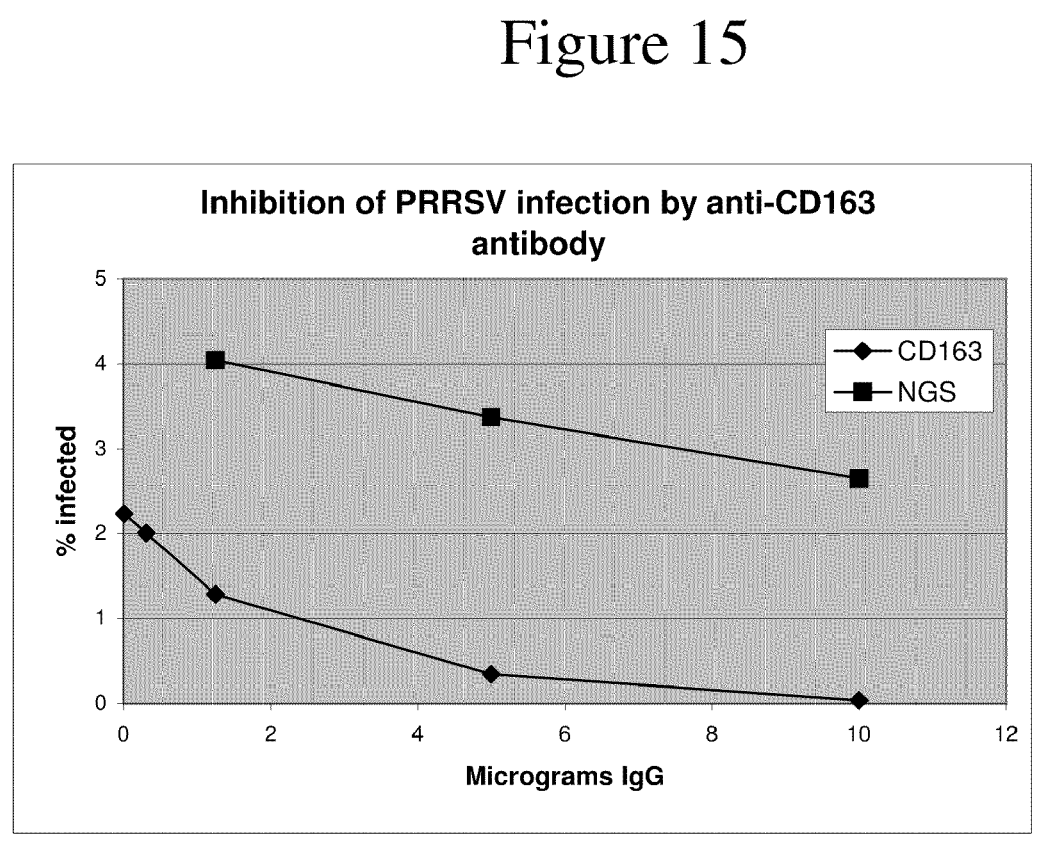

Blocking PRRSV Infection with Anti-CD163 Antibody: Transiently Transfected Cells BHK-21 cells, seeded in 24 well plates, were transiently transfected with the plasmid pcDNA3.1D-MARC-CD163v2 described in example 8, using Lipofectamine 2000 as described in example 14. After overnight incubation to allow expression of CD163, a titration of goat polyclonal antibody specific for human CD163 (R&D Systems, cat # AF1607) in PBS was added to the cells in a volume of 1004 As a control, equivalent amounts of normal goat IgG (R&D Systems, cat # AB-108-C) were used. Following a one-hour incubation at 37° C., the monolayers were infected with approximately $1\times10^7$ pfu of a recombinant P129 strain of PRRSV that expresses GFP. The cell monolayers, with anti-CD163 antibody and PRRSV, were incubated at 37° C. for one hour at which time the virus inoculum/antibody mixture was aspirated, the cell monolayer washed once with PBS, and 1 ml of growth medium added to the wells. The cells were incubated for 24 hours at 37° C. to allow PRRSV directed GFP expression. For analysis, the cells were trypsinized, resuspended in 500 μl of PBS and analyzed by flow cytometry to innumerate the PRRSV infected cells via GFP expression. For flow cytometry, uninfected BHK-21 cells were used to set the baseline for fluorescence detection, and approximately 100,000 cells were analyzed from each subsequent sample. The results of this analysis, shown in FIG. 15, show that the CD163 specific antibody was able to significantly reduce the number of infected cells when compared to cells incubated with normal goat IgG.

Example 28

Blocking PRRSV Infection by Anti CD163 Antibody: Stably Transfected Cells

Figure 16:
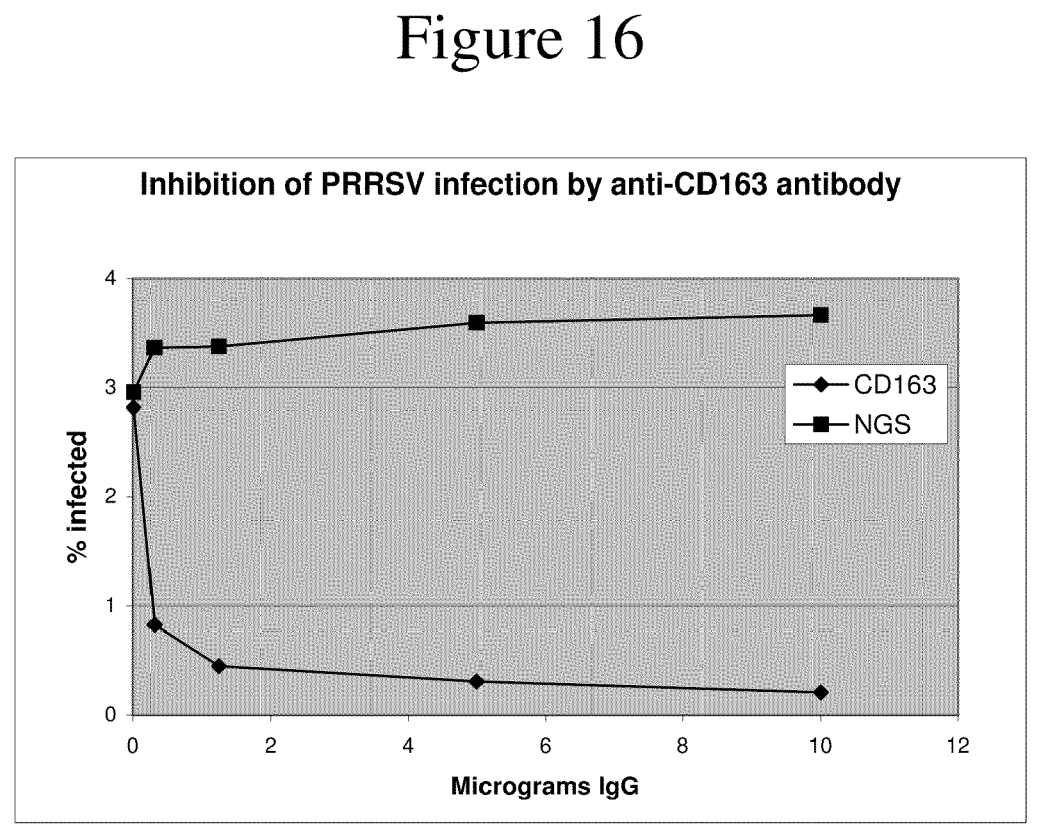

The NLFK cells that stably express human CD163 (FK-cDNA3.1D-humCD163v2-A6), described in Example 23, were seeded into 24 wells plates. After allowing the cells to attach overnight, a titration of goat polyclonal antibody specific for human CD163 (R&D Systems, cat # AF1607) in PBS was added to the cells in a volume of 100 μl. As a control, equivalent amounts of normal goat IgG (R&D Systems, cat # AB-108-C) were used. Following a one-hour incubation at 37° C., the monolayers were infected with approximately $1\times10^7$ pfu of a recombinant P129 strain of PRRSV that expresses GFP. The cell monolayers, with anti-CD163 antibody and PRRSV, were incubated at 37° C. for one hour at which time the virus inoculum/antibody mixture was aspirated, the cell monolayer washed once with PBS, and 1 ml of growth medium added to the wells. The cells were incubated for 24 hours at 37° C. to allow PRRSV directed GFP expression. For analysis, the cells were trypsinized, resuspended in 500 μl of PBS, and analyzed by flow cytometry to innumerate the PRRSV infected cells via GFP expression. Approximately 100,000 cells were analyzed from each sample. The results of this analysis, shown in FIG. 16, show that the CD163 specific antibody was able to significantly reduce the number of infected cells when compared to cells incubated with normal goat IgG.

Example 29

Generation of PRRSV-Permissive Porcine Kidney Stable Cell Lines Using pRSV-susCD163v2

Figure 18:
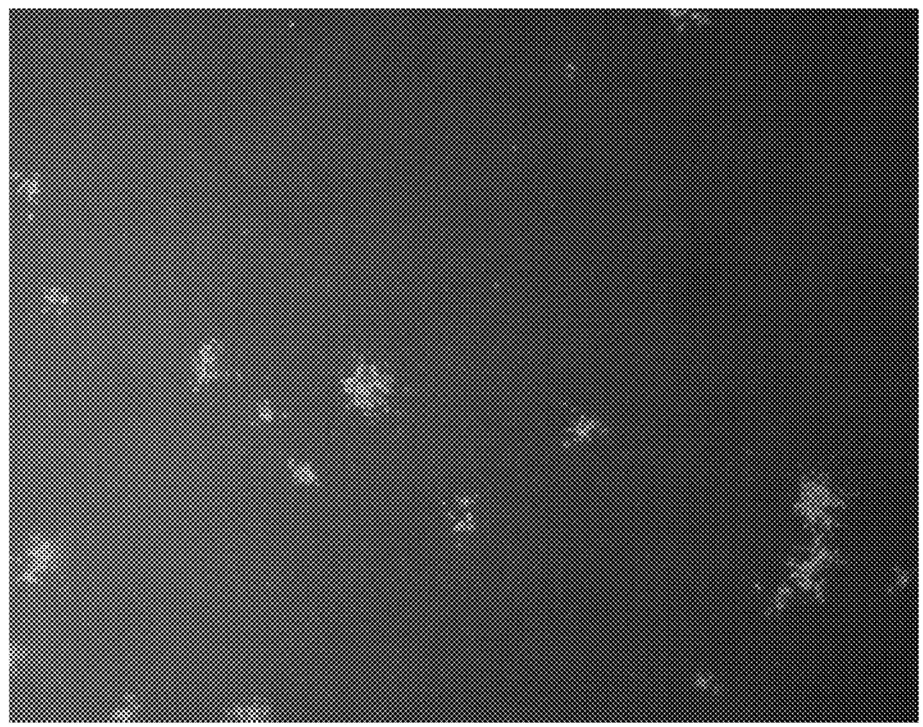
FIG. 18. PK-RSVScript-susCD163v2 #9 cells infected with PRRSV isolate P129. Undiluted supernatant from PRRSV isolate P201 infected PAMs was used to infect PK-RSVScript-susCD163v2 #9 cells. After two days of incubation the cells were fixed and stained with monoclonal antibody SDOW17 as described in Example 11.

Porcine kidney cells (PK032495) were cultured as described in Example 21. For transfection, cells were seeded in a 24 well plate at 80% confluency and allowed to recover overnight. Transfection of ligated pRSV-susCD163v2 DNA described in Example 5 was performed using Lipofectamine 2000 (Invitrogen) following the manufacturer's instructions. Subsequent cloning and selection of PRRSV permissive cells was performed essentially as described in Example 14. The initial cloning by limiting dilution failed to yield single cell derived clones, so 5 wells with PRRSV permissive cells were recloned by limiting dilution to yield clonal cell lines. 10 clones were selected for further study and one of these clones, PK-RSVScript-susCD163v2 #9 showed the ability to support foci growth of PRRSV early after infection (see FIG. 18).

Example 30

Generation of PRRSV-Permissive Feline Kidney Stable Cell Lines Using pRSV-susCD163v2

Figure 19:
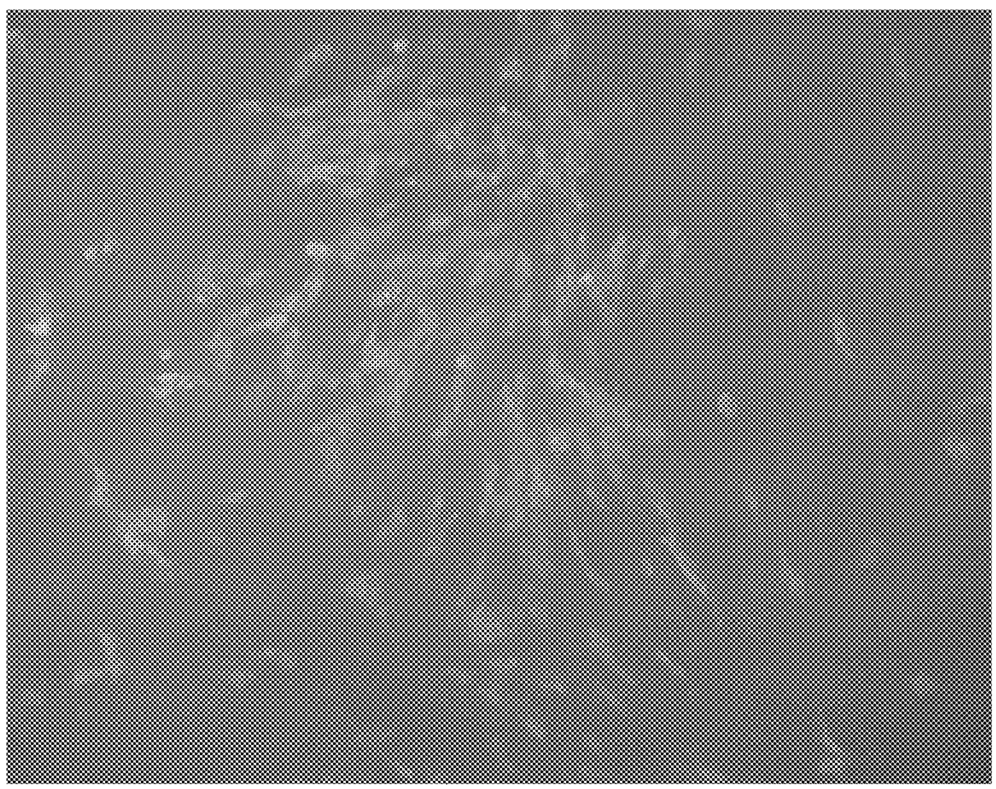
FIG. 19. FK-RSVScript-susCD163v2 #51 cells infected with PRRSV isolate P129. Undiluted supernatant from PRRSV isolate P201 infected PAMs was used to infect FK-RSVScript-susCD163v2 #51 cells. Two days post infection the cells were acetone fixed and stained with monoclonal antibody SDOW17 as described in Example 11.

NLFK feline kidney cells were cultured as described in Example 17. For transfection, cells were seeded at approximately 80% of maximal density in 24 well plates. After overnight incubation the monolayers were transfected with ligation derived RSV/susCD163v2 (see example 5) using Lipofectamine following the manufacturer's instructions. Cloning of the transfected cells and selection of PRRSV permissive cell clones was performed essentially as described in Example 14. Of the 67 cell clones tested for PRRSV permissivity, 20 were found to be positive. An example of the staining observed is shown in FIG. 19.

Example 31

Passage of PRRSV Isolate P201 in PK-RSVScript-susCD163v2 Cells

Figure 20A:
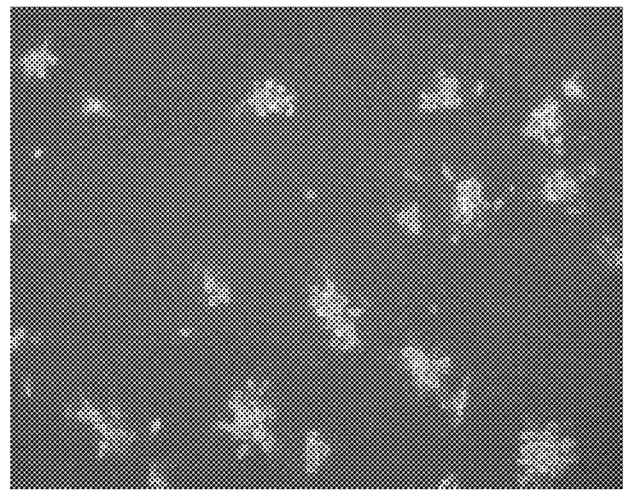
FIG. 20. Infection of PK-RSVScript-susCD163v2 clone #9 cells with PRRSV isolate P201. Panel A shows a monolayer of cells infected with PRRSV P201 at passage 1, twenty-four hours post infection. Panel B shows a monolayer of cells 2 days post infection with cell free supernatant PRRSV P201 at passage 10.
Figure 20B:
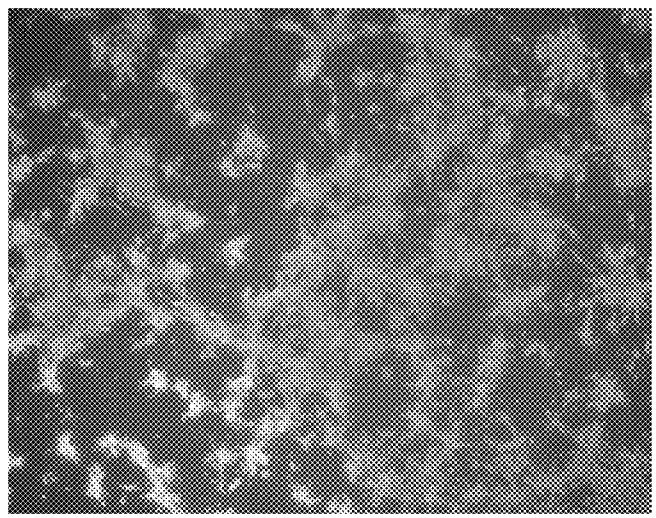

Amplification of a PRRSV clinical isolate was performed as follows. Peripheral alveolar macrophage (PAM) cells were seeded at 5.4E6 cells per 10 cm2 in a 6 well dish using OptiMEM media supplemented with 2% FBS. After 6 hours the media was aspirated and a 2 ml aliquot of serum harvested from a PRRSV infected pig was added to the cells. Following a 90 minute adsorption, the serum inoculum was removed and replaced with OptiMEM. At approximately 40 post infection the supernatant was harvested and clarified with a 10 minute centrifugation. The supernatant was directly used to infect PK-RSVScript-susCD163v2 clone #9 cells using a 6 hour adsorption. After removal of the inoculum the cells were refed with D-MEM. The P201 virus was serially passaged on the PK-RSVScript-susCD163v2 #9 cell line using alternating infected cell and cell free supernatant passes. We observed that for efficient spread of the virus, the cells should be seeded at 50-70% confluency the day before infection, using flasks of cells that were kept at sub-confluency. To follow the progression of infection, each passage was replicated in multiple wells of identically infected cells and at each day one of the wells was acetone fixed and stained with the FITC labeled monoclonal antibody SDOW17. If the percentage of infected cells was not greater than 50% and significant progression of foci development over the prior days observations were not seen, the cells in an equivalent well were trypsinized and passed to multiple fresh wells. These infected cell passages were typically at a 1:4 split and sometimes included the addition of an equivalent number of cells from an uninfected culture. Alternatively, if the SDOW17 staining revealed that the infected cell foci had spread sufficiently to account for greater than 50% of the total cells, cell free supernatant was harvested and used to infect multiple wells of freshly seeded cells (FIG. 20). After 11 passages the intervening cell passages were not necessary as the virus was able to grow to sufficient titer to allow consecutive cell free supernatant passaging of the virus.

Example 32

Screening Various CD163 Cell Lines for Permissivity to Various European and North American PRRSV Isolates Various CD163 transgenic cell lines were assessed for permissivity to low passage European and North American PRRSV isolates (see Table 7). Transgenic CD163 cell lines as described in earlier examples included NLFK-MARC CD163 D4, PK-RSVScript-susCD163v2clone #9 and PK-CMV-susCD163v1-A10. Each CD163 cell line along with cell lines MARC-145, parental feline kidney, parental porcine kidney cell lines (serving as controls) were planted onto 96-well tissue culture plates. Growth media was removed from monolayers and inoculated with 0.1 mL per well of each PRRSV isolate. At day 3 post infection, the plates were fixed with 80% acetone and stained with FITC-conjugated monoclonal antibody SDOW17 (Rural Technologies Inc.) which is specific for the nucleocapsid. Results of the fluorescent antibody (FA) assay are in Table 7.

TABLE 7

FA results of screening of various CD163 cell lines for permissivity to European and North American PRRSV isolates

| | PRRSV Isolate[a] | | | | | |
|---|---|---|---|---|---|---|
| CD163 Cell Line | EU98V226 | P129 | P201 | 1151 | 94-3 | IND5 |
| NLFK-MARC CD163 D4 | ++ | + | +++ | +++ | ++ | ++++ |
| PK-RSVScript-susCD163v2clone #9 | + | + | ++ | + | + | ++ |
| PK-CMV-susCD163v1-A10 | + | + | ++ | ++ | ++ | ++ |
| MARC-145 | ++ | + | +++ | + | ++++ | +++ |
| Porcine Kidney (parental) | – | – | – | – | – | – |
| Feline Kidney (parental) | – | – | – | – | – | – |

[a]All PRRSV isolates are North American except EU98V226 is a European isolate.

Example 33

Phorbol 12-Myristate 13-Acetate (PMA) Induction of CD163 Renders Human U937 Cells Permissive to PRRSV Infection Human U937 cells obtained from ATCC (CRL-1593.2) were propagated in RPMI medium containing serum and additives according to ATCC specifications. These cells are known to express CD163 when activated by PMA treatment (Gronlund et al., 2000). U937 cells were seeded in duplicate in wells of a 6-well plate. One set of wells was treated with 100 ng/ml of PMA and the other set was left untreated. Three days after PMA stimulation, one well from each set was infected with the P129 isolate of PRRSV. The other well from each set was fixed and stained for expression of CD163 in an indirect immunofluorescent antibody assay using goat-anti human CD163 (R&D System) and donkey anti-goat IgG conjugated with FITC (BioDesign International).

Untreated U937 cells continued propagation to high density 3 days after initial planting. PMA-treated U937 cells stopped propagating, became enlarged, and attached to the surface of the culture wells. A small fraction of untreated U937 were positive for CD163 staining, whereas almost all PMA-treated U937 were positive for CD163 staining. In untreated U937 no PRRSV infected cells were observed. However, hundreds of PMA treated U937 cells became infected by PRRSV. This demonstrates that non-permissive cells can be rendered permissive for PRRSV infection following chemical induction of CD163 expression.

Additional features and variations of the invention will be apparent to those skilled in the art from the entirety of this application, including the detailed description, and all such features are intended as aspects of the invention Likewise, features of the invention described herein can be re-combined into additional embodiments that also are intended as aspects of the invention, irrespective of whether the combination of features is specifically mentioned above as an aspect or embodiment of the invention. Also, only such limitations that are described herein as critical to the invention should be viewed as such; variations of the invention lacking limitations that have not been described herein as critical are intended as aspects of the invention.

It will be clear that the invention may be practiced otherwise than as particularly described in the foregoing description and examples.

Numerous modifications and variations of the present invention are possible in light of the above teachings and, therefore, are within the scope of the invention.

The entire disclosure of all publications cited herein are hereby incorporated by reference to the extent they are not inconsistent to the disclosure herein.

What is claimed is:

1. A method of facilitating production of Porcine Reproductive and Respiratory Syndrome Virus (PRRSV) from a culture of vertebrate cells, comprising the steps of:

(a) providing a recombinant vertebrate cell transfected with an exogenous polynucleotide that encodes a polypeptide having a transmembrane domain and at least 85% sequence identity to SEQ ID NO:2, so that expression of the polypeptide in said cell is increased;

(b) contacting a culture of said cell with PRRSV virus under conditions which permit infection of the cells and growth of the virus; and (c) recovering virus from said culture.

2. The method of claim 1, wherein the cell was previously PRRSV permissive and is rendered more PRRSV permissive.

3. The method of claim 1, wherein the cell is selected from the group consisting of baby hamster kidney cells (BHK21), porcine kidney cells, feline kidney cells, avian cells, and swine testicular cells.

4. The method of claim 1, wherein the PRRSV is of the European genotype.

5. The method of claim 1, wherein the PRRSV is of the North American genotype.

6. The method of claim 1, wherein the polynucleotide encodes a polypeptide having a transmembrane domain, and at least 90% sequence identity to SEQ ID NO:2.

7. The method of claim 1, wherein the polynucleotide encodes a polypeptide having a transmembrane domain and at least 95% sequence identity to SEQ ID NO:2.

8. The method of claim 1, wherein the polynucleotide encodes a polypeptide having a transmembrane domain and at least 99% sequence identity to SEQ ID NO:2.

9. The method of claim 1, further comprising the step of producing a vaccine from the recovered virus.

10. The method of claim 9, wherein the vaccine comprises inactivated virus.

11. The method of claim 9, wherein the vaccine comprises live attenuated virus.

12. The method of claim 1, wherein transfection with the exogenous polynucleotide is accomplished by electroporation.

13. The method of claim 1, wherein said exogenous polynucleotide encodes a fusion protein.

* * * * *

SEQUENCE LISTING

<160> NUMBER OF SEQ ID NOS: 48

<210> SEQ ID NO 1
<211> LENGTH: 2607
<212> TYPE: DNA
<213> ORGANISM: Sus scrofa

<400> SEQUENCE: 1
atggacaaac tcagaatggt gctacatgaa aactctggat ctgcagacct gaaactgaga 60
gtggtagatg gagtcactga atgttcagga agattggaag tgaaattcca aggagaatgg 120
ggaacaatct gtgatgatgg ctgggatagt gatgatgccg ctgtggcatg taagcaactg 180
ggatgtccaa ctgctgtcac tgccattggt cgagttaacg ccagtgaggg aactggacac 240
atttggcttg acagtgtttc ttgccatgga cacgagtctg ctctctggca gtgtagacac 300
catgaatggg gaaagcatta ttgcaatcat aatgaagatg ctggtgtgac atgttctgat 360
ggatcagatc tggaactgag acttaaaggt ggaggcagcc actgtgctgg gacagtggag 420
gtggaaattc agaaactggt aggaaaagtg tgtgatagaa gctggggact gaaagaagct 480
gatgtggttt gcaggcagct gggatgtgga tctgcactca aaacatcata tcaagtttat 540
tccaaaacca aggcaacaaa cacatggctg tttgtaagca gctgtaatgg aaatgaaact 600
tctctttggg actgcaagaa ttggcagtgg ggtggactta gttgtgatca ctatgacgaa 660
gccaaaatta cctgctcagc ccacaggaaa cccaggctgg ttggagggga cattccctgc 720
tctggtcgtg ttgaagtaca acatggagac acgtggggca ccgtctgtga ttctgacttc 780
tctctggagg cggccagcgt gctgtgcagg gaactacagt gcggcactgt ggtttccctc 840
ctggggggag ctcactttgg agaaggaagt ggacagatct gggctgaaga attccagtgt 900
gaggggcacg agtcccacct ttcactctgc ccagtagcac cccgccctga cgggacatgt 960
agccacagca gggacgtcgg cgtagtctgc tcaagataca cacaaatccg cttggtgaat 1020
ggcaagaccc catgtgaagg aagagtggag ctcaacattc ttgggtcctg gggggtccctc 1080 tgcaactctc actgggacat ggaagatgcc catgttttat gccagcagct taaatgtgga 1140
gttgcccttt ctatcccggg aggagcacct tttgggaaag gaagtgagca ggtctggagg 1200
cacatgtttc actgcactgg gactgagaag cacatgggag attgttccgt cactgctctg 1260
ggcgcatcac tctgttcttc agggcaagtg gcctctgtaa tctgctcagg gaaccagagt 1320
cagacactat ccccgtgcaa ttcatcatcc tcggacccat caagctctat tatttcagaa 1380
gaaaatggtg ttgcctgcat agggagtggt caacttcgcc tggtcgatgg aggtggtcgt 1440
tgtgctggga gagtagaggt ctatcatgag ggctcctggg gcaccatctg tgatgacagc 1500
tgggacctga atgatgccca tgtggtgtgc aaacagctga gctgtggatg ggccattaat 1560
gccactggtt ctgctcattt tggggaagga acagggccca tttggctgga tgagataaac 1620
tgtaatggaa aagaatctca tatttggcaa tgccactcac atggttgggg gcggcacaat 1680
tgcaggcata aggaggatgc aggagtcatc tgctcggagt tcatgtctct cagactgatc 1740
agtgaaaaca gcagagagac ctgtgcaggg cgcctggaag ttttttacaa cggagcttgg 1800
ggcagcgttg gcaagaatag catgtctcca gccacagtgg gggtggtatg caggcagctg 1860
ggctgtgcag acagagggga catcagccct gcatcttcag acaagacagt gtccaggcac 1920
atgtgggtgg acaatgttca gtgtcctaaa ggacctgaca ccctatggca gtgcccatca 1980
tctccatgga agaagagact ggccagcccc tcagaggaga catggatcac atgtgccaac 2040

```
aaaataagac ttcaagaagg aaacactaat tgttctggac gtgtggagat ctggtacgga   2100

ggttcctggg gcactgtgtg tgacgactcc tgggaccttg aagatgctca ggtggtgtgc   2160

cgacagctgg gctgtggctc agctttggag gcaggaaaag aggccgcatt tggccagggg   2220

actgggccca tatggctcaa tgaagtgaag tgcaagggga atgaaacctc cttgtgggat   2280

tgtcctgcca gatcctgggg ccacagtgac tgtggacaca aggaggatgc tgctgtgacg   2340

tgttcagaaa ttgcaaagag ccgagaatcc ctacatgcca caggtcgctc atcttttgtt   2400

gcacttgcaa tctttggggt cattctgttg gcctgtctca tcgcattcct catttggact   2460

cagaagcgaa gacagaggca gcggctctca gttttctcag gaggagagaa ttctgtccat   2520

caaattcaat accgggagat gaattcttgc ctgaaagcag atgaaacgga tatgctaaat   2580

ccctcaggag accactctga agtacaa                                      2607
```

<210> SEQ ID NO 2
<211> LENGTH: 869
<212> TYPE: PRT
<213> ORGANISM: Sus scrofa

<400> SEQUENCE: 2

```
Met Asp Lys Leu Arg Met Val Leu His Glu Asn Ser Gly Ser Ala Asp
1               5                   10                  15

Leu Lys Leu Arg Val Val Asp Gly Val Thr Glu Cys Ser Gly Arg Leu
            20                  25                  30

Glu Val Lys Phe Gln Gly Glu Trp Gly Thr Ile Cys Asp Asp Gly Trp
        35                  40                  45

Asp Ser Asp Asp Ala Ala Val Ala Cys Lys Gln Leu Gly Cys Pro Thr
    50                  55                  60

Ala Val Thr Ala Ile Gly Arg Val Asn Ala Ser Glu Gly Thr Gly His
65                  70                  75                  80

Ile Trp Leu Asp Ser Val Ser Cys His Gly His Glu Ser Ala Leu Trp
                85                  90                  95

Gln Cys Arg His His Glu Trp Gly Lys His Tyr Cys Asn His Asn Glu
            100                 105                 110

Asp Ala Gly Val Thr Cys Ser Asp Gly Ser Asp Leu Glu Leu Arg Leu
        115                 120                 125

Lys Gly Gly Gly Ser His Cys Ala Gly Thr Val Glu Val Glu Ile Gln
    130                 135                 140

Lys Leu Val Gly Lys Val Cys Asp Arg Ser Trp Gly Leu Lys Glu Ala
145                 150                 155                 160

Asp Val Val Cys Arg Gln Leu Gly Cys Gly Ser Ala Leu Lys Thr Ser
                165                 170                 175

Tyr Gln Val Tyr Ser Lys Thr Lys Ala Thr Asn Thr Trp Leu Phe Val
            180                 185                 190

Ser Ser Cys Asn Gly Asn Glu Thr Ser Leu Trp Asp Cys Lys Asn Trp
        195                 200                 205

Gln Trp Gly Gly Leu Ser Cys Asp His Tyr Asp Glu Ala Lys Ile Thr
    210                 215                 220

Cys Ser Ala His Arg Lys Pro Arg Leu Val Gly Gly Asp Ile Pro Cys
225                 230                 235                 240

Ser Gly Arg Val Glu Val Gln His Gly Asp Thr Trp Gly Thr Val Cys
                245                 250                 255

Asp Ser Asp Phe Ser Leu Glu Ala Ala Ser Val Leu Cys Arg Glu Leu
            260                 265                 270

Gln Cys Gly Thr Val Val Ser Leu Leu Gly Gly Ala His Phe Gly Glu
```

```
        275                 280                 285

Gly Ser Gly Gln Ile Trp Ala Glu Glu Phe Gln Cys Glu Gly His Glu
    290                 295                 300

Ser His Leu Ser Leu Cys Pro Val Ala Pro Arg Pro Asp Gly Thr Cys
305                 310                 315                 320

Ser His Ser Arg Asp Val Gly Val Val Cys Ser Arg Tyr Thr Gln Ile
                325                 330                 335

Arg Leu Val Asn Gly Lys Thr Pro Cys Glu Gly Arg Val Glu Leu Asn
            340                 345                 350

Ile Leu Gly Ser Trp Gly Ser Leu Cys Asn Ser His Trp Asp Met Glu
        355                 360                 365

Asp Ala His Val Leu Cys Gln Gln Leu Lys Cys Gly Val Ala Leu Ser
    370                 375                 380

Ile Pro Gly Gly Ala Pro Phe Gly Lys Gly Ser Glu Gln Val Trp Arg
385                 390                 395                 400

His Met Phe His Cys Thr Gly Thr Glu Lys His Met Gly Asp Cys Ser
                405                 410                 415

Val Thr Ala Leu Gly Ala Ser Leu Cys Ser Ser Gly Gln Val Ala Ser
            420                 425                 430

Val Ile Cys Ser Gly Asn Gln Ser Gln Thr Leu Ser Pro Cys Asn Ser
        435                 440                 445

Ser Ser Ser Asp Pro Ser Ser Ser Ile Ile Ser Glu Glu Asn Gly Val
    450                 455                 460

Ala Cys Ile Gly Ser Gly Gln Leu Arg Leu Val Asp Gly Gly Gly Arg
465                 470                 475                 480

Cys Ala Gly Arg Val Glu Val Tyr His Glu Gly Ser Trp Gly Thr Ile
                485                 490                 495

Cys Asp Asp Ser Trp Asp Leu Asn Asp Ala His Val Val Cys Lys Gln
            500                 505                 510

Leu Ser Cys Gly Trp Ala Ile Asn Ala Thr Gly Ser Ala His Phe Gly
        515                 520                 525

Glu Gly Thr Gly Pro Ile Trp Leu Asp Glu Ile Asn Cys Asn Gly Lys
    530                 535                 540

Glu Ser His Ile Trp Gln Cys His Ser His Gly Trp Gly Arg His Asn
545                 550                 555                 560

Cys Arg His Lys Glu Asp Ala Gly Val Ile Cys Ser Glu Phe Met Ser
                565                 570                 575

Leu Arg Leu Ile Ser Glu Asn Ser Arg Glu Thr Cys Ala Gly Arg Leu
            580                 585                 590

Glu Val Phe Tyr Asn Gly Ala Trp Gly Ser Val Gly Lys Asn Ser Met
        595                 600                 605

Ser Pro Ala Thr Val Gly Val Val Cys Arg Gln Leu Gly Cys Ala Asp
    610                 615                 620

Arg Gly Asp Ile Ser Pro Ala Ser Ser Asp Lys Thr Val Ser Arg His
625                 630                 635                 640

Met Trp Val Asp Asn Val Gln Cys Pro Lys Gly Pro Asp Thr Leu Trp
                645                 650                 655

Gln Cys Pro Ser Ser Pro Trp Lys Lys Arg Leu Ala Ser Pro Ser Glu
            660                 665                 670

Glu Thr Trp Ile Thr Cys Ala Asn Lys Ile Arg Leu Gln Glu Gly Asn
        675                 680                 685

Thr Asn Cys Ser Gly Arg Val Glu Ile Trp Tyr Gly Gly Ser Trp Gly
    690                 695                 700
```

```
Thr Val Cys Asp Asp Ser Trp Asp Leu Glu Asp Ala Gln Val Val Cys
705                 710                 715                 720

Arg Gln Leu Gly Cys Gly Ser Ala Leu Glu Ala Gly Lys Glu Ala Ala
                725                 730                 735

Phe Gly Gln Gly Thr Gly Pro Ile Trp Leu Asn Glu Val Lys Cys Lys
            740                 745                 750

Gly Asn Glu Thr Ser Leu Trp Asp Cys Pro Ala Arg Ser Trp Gly His
        755                 760                 765

Ser Asp Cys Gly His Lys Glu Asp Ala Ala Val Thr Cys Ser Glu Ile
    770                 775                 780

Ala Lys Ser Arg Glu Ser Leu His Ala Thr Gly Arg Ser Ser Phe Val
785                 790                 795                 800

Ala Leu Ala Ile Phe Gly Val Ile Leu Leu Ala Cys Leu Ile Ala Phe
                805                 810                 815

Leu Ile Trp Thr Gln Lys Arg Arg Gln Arg Gln Arg Leu Ser Val Phe
            820                 825                 830

Ser Gly Gly Glu Asn Ser Val His Gln Ile Gln Tyr Arg Glu Met Asn
        835                 840                 845

Ser Cys Leu Lys Ala Asp Glu Thr Asp Met Leu Asn Pro Ser Gly Asp
    850                 855                 860

His Ser Glu Val Gln
865


<210> SEQ ID NO 3
<211> LENGTH: 3400
<212> TYPE: DNA
<213> ORGANISM: Sus scrofa

<400> SEQUENCE: 3

atggtgctac ttgaagactc tggatctgca gactttagaa gatgttctgc ccatttaagt     60

tccttcactt ttgctgtagt cgctgttctc agtgcctgct tggtcactag ttctcttgga    120

ggaaaagaca aggagctgag gctaacgggt ggtgaaaaca agtgctctgg aagagtggag    180

gtgaaagtgc aggaggagtg ggaactgtg tgtaataatg gctgggacat ggatgtggtc    240

tctgttgttt gtaggcagct gggatgtcca actgctatca aagccactgg atgggctaat    300

tttagtgcag gttctggacg catttggatg gatcatgttt cttgtcgagg gaatgagtca    360

gctctctggg actgcaaaca tgatggatgg ggaaagcata actgtactca ccaacaggat    420

gctggagtaa cctgctcaga tggatctgat ttagagatga ggctggtgaa tggaggaaac    480

cggtgcttag gaagaataga agtcaaattt caagagcggt ggggaacagt gtgtgatgat    540

aacttcaaca taaatcatgc ttctgtggtt tgtaaacaac ttgaatgtgg aagtgctgtc    600

agtttctctg gttcagctaa ttttggagaa ggttctggac caatctggtt tgatgatctt    660

gtatgcaatg gaaatgagtc agctctctgg aactgcaaac atgaaggatg gggaaagcac    720

aattgcgatc atgctgagga tgctggagtg atttgcttaa atggagcaga cctgaaactg    780

agagtggtag atggactcac tgaatgttca ggaagattgg aagtgaaatt ccaaggagaa    840

tggggaacaa tctgtgatga tggctgggat agtgatgatg ccgctgtggc atgtaagcaa    900

ctgggatgtc caactgctgt cactgccatt ggtcgagtta acgccagtga gggaactgga    960

cacatttggc ttgacagtgt ttcttgccat ggacacgagt ctgctctctg gcagtgtaga   1020

caccatgaat ggggaaagca ttattgcaat cataatgaag atgctggtgt gacatgttct   1080

gatggatcag atctggaact gagacttaaa ggtggaggca gccactgtgc tgggacagtg   1140

gaggtggaaa ttcagaaact ggtaggaaaa gtgtgtgata gaagctgggg actgaaagaa   1200
```

```
gctgatgtgg tttgcaggca gctgggatgt ggatctgcac tcaaaacatc atatcaagtt   1260

tattccaaaa ccaaggcaac aaacacatgg ctgtttgtaa gcagctgtaa tggaaatgaa   1320

acttctcttt gggactgcaa gaattggcag tggggtggac ttagttgtga tcactatgac   1380

gaagccaaaa ttacctgctc agcccacagg aaacccaggc tggttggagg ggacattccc   1440

tgctctggtc gtgttgaagt acaacatgga gacacgtggg gcaccgtctg tgattctgac   1500

ttctctctgg aggcggccag cgtgctgtgc agggaactac agtgcggcac tgtggtttcc   1560

ctcctggggg gagctcactt tggagaagga agtggacaga tctgggctga agaattccag   1620

tgtgaggggc acgagtccca cctttcactc tgcccagtag caccccgccc tgacgggaca   1680

tgtagccaca gcagggacgt cggcgtagtc tgctcaagat acacacaaat ccgcttggtg   1740

aatggcaaga ccccatgtga aggaagagtg gagctcaaca ttcttgggtc ctgggggtcc   1800

ctctgcaact ctcactggga catggaagat gcccatgttt tatgccagca gcttaaatgt   1860

ggagttgccc tttctatccc gggaggagca cctttttggga aaggaagtga gcaggtctgg   1920

aggcacatgt ttcactgcac tgggactgag aagcacatgg gagattgttc cgtcactgct   1980

ctgggcgcat cactctgttc ttcagggcaa gtggcctctg taatctgctc agggaaccag   2040

agtcagacac tatccccgtg caattcatca tcctcggacc catcaagctc tattatttca   2100

gaagaaagtg gtgttgcctg catagggagt ggtcaacttc gcctggtcga tggaggtggt   2160

cgttgtgctg ggagagtaga ggtctatcct ggggcatcct ggggcaccat ctgtgatgac   2220

agctgggacc tgaatgatgc ccatgtggtg tgcaaacagc tgagctgtgg atgggccatt   2280

aatgccactg gttctgctca ttttggggaa ggaacagggc ccatttggct ggatgagata   2340

aactgtaatg gaaaagaatc tcatatttgg caatgccact cacatggttg gggcggcac   2400

aattgcaggc ataaggagga tgcaggagtc atctgctcag agttcatgtc tctgagactg   2460

atcagtgaaa acagcagaga gacctgtgca gggcgcctgg aagtttttta caacggagct   2520

tggggcagcg ttggcaggaa tagcatgtct ccagccacag tgggggtggt atgcaggcag   2580

ctgggctgtg cagacagagg ggacatcagc cctgcatctt cagacaagac agtgtccagg   2640

cacatgtggg tggacaatgt tcagtgtcct aaaggacctg acacactatg gcagtgcccc   2700

tcatctccat ggaagaagag actggccagc ccctcagagg agacatggat cacatgtgcc   2760

aacaaaataa gacttcaaga aggaaacact aattgttctg gacgtgtgga gatctggtac   2820

ggaggttcct ggggcactgt gtgtgacgac tcctgggacc ttgaagatgc tcaggtggtg   2880

tgccgacagc tgggctgtgg ctcagctttg gaggcaggaa aagagcccgc atttggccag   2940

gggactgggc ccatatggct caatgaagtg aagtgcaagg ggaatgaacc ctccttgtgg   3000

gattgtcctg ccagatcctg gggccacagt gactgtggac acaaggagga tgctgctgtg   3060

acgtgctcag aaattgcaaa gagccgagaa tccctacatg ccacaggtcg ctcatctttt   3120

gttgcacttg caatctttgg ggtcattctg ttggcctgtc tcatcgcatt cctcatttgg   3180

actcagaagc gaagacagag gcagcggctc tcagttttct caggaggaga gaattctgtc   3240

catcaaattc aataccggga gatgaattct tgcctgaaag cagatgaaac ggatatgcta   3300

aatccctcag gagaccactc tgaagtacaa tgaaaaggaa aatgggaatt ataacctggt   3360

gagttcagcc tttaagatac cttgatgaag acctggacta                         3400
```

<210> SEQ ID NO 4
<211> LENGTH: 1110
<212> TYPE: PRT
<213> ORGANISM: Sus scrofa

<400> SEQUENCE: 4

```
Met Val Leu Leu Glu Asp Ser Gly Ser Ala Asp Phe Arg Arg Cys Ser
1               5                   10                  15

Ala His Leu Ser Ser Phe Thr Phe Ala Val Val Ala Val Leu Ser Ala
            20                  25                  30

Cys Leu Val Thr Ser Ser Leu Gly Gly Lys Asp Lys Glu Leu Arg Leu
        35                  40                  45

Thr Gly Gly Glu Asn Lys Cys Ser Gly Arg Val Glu Val Lys Val Gln
    50                  55                  60

Glu Glu Trp Gly Thr Val Cys Asn Asn Gly Trp Asp Met Asp Val Val
65                  70                  75                  80

Ser Val Val Cys Arg Gln Leu Gly Cys Pro Thr Ala Ile Lys Ala Thr
                85                  90                  95

Gly Trp Ala Asn Phe Ser Ala Gly Ser Gly Arg Ile Trp Met Asp His
            100                 105                 110

Val Ser Cys Arg Gly Asn Glu Ser Ala Leu Trp Asp Cys Lys His Asp
        115                 120                 125

Gly Trp Gly Lys His Asn Cys Thr His Gln Gln Asp Ala Gly Val Thr
    130                 135                 140

Cys Ser Asp Gly Ser Asp Leu Glu Met Arg Leu Val Asn Gly Gly Asn
145                 150                 155                 160

Arg Cys Leu Gly Arg Ile Glu Val Lys Phe Gln Glu Arg Trp Gly Thr
                165                 170                 175

Val Cys Asp Asp Asn Phe Asn Ile Asn His Ala Ser Val Val Cys Lys
            180                 185                 190

Gln Leu Glu Cys Gly Ser Ala Val Ser Phe Ser Gly Ser Ala Asn Phe
        195                 200                 205

Gly Glu Gly Ser Gly Pro Ile Trp Phe Asp Asp Leu Val Cys Asn Gly
    210                 215                 220

Asn Glu Ser Ala Leu Trp Asn Cys Lys His Glu Gly Trp Gly Lys His
225                 230                 235                 240

Asn Cys Asp His Ala Glu Asp Ala Gly Val Ile Cys Leu Asn Gly Ala
                245                 250                 255

Asp Leu Lys Leu Arg Val Val Asp Gly Leu Thr Glu Cys Ser Gly Arg
            260                 265                 270

Leu Glu Val Lys Phe Gln Gly Glu Trp Gly Thr Ile Cys Asp Asp Gly
        275                 280                 285

Trp Asp Ser Asp Asp Ala Ala Val Ala Cys Lys Gln Leu Gly Cys Pro
    290                 295                 300

Thr Ala Val Thr Ala Ile Gly Arg Val Asn Ala Ser Glu Gly Thr Gly
305                 310                 315                 320

His Ile Trp Leu Asp Ser Val Ser Cys His Gly His Glu Ser Ala Leu
                325                 330                 335

Trp Gln Cys Arg His His Glu Trp Gly Lys His Tyr Cys Asn His Asn
            340                 345                 350

Glu Asp Ala Gly Val Thr Cys Ser Asp Gly Ser Asp Leu Glu Leu Arg
        355                 360                 365

Leu Lys Gly Gly Gly Ser His Cys Ala Gly Thr Val Glu Val Glu Ile
    370                 375                 380

Gln Lys Leu Val Gly Lys Val Cys Asp Arg Ser Trp Gly Leu Lys Glu
385                 390                 395                 400

Ala Asp Val Val Cys Arg Gln Leu Gly Cys Gly Ser Ala Leu Lys Thr
                405                 410                 415
```

```
Ser Tyr Gln Val Tyr Ser Lys Thr Lys Ala Thr Asn Thr Trp Leu Phe
            420                 425                 430

Val Ser Ser Cys Asn Gly Asn Glu Thr Ser Leu Trp Asp Cys Lys Asn
        435                 440                 445

Trp Gln Trp Gly Gly Leu Ser Cys Asp His Tyr Asp Glu Ala Lys Ile
    450                 455                 460

Thr Cys Ser Ala His Arg Lys Pro Arg Leu Val Gly Gly Asp Ile Pro
465                 470                 475                 480

Cys Ser Gly Arg Val Glu Val Gln His Gly Asp Thr Trp Gly Thr Val
                485                 490                 495

Cys Asp Ser Asp Phe Ser Leu Glu Ala Ala Ser Val Leu Cys Arg Glu
            500                 505                 510

Leu Gln Cys Gly Thr Val Val Ser Leu Leu Gly Gly Ala His Phe Gly
        515                 520                 525

Glu Gly Ser Gly Gln Ile Trp Ala Glu Glu Phe Gln Cys Glu Gly His
    530                 535                 540

Glu Ser His Leu Ser Leu Cys Pro Val Ala Pro Arg Pro Asp Gly Thr
545                 550                 555                 560

Cys Ser His Ser Arg Asp Val Gly Val Val Cys Ser Arg Tyr Thr Gln
                565                 570                 575

Ile Arg Leu Val Asn Gly Lys Thr Pro Cys Glu Gly Arg Val Glu Leu
            580                 585                 590

Asn Ile Leu Gly Ser Trp Gly Ser Leu Cys Asn Ser His Trp Asp Met
        595                 600                 605

Glu Asp Ala His Val Leu Cys Gln Gln Leu Lys Cys Gly Val Ala Leu
    610                 615                 620

Ser Ile Pro Gly Gly Ala Pro Phe Gly Lys Gly Ser Glu Gln Val Trp
625                 630                 635                 640

Arg His Met Phe His Cys Thr Gly Thr Glu Lys His Met Gly Asp Cys
                645                 650                 655

Ser Val Thr Ala Leu Gly Ala Ser Leu Cys Ser Ser Gly Gln Val Ala
            660                 665                 670

Ser Val Ile Cys Ser Gly Asn Gln Ser Gln Thr Leu Ser Pro Cys Asn
        675                 680                 685

Ser Ser Ser Ser Asp Pro Ser Ser Ser Ile Ile Ser Glu Glu Ser Gly
    690                 695                 700

Val Ala Cys Ile Gly Ser Gly Gln Leu Arg Leu Val Asp Gly Gly Gly
705                 710                 715                 720

Arg Cys Ala Gly Arg Val Glu Val Tyr Pro Gly Ala Ser Trp Gly Thr
                725                 730                 735

Ile Cys Asp Asp Ser Trp Asp Leu Asn Asp Ala His Val Val Cys Lys
            740                 745                 750

Gln Leu Ser Cys Gly Trp Ala Ile Asn Ala Thr Gly Ser Ala His Phe
        755                 760                 765

Gly Glu Gly Thr Gly Pro Ile Trp Leu Asp Glu Ile Asn Cys Asn Gly
    770                 775                 780

Lys Glu Ser His Ile Trp Gln Cys His Ser His Gly Trp Gly Arg His
785                 790                 795                 800

Asn Cys Arg His Lys Glu Asp Ala Gly Val Ile Cys Ser Glu Phe Met
                805                 810                 815

Ser Leu Arg Leu Ile Ser Glu Asn Ser Arg Glu Thr Cys Ala Gly Arg
            820                 825                 830

Leu Glu Val Phe Tyr Asn Gly Ala Trp Gly Ser Val Gly Arg Asn Ser
```

```
        835                 840                 845

Met Ser Pro Ala Thr Val Gly Val Val Cys Arg Gln Leu Gly Cys Ala
    850                 855                 860

Asp Arg Gly Asp Ile Ser Pro Ala Ser Ser Asp Lys Thr Val Ser Arg
865                 870                 875                 880

His Met Trp Val Asp Asn Val Gln Cys Pro Lys Gly Pro Asp Thr Leu
                885                 890                 895

Trp Gln Cys Pro Ser Ser Pro Trp Lys Lys Arg Leu Ala Ser Pro Ser
            900                 905                 910

Glu Glu Thr Trp Ile Thr Cys Ala Asn Lys Ile Arg Leu Gln Glu Gly
        915                 920                 925

Asn Thr Asn Cys Ser Gly Arg Val Glu Ile Trp Tyr Gly Gly Ser Trp
    930                 935                 940

Gly Thr Val Cys Asp Asp Ser Trp Asp Leu Glu Asp Ala Gln Val Val
945                 950                 955                 960

Cys Arg Gln Leu Gly Cys Gly Ser Ala Leu Glu Ala Gly Lys Glu Pro
                965                 970                 975

Ala Phe Gly Gln Gly Thr Gly Pro Ile Trp Leu Asn Glu Val Lys Cys
            980                 985                 990

Lys Gly Asn Glu Pro Ser Leu Trp  Asp Cys Pro Ala Arg  Ser Trp Gly
        995                 1000                1005

His Ser  Asp Cys Gly His Lys  Glu Asp Ala Ala Val  Thr Cys Ser
    1010                 1015                 1020

Glu Ile  Ala Lys Ser Arg Glu  Ser Leu His Ala Thr  Gly Arg Ser
    1025                 1030                 1035

Ser Phe  Val Ala Leu Ala Ile  Phe Gly Val Ile Leu  Leu Ala Cys
    1040                 1045                 1050

Leu Ile  Ala Phe Leu Ile Trp  Thr Gln Lys Arg Arg  Gln Arg Gln
    1055                 1060                 1065

Arg Leu  Ser Val Phe Ser Gly  Gly Glu Asn Ser Val  His Gln Ile
    1070                 1075                 1080

Gln Tyr  Arg Glu Met Asn Ser  Cys Leu Lys Ala Asp  Glu Thr Asp
    1085                 1090                 1095

Met Leu  Asn Pro Ser Gly Asp  His Ser Glu Val Gln
    1100                 1105                 1110


<210> SEQ ID NO 5
<211> LENGTH: 2930
<212> TYPE: DNA
<213> ORGANISM: Sus scrofa

<400> SEQUENCE: 5

gtaataatac aagaagattt aaatgggcat aaaaccttgg aatggacaaa ctcagaatgg      60

tgctacatga aaactctgga tctgcagacc tgaaactgag agtggtagat ggagtcactg     120

aatgttcagg aagattggaa gtgaaattcc aaggagaatg ggaacaatc tgtgatgatg     180

gctgggatag tgatgatgcc gctgtggcat gtaagcaact gggatgtcca actgctgtca     240

ctgccattgg tcgagttaac gccagtgagg gaactggaca catttggctt gacagtgttt     300

cttgccatgg acacgagtct gctctctggc agtgtagaca ccatgaatgg ggaaagcatt     360

attgcaatca taatgaagat gctggtgtga catgttctga tggatcagat ctggaactga     420

gacttaaagg tggaggcagc cactgtgctg ggacagtgga ggtggaaatt cagaaactgg     480

taggaaaagt gtgtgataga agctggggac tgaaagaagc tgatgtggtt tgcaggcagc     540

tgggatgtgg atctgcactc aaaacatcat atcaagttta ttccaaaacc aaggcaacaa     600
```

```
acacatggct gtttgtaagc agctgtaatg gaaatgaaac ttctctttgg gactgcaaga    660
attggcagtg gggtggactt agttgtgatc actatgacga agccaaaatt acctgctcag    720
cccacaggaa acccaggctg gttggagggg acattccctg ctctggtcgt gttgaagtac    780
aacatggaga cacgtggggc accgtctgtg attctgactt ctctctggag gcggccagcg    840
tgctgtgcag ggaactacag tgcggcactg tggtttccct cctgggggga gctcactttg    900
gagaaggaag tggacagatc tgggctgaag aattccagtg tgaggggcac gagtcccacc    960
tttcactctg cccagtagca ccccgccctg acgggacatg tagccacagc agggacgtcg   1020
gcgtagtctg ctcaagatac acacaaatcc gcttggtgaa tggcaagacc ccatgtgaag   1080
gaagagtgga gctcaacatt cttgggtcct gggggtccct ctgcaactct cactgggaca   1140
tggaagatgc ccatgtttta tgccagcagc ttaaatgtgg agttgccctt tctatcccgg   1200
gaggagcacc ttttgggaaa ggaagtgagc aggtctggag gcacatgttt cactgcactg   1260
ggactgagaa gcacatggga gattgttccg tcactgctct gggcgcatca ctctgttctt   1320
cagggcaagt ggcctctgta atctgctcag ggaaccagag tcagacacta tccccgtgca   1380
attcatcatc ctcggaccca tcaagctcta ttatttcaga agaaaatggt gttgcctgca   1440
tagggagtgg tcaacttcgc ctggtcgatg gaggtggtcg ttgtgctggg agagtagagg   1500
tctatcatga gggctcctgg ggcaccatct gtgatgacag ctgggacctg aatgatgccc   1560
atgtggtgtg caaacagctg agctgtggat gggccattaa tgccactggt tctgctcatt   1620
ttggggaagg aacagggccc atttggctgg atgagataaa ctgtaatgga aaagaatctc   1680
atatttggca atgccactca catggttggg ggcggcacaa ttgcaggcat aaggaggatg   1740
caggagtcat ctgctcggag ttcatgtctc tcagactgat cagtgaaaac agcagagaga   1800
cctgtgcagg gcgcctggaa gtttttttaca acggagcttg ggcagcgtt ggcaagaata   1860
gcatgtctcc agccacagtg gggtggtat gcaggcagct gggctgtgca gacagagggg   1920
acatcagccc tgcatcttca gacaagacag tgtccaggca catgtgggtg gacaatgttc   1980
agtgtcctaa aggacctgac accctatggc agtgcccatc atctccatgg aagaagagac   2040
tggccagccc ctcagaggag acatggatca catgtgccaa caaaataaga cttcaagaag   2100
gaaacactaa ttgttctgga cgtgtggaga tctggtacgg aggttcctgg ggcactgtgt   2160
gtgacgactc ctgggacctt gaagatgctc aggtggtgtg ccgacagctg ggctgtggct   2220
cagctttgga ggcaggaaaa gaggccgcat ttggccaggg gactgggccc atatggctca   2280
atgaagtgaa gtgcaagggg aatgaaacct ccttgtggga ttgtcctgcc agatcctggg   2340
gccacagtga ctgtggacac aaggaggatg ctgctgtgac gtgttcagaa attgcaaaga   2400
gccgagaatc cctacatgcc acaggtcgct catcttttgt tgcacttgca atctttgggg   2460
tcattctgtt ggcctgtctc atcgcattcc tcatttggac tcagaagcga agacagaggc   2520
agcggctctc agttttctca ggaggagaga attctgtcca tcaaattcaa taccgggaga   2580
tgaattcttg cctgaaagca gatgaaacgg atatgctaaa tccctcagga gaccactctg   2640
aagtacaatg aaaaggaaaa tgggaattat aacctggtga gttcagcctt taagatacct   2700
tgatgaagac ctggactatt gaatgagcaa gaatctgcct cttacactga agattacaat   2760
acagtcctct gtctcctggt attccaaaga ctgctgttga atttctaaaa aatagattgg   2820
tgaatgtgac tactcaaagt tgtatgtaag actttcaagg gcattaaata aaaaagaata   2880
ttgctgaaaa aaaaaaaaaa aaaaaaaaaa aaaaaaaaaa aaaaaaaaaa              2930
```

<210> SEQ ID NO 6
<211> LENGTH: 32
<212> TYPE: DNA
<213> ORGANISM: Artificial
<220> FEATURE:
<223> OTHER INFORMATION: PCR primer

<400> SEQUENCE: 6
cggaattccg cggatgtaat aatacaagaa ga 32

<210> SEQ ID NO 7
<211> LENGTH: 36
<212> TYPE: DNA
<213> ORGANISM: Artificial
<220> FEATURE:
<223> OTHER INFORMATION: PCR Primer

<400> SEQUENCE: 7
ccgctcgagt agtccaggtc ttcatcaagg tatctt 36

<210> SEQ ID NO 8
<211> LENGTH: 38
<212> TYPE: DNA
<213> ORGANISM: Artificial
<220> FEATURE:
<223> OTHER INFORMATION: PCR Primer

<400> SEQUENCE: 8
acactcgaca tgtcgatgta cgggccagat atacgcgt 38

<210> SEQ ID NO 9
<211> LENGTH: 38
<212> TYPE: DNA
<213> ORGANISM: Artificial
<220> FEATURE:
<223> OTHER INFORMATION: PCR Primer

<400> SEQUENCE: 9
ttccttacag agctcgaggt gcacaccaat gtggtgaa 38

<210> SEQ ID NO 10
<211> LENGTH: 46
<212> TYPE: DNA
<213> ORGANISM: Artificial
<220> FEATURE:
<223> OTHER INFORMATION: PCR Primer

<400> SEQUENCE: 10
cggtccggag cggccgcgat gtaataatac aagaagattt aaatgg 46

<210> SEQ ID NO 11
<211> LENGTH: 38
<212> TYPE: DNA
<213> ORGANISM: Artificial
<220> FEATURE:
<223> OTHER INFORMATION: PCR Primer

<400> SEQUENCE: 11
cggttggtac ccagcaatat tctttttat ttaatgcc 38

<210> SEQ ID NO 12
<211> LENGTH: 3623
<212> TYPE: DNA
<213> ORGANISM: Sus scrofa

<400> SEQUENCE: 12
gtaataatac aagaagattt aaatggcata aaaccttgga atggacaaac tcagaatggt 60

```
gctacatgaa aactctggat ctgcagactt tagaagatgt tctgcccatt taagttcctt    120
cacttttgct gtagtcgctg ttctcagtgc ctgcttggtc actagttctc ttggaggaaa    180
agacaaggag ctgaggctaa cgggtggtga aaacaagtgc tctggaagag tggaggtgaa    240
agtgcaggag gagtggggaa ctgtgtgtaa taatggctgg gacatggatg tggtctctgt    300
tgtttgtagg cagctgggat gtccaactgc tatcaaagcc actggatggg ctaattttag    360
tgcaggttct ggacgcattt ggatggatca tgtttcttgt cgagggaatg agtcagctct    420
ctgggactgc aaacatgatg gatggggaaa gcataactgt actcaccaac aggatgctgg    480
agtaacctgc tcagatggat ctgatttaga gatggggctg gtgaatggag gaaaccggtg    540
cttaggaaga atagaagtca aatttcaagg acggtgggga acagtgtgtg atgataactt    600
caacataaat catgcttctg tggtttgtaa acaacttgaa tgtggaagtg ctgtcagttt    660
ctctggttca gctaattttg gagaaggttc tggaccaatc tggtttgatg atcttgtatg    720
caatggaaat gagtcagctc tctggaactg caaacatgaa ggatggggaa agcacaattg    780
cgatcatgct gaggatgctg gagtgatttg cttaaatgga gcagacctga aactgagagt    840
ggtagatgga gtcactgaat gttcaggaag attggaagtg aaattccaag gagaatgggg    900
aacaatctgt gatgatggct gggatagtga tgatgccgct gtggcatgta agcaactggg    960
atgtccaact gctgtcactg ccattggtcg agttaacgcc agtgagggaa ctggacacat   1020
ttggcttgac agtgtttctt gccatggaca cgagtctgct ctctggcagt gtagacacca   1080
tgaatgggga aagcattatt gcaatcatga tgaagatgct ggtgtgacat gttctgatgg   1140
atcagatctg gaactgagac ttaaaggtgg aggcagccac tgtgctggga cagtggaggt   1200
ggaaattcag aaactggtag gaaaagtgtg tgatagaagc tggggactga aagaagctga   1260
tgtggtttgc aggcagctgg gatgtggatc tgcactcaaa acatcatatc aagtttattc   1320
caaaaccaag gcaacaaaca catggctgtt tgtaagcagc tgtaatggaa atgaaacttc   1380
tctttgggac tgcaagaatt ggcagtgggg tggacttagt tgtgatcact atgacgaagc   1440
caaaattacc tgctcagccc acaggaaacc caggctggtt ggaggggaca ttccctgctc   1500
tggtcgtgtt gaagtacaac atggagacac gtggggcacc gtctgtgatt ctgacttctc   1560
tctggaggcg gccagcgtgc tgtgcaggga actacagtgc ggcactgtgg tttccctcct   1620
ggggggagct cactttggag aaggaagtgg acagatctgg gctgaagaat tccagtgtga   1680
ggggcacgag tcccaccttt cactctgccc agtagcaccc cgccctgacg ggacatgtag   1740
ccacagcagg gacgtcggcg tagtctgctc aagatacaca caaatccgct tggtgaatgg   1800
caagacccca tgtgaaggaa gagtggagct caacattctt gggtcctggg ggtccctctg   1860
caactctcac tgggacatgg aagatgccca tgttttatgc cagcagctta aatgtggagt   1920
tgccctttct atcccgggag gagcaccttt tgggaaagga agtgagcagg tctggaggca   1980
catgtttcac tgcactggga ctgagaagca catgggagat tgttccgtca ctgctctggg   2040
cgcatcactc tgttcttcag ggcaagtggc ctctgtaatc tgctcaggga accagagtca   2100
gacactatct ccgtgcaatt catcatcctc ggacccatca agctctatta tttcagaaga   2160
aaatggtgtt gcctgcatag ggagtggtca acttcgcctg gtcgatggag gtggtcgttg   2220
tgctgggaga gtagaggtct atcatgaggg ctcctggggc accatctgtg atgacagctg   2280
ggacctgaat gatgcccatg tggtgtgcaa acagctgagc tgtggatggg ccattaatgc   2340
cactggttct gctcattttg gggaaggaac agggcccatt tggctggatg agataaactg   2400
taatggaaaa gaatctcata tttggcaatg ccactcacat ggttgggggc ggcacaattg   2460
```

```
caggcataag gaggatgcag gagtcatctg ctcagagttc atgtctctga gactgatcag   2520
tgaaaacagc agagagacct gtgcagggcg cctggaagtt ttttacaacg gagcttgggg   2580
cagcgttggc aggaatagca tgtctccagc cacagtgggg gtggtatgca ggcagctggg   2640
ctgtgcagac agaggggaca tcagccctgc atcttcagac aagacagtgt ccaggcacat   2700
gtgggtggac aatgttcagt gtcctaaagg acctgacaca ctatggcagt gcccatcatc   2760
tccatggaag aagagactgg ccagcccctc agaggagaca tggatcacat gtgccaacaa   2820
aataagactt caagaaggaa acactaattg ttctggacgt gtggagatct ggtacggagg   2880
ttcctggggc actgtgtgtg acgactcctg ggaccttgaa gatgctcagg tggtgtgccg   2940
acagctgggc tgtggctcag ctttggaggc aggaaaagag gccgcatttg gccaggggac   3000
tgggcccata tggctcaatg aagtgaagtg caaggggaat gaaacctcct tgtgggattg   3060
tcctgccaga tcctggggcc acagtgactg tggacacaag gaggatgctg ctgtgacgtg   3120
ctcagaaatt gcaaagagcc gagaatccct acatgccaca ggtcgctcat cttttgttgc   3180
acttgcaatc tttggggtca ttctgttggc ctgtctcatc gcattcctca tttggactca   3240
gaagcgaaga cagaggcagc ggctctcagt tttctcagga ggagagaatt ctgtccatca   3300
aattcaatac cgggagatga attcttgcct gaaagcagat gaaacggata tgctaaatcc   3360
ctcaggagac cactctgaag tacaatgaaa aggaaaatgg gaattataac ctggtgagtt   3420
cagcctttaa gataccttga tgaagacctg gactattgaa tgagcaagaa tctgcctctt   3480
acactgaaga ttacaataca gtcctctgtc tcctggtatt ccaaagactg ctgctgaatt   3540
tctaaagaat agattggtga atgtgactac tcaaagttgt atgtaagact ttcaagggca   3600
ttaaataaaa aagaatattg ctg                                          3623
```

<210> SEQ ID NO 13
<211> LENGTH: 3345
<212> TYPE: DNA
<213> ORGANISM: Sus scrofa

<400> SEQUENCE: 13

```
atggacaaac tcagaatggt gctacatgaa aactctggat ctgcagactt tagaagatgt     60
tctgcccatt taagttcctt cacttttgct gtagtcgctg ttctcagtgc ctgcttggtc    120
actagttctc ttggaggaaa agacaaggag ctgaggctaa cgggtggtga aaacaagtgc    180
tctggaagag tggaggtgaa agtgcaggag gagtggggaa ctgtgtgtaa taatggctgg    240
gacatggatg tggtctctgt tgtttgtagg cagctgggat gtccaactgc tatcaaagcc    300
actggatggg ctaattttag tgcaggttct ggacgcattt ggatggatca tgtttcttgt    360
cgagggaatg agtcagctct ctgggactgc aaacatgatg gatggggaaa gcataactgt    420
actcaccaac aggatgctgg agtaacctgc tcagatggat ctgatttaga gatggggctg    480
gtgaatggag gaaaccggtg cttaggaaga atagaagtca aatttcaagg acggtgggga    540
acagtgtgtg atgataactt caacataaat catgcttctg tggtttgtaa acaacttgaa    600
tgtggaagtg ctgtcagttt ctctggttca gctaattttg gagaaggttc tggaccaatc    660
tggtttgatg atcttgtatg caatggaaat gagtcagctc tctggaactg caaacatgaa    720
ggatggggaa agcacaattg cgatcatgct gaggatgctg gagtgatttg cttaaatgga    780
gcagacctga aactgagagt ggtagatgga gtcactgaat gttcaggaag attggaagtg    840
aaattccaag gagaatgggg aacaatctgt gatgatggct gggatagtga tgatgccgct    900
gtggcatgta agcaactggg atgtccaact gctgtcactg ccattggtcg agttaacgcc    960
```

```
agtgagggaa ctggacacat ttggcttgac agtgtttctt gccatggaca cgagtctgct   1020
ctctggcagt gtagacacca tgaatgggga aagcattatt gcaatcatga tgaagatgct   1080
ggtgtgacat gttctgatgg atcagatctg gaactgagac ttaaaggtgg aggcagccac   1140
tgtgctggga cagtggaggt ggaaattcag aaactggtag gaaaagtgtg tgatagaagc   1200
tggggactga aagaagctga tgtggtttgc aggcagctgg gatgtggatc tgcactcaaa   1260
acatcatatc aagtttattc caaaaccaag gcaacaaaca catggctgtt tgtaagcagc   1320
tgtaatggaa atgaaacttc tctttgggac tgcaagaatt ggcagtgggg tggacttagt   1380
tgtgatcact atgacgaagc caaaattacc tgctcagccc acaggaaacc caggctggtt   1440
ggaggggaca ttccctgctc tggtcgtgtt gaagtacaac atggagacac gtggggcacc   1500
gtctgtgatt ctgacttctc tctggaggcg gccagcgtgc tgtgcaggga actacagtgc   1560
ggcactgtgg tttccctcct ggggggagct cactttggag aaggaagtgg acagatctgg   1620
gctgaagaat tccagtgtga ggggcacgag tcccaccttt cactctgccc agtagcaccc   1680
cgccctgacg ggacatgtag ccacagcagg gacgtcggcg tagtctgctc aagatacaca   1740
caaatccgct tggtgaatgg caagacccca tgtgaaggaa gagtggagct caacattctt   1800
gggtcctggg ggtccctctg caactctcac tgggacatgg aagatgccca tgttttatgc   1860
cagcagctta aatgtggagt tgccctttct atcccgggag gagcaccttt tgggaaagga   1920
agtgagcagg tctggaggca catgtttcac tgcactggga ctgagaagca catgggagat   1980
tgttccgtca ctgctctggg cgcatcactc tgttcttcag ggcaagtggc ctctgtaatc   2040
tgctcaggga accagagtca gacactatct ccgtgcaatt catcatcctc ggacccatca   2100
agctctatta tttcagaaga aaatggtgtt gcctgcatag ggagtggtca acttcgcctg   2160
gtcgatggag gtggtcgttg tgctgggaga gtagaggtct atcatgaggg ctcctggggc   2220
accatctgtg atgacagctg ggacctgaat gatgcccatg tggtgtgcaa acagctgagc   2280
tgtggatggg ccattaatgc cactggttct gctcattttg gggaaggaac agggcccatt   2340
tggctggatg agataaactg taatggaaaa gaatctcata tttggcaatg ccactcacat   2400
ggttgggggc ggcacaattg caggcataag gaggatgcag gagtcatctg ctcagagttc   2460
atgtctctga gactgatcag tgaaaacagc agagagacct gtgcagggcg cctggaagtt   2520
ttttacaacg gagcttgggg cagcgttggc aggaatagca tgtctccagc cacagtgggg   2580
gtggtatgca ggcagctggg ctgtgcagac agaggggaca tcagccctgc atcttcagac   2640
aagacagtgt ccaggcacat gtgggtggac aatgttcagt gtcctaaagg acctgacaca   2700
ctatggcagt gcccatcatc tccatggaag aagagactgg ccagcccctc agaggagaca   2760
tggatcacat gtgccaacaa aataagactt caagaaggaa acactaattg ttctggacgt   2820
gtggagatct ggtacggagg ttcctggggc actgtgtgtg acgactcctg ggaccttgaa   2880
gatgctcagg tggtgtgccg acagctgggc tgtggctcag ctttggaggc aggaaaagag   2940
gccgcatttg gccaggggac tgggcccata tggctcaatg aagtgaagtg caaggggaat   3000
gaaacctcct tgtgggattg tcctgccaga tcctggggcc acagtgactg tggacacaag   3060
gaggatgctg ctgtgacgtg ctcagaaatt gcaaagagcc gagaatccct acatgccaca   3120
ggtcgctcat cttttgttgc acttgcaatc tttggggtca ttctgttggc ctgtctcatc   3180
gcattcctca tttggactca gaagcgaaga cagaggcagc ggctctcagt tttctcagga   3240
ggagagaatt ctgtccatca aattcaatac cgggagatga attcttgcct gaaagcagat   3300
gaaacggata tgctaaatcc ctcaggagac cactctgaag tacaa                   3345
```

<210> SEQ ID NO 14
<211> LENGTH: 1115
<212> TYPE: PRT
<213> ORGANISM: Sus scrofa

<400> SEQUENCE: 14

```
Met Asp Lys Leu Arg Met Val Leu His Glu Asn Ser Gly Ser Ala Asp
1               5                   10                  15

Phe Arg Arg Cys Ser Ala His Leu Ser Ser Phe Thr Phe Ala Val Val
            20                  25                  30

Ala Val Leu Ser Ala Cys Leu Val Thr Ser Ser Leu Gly Gly Lys Asp
        35                  40                  45

Lys Glu Leu Arg Leu Thr Gly Gly Glu Asn Lys Cys Ser Gly Arg Val
    50                  55                  60

Glu Val Lys Val Gln Glu Glu Trp Gly Thr Val Cys Asn Asn Gly Trp
65                  70                  75                  80

Asp Met Asp Val Val Ser Val Val Cys Arg Gln Leu Gly Cys Pro Thr
                85                  90                  95

Ala Ile Lys Ala Thr Gly Trp Ala Asn Phe Ser Ala Gly Ser Gly Arg
            100                 105                 110

Ile Trp Met Asp His Val Ser Cys Arg Gly Asn Glu Ser Ala Leu Trp
        115                 120                 125

Asp Cys Lys His Asp Gly Trp Gly Lys His Asn Cys Thr His Gln Gln
    130                 135                 140

Asp Ala Gly Val Thr Cys Ser Asp Gly Ser Asp Leu Glu Met Gly Leu
145                 150                 155                 160

Val Asn Gly Gly Asn Arg Cys Leu Gly Arg Ile Glu Val Lys Phe Gln
                165                 170                 175

Gly Arg Trp Gly Thr Val Cys Asp Asp Asn Phe Asn Ile Asn His Ala
            180                 185                 190

Ser Val Val Cys Lys Gln Leu Glu Cys Gly Ser Ala Val Ser Phe Ser
        195                 200                 205

Gly Ser Ala Asn Phe Gly Glu Gly Ser Gly Pro Ile Trp Phe Asp Asp
    210                 215                 220

Leu Val Cys Asn Gly Asn Glu Ser Ala Leu Trp Asn Cys Lys His Glu
225                 230                 235                 240

Gly Trp Gly Lys His Asn Cys Asp His Ala Glu Asp Ala Gly Val Ile
                245                 250                 255

Cys Leu Asn Gly Ala Asp Leu Lys Leu Arg Val Val Asp Gly Val Thr
            260                 265                 270

Glu Cys Ser Gly Arg Leu Glu Val Lys Phe Gln Gly Glu Trp Gly Thr
        275                 280                 285

Ile Cys Asp Asp Gly Trp Asp Ser Asp Asp Ala Ala Val Ala Cys Lys
    290                 295                 300

Gln Leu Gly Cys Pro Thr Ala Val Thr Ala Ile Gly Arg Val Asn Ala
305                 310                 315                 320

Ser Glu Gly Thr Gly His Ile Trp Leu Asp Ser Val Ser Cys His Gly
                325                 330                 335

His Glu Ser Ala Leu Trp Gln Cys Arg His His Glu Trp Gly Lys His
            340                 345                 350

Tyr Cys Asn His Asp Glu Asp Ala Gly Val Thr Cys Ser Asp Gly Ser
        355                 360                 365

Asp Leu Glu Leu Arg Leu Lys Gly Gly Gly Ser His Cys Ala Gly Thr
    370                 375                 380
```

```
Val Glu Val Glu Ile Gln Lys Leu Val Gly Lys Val Cys Asp Arg Ser
385                 390                 395                 400

Trp Gly Leu Lys Glu Ala Asp Val Val Cys Arg Gln Leu Gly Cys Gly
                405                 410                 415

Ser Ala Leu Lys Thr Ser Tyr Gln Val Tyr Ser Lys Thr Lys Ala Thr
            420                 425                 430

Asn Thr Trp Leu Phe Val Ser Ser Cys Asn Gly Asn Glu Thr Ser Leu
        435                 440                 445

Trp Asp Cys Lys Asn Trp Gln Trp Gly Gly Leu Ser Cys Asp His Tyr
    450                 455                 460

Asp Glu Ala Lys Ile Thr Cys Ser Ala His Arg Lys Pro Arg Leu Val
465                 470                 475                 480

Gly Gly Asp Ile Pro Cys Ser Gly Arg Val Glu Val Gln His Gly Asp
                485                 490                 495

Thr Trp Gly Thr Val Cys Asp Ser Asp Phe Ser Leu Glu Ala Ala Ser
            500                 505                 510

Val Leu Cys Arg Glu Leu Gln Cys Gly Thr Val Val Ser Leu Leu Gly
        515                 520                 525

Gly Ala His Phe Gly Glu Gly Ser Gly Gln Ile Trp Ala Glu Glu Phe
    530                 535                 540

Gln Cys Glu Gly His Glu Ser His Leu Ser Leu Cys Pro Val Ala Pro
545                 550                 555                 560

Arg Pro Asp Gly Thr Cys Ser His Ser Arg Asp Val Gly Val Val Cys
                565                 570                 575

Ser Arg Tyr Thr Gln Ile Arg Leu Val Asn Gly Lys Thr Pro Cys Glu
            580                 585                 590

Gly Arg Val Glu Leu Asn Ile Leu Gly Ser Trp Gly Ser Leu Cys Asn
        595                 600                 605

Ser His Trp Asp Met Glu Asp Ala His Val Leu Cys Gln Gln Leu Lys
    610                 615                 620

Cys Gly Val Ala Leu Ser Ile Pro Gly Gly Ala Pro Phe Gly Lys Gly
625                 630                 635                 640

Ser Glu Gln Val Trp Arg His Met Phe His Cys Thr Gly Thr Glu Lys
                645                 650                 655

His Met Gly Asp Cys Ser Val Thr Ala Leu Gly Ala Ser Leu Cys Ser
            660                 665                 670

Ser Gly Gln Val Ala Ser Val Ile Cys Ser Gly Asn Gln Ser Gln Thr
        675                 680                 685

Leu Ser Pro Cys Asn Ser Ser Ser Ser Asp Pro Ser Ser Ser Ile Ile
    690                 695                 700

Ser Glu Glu Asn Gly Val Ala Cys Ile Gly Ser Gly Gln Leu Arg Leu
705                 710                 715                 720

Val Asp Gly Gly Gly Arg Cys Ala Gly Arg Val Glu Val Tyr His Glu
                725                 730                 735

Gly Ser Trp Gly Thr Ile Cys Asp Asp Ser Trp Asp Leu Asn Asp Ala
            740                 745                 750

His Val Val Cys Lys Gln Leu Ser Cys Gly Trp Ala Ile Asn Ala Thr
        755                 760                 765

Gly Ser Ala His Phe Gly Glu Gly Thr Gly Pro Ile Trp Leu Asp Glu
    770                 775                 780

Ile Asn Cys Asn Gly Lys Glu Ser His Ile Trp Gln Cys His Ser His
785                 790                 795                 800

Gly Trp Gly Arg His Asn Cys Arg His Lys Glu Asp Ala Gly Val Ile
```

```
                805                 810                 815

Cys Ser Glu Phe Met Ser Leu Arg Leu Ile Ser Glu Asn Ser Arg Glu
            820                 825                 830

Thr Cys Ala Gly Arg Leu Glu Val Phe Tyr Asn Gly Ala Trp Gly Ser
        835                 840                 845

Val Gly Arg Asn Ser Met Ser Pro Ala Thr Val Gly Val Val Cys Arg
    850                 855                 860

Gln Leu Gly Cys Ala Asp Arg Gly Asp Ile Ser Pro Ala Ser Ser Asp
865                 870                 875                 880

Lys Thr Val Ser Arg His Met Trp Val Asp Asn Val Gln Cys Pro Lys
                885                 890                 895

Gly Pro Asp Thr Leu Trp Gln Cys Pro Ser Ser Pro Trp Lys Lys Arg
            900                 905                 910

Leu Ala Ser Pro Ser Glu Glu Thr Trp Ile Thr Cys Ala Asn Lys Ile
        915                 920                 925

Arg Leu Gln Glu Gly Asn Thr Asn Cys Ser Gly Arg Val Glu Ile Trp
    930                 935                 940

Tyr Gly Gly Ser Trp Gly Thr Val Cys Asp Asp Ser Trp Asp Leu Glu
945                 950                 955                 960

Asp Ala Gln Val Val Cys Arg Gln Leu Gly Cys Gly Ser Ala Leu Glu
                965                 970                 975

Ala Gly Lys Glu Ala Ala Phe Gly Gln Gly Thr Gly Pro Ile Trp Leu
            980                 985                 990

Asn Glu Val Lys Cys Lys Gly Asn  Glu Thr Ser Leu Trp  Asp Cys Pro
        995                 1000                1005

Ala Arg  Ser Trp Gly His Ser  Asp Cys Gly His Lys  Glu Asp Ala
    1010                 1015                 1020

Ala Val  Thr Cys Ser Glu Ile  Ala Lys Ser Arg Glu  Ser Leu His
    1025                 1030                 1035

Ala Thr  Gly Arg Ser Ser Phe  Val Ala Leu Ala Ile  Phe Gly Val
    1040                 1045                 1050

Ile Leu  Leu Ala Cys Leu Ile  Ala Phe Leu Ile Trp  Thr Gln Lys
    1055                 1060                 1065

Arg Arg  Gln Arg Gln Arg Leu  Ser Val Phe Ser Gly  Gly Glu Asn
    1070                 1075                 1080

Ser Val  His Gln Ile Gln Tyr  Arg Glu Met Asn Ser  Cys Leu Lys
    1085                 1090                 1095

Ala Asp  Glu Thr Asp Met Leu  Asn Pro Ser Gly Asp  His Ser Glu
    1100                 1105                 1110

Val Gln
    1115
```

<210> SEQ ID NO 15
<211> LENGTH: 50
<212> TYPE: DNA
<213> ORGANISM: Artificial
<220> FEATURE:
<223> OTHER INFORMATION: PCR Primer

<400> SEQUENCE: 15
caccgcggcc gcgaagttat aaatcgccac catgagcaaa ctcagaatgg 50

<210> SEQ ID NO 16
<211> LENGTH: 40
<212> TYPE: DNA
<213> ORGANISM: Artificial
<220> FEATURE:

<223> OTHER INFORMATION: PCR Primer

<400> SEQUENCE: 16
tgctccggta cctagtccag gtcttcatca aggtatctta 40

<210> SEQ ID NO 17
<211> LENGTH: 3434
<212> TYPE: DNA
<213> ORGANISM: Homo sapiens

<400> SEQUENCE: 17
atgagcaaac tcagaatggt gctacttgaa gactctggat ctgctgactt cagaagacat 60
tttgtcaacc tgagtccctt caccattact gtggtcttac ttctcagtgc ctgttttgtc 120
accagttctc ttggaggaac agacaaggag ctgaggctag tggatggtga aaacaagtgt 180
agcgggagag tggaagtgaa agtccaggag gagtggggaa cggtgtgtaa taatggctgg 240
agcatggaag cggtctctgt gatttgtaac cagctgggat gtccaactgc tatcaaagcc 300
cctggatggg ctaattccag tgcaggttct ggacgcattt ggatggatca tgtttcttgt 360
cgtgggaatg agtcagctct ttgggattgc aaacatgatg gatggggaaa gcatagtaac 420
tgtactcacc aacaagatgc tggagtgacc tgctcagatg gatccaattt ggaaatgagg 480
ctgacgcgtg gagggaatat gtgttctgga agaatagaga tcaaattcca aggacggtgg 540
ggaacagtgt gtgatgataa cttcaacata gatcatgcat ctgtcatttg tagacaactt 600
gaatgtggaa gtgctgtcag tttctctggt tcatctaatt ttggagaagg ctctggacca 660
atctggtttg atgatcttat atgcaacgga aatgagtcag ctctctggaa ctgcaaacat 720
caaggatggg gaaagcataa ctgtgaccat gctgaggatg ctggagtgat ttgctcaaag 780
ggagcagatc tgagcctgag actggtagat ggagtcactg aatgttcagg aagattagaa 840
gtgagattcc aaggggaatg gggacaaata tgtgatgacg gctgggacag ttacgatgct 900
gctgtggcat gcaagcaact gggatgtcca actgccgtca cagccattgg tcgagttaac 960
gccagtaagg gatttggaca catctggctt gacagcgttt cttgccaggg acatgaacct 1020
gctgtctggc aatgtaaaca ccatgaatgg ggaaagcatt attgcaatca caatgaagat 1080
gctggcgtga catgttctga tggatcagat ctggagctaa gacttagagg tggaggcagc 1140
cgctgtgctg ggacagttga ggtggagatt cagagactgt tagggaaggt gtgtgacaga 1200
ggctggggac tgaaagaagc tgatgtggtt tgcaggcagc tgggatgtgg atctgcactc 1260
aaaacatctt atcaagtgta ctccaaaatc caggcaacaa acacatggct gtttctaagt 1320
agctgtaacg gaaatgaaac ttctctttgg gactgcaaga actggcaatg gggtggactt 1380
acctgtgatc actatgaaga agccaaaatt acctgctcag cccacaggga acccagactg 1440
gttggagggg acattccctg ttctggacgt gttgaagtga agcatggtga cacgtggggc 1500
tccatctgtg attcggactt ctctctggaa gctgccagcg ttctatgcag ggaattacag 1560
tgtggcacag ttgtctctat cctgggggga gctcactttg gagagggaaa tggacagatc 1620
tgggctgaag aattccagtg tgagggacat gagtcccatc tttcactctg cccagtagca 1680
ccccgcccag aaggaacttg tagccacagc agggatgttg gagtagtctg ctcaagatac 1740
acagaaattc gcttggtgaa tggcaagacc ccgtgtgagg gcagagtgga gctcaaaacg 1800
cttggtgcct ggggatccct ctgtaactct cactgggaca tagaagatgc ccatgttctt 1860
tgccagcagc ttaaatgtgg agttgccctt tctaccccag gaggagcacg ttttggaaaa 1920
ggaaatggtc agatctggag gcatatgttt cactgcactg ggactgagca gcacatggga 1980

-continued

```
gattgtcctg taactgctct aggtgcttca ttatgtcctt cagagcaagt ggcctctgta   2040
atctgctcag gaaaccagtc ccaaacactg tcctcgtgca attcatcgtc tttgggccca   2100
acaaggccta ccattccaga agaaagtgct gtggcctgca tagagagtgg tcaacttcgc   2160
ctggtaaatg gaggaggtcg ctgtgctggg agagtagaga tctatcatga gggctcctgg   2220
ggcaccatct gtgatgacag ctgggacctg agtgatgccc acgtggtttg cagacagctg   2280
ggctgtggag aggccattaa tgccactggt tctgctcatt ttggggaagg aacagggccc   2340
atctggctgg atgagatgaa atgcaatgga aaagaatccc gcatttggca gtgccattca   2400
cacggctggg ggcagcaaaa ttgcaggcac aaggaggatg cgggagttat ctgctcagaa   2460
ttcatgtctc tgagactgac cagtgaagcc agcagagagg cctgtgcagg gcgtctggaa   2520
gtttttaca atggagcttg gggcactgtt ggcaagagta gcatgtctga aaccactgtg    2580
ggtgtggtgt gcaggcagct gggctgtgca gacaaaggga aaatcaaccc tgcatcttta   2640
gacaaggcca tgtccattcc catgtgggtg gacaatgttc agtgtccaaa aggacctgac   2700
acgctgtggc agtgcccatc atctccatgg gagaagagac tggccagccc ctcggaggag   2760
acctggatca catgtgacaa caagataaga cttcaggaag gacccacttc ctgttctgga   2820
cgtgtggaga tctggcatgg aggttcctgg gggacagtgt gtgatgactc ttgggacttg   2880
gacgatgctc aggtggtgtg tcaacaactt ggctgtggtc cagctttgaa agcattcaaa   2940
gaagcagagt ttggtcaggg gactggaccg atatggctca atgaagtgaa gtgcaaaggg   3000
aatgagtctt ccttgtggga ttgtcctgcc agacgctggg gccatagtga gtgtgggcac   3060
aaggaagacg ctgcagtgaa ttgcacagat atttcagtgc agaaaacccc acaaaaagcc   3120
acaacaggtc gctcatcccg tcagtcatcc tttattgcag tcgggatcct tggggttgtt   3180
ctgttggcca ttttcgtcgc attattcttc ttgactaaaa agcgaagaca gagacagcgg   3240
cttgcagttt cctcaagagg agagaactta gtccaccaaa ttcaataccg ggagatgaat   3300
tcttgcctga atgcagatga tctggaccta atgaattcct caggaggcca ttctgagcca   3360
cactgaaaag gaaaatggga atttataacc cagtgagttc agcctttaag ataccttgat   3420
gaagacctgg acta                                                     3434
```

<210> SEQ ID NO 18
<211> LENGTH: 3363
<212> TYPE: DNA
<213> ORGANISM: Homo sapiens

<400> SEQUENCE: 18

```
atgagcaaac tcagaatggt gctacttgaa gactctggat ctgctgactt cagaagacat     60
tttgtcaacc tgagtccctt caccattact gtggtcttac ttctcagtgc ctgttttgtc    120
accagttctc ttggaggaac agacaaggag ctgaggctag tggatggtga aaacaagtgt    180
agcgggagag tggaagtgaa agtccaggag gagtggggaa cggtgtgtaa taatggctgg    240
agcatggaag cggtctctgt gatttgtaac cagctgggat gtccaactgc tatcaaagcc    300
cctggatggg ctaattccag tgcaggttct ggacgcattt ggatggatca tgtttcttgt    360
cgtgggaatg agtcagctct ttgggattgc aaacatgatg gatggggaaa gcatagtaac    420
tgtactcacc aacaagatgc tggagtgacc tgctcagatg gatccaattt ggaaatgagg    480
ctgacgcgtg gagggaatat gtgttctgga agaatagaga tcaaattcca aggacggtgg    540
ggaacagtgt gtgatgataa cttcaacata gatcatgcat ctgtcatttg tagacaactt    600
gaatgtggaa gtgctgtcag tttctctggt tcatctaatt ttggagaagg ctctggacca    660
```

```
atctggtttg atgatcttat atgcaacgga aatgagtcag ctctctggaa ctgcaaacat    720
caaggatggg gaaagcataa ctgtgaccat gctgaggatg ctggagtgat ttgctcaaag    780
ggagcagatc tgagcctgag actggtagat ggagtcactg aatgttcagg aagattagaa    840
gtgagattcc aaggggaatg gggacaata tgtgatgacg gctgggacag ttacgatgct    900
gctgtggcat gcaagcaact gggatgtcca actgccgtca cagccattgg tcgagttaac    960
gccagtaagg gatttggaca catctggctt gacagcgttt cttgccaggg acatgaacct   1020
gctgtctggc aatgtaaaca ccatgaatgg ggaaagcatt attgcaatca caatgaagat   1080
gctggcgtga catgttctga tggatcagat ctggagctaa gacttagagg tggaggcagc   1140
cgctgtgctg ggacagttga ggtggagatt cagagactgt tagggaaggt gtgtgacaga   1200
ggctggggac tgaaagaagc tgatgtggtt tgcaggcagc tgggatgtgg atctgcactc   1260
aaaacatctt atcaagtgta ctccaaaatc caggcaacaa acacatggct gtttctaagt   1320
agctgtaacg gaaatgaaac ttctctttgg gactgcaaga actggcaatg gggtggactt   1380
acctgtgatc actatgaaga agccaaaatt acctgctcag cccacaggga acccagactg   1440
gttggagggg acattccctg ttctggacgt gttgaagtga agcatggtga cacgtggggc   1500
tccatctgtg attcggactt ctctctggaa gctgccagcg ttctatgcag ggaattacag   1560
tgtggcacag ttgtctctat cctgggggga gctcactttg gagagggaaa tggacagatc   1620
tgggctgaag aattccagtg tgagggacat gagtcccatc tttcactctg cccagtagca   1680
ccccgcccag aaggaacttg tagccacagc agggatgttg gagtagtctg ctcaagatac   1740
acagaaattc gcttggtgaa tggcaagacc ccgtgtgagg gcagagtgga gctcaaaacg   1800
cttggtgcct ggggatccct ctgtaactct cactgggaca tagaagatgc ccatgttctt   1860
tgccagcagc ttaaatgtgg agttgccctt tctaccccag gaggagcacg ttttggaaaa   1920
ggaaatggtc agatctggag gcatatgttt cactgcactg ggactgagca gcacatggga   1980
gattgtcctg taactgctct aggtgcttca ttatgtcctt cagagcaagt ggcctctgta   2040
atctgctcag gaaaccagtc ccaaacactg tcctcgtgca attcatcgtc tttgggccca   2100
acaaggccta ccattccaga agaaagtgct gtggcctgca tagagagtgg tcaacttcgc   2160
ctggtaaatg gaggaggtcg ctgtgctggg agagtagaga tctatcatga gggctcctgg   2220
ggcaccatct gtgatgacag ctgggacctg agtgatgccc acgtggtttg cagacagctg   2280
ggctgtggag aggccattaa tgccactggt tctgctcatt ttggggaagg aacagggccc   2340
atctggctgg atgagatgaa atgcaatgga aaagaatccc gcatttggca gtgccattca   2400
cacggctggg ggcagcaaaa ttgcaggcac aaggaggatg cgggagttat ctgctcagaa   2460
ttcatgtctc tgagactgac cagtgaagcc agcagagagg cctgtgcagg gcgtctggaa   2520
gtttttttaca atggagcttg gggcactgtt ggcaagagta gcatgtctga aaccactgtg   2580
ggtgtggtgt gcaggcagct gggctgtgca gacaaaggga aaatcaaccc tgcatcttta   2640
gacaaggcca tgtccattcc catgtgggtg gacaatgttc agtgtccaaa aggacctgac   2700
acgctgtggc agtgcccatc atctccatgg gagaagagac tggccagccc ctcggaggag   2760
acctggatca catgtgacaa caagataaga cttcaggaag gacccacttc ctgttctgga   2820
cgtgtggaga tctggcatgg aggttcctgg gggacagtgt gtgatgactc ttgggacttg   2880
gacgatgctc aggtggtgtg tcaacaactt ggctgtggtc cagctttgaa agcattcaaa   2940
gaagcagagt ttggtcaggg gactggaccg atatggctca atgaagtgaa gtgcaaaggg   3000
aatgagtctt ccttgtggga ttgtcctgcc agacgctggg gccatagtga gtgtgggcac   3060
```

```
aaggaagacg ctgcagtgaa ttgcacagat atttcagtgc agaaaacccc acaaaaagcc   3120

acaacaggtc gctcatcccg tcagtcatcc tttattgcag tcgggatcct tggggttgtt   3180

ctgttggcca ttttcgtcgc attattcttc ttgactaaaa agcgaagaca gagacagcgg   3240

cttgcagttt cctcaagagg agagaactta gtccaccaaa ttcaataccg ggagatgaat   3300

tcttgcctga atgcagatga tctggaccta atgaattcct caggaggcca ttctgagcca   3360

cac                                                                 3363
```

```
<210> SEQ ID NO 19
<211> LENGTH: 1121
<212> TYPE: PRT
<213> ORGANISM: Homo sapiens

<400> SEQUENCE: 19

Met Ser Lys Leu Arg Met Val Leu Leu Glu Asp Ser Gly Ser Ala Asp
1               5                   10                  15

Phe Arg Arg His Phe Val Asn Leu Ser Pro Phe Thr Ile Thr Val Val
            20                  25                  30

Leu Leu Leu Ser Ala Cys Phe Val Thr Ser Ser Leu Gly Gly Thr Asp
        35                  40                  45

Lys Glu Leu Arg Leu Val Asp Gly Glu Asn Lys Cys Ser Gly Arg Val
    50                  55                  60

Glu Val Lys Val Gln Glu Glu Trp Gly Thr Val Cys Asn Asn Gly Trp
65                  70                  75                  80

Ser Met Glu Ala Val Ser Val Ile Cys Asn Gln Leu Gly Cys Pro Thr
                85                  90                  95

Ala Ile Lys Ala Pro Gly Trp Ala Asn Ser Ser Ala Gly Ser Gly Arg
            100                 105                 110

Ile Trp Met Asp His Val Ser Cys Arg Gly Asn Glu Ser Ala Leu Trp
        115                 120                 125

Asp Cys Lys His Asp Gly Trp Gly Lys His Ser Asn Cys Thr His Gln
    130                 135                 140

Gln Asp Ala Gly Val Thr Cys Ser Asp Gly Ser Asn Leu Glu Met Arg
145                 150                 155                 160

Leu Thr Arg Gly Gly Asn Met Cys Ser Gly Arg Ile Glu Ile Lys Phe
                165                 170                 175

Gln Gly Arg Trp Gly Thr Val Cys Asp Asp Asn Phe Asn Ile Asp His
            180                 185                 190

Ala Ser Val Ile Cys Arg Gln Leu Glu Cys Gly Ser Ala Val Ser Phe
        195                 200                 205

Ser Gly Ser Ser Asn Phe Gly Glu Gly Ser Gly Pro Ile Trp Phe Asp
    210                 215                 220

Asp Leu Ile Cys Asn Gly Asn Glu Ser Ala Leu Trp Asn Cys Lys His
225                 230                 235                 240

Gln Gly Trp Gly Lys His Asn Cys Asp His Ala Glu Asp Ala Gly Val
                245                 250                 255

Ile Cys Ser Lys Gly Ala Asp Leu Ser Leu Arg Leu Val Asp Gly Val
            260                 265                 270

Thr Glu Cys Ser Gly Arg Leu Glu Val Arg Phe Gln Gly Glu Trp Gly
        275                 280                 285

Thr Ile Cys Asp Asp Gly Trp Asp Ser Tyr Asp Ala Ala Val Ala Cys
    290                 295                 300

Lys Gln Leu Gly Cys Pro Thr Ala Val Thr Ala Ile Gly Arg Val Asn
305                 310                 315                 320
```

```
Ala Ser Lys Gly Phe Gly His Ile Trp Leu Asp Ser Val Ser Cys Gln
                325                 330                 335

Gly His Glu Pro Ala Val Trp Gln Cys Lys His His Glu Trp Gly Lys
            340                 345                 350

His Tyr Cys Asn His Asn Glu Asp Ala Gly Val Thr Cys Ser Asp Gly
        355                 360                 365

Ser Asp Leu Glu Leu Arg Leu Arg Gly Gly Gly Ser Arg Cys Ala Gly
    370                 375                 380

Thr Val Glu Val Glu Ile Gln Arg Leu Leu Gly Lys Val Cys Asp Arg
385                 390                 395                 400

Gly Trp Gly Leu Lys Glu Ala Asp Val Val Cys Arg Gln Leu Gly Cys
                405                 410                 415

Gly Ser Ala Leu Lys Thr Ser Tyr Gln Val Tyr Ser Lys Ile Gln Ala
            420                 425                 430

Thr Asn Thr Trp Leu Phe Leu Ser Ser Cys Asn Gly Asn Glu Thr Ser
        435                 440                 445

Leu Trp Asp Cys Lys Asn Trp Gln Trp Gly Gly Leu Thr Cys Asp His
    450                 455                 460

Tyr Glu Glu Ala Lys Ile Thr Cys Ser Ala His Arg Glu Pro Arg Leu
465                 470                 475                 480

Val Gly Gly Asp Ile Pro Cys Ser Gly Arg Val Glu Val Lys His Gly
                485                 490                 495

Asp Thr Trp Gly Ser Ile Cys Asp Ser Asp Phe Ser Leu Glu Ala Ala
            500                 505                 510

Ser Val Leu Cys Arg Glu Leu Gln Cys Gly Thr Val Val Ser Ile Leu
        515                 520                 525

Gly Gly Ala His Phe Gly Glu Gly Asn Gly Gln Ile Trp Ala Glu Glu
    530                 535                 540

Phe Gln Cys Glu Gly His Glu Ser His Leu Ser Leu Cys Pro Val Ala
545                 550                 555                 560

Pro Arg Pro Glu Gly Thr Cys Ser His Ser Arg Asp Val Gly Val Val
                565                 570                 575

Cys Ser Arg Tyr Thr Glu Ile Arg Leu Val Asn Gly Lys Thr Pro Cys
            580                 585                 590

Glu Gly Arg Val Glu Leu Lys Thr Leu Gly Ala Trp Gly Ser Leu Cys
        595                 600                 605

Asn Ser His Trp Asp Ile Glu Asp Ala His Val Leu Cys Gln Gln Leu
    610                 615                 620

Lys Cys Gly Val Ala Leu Ser Thr Pro Gly Gly Ala Arg Phe Gly Lys
625                 630                 635                 640

Gly Asn Gly Gln Ile Trp Arg His Met Phe His Cys Thr Gly Thr Glu
                645                 650                 655

Gln His Met Gly Asp Cys Pro Val Thr Ala Leu Gly Ala Ser Leu Cys
            660                 665                 670

Pro Ser Glu Gln Val Ala Ser Val Ile Cys Ser Gly Asn Gln Ser Gln
        675                 680                 685

Thr Leu Ser Ser Cys Asn Ser Ser Ser Leu Gly Pro Thr Arg Pro Thr
    690                 695                 700

Ile Pro Glu Glu Ser Ala Val Ala Cys Ile Glu Ser Gly Gln Leu Arg
705                 710                 715                 720

Leu Val Asn Gly Gly Gly Arg Cys Ala Gly Arg Val Glu Ile Tyr His
                725                 730                 735

Glu Gly Ser Trp Gly Thr Ile Cys Asp Asp Ser Trp Asp Leu Ser Asp
            740                 745                 750
```

```
Ala His Val Val Cys Arg Gln Leu Gly Cys Gly Glu Ala Ile Asn Ala
        755                 760                 765

Thr Gly Ser Ala His Phe Gly Glu Gly Thr Gly Pro Ile Trp Leu Asp
    770                 775                 780

Glu Met Lys Cys Asn Gly Lys Glu Ser Arg Ile Trp Gln Cys His Ser
785                 790                 795                 800

His Gly Trp Gly Gln Gln Asn Cys Arg His Lys Glu Asp Ala Gly Val
                805                 810                 815

Ile Cys Ser Glu Phe Met Ser Leu Arg Leu Thr Ser Glu Ala Ser Arg
            820                 825                 830

Glu Ala Cys Ala Gly Arg Leu Glu Val Phe Tyr Asn Gly Ala Trp Gly
        835                 840                 845

Thr Val Gly Lys Ser Ser Met Ser Glu Thr Thr Val Gly Val Val Cys
    850                 855                 860

Arg Gln Leu Gly Cys Ala Asp Lys Gly Lys Ile Asn Pro Ala Ser Leu
865                 870                 875                 880

Asp Lys Ala Met Ser Ile Pro Met Trp Val Asp Asn Val Gln Cys Pro
                885                 890                 895

Lys Gly Pro Asp Thr Leu Trp Gln Cys Pro Ser Ser Pro Trp Glu Lys
            900                 905                 910

Arg Leu Ala Ser Pro Ser Glu Glu Thr Trp Ile Thr Cys Asp Asn Lys
        915                 920                 925

Ile Arg Leu Gln Glu Gly Pro Thr Ser Cys Ser Gly Arg Val Glu Ile
    930                 935                 940

Trp His Gly Gly Ser Trp Gly Thr Val Cys Asp Asp Ser Trp Asp Leu
945                 950                 955                 960

Asp Asp Ala Gln Val Val Cys Gln Gln Leu Gly Cys Gly Pro Ala Leu
                965                 970                 975

Lys Ala Phe Lys Glu Ala Glu Phe Gly Gln Gly Thr Gly Pro Ile Trp
            980                 985                 990

Leu Asn Glu Val Lys Cys Lys Gly  Asn Glu Ser Ser Leu  Trp Asp Cys
        995                 1000                 1005

Pro Ala  Arg Arg Trp Gly His  Ser Glu Cys Gly His  Lys Glu Asp
    1010                 1015                 1020

Ala Ala  Val Asn Cys Thr Asp  Ile Ser Val Gln Lys  Thr Pro Gln
    1025                 1030                 1035

Lys Ala  Thr Thr Gly Arg Ser  Ser Arg Gln Ser Ser  Phe Ile Ala
    1040                 1045                 1050

Val Gly  Ile Leu Gly Val Val  Leu Leu Ala Ile Phe  Val Ala Leu
    1055                 1060                 1065

Phe Phe  Leu Thr Lys Lys Arg  Arg Gln Arg Gln Arg  Leu Ala Val
    1070                 1075                 1080

Ser Ser  Arg Gly Glu Asn Leu  Val His Gln Ile Gln  Tyr Arg Glu
    1085                 1090                 1095

Met Asn  Ser Cys Leu Asn Ala  Asp Asp Leu Asp Leu  Met Asn Ser
    1100                 1105                 1110

Ser Gly  Gly His Ser Glu Pro  His
    1115                 1120
```

```
<210> SEQ ID NO 20
<211> LENGTH: 37
<212> TYPE: DNA
<213> ORGANISM: Artificial
<220> FEATURE:
<223> OTHER INFORMATION: PCR Primer
```

<400> SEQUENCE: 20
caccgcggcc gccacacgga gccatcaaaa tcatcaa 37

<210> SEQ ID NO 21
<211> LENGTH: 46
<212> TYPE: DNA
<213> ORGANISM: Artificial
<220> FEATURE:
<223> OTHER INFORMATION: PCR Primer

<400> SEQUENCE: 21
ggtaccgcga acaagcaaac caatagcaat attgtttaat tccctc 46

<210> SEQ ID NO 22
<211> LENGTH: 3556
<212> TYPE: DNA
<213> ORGANISM: Mus musculus

<400> SEQUENCE: 22
gctttggaat gggtggacac agaatggttc ttcttggagg tgctggatct cctggttgta 60
aaaggtttgt ccatctaggt ttctttgttg tggctgtgag ctcacttctc agtgcctctg 120
ctgtcactaa cgctcctgga gaaatgaaga aggaactgag actggcgggt ggtgaaaaca 180
actgtagtgg gagagtggaa cttaagatcc atgacaagtg gggcacagtg tgcagtaacg 240
gctggagcat gaatgaagtg tccgtggttt gccagcagct gggatgccca acttctatta 300
aagcccttgg atgggctaac tccagcgccg gctctggata tatctggatg gacaaagttt 360
cttgtacagg gaatgagtca gctctttggg actgcaaaca tgatgggtgg ggaaagcata 420
actgtaccca tgaaaaagat gctggagtga cctgctcaga tggatctaat ttggagatga 480
gactggtgaa cagtgcgggc caccgatgct taggaagagt agaaataaag ttccagggaa 540
agtgggggac ggtgtgtgac gacaacttca gcaaagatca cgcttctgtg atttgtaaac 600
agcttggatg tggaagtgcc attagtttct ctggctcagc taaattggga gctggttctg 660
gaccaatctg gctcgatgac ctggcatgca atggaaatga gtcagctctc tgggactgca 720
aacaccgggg atggggcaag cataactgtg accatgctga ggatgtcggt gtgatttgct 780
tagagggagc agatctgagc ctgagactag tggatggagt gtccagatgt tcaggaagat 840
tggaagtgag attccaagga gaatggggga ccgtgtgtga tgataactgg gatctccggg 900
atgcttctgt ggtgtgcaag caactgggat gtccaactgc catcagtgcc attggtcgag 960
ttaatgccag tgagggatct ggacagattt ggcttgacaa catttcatgc gaaggacatg 1020
aggcaactct ttgggagtgt aaacaccaag agtggggaaa gcattactgt catcatagag 1080
aagacgctgg cgtgacatgt tctgatggag cagatctgga acttagactt gtaggtggag 1140
gcagtcgctg tgctggcatt gtggaggtgg agattcagaa gctgactggg aagatgtgta 1200
gccgaggctg gacactggca gatgcggatg tggtttgcag acagcttgga tgtggatctg 1260
cgcttcaaac ccaggctaag atctactcta aaactggggc aacaaatacg tggctctttc 1320
ctggatcttg taatggaaat gaaactactt tttggcaatg caaaaactgg cagtggggcg 1380
gcctttcctg tgataatttc gaagaagcca aagttacctg ctcaggccac agggaaccca 1440
gactggttgg aggagaaatc ccatgctctg gtcgtgtgga agtgaaacac ggagacgtgt 1500
ggggctccgt ctgtgatttt gacttgtctc tggaagctgc cagtgtggtg tgcagggaat 1560
tacaatgtgg aacagtcgtc tctatcctag ggggagcaca ttttggagaa ggaagtggac 1620
agatctgggg tgaagaattc cagtgtagtg ggatgagtc ccatctttca ctatgctcag 1680

```
tggcgccccc gctagacaga acttgtaccc acagcaggga tgtcagcgta gtctgctcac   1740

gatacataga tattcgtctg gcaggcggcg agtcctcctg tgagggaaga gtggagctca   1800

agacactcgg agcctggggt cccctctgca gttctcattg ggacatggaa gatgctcatg   1860

tcttatgtca gcagctgaag tgtggggttg cccaatctat tccagaagga gcacattttg   1920

ggaaaggagc tggtcaggtc tggagtcaca tgttccactg cactggaact gaggaacata   1980

taggagattg cctcatgact gctctgggtg cgccgacgtg ttccgaagga caggtggcct   2040

ctgtcatctg ctcaggaaac caatcccaga cactattgcc atgtagttca ttgtctccag   2100

tccaaacaac aagctctaca attccaaagg agagtgaagt tccctgcata gcaagtggcc   2160

agcttcgctt ggtaggtgga ggtggtcgct gcgctggaag agtggaggtc taccacgagg   2220

gctcttgggg caccgtctgt gatgacaatt gggatatgac tgatgccaat gtggtgtgca   2280

agcagctgga ctgtggcgtg gcaattaacg ccactggctc tgcttacttc ggggaaggag   2340

caggagctat ctggctagac gaagtcatct gcactgggaa agagtctcat atttggcagt   2400

gccattcaca tggctgggga cgccataact gcaggcacaa agaagatgca ggtgttatct   2460

gctccgagtt catgtctctg aggctgacca acgaagccca caaagaaaac tgcacaggtc   2520

gccttgaagt gttttacaat ggtacatggg gcagtattgg cagtagcaat atgtctccaa   2580

ccactgtggg ggtggtgtgc cgtcagctgg gctgtgcaga caacgggact gtgaaaccca   2640

taccttcaga caagacacca tccaggccca tgtgggtaga tcgtgtgcag tgtccaaaag   2700

gagttgacac tttgtggcag tgcccctcgt caccttggaa acagagacag gccagcccct   2760

cctcccagga gtcctggatc atctgtgaca acaaaataag actccaggaa gggcatacag   2820

actgttctgg acgtgtggag atctggcaca aaggttcctg ggaacagtg tgtgatgact   2880

cctgggatct taatgatgct aaggttgtat gtaagcagtt gggctgtggc caagctgtga   2940

aggcactaaa agaagcagca tttggtccag gaactgggcc catatggctc aatgaaatta   3000

agtgtagagg gaatgagtct tccctgtggg attgtcctgc caaaccgtgg agtcacagcg   3060

actgtgggca caaagaagat gcttccatcc agtgcctccc aaaaatgact tcagaatcac   3120

atcatggcac aggtcacccc accctcacgg cactcttggt ttgtggagcc attctattgg   3180

tcctcctcat tgtcttcctc ctgtggactc tgaagcgacg acagattcag cgacttacag   3240

tttcctcaag aggagaggtc ttgatacatc aagttcagta ccaagagatg gattcaaagg   3300

cggatgatct ggacttgctg aaatcctcgg gggtcattca gaggcacact gagaaggaaa   3360

atgataattt ataatccact gaggttggag tttaagaagc cttgacagga cagccagcta   3420

aatggaacaa gagcccaggc aacgcacgga tgaccacagc tgcatcttca tgcagtcctt   3480

tgtttcctgg aactctgctg aacctgcaaa aaccatattt gtgaatgtga ccacttaata   3540

gagatgggag actttt                                                    3556
```

```
<210> SEQ ID NO 23
<211> LENGTH: 3363
<212> TYPE: DNA
<213> ORGANISM: Mus musculus

<400> SEQUENCE: 23

atgggtggac acagaatggt tcttcttgga ggtgctggat ctcctggttg taaaaggttt     60

gtccatctag gtttctttgt tgtggctgtg agctcacttc tcagtgcctc tgctgtcact    120

aacgctcctg gagaaatgaa gaaggaactg agactggcgg gtggtgaaaa caactgtagt    180

gggagagtgg aacttaagat ccatgacaag tggggcacag tgtgcagtaa cggctggagc    240
```

```
atgaatgaag tgtccgtggt ttgccagcag ctgggatgcc caacttctat taaagccctt    300
ggatgggcta actccagcgc cggctctgga tatatctgga tggacaaagt ttcttgtaca    360
gggaatgagt cagctctttg ggactgcaaa catgatgggt ggggaaagca taactgtacc    420
catgaaaaag atgctggagt gacctgctca gatggatcta atttggagat gagactggtg    480
aacagtgcgg gccaccgatg cttaggaaga gtagaaataa agttccaggg aaagtggggg    540
acggtgtgtg acgacaactt cagcaaagat cacgcttctg tgatttgtaa acagcttgga    600
tgtggaagtg ccattagttt ctctggctca gctaaattgg gagctggttc tggaccaatc    660
tggctcgatg acctggcatg caatggaaat gagtcagctc tctgggactg caaacaccgg    720
ggatggggca agcataactg tgaccatgct gaggatgtcg gtgtgatttg cttagaggga    780
gcagatctga gcctgagact agtggatgga gtgtccagat gttcaggaag attggaagtg    840
agattccaag gagaatgggg gaccgtgtgt gatgataact gggatctccg ggatgcttct    900
gtggtgtgca agcaactggg atgtccaact gccatcagtg ccattggtcg agttaatgcc    960
agtgagggat ctggacagat ttggcttgac aacatttcat gcgaaggaca tgaggcaact   1020
ctttgggagt gtaaacacca agagtgggga aagcattact gtcatcatag agaagacgct   1080
ggcgtgacat gttctgatgg agcagatctg gaacttagac ttgtaggtgg aggcagtcgc   1140
tgtgctggca ttgtggaggt ggagattcag aagctgactg ggaagatgtg tagccgaggc   1200
tggacactgg cagatgcgga tgtggtttgc agacagcttg gatgtggatc tgcgcttcaa   1260
acccaggcta agatctactc taaaactggg gcaacaaata cgtggctctt tcctggatct   1320
tgtaatggaa atgaaactac tttttggcaa tgcaaaaact ggcagtgggg cggcctttcc   1380
tgtgataatt tcgaagaagc caaagttacc tgctcaggcc acagggaacc cagactggtt   1440
ggaggagaaa tcccatgctc tggtcgtgtg gaagtgaaac acggagacgt gtggggctcc   1500
gtctgtgatt ttgacttgtc tctggaagct gccagtgtgg tgtgcaggga attacaatgt   1560
ggaacagtcg tctctatcct aggggggagca catttggag aaggaagtgg acagatctgg   1620
ggtgaagaat tccagtgtag tggggatgag tcccatcttt cactatgctc agtggcgccc   1680
ccgctagaca gaacttgtac ccacagcagg gatgtcagcg tagtctgctc acgatacata   1740
gatattcgtc tggcaggcgg cgagtcctcc tgtgagggaa gagtggagct caagacactc   1800
ggagcctggg gtcccctctg cagttctcat tgggacatgg aagatgctca tgtcttatgt   1860
cagcagctga agtgtggggt tgcccaatct attccagaag gagcacattt tgggaaagga   1920
gctggtcagg tctggagtca catgttccac tgcactggaa ctgaggaaca tataggagat   1980
tgcctcatga ctgctctggg tgcgccgacg tgttccgaag gacaggtggc ctctgtcatc   2040
tgctcaggaa accaatccca gacactattg ccatgtagtt cattgtctcc agtccaaaca   2100
acaagctcta caattccaaa ggagagtgaa gttccctgca tagcaagtgg ccagcttcgc   2160
ttggtaggtg gaggtggtcg ctgcgctgga agagtggagg tctaccacga gggctcttgg   2220
ggcaccgtct gtgatgacaa ttgggatatg actgatgcca atgtggtgtg caagcagctg   2280
gactgtggcg tggcaattaa cgccactggc tctgcttact tcggggaagg agcaggagct   2340
atctggctag acgaagtcat ctgcactggg aaagagtctc atatttggca gtgccattca   2400
catggctggg gacgccataa ctgcaggcac aaagaagatg caggtgttat ctgctccgag   2460
ttcatgtctc tgaggctgac caacgaagcc cacaaagaaa actgcacagg tcgccttgaa   2520
gtgttttaca atggtacatg gggcagtatt ggcagtagca atatgtctcc aaccactgtg   2580
ggggtggtgt gccgtcagct gggctgtgca gacaacggga ctgtgaaacc cataccttca   2640
```

```
gacaagacac catccaggcc catgtgggta gatcgtgtgc agtgtccaaa aggagttgac   2700
actttgtggc agtgcccctc gtcaccttgg aaacagagac aggccagccc ctcctcccag   2760
gagtcctgga tcatctgtga caacaaaata agactccagg aagggcatac agactgttct   2820
ggacgtgtgg agatctggca caaaggttcc tggggaacag tgtgtgatga ctcctgggat   2880
cttaatgatg ctaaggttgt atgtaagcag ttgggctgtg gccaagctgt gaaggcacta   2940
aaagaagcag catttggtcc aggaactggg cccatatggc tcaatgaaat taagtgtaga   3000
gggaatgagt cttccctgtg ggattgtcct gccaaaccgt ggagtcacag cgactgtggg   3060
cacaaagaag atgcttccat ccagtgcctc ccaaaaatga cttcagaatc acatcatggc   3120
acaggtcacc ccaccctcac ggcactcttg gtttgtggag ccattctatt ggtcctcctc   3180
attgtcttcc tcctgtggac tctgaagcga cgacagattc agcgacttac agtttcctca   3240
agaggagagg tcttgataca tcaagttcag taccaagaga tggattcaaa ggcggatgat   3300
ctggacttgc tgaaatcctc gggggtcatt cagaggcaca ctgagaagga aaatgataat   3360
tta                                                                 3363
```

<210> SEQ ID NO 24
<211> LENGTH: 1121
<212> TYPE: PRT
<213> ORGANISM: Mus musculus

<400> SEQUENCE: 24

```
Met Gly Gly His Arg Met Val Leu Leu Gly Gly Ala Gly Ser Pro Gly
1               5                   10                  15

Cys Lys Arg Phe Val His Leu Gly Phe Phe Val Val Ala Val Ser Ser
            20                  25                  30

Leu Leu Ser Ala Ser Ala Val Thr Asn Ala Pro Gly Glu Met Lys Lys
        35                  40                  45

Glu Leu Arg Leu Ala Gly Gly Glu Asn Asn Cys Ser Gly Arg Val Glu
    50                  55                  60

Leu Lys Ile His Asp Lys Trp Gly Thr Val Cys Ser Asn Gly Trp Ser
65                  70                  75                  80

Met Asn Glu Val Ser Val Val Cys Gln Gln Leu Gly Cys Pro Thr Ser
                85                  90                  95

Ile Lys Ala Leu Gly Trp Ala Asn Ser Ser Ala Gly Ser Gly Tyr Ile
            100                 105                 110

Trp Met Asp Lys Val Ser Cys Thr Gly Asn Glu Ser Ala Leu Trp Asp
        115                 120                 125

Cys Lys His Asp Gly Trp Gly Lys His Asn Cys Thr His Glu Lys Asp
    130                 135                 140

Ala Gly Val Thr Cys Ser Asp Gly Ser Asn Leu Glu Met Arg Leu Val
145                 150                 155                 160

Asn Ser Ala Gly His Arg Cys Leu Gly Arg Val Glu Ile Lys Phe Gln
                165                 170                 175

Gly Lys Trp Gly Thr Val Cys Asp Asp Asn Phe Ser Lys Asp His Ala
            180                 185                 190

Ser Val Ile Cys Lys Gln Leu Gly Cys Gly Ser Ala Ile Ser Phe Ser
        195                 200                 205

Gly Ser Ala Lys Leu Gly Ala Gly Ser Gly Pro Ile Trp Leu Asp Asp
    210                 215                 220

Leu Ala Cys Asn Gly Asn Glu Ser Ala Leu Trp Asp Cys Lys His Arg
225                 230                 235                 240
```

```
Gly Trp Gly Lys His Asn Cys Asp His Ala Glu Asp Val Gly Val Ile
                245                 250                 255

Cys Leu Glu Gly Ala Asp Leu Ser Leu Arg Leu Val Asp Gly Val Ser
            260                 265                 270

Arg Cys Ser Gly Arg Leu Glu Val Arg Phe Gln Gly Glu Trp Gly Thr
        275                 280                 285

Val Cys Asp Asp Asn Trp Asp Leu Arg Asp Ala Ser Val Val Cys Lys
    290                 295                 300

Gln Leu Gly Cys Pro Thr Ala Ile Ser Ala Ile Gly Arg Val Asn Ala
305                 310                 315                 320

Ser Glu Gly Ser Gly Gln Ile Trp Leu Asp Asn Ile Ser Cys Glu Gly
                325                 330                 335

His Glu Ala Thr Leu Trp Glu Cys Lys His Gln Glu Trp Gly Lys His
            340                 345                 350

Tyr Cys His His Arg Glu Asp Ala Gly Val Thr Cys Ser Asp Gly Ala
        355                 360                 365

Asp Leu Glu Leu Arg Leu Val Gly Gly Gly Ser Arg Cys Ala Gly Ile
    370                 375                 380

Val Glu Val Glu Ile Gln Lys Leu Thr Gly Lys Met Cys Ser Arg Gly
385                 390                 395                 400

Trp Thr Leu Ala Asp Ala Asp Val Val Cys Arg Gln Leu Gly Cys Gly
                405                 410                 415

Ser Ala Leu Gln Thr Gln Ala Lys Ile Tyr Ser Lys Thr Gly Ala Thr
            420                 425                 430

Asn Thr Trp Leu Phe Pro Gly Ser Cys Asn Gly Asn Glu Thr Thr Phe
        435                 440                 445

Trp Gln Cys Lys Asn Trp Gln Trp Gly Gly Leu Ser Cys Asp Asn Phe
    450                 455                 460

Glu Glu Ala Lys Val Thr Cys Ser Gly His Arg Glu Pro Arg Leu Val
465                 470                 475                 480

Gly Gly Glu Ile Pro Cys Ser Gly Arg Val Glu Val Lys His Gly Asp
                485                 490                 495

Val Trp Gly Ser Val Cys Asp Phe Asp Leu Ser Leu Glu Ala Ala Ser
            500                 505                 510

Val Val Cys Arg Glu Leu Gln Cys Gly Thr Val Val Ser Ile Leu Gly
        515                 520                 525

Gly Ala His Phe Gly Glu Gly Ser Gly Gln Ile Trp Gly Glu Glu Phe
    530                 535                 540

Gln Cys Ser Gly Asp Glu Ser His Leu Ser Leu Cys Ser Val Ala Pro
545                 550                 555                 560

Pro Leu Asp Arg Thr Cys Thr His Ser Arg Asp Val Ser Val Val Cys
                565                 570                 575

Ser Arg Tyr Ile Asp Ile Arg Leu Ala Gly Gly Glu Ser Ser Cys Glu
            580                 585                 590

Gly Arg Val Glu Leu Lys Thr Leu Gly Ala Trp Gly Pro Leu Cys Ser
        595                 600                 605

Ser His Trp Asp Met Glu Asp Ala His Val Leu Cys Gln Gln Leu Lys
    610                 615                 620

Cys Gly Val Ala Gln Ser Ile Pro Glu Gly Ala His Phe Gly Lys Gly
625                 630                 635                 640

Ala Gly Gln Val Trp Ser His Met Phe His Cys Thr Gly Thr Glu Glu
                645                 650                 655

His Ile Gly Asp Cys Leu Met Thr Ala Leu Gly Ala Pro Thr Cys Ser
            660                 665                 670
```

```
Glu Gly Gln Val Ala Ser Val Ile Cys Ser Gly Asn Gln Ser Gln Thr
        675                 680                 685

Leu Leu Pro Cys Ser Ser Leu Ser Pro Val Gln Thr Thr Ser Ser Thr
    690                 695                 700

Ile Pro Lys Glu Ser Glu Val Pro Cys Ile Ala Ser Gly Gln Leu Arg
705                 710                 715                 720

Leu Val Gly Gly Gly Gly Arg Cys Ala Gly Arg Val Glu Val Tyr His
                725                 730                 735

Glu Gly Ser Trp Gly Thr Val Cys Asp Asp Asn Trp Asp Met Thr Asp
            740                 745                 750

Ala Asn Val Val Cys Lys Gln Leu Asp Cys Gly Val Ala Ile Asn Ala
        755                 760                 765

Thr Gly Ser Ala Tyr Phe Gly Glu Gly Ala Gly Ala Ile Trp Leu Asp
    770                 775                 780

Glu Val Ile Cys Thr Gly Lys Glu Ser His Ile Trp Gln Cys His Ser
785                 790                 795                 800

His Gly Trp Gly Arg His Asn Cys Arg His Lys Glu Asp Ala Gly Val
                805                 810                 815

Ile Cys Ser Glu Phe Met Ser Leu Arg Leu Thr Asn Glu Ala His Lys
            820                 825                 830

Glu Asn Cys Thr Gly Arg Leu Glu Val Phe Tyr Asn Gly Thr Trp Gly
        835                 840                 845

Ser Ile Gly Ser Ser Asn Met Ser Pro Thr Thr Val Gly Val Val Cys
    850                 855                 860

Arg Gln Leu Gly Cys Ala Asp Asn Gly Thr Val Lys Pro Ile Pro Ser
865                 870                 875                 880

Asp Lys Thr Pro Ser Arg Pro Met Trp Val Asp Arg Val Gln Cys Pro
                885                 890                 895

Lys Gly Val Asp Thr Leu Trp Gln Cys Pro Ser Ser Pro Trp Lys Gln
            900                 905                 910

Arg Gln Ala Ser Pro Ser Ser Gln Glu Ser Trp Ile Ile Cys Asp Asn
        915                 920                 925

Lys Ile Arg Leu Gln Glu Gly His Thr Asp Cys Ser Gly Arg Val Glu
    930                 935                 940

Ile Trp His Lys Gly Ser Trp Gly Thr Val Cys Asp Asp Ser Trp Asp
945                 950                 955                 960

Leu Asn Asp Ala Lys Val Val Cys Lys Gln Leu Gly Cys Gly Gln Ala
                965                 970                 975

Val Lys Ala Leu Lys Glu Ala Ala Phe Gly Pro Gly Thr Gly Pro Ile
            980                 985                 990

Trp Leu Asn Glu Ile Lys Cys Arg  Gly Asn Glu Ser Ser  Leu Trp Asp
        995                 1000                 1005

Cys Pro  Ala Lys Pro Trp Ser  His Ser Asp Cys Gly  His Lys Glu
    1010                 1015                 1020

Asp Ala  Ser Ile Gln Cys Leu  Pro Lys Met Thr Ser  Glu Ser His
    1025                 1030                 1035

His Gly  Thr Gly His Pro Thr  Leu Thr Ala Leu Leu  Val Cys Gly
    1040                 1045                 1050

Ala Ile  Leu Leu Val Leu Leu  Ile Val Phe Leu Leu  Trp Thr Leu
    1055                 1060                 1065

Lys Arg  Arg Gln Ile Gln Arg  Leu Thr Val Ser Ser  Arg Gly Glu
    1070                 1075                 1080

Val Leu  Ile His Gln Val Gln  Tyr Gln Glu Met Asp  Ser Lys Ala
```

```
    1085                1090                1095

Asp Asp  Leu Asp Leu Leu Lys  Ser Ser Gly Val Ile  Gln Arg His
    1100                1105                1110

Thr Glu  Lys Glu Asn Asp Asn  Leu
    1115                1120


<210> SEQ ID NO 25
<211> LENGTH: 3639
<212> TYPE: DNA
<213> ORGANISM: Mus musculus

<400> SEQUENCE: 25

gctttggaat gggtggacac agaatggttc ttcttggagg tgctggatct cctggttgta     60

aaaggtttgt ccatctaggt ttctttgttg tggctgtgag ctcacttctc agtgcctctg    120

ctgtcactaa cgctcctgga gaaatgaaga aggaactgag actggcgggt ggtgaaaaca    180

actgtagtgg gagagtggaa cttaagatcc atgacaagtg ggcacagtg tgcagtaacg    240

gctggagcat gaatgaagtg tccgtggttt gccagcagct gggatgccca acttctatta    300

aagcccttgg atgggctaac tccagcgccg gctctggata tatctggatg gacaaagttt    360

cttgtacagg gaatgagtca gctctttggg actgcaaaca tgatgggtgg ggaaagcata    420

actgtaccca tgaaaaagat gctggagtga cctgctcaga tggatctaat ttggagatga    480

gactggtgaa cagtgcgggc caccgatgct taggaagagt agaaataaag ttccagggaa    540

agtgggggac ggtgtgtgac gacaacttca gcaaagatca cgcttctgtg atttgtaaac    600

agcttggatg tggaagtgcc attagtttct ctggctcagc taaattggga gctggttctg    660

gaccaatctg gctcgatgac ctggcatgca atggaaatga gtcagctctc tgggactgca    720

aacaccgggg atggggcaag cataactgtg accatgctga ggatgtcggt gtgatttgct    780

tagagggagc agatctgagc ctgagactag tggatggagt gtccagatgt tcaggaagat    840

tggaagtgag attccaagga gaatggggga ccgtgtgtga tgataactgg gatctccggg    900

atgcttctgt ggtgtgcaag caactgggat gtccaactgc catcagtgcc attggtcgag    960

ttaatgccag tgagggatct ggacagattt ggcttgacaa catttcatgc gaaggacatg   1020

aggcaactct ttgggagtgt aaacaccaag agtggggaaa gcattactgt catcatagag   1080

aagacgctgg cgtgacatgt tctgatggag cagatctgga acttagactt gtaggtggag   1140

gcagtcgctg tgctggcatt gtggaggtgg agattcagaa gctgactggg aagatgtgta   1200

gccgaggctg gacactggca gatgcggatg tggtttgcag acagcttgga tgtggatctg   1260

cgcttcaaac ccaggctaag atctactcta aaactggggc aacaaatacg tggctctttc   1320

ctggatcttg taatggaaat gaaactactt tttggcaatg caaaaactgg cagtggggcg   1380

gcctttcctg tgataatttc gaagaagcca aagttacctg ctcaggccac agggaaccca   1440

gactggttgg aggagaaatc ccatgctctg gtcgtgtgga aatgaaacac ggagacgtgt   1500

ggggctccgt ctgtgatttt gacttgtctc tggaagctgc cagtgtggtg tgcagggaat   1560

tacaatgtgg aacagtcgtc tctatcctag gggagcaca ttttggagaa ggaagtggac   1620

agatctgggg tgaagaattc cagtgtagtg ggatgagtc ccatctttca ctatgctcag   1680

tggcgccccc gctagacaga acttgtaccc acagcaggga tgtcagcgta gtctgctcac   1740

gatacataga tattcgtctg gcaggcggcg agtcctcctg tgagggaaga gtggagctca   1800

agacactcgg agcctggggt cccctctgca gttctcattg ggacatggaa gatgctcatg   1860

tcttatgtca gcagctgaag tgtggggttg cccaatctat tccagaagga gcacattttg   1920
```

```
ggaaaggagc tggtcaggtc tggagtcaca tgttccactg cactggaact gaggaacata   1980

taggagattg cctcatgact gctctgggtg cgccgacgtg ttccgaagga caggtggcct   2040

ctgtcatctg ctcaggaaac caatcccaga cactattgcc atgtagttca ttgtctccag   2100

tccaaacaac aagctctaca attccaaagg agagtgaagt tccctgcata gcaagtggcc   2160

agcttcgctt ggtaggtgga ggtggtcgct gcgctggaag agtggaggtc taccacgagg   2220

gctcttgggg caccgtctgt gatgacaatt gggatatgac tgatgccaat gtggtgtgca   2280

agcagctgga ctgtggcgtg gcaattaacg ccactggctc tgcttacttc ggggaaggag   2340

caggagctat ctggctagac gaagtcatct gcactgggaa agagtctcat atttggcagt   2400

gccattcaca tggctgggga cgccataact gcaggcacaa agaagatgca ggtgttatct   2460

gctccgagtt catgtctctg aggctgacca acgaagccca caaagaaaac tgcacaggtc   2520

gccttgaagt gttttacaat ggtacatggg gcagtattgg cagtagcaat atgtctccaa   2580

ccactgtggg ggtggtgtgc cgtcagctgg gctgtgcaga caacgggact gtgaaaccca   2640

taccttcaga caagacacca tccaggccca tgtgggtaga tcgtgtgcag tgtccaaaag   2700

gagttgacac tttgtggcag tgcccctcgt caccttggaa acagagacag gccagcccct   2760

cctcccagga gtcctggatc atctgtgaca acaaaataag actccaggaa gggcatacag   2820

actgttctgg acgtgtggag atctggcaca aaggttcctg ggaacagtg tgtgatgact    2880

cctgggatct taatgatgct aaggttgtat gtaagcagtt gggctgtggc caagctgtga   2940

aggcactaaa agaagcagca tttggtccag gaactgggcc catatggctc aatgaaatta   3000

agtgtagagg gaatgagtct tccctgtggg attgtcctgc caaaccgtgg agtcacagcg   3060

actgtgggca caaagaagat gcttccatcc agtgcctccc caaaatgact tcagaatcac   3120

atcatggcac aggtcacccc accctcacgg cactcttggt ttgtggagcc attctattgg   3180

tcctcctcat tgtcttcctc ctgtggactc tgaagcgacg acagattcag cgacttacag   3240

tttcctcaag aggagaggtc ttgatacatc aagttcagta ccaagagatg gattcaaagg   3300

cggatgatct ggacttgctg aaatcctcgg aaaattccaa caattcatat gattttaatg   3360

atgatggact gacatctttg tctaaatatc ttcctatttc tggaattaaa aaggggtcat   3420

tcagaggcac actgagaagg aaaatgataa tttataatcc actgaggttg gagtttaaga   3480

agccttgaca ggacagccag ctaaatggaa caagagccca ggcaacgcac ggatgaccac   3540

agctgcatct tcatgcagtc ctttgtttcc tggaactctg ctgaacctgc aaaaaccata   3600

tttgtgaatg tgaccactta atagagatgg gagactttt                          3639
```

<210> SEQ ID NO 26
<211> LENGTH: 3477
<212> TYPE: DNA
<213> ORGANISM: Mus musculus

<400> SEQUENCE: 26

```
atgggtggac acagaatggt tcttcttgga ggtgctggat ctcctggttg taaaaggttt     60

gtccatctag gtttctttgt tgtggctgtg agctcacttc tcagtgcctc tgctgtcact    120

aacgctcctg gagaaatgaa gaaggaactg agactggcgg gtggtgaaaa caactgtagt    180

gggagagtgg aacttaagat ccatgacaag tggggcacag tgtgcagtaa cggctggagc    240

atgaatgaag tgtccgtggt ttgccagcag ctgggatgcc caacttctat taaagccctt    300

ggatgggcta actccagcgc cggctctgga tatatctgga tggacaaagt ttcttgtaca    360

gggaatgagt cagctctttg ggactgcaaa catgatgggt ggggaaagca taactgtacc    420
```

-continued

```
catgaaaaag atgctggagt gacctgctca gatggatcta atttggagat gagactggtg    480
aacagtgcgg gccaccgatg cttaggaaga gtagaaataa agttccaggg aaagtggggg    540
acggtgtgtg acgacaactt cagcaaagat cacgcttctg tgatttgtaa acagcttgga    600
tgtggaagtg ccattagttt ctctggctca gctaaattgg gagctggttc tggaccaatc    660
tggctcgatg acctggcatg caatggaaat gagtcagctc tctgggactg caaacaccgg    720
ggatggggca agcataactg tgaccatgct gaggatgtcg gtgtgatttg cttagaggga    780
gcagatctga gcctgagact agtggatgga gtgtccagat gttcaggaag attggaagtg    840
agattccaag gagaatgggg gaccgtgtgt gatgataact gggatctccg ggatgcttct    900
gtggtgtgca agcaactggg atgtccaact gccatcagtg ccattggtcg agttaatgcc    960
agtgagggat ctggacagat ttggcttgac aacatttcat gcgaaggaca tgaggcaact   1020
ctttgggagt gtaaacacca agagtgggga aagcattact gtcatcatag agaagacgct   1080
ggcgtgacat gttctgatgg agcagatctg gaacttagac ttgtaggtgg aggcagtcgc   1140
tgtgctggca ttgtggaggt ggagattcag aagctgactg ggaagatgtg tagccgaggc   1200
tggacactgg cagatgcgga tgtggtttgc agacagcttg gatgtggatc tgcgcttcaa   1260
acccaggcta agatctactc taaaactggg gcaacaaata cgtggctctt tcctggatct   1320
tgtaatggaa atgaaactac tttttggcaa tgcaaaaact ggcagtgggg cggcctttcc   1380
tgtgataatt tcgaagaagc caaagttacc tgctcaggcc acagggaacc cagactggtt   1440
ggaggagaaa tcccatgctc tggtcgtgtg gaaatgaaac acggagacgt gtggggctcc   1500
gtctgtgatt ttgacttgtc tctggaagct gccagtgtgg tgtgcaggga attacaatgt   1560
ggaacagtcg tctctatcct aggggggagca cattttggag aaggaagtgg acagatctgg   1620
ggtgaagaat tccagtgtag tggggatgag tcccatcttt cactatgctc agtggcgccc   1680
ccgctagaca gaacttgtac ccacagcagg gatgtcagcg tagtctgctc acgatacata   1740
gatattcgtc tggcaggcgg cgagtcctcc tgtgagggaa gagtggagct caagacactc   1800
ggagcctggg gtcccctctg cagttctcat tgggacatgg aagatgctca tgtcttatgt   1860
cagcagctga agtgtggggt tgcccaatct attccagaag gagcacattt tgggaaagga   1920
gctggtcagg tctggagtca catgttccac tgcactggaa ctgaggaaca tataggagat   1980
tgcctcatga ctgctctggg tgcgccgacg tgttccgaag gacaggtggc ctctgtcatc   2040
tgctcaggaa accaatccca gacactattg ccatgtagtt cattgtctcc agtccaaaca   2100
acaagctcta caattccaaa ggagagtgaa gttccctgca tagcaagtgg ccagcttcgc   2160
ttggtaggtg gaggtggtcg ctgcgctgga agagtggagg tctaccacga gggctcttgg   2220
ggcaccgtct gtgatgacaa ttgggatatg actgatgcca atgtggtgtg caagcagctg   2280
gactgtggcg tggcaattaa cgccactggc tctgcttact tcggggaagg agcaggagct   2340
atctggctag acgaagtcat ctgcactggg aaagagtctc atatttggca gtgccattca   2400
catggctggg gacgccataa ctgcaggcac aaagaagatg caggtgttat ctgctccgag   2460
ttcatgtctc tgaggctgac caacgaagcc cacaaagaaa actgcacagg tcgccttgaa   2520
gtgttttaca atggtacatg gggcagtatt ggcagtagca atatgtctcc aaccactgtg   2580
ggggtggtgt gccgtcagct gggctgtgca gacaacggga ctgtgaaacc cataccttca   2640
gacaagacac catccaggcc catgtgggta gatcgtgtgc agtgtccaaa aggagttgac   2700
actttgtggc agtgcccctc gtcaccttgg aaacagagac aggccagccc ctcctcccag   2760
gagtcctgga tcatctgtga caacaaaata agactccagg aagggcatac agactgttct   2820
```

```
ggacgtgtgg agatctggca caaaggttcc tggggaacag tgtgtgatga ctcctgggat   2880

cttaatgatg ctaaggttgt atgtaagcag ttgggctgtg gccaagctgt gaaggcacta   2940

aaagaagcag catttggtcc aggaactggg cccatatggc tcaatgaaat taagtgtaga   3000

gggaatgagt cttccctgtg ggattgtcct gccaaaccgt ggagtcacag cgactgtggg   3060

cacaaagaag atgcttccat ccagtgcctc cccaaaatga cttcagaatc acatcatggc   3120

acaggtcacc ccaccctcac ggcactcttg gtttgtggag ccattctatt ggtcctcctc   3180

attgtcttcc tcctgtggac tctgaagcga cgacagattc agcgacttac agtttcctca   3240

agaggagagg tcttgataca tcaagttcag taccaagaga tggattcaaa ggcggatgat   3300

ctggacttgc tgaaatcctc ggaaaattcc aacaattcat atgattttaa tgatgatgga   3360

ctgacatctt tgtctaaata tcttcctatt tctggaatta aaaaggggtc attcagaggc   3420

acactgagaa ggaaaatgat aatttataat ccactgaggt tggagtttaa gaagcct      3477


<210> SEQ ID NO 27
<211> LENGTH: 1159
<212> TYPE: PRT
<213> ORGANISM: Mus musculus

<400> SEQUENCE: 27

Met Gly Gly His Arg Met Val Leu Leu Gly Gly Ala Gly Ser Pro Gly
1               5                   10                  15

Cys Lys Arg Phe Val His Leu Gly Phe Phe Val Val Ala Val Ser Ser
            20                  25                  30

Leu Leu Ser Ala Ser Ala Val Thr Asn Ala Pro Gly Glu Met Lys Lys
        35                  40                  45

Glu Leu Arg Leu Ala Gly Gly Glu Asn Asn Cys Ser Gly Arg Val Glu
    50                  55                  60

Leu Lys Ile His Asp Lys Trp Gly Thr Val Cys Ser Asn Gly Trp Ser
65                  70                  75                  80

Met Asn Glu Val Ser Val Val Cys Gln Gln Leu Gly Cys Pro Thr Ser
                85                  90                  95

Ile Lys Ala Leu Gly Trp Ala Asn Ser Ser Ala Gly Ser Gly Tyr Ile
            100                 105                 110

Trp Met Asp Lys Val Ser Cys Thr Gly Asn Glu Ser Ala Leu Trp Asp
        115                 120                 125

Cys Lys His Asp Gly Trp Gly Lys His Asn Cys Thr His Glu Lys Asp
    130                 135                 140

Ala Gly Val Thr Cys Ser Asp Gly Ser Asn Leu Glu Met Arg Leu Val
145                 150                 155                 160

Asn Ser Ala Gly His Arg Cys Leu Gly Arg Val Glu Ile Lys Phe Gln
                165                 170                 175

Gly Lys Trp Gly Thr Val Cys Asp Asp Asn Phe Ser Lys Asp His Ala
            180                 185                 190

Ser Val Ile Cys Lys Gln Leu Gly Cys Gly Ser Ala Ile Ser Phe Ser
        195                 200                 205

Gly Ser Ala Lys Leu Gly Ala Gly Ser Gly Pro Ile Trp Leu Asp Asp
    210                 215                 220

Leu Ala Cys Asn Gly Asn Glu Ser Ala Leu Trp Asp Cys Lys His Arg
225                 230                 235                 240

Gly Trp Gly Lys His Asn Cys Asp His Ala Glu Asp Val Gly Val Ile
                245                 250                 255

Cys Leu Glu Gly Ala Asp Leu Ser Leu Arg Leu Val Asp Gly Val Ser
            260                 265                 270
```

```
Arg Cys Ser Gly Arg Leu Glu Val Arg Phe Gln Gly Glu Trp Gly Thr
        275                 280                 285

Val Cys Asp Asp Asn Trp Asp Leu Arg Asp Ala Ser Val Val Cys Lys
    290                 295                 300

Gln Leu Gly Cys Pro Thr Ala Ile Ser Ala Ile Gly Arg Val Asn Ala
305                 310                 315                 320

Ser Glu Gly Ser Gly Gln Ile Trp Leu Asp Asn Ile Ser Cys Glu Gly
                325                 330                 335

His Glu Ala Thr Leu Trp Glu Cys Lys His Gln Glu Trp Gly Lys His
            340                 345                 350

Tyr Cys His His Arg Glu Asp Ala Gly Val Thr Cys Ser Asp Gly Ala
        355                 360                 365

Asp Leu Glu Leu Arg Leu Val Gly Gly Gly Ser Arg Cys Ala Gly Ile
    370                 375                 380

Val Glu Val Glu Ile Gln Lys Leu Thr Gly Lys Met Cys Ser Arg Gly
385                 390                 395                 400

Trp Thr Leu Ala Asp Ala Asp Val Val Cys Arg Gln Leu Gly Cys Gly
                405                 410                 415

Ser Ala Leu Gln Thr Gln Ala Lys Ile Tyr Ser Lys Thr Gly Ala Thr
            420                 425                 430

Asn Thr Trp Leu Phe Pro Gly Ser Cys Asn Gly Asn Glu Thr Thr Phe
        435                 440                 445

Trp Gln Cys Lys Asn Trp Gln Trp Gly Gly Leu Ser Cys Asp Asn Phe
    450                 455                 460

Glu Glu Ala Lys Val Thr Cys Ser Gly His Arg Glu Pro Arg Leu Val
465                 470                 475                 480

Gly Gly Glu Ile Pro Cys Ser Gly Arg Val Glu Met Lys His Gly Asp
                485                 490                 495

Val Trp Gly Ser Val Cys Asp Phe Asp Leu Ser Leu Glu Ala Ala Ser
            500                 505                 510

Val Val Cys Arg Glu Leu Gln Cys Gly Thr Val Val Ser Ile Leu Gly
        515                 520                 525

Gly Ala His Phe Gly Glu Gly Ser Gly Gln Ile Trp Gly Glu Glu Phe
    530                 535                 540

Gln Cys Ser Gly Asp Glu Ser His Leu Ser Leu Cys Ser Val Ala Pro
545                 550                 555                 560

Pro Leu Asp Arg Thr Cys Thr His Ser Arg Asp Val Ser Val Val Cys
                565                 570                 575

Ser Arg Tyr Ile Asp Ile Arg Leu Ala Gly Gly Glu Ser Ser Cys Glu
            580                 585                 590

Gly Arg Val Glu Leu Lys Thr Leu Gly Ala Trp Gly Pro Leu Cys Ser
        595                 600                 605

Ser His Trp Asp Met Glu Asp Ala His Val Leu Cys Gln Gln Leu Lys
    610                 615                 620

Cys Gly Val Ala Gln Ser Ile Pro Glu Gly Ala His Phe Gly Lys Gly
625                 630                 635                 640

Ala Gly Gln Val Trp Ser His Met Phe His Cys Thr Gly Thr Glu Glu
                645                 650                 655

His Ile Gly Asp Cys Leu Met Thr Ala Leu Gly Ala Pro Thr Cys Ser
            660                 665                 670

Glu Gly Gln Val Ala Ser Val Ile Cys Ser Gly Asn Gln Ser Gln Thr
        675                 680                 685

Leu Leu Pro Cys Ser Ser Leu Ser Pro Val Gln Thr Thr Ser Ser Thr
```

```
    690                 695                 700

Ile Pro Lys Glu Ser Glu Val Pro Cys Ile Ala Ser Gly Gln Leu Arg
705                 710                 715                 720

Leu Val Gly Gly Gly Gly Arg Cys Ala Gly Arg Val Glu Val Tyr His
                725                 730                 735

Glu Gly Ser Trp Gly Thr Val Cys Asp Asp Asn Trp Asp Met Thr Asp
            740                 745                 750

Ala Asn Val Val Cys Lys Gln Leu Asp Cys Gly Val Ala Ile Asn Ala
        755                 760                 765

Thr Gly Ser Ala Tyr Phe Gly Glu Gly Ala Gly Ala Ile Trp Leu Asp
    770                 775                 780

Glu Val Ile Cys Thr Gly Lys Glu Ser His Ile Trp Gln Cys His Ser
785                 790                 795                 800

His Gly Trp Gly Arg His Asn Cys Arg His Lys Glu Asp Ala Gly Val
                805                 810                 815

Ile Cys Ser Glu Phe Met Ser Leu Arg Leu Thr Asn Glu Ala His Lys
            820                 825                 830

Glu Asn Cys Thr Gly Arg Leu Glu Val Phe Tyr Asn Gly Thr Trp Gly
        835                 840                 845

Ser Ile Gly Ser Ser Asn Met Ser Pro Thr Thr Val Gly Val Val Cys
    850                 855                 860

Arg Gln Leu Gly Cys Ala Asp Asn Gly Thr Val Lys Pro Ile Pro Ser
865                 870                 875                 880

Asp Lys Thr Pro Ser Arg Pro Met Trp Val Asp Arg Val Gln Cys Pro
                885                 890                 895

Lys Gly Val Asp Thr Leu Trp Gln Cys Pro Ser Ser Pro Trp Lys Gln
            900                 905                 910

Arg Gln Ala Ser Pro Ser Ser Gln Glu Ser Trp Ile Ile Cys Asp Asn
        915                 920                 925

Lys Ile Arg Leu Gln Glu Gly His Thr Asp Cys Ser Gly Arg Val Glu
    930                 935                 940

Ile Trp His Lys Gly Ser Trp Gly Thr Val Cys Asp Asp Ser Trp Asp
945                 950                 955                 960

Leu Asn Asp Ala Lys Val Val Cys Lys Gln Leu Gly Cys Gly Gln Ala
                965                 970                 975

Val Lys Ala Leu Lys Glu Ala Ala Phe Gly Pro Gly Thr Gly Pro Ile
            980                 985                 990

Trp Leu Asn Glu Ile Lys Cys Arg  Gly Asn Glu Ser Ser  Leu Trp Asp
        995                 1000                1005

Cys Pro  Ala Lys Pro Trp Ser  His Ser Asp Cys Gly  His Lys Glu
    1010                1015                1020

Asp Ala  Ser Ile Gln Cys Leu  Pro Lys Met Thr Ser  Glu Ser His
    1025                1030                1035

His Gly  Thr Gly His Pro Thr  Leu Thr Ala Leu Leu  Val Cys Gly
    1040                1045                1050

Ala Ile  Leu Leu Val Leu Leu  Ile Val Phe Leu Leu  Trp Thr Leu
    1055                1060                1065

Lys Arg  Arg Gln Ile Gln Arg  Leu Thr Val Ser Ser  Arg Gly Glu
    1070                1075                1080

Val Leu  Ile His Gln Val Gln  Tyr Gln Glu Met Asp  Ser Lys Ala
    1085                1090                1095

Asp Asp  Leu Asp Leu Leu Lys  Ser Ser Glu Asn Ser  Asn Asn Ser
    1100                1105                1110
```

```
Tyr Asp  Phe Asn Asp Asp Gly  Leu Thr Ser Leu Ser  Lys Tyr Leu
    1115                 1120                 1125

Pro Ile  Ser Gly Ile Lys Lys  Gly Ser Phe Arg Gly  Thr Leu Arg
    1130                 1135                 1140

Arg Lys  Met Ile Ile Tyr Asn  Pro Leu Arg Leu Glu  Phe Lys Lys
    1145                 1150                 1155

Pro
```

<210> SEQ ID NO 28
<211> LENGTH: 26
<212> TYPE: DNA
<213> ORGANISM: Artificial
<220> FEATURE:
<223> OTHER INFORMATION: PCR Primer

<400> SEQUENCE: 28

```
caccggaatg agcaaactca gaatgg                                          26
```

<210> SEQ ID NO 29
<211> LENGTH: 40
<212> TYPE: DNA
<213> ORGANISM: Artificial
<220> FEATURE:
<223> OTHER INFORMATION: PCR Primer

<400> SEQUENCE: 29

```
tgctccggta cctagtccag gtcttcatca aggtatctta                            40
```

<210> SEQ ID NO 30
<211> LENGTH: 3414
<212> TYPE: DNA
<213> ORGANISM: African green monkey

<400> SEQUENCE: 30

```
atgagcaaac tcagaatggt gctacttgaa gactctggat ctgctgacgt cagaagacat     60

tttgtcaact tgagtccctt cactattgct gtggtcttac ttctccgtgc ctgttttgtc    120

accagttctc ttggaggaac aaccaaggag ctgaggctag tggatggtga aaacaagtgt    180

agtgggagag tggaagtgaa aatccaggag gagtggggaa cggtgtgtaa taatggctgg    240

agcatggaag cagtctctgt gatttgtaac cagctgggat gtccaactgc tatcaaagcc    300

actggatggg ctaattccag tgcaggttct ggacgcattt ggatggatca tgtttcttgt    360

cgtgggaatg agtcagctct ttgggactgc aaacatgatg gatggggaaa gcatagtaac    420

tgtactcacc aacaagatgc tggagtgact tgctcagatg gatccgattt ggaaatgagg    480

ctgacgaatg gagggaatat gtgttctgga agaatagaga tcaaattcca aggacagtgg    540

ggaacagtgt gtgatgataa cttcaacatc aatcatgcat ctgtggtttg taaacaactt    600

gaatgtggaa gtgctgtcag tttctctggt tcagctaatt ttggagaagg ctctggacca    660

atctggtttg atgatcttat atgcaacgga aatgagtcag ctctctggaa ctgcaaacat    720

caaggatggg gaaagcataa ctgtgatcat gctgaggatg ctggagtgat ttgctcaaag    780

ggagcagatc tgagcctgag actggtagat ggagtcactg aatgttcagg aagattagaa    840

gtgagattcc aaggagaatg gggacaata tgtgatgacg gctgggacag tcatgatgct    900

gctgtggcat gcaagcaact gggatgtcca actgctatca ccgccattgg tcgagttaac    960

gccagtgagg gatttggaca catctggctt gacagtgttt cttgccaggg acatgaacct   1020

gcggtctggc aatgtaaaca ccatgaatgg ggaaagcatt attgcaatca caatgaagat   1080

gctggcgtaa catgttctga tggatcagat ctggagctaa gacttagagg tggaggcagc   1140
```

```
cgctgtgctg ggacagttga ggtggagatt cagagactgt tagggaaggt gtgtgacaga   1200

ggctggggac tgaaagaagc tgatgtggtt tgcaggcagc tgggatgtgg atctgcactc   1260

aaaacatcct atcaagtata ctccaaaatc caggcaacaa acatgtggct gtttctaagt   1320

agctgtaacg gaaatgaaac ttctctttgg gactgcaaga actggcaatg ggtggactt    1380

acctgtgatc actatgaaga agccaaaatt acctgctcag cccacaggga acccagactg   1440

gttggaggag acattccctg ttctggacgc gttgaagtga agcatggtga cacatggggc   1500

tccgtctgtg attcggattt ctctctggaa gctgccagcg ttctatgcag ggaattacag   1560

tgtggcacag tcgtctctat cctgggggga gctcactttg gagagggaaa tggacagatc   1620

tgggctgaag aattccagtg tgagggacat gagtcccatc tttcactctg cccagtagca   1680

ccccgcccag aaggaacttg tagccacagc agggatgttg gagtagtctg ctcaagatac   1740

acagaaattc gcttggtgaa tggcaagacc ccatgtgagg gcagagtgga gctcaaaacg   1800

cttaatgcct ggggatccct ctgcaactct cactgggaca tagaagatgc ccacgttctt   1860

tgccaacaac ttaaatgtgg agttgccctt tctaccccag gaggagcaca ttttggaaaa   1920

ggaaatggtc aggtctggag gcatatgttt cactgcactg ggactgagca gcacatggga   1980

gattgtcctg taactgctct gggtgcttca ctatgtcctt cagggcaagt ggcctctgta   2040

atttgctcag gaaaccagtc ccaaacactg tcctcgtgca attcatcatc tctgggccca   2100

acaaggccta ccattccaga agaaagtgct gtggcctgca tagagagtgg tcaacttcgc   2160

ttggtaaatg gaggaggtcg ctgtgctggg agagtagaga tttatcatga gggctcctgg   2220

ggcaccatct gtgatgacag ctgggacctg agcgatgccc acgtggtgtg cagacagctg   2280

ggctgtggag aggccattaa tgccactggt tctgctcatt ttggagaagg aacagggccc   2340

atctggctgg atgagatgaa atgcaatgga aaagaatccc gcatttggca gtgccattca   2400

catggctggg ggcagcaaaa ctgcaggcac aaggaggatg caggagttat ctgctcagag   2460

ttcatgtctc tgagactgac cagtgaagcc agcagagagg cctgtgcagg gcgtctagaa   2520

gtttttttaca acggagcttg gggcagtgtt ggcaggagta acatgtctga aaccactgtg   2580

ggtgtggtgt gcaggcagct gggctgtgca gacaaaggga aaatcaaccc tgcatcttta   2640

gacaaggcca tgtccattcc catgtgggtg gacaatgttc agtgtccaaa aggacctgac   2700

acgctgtggc agtgcccatc atctccatgg gagaagagac tggccaggcc ctcggaggag   2760

acctggatca catgtgacaa caagatgaga ctacaagaag gacccacttc ctgttctgga   2820

cgtgtggaga tctggcacgg aggttcctgg gggacagtgt gtgatgactc ctgggacttg   2880

aacgatgctc aggtggtgtg tcaacaactt ggctgtggtc cagctttgaa agcattcaaa   2940

gaagcagagt ttggtcaggg gactggaccc atatggctca atgaagtgaa gtgcaaaggg   3000

aatgagtctt ccttgtggga ttgtcctgcc agacgctggg gccacagtga gtgtggacac   3060

aaggaagacg ctgcagtgaa ttgcacagat atttcaacga acaaaacccc acaaaaagcc   3120

acaacaggtc agtcatccct tattgcagtc ggaatccttg gagttgttct cttggtcatt   3180

ttcgtcgcat tattcttgac tcaaaagcga agacagagac agcggcttac agtttcctca   3240

agaggagaga acttagtcca ccaaattcaa taccgggaga tgaattcttg cctgaatgca   3300

gatgatctgg acctaatgaa ttcctcagga ggccattctg aggcacactg aaaaggaaaa   3360

tgggaattta taacccagtg agccttgaag ataccttgat gaagacctgg acta         3414
```

<210> SEQ ID NO 31
<211> LENGTH: 3348

<212> TYPE: DNA
<213> ORGANISM: African green monkey

<400> SEQUENCE: 31

```
atgagcaaac tcagaatggt gctacttgaa gactctggat ctgctgacgt cagaagacat     60
tttgtcaact tgagtccctt cactattgct gtggtcttac ttctccgtgc ctgttttgtc    120
accagttctc ttggaggaac aaccaaggag ctgaggctag tggatggtga aaacaagtgt    180
agtgggagag tggaagtgaa aatccaggag gagtggggaa cggtgtgtaa taatggctgg    240
agcatggaag cagtctctgt gatttgtaac cagctgggat gtccaactgc tatcaaagcc    300
actggatggg ctaattccag tgcaggttct ggacgcattt ggatggatca tgtttcttgt    360
cgtgggaatg agtcagctct ttgggactgc aaacatgatg gatggggaaa gcatagtaac    420
tgtactcacc aacaagatgc tggagtgact tgctcagatg gatccgattt ggaaatgagg    480
ctgacgaatg gagggaatat gtgttctgga agaatagaga tcaaattcca aggacagtgg    540
ggaacagtgt gtgatgataa cttcaacatc aatcatgcat ctgtggtttg taaacaactt    600
gaatgtggaa gtgctgtcag tttctctggt tcagctaatt ttggagaagg ctctggacca    660
atctggtttg atgatcttat atgcaacgga aatgagtcag ctctctggaa ctgcaaacat    720
caaggatggg gaaagcataa ctgtgatcat gctgaggatg ctggagtgat ttgctcaaag    780
ggagcagatc tgagcctgag actggtagat ggagtcactg aatgttcagg aagattagaa    840
gtgagattcc aaggagaatg gggacaata tgtgatgacg gctgggacag tcatgatgct     900
gctgtggcat gcaagcaact gggatgtcca actgctatca ccgccattgg tcgagttaac    960
gccagtgagg gatttggaca catctggctt gacagtgttt cttgccaggg acatgaacct   1020
gcggtctggc aatgtaaaca ccatgaatgg ggaaagcatt attgcaatca caatgaagat   1080
gctggcgtaa catgttctga tggatcagat ctggagctaa gacttagagg tggaggcagc   1140
cgctgtgctg ggacagttga ggtggagatt cagagactgt tagggaaggt gtgtgacaga   1200
ggctggggac tgaaagaagc tgatgtggtt tgcaggcagc tgggatgtgg atctgcactc   1260
aaaacatcct atcaagtata ctccaaaatc caggcaacaa acatgtggct gtttctaagt   1320
agctgtaacg gaaatgaaac ttctctttgg gactgcaaga actggcaatg gggtggactt   1380
acctgtgatc actatgaaga agccaaaatt acctgctcag cccacaggga acccagactg   1440
gttggaggag acattccctg ttctggacgc gttgaagtga agcatggtga cacatggggc   1500
tccgtctgtg attcggattt ctctctggaa gctgccagcg ttctatgcag ggaattacag   1560
tgtggcacag tcgtctctat cctgggggga gctcactttg gagagggaaa tggacagatc   1620
tgggctgaag aattccagtg tgagggacat gagtcccatc tttcactctg cccagtagca   1680
ccccgcccag aaggaacttg tagccacagc agggatgttg gagtagtctg ctcaagatac   1740
acagaaattc gcttggtgaa tggcaagacc ccatgtgagg gcagagtgga gctcaaaacg   1800
cttaatgcct ggggatccct ctgcaactct cactgggaca tagaagatgc ccacgttctt   1860
tgccaacaac ttaaatgtgg agttgccctt tctaccccag gaggagcaca ttttggaaaa   1920
ggaaatggtc aggtctggag gcatatgttt cactgcactg ggactgagca gcacatggga   1980
gattgtcctg taactgctct gggtgcttca ctatgtcctt cagggcaagt ggcctctgta   2040
atttgctcag gaaaccagtc ccaaacactg tcctcgtgca attcatcatc tctgggccca   2100
acaaggccta ccattccaga agaaagtgct gtggcctgca tagagagtgg tcaacttcgc   2160
ttggtaaatg gaggaggtcg ctgtgctggg agagtagaga tttatcatga gggctcctgg   2220
ggcaccatct gtgatgacag ctgggacctg agcgatgccc acgtggtgtg cagacagctg   2280
```

```
ggctgtggag aggccattaa tgccactggt tctgctcatt ttggagaagg aacagggccc   2340

atctggctgg atgagatgaa atgcaatgga aaagaatccc gcatttggca gtgccattca   2400

catggctggg ggcagcaaaa ctgcaggcac aaggaggatg caggagttat ctgctcagag   2460

ttcatgtctc tgagactgac cagtgaagcc agcagagagg cctgtgcagg gcgtctagaa   2520

gtttttttaca acggagcttg gggcagtgtt ggcaggagta acatgtctga aaccactgtg   2580

ggtgtggtgt gcaggcagct gggctgtgca gacaaaggga aaatcaaccc tgcatcttta   2640

gacaaggcca tgtccattcc catgtgggtg gacaatgttc agtgtccaaa aggacctgac   2700

acgctgtggc agtgcccatc atctccatgg gagaagagac tggccaggcc ctcggaggag   2760

acctggatca catgtgacaa caagatgaga ctacaagaag gacccacttc ctgttctgga   2820

cgtgtggaga tctggcacgg aggttcctgg gggacagtgt gtgatgactc ctgggacttg   2880

aacgatgctc aggtggtgtg tcaacaactt ggctgtggtc cagctttgaa agcattcaaa   2940

gaagcagagt ttggtcaggg gactggaccc atatggctca atgaagtgaa gtgcaaaggg   3000

aatgagtctt ccttgtggga ttgtcctgcc agacgctggg gccacagtga gtgtggacac   3060

aaggaagacg ctgcagtgaa ttgcacagat atttcaacga acaaaacccc acaaaaagcc   3120

acaacaggtc agtcatccct tattgcagtc ggaatccttg gagttgttct cttggtcatt   3180

ttcgtcgcat tattcttgac tcaaaagcga agacagagac agcggcttac agtttcctca   3240

agaggagaga acttagtcca ccaaattcaa taccgggaga tgaattcttg cctgaatgca   3300

gatgatctgg acctaatgaa ttcctcagga ggccattctg aggcacac               3348
```

<210> SEQ ID NO 32
<211> LENGTH: 1116
<212> TYPE: PRT
<213> ORGANISM: African green monkey

<400> SEQUENCE: 32

```
Met Ser Lys Leu Arg Met Val Leu Leu Glu Asp Ser Gly Ser Ala Asp
1               5                   10                  15

Val Arg Arg His Phe Val Asn Leu Ser Pro Phe Thr Ile Ala Val Val
            20                  25                  30

Leu Leu Leu Arg Ala Cys Phe Val Thr Ser Ser Leu Gly Gly Thr Thr
        35                  40                  45

Lys Glu Leu Arg Leu Val Asp Gly Glu Asn Lys Cys Ser Gly Arg Val
    50                  55                  60

Glu Val Lys Ile Gln Glu Glu Trp Gly Thr Val Cys Asn Asn Gly Trp
65                  70                  75                  80

Ser Met Glu Ala Val Ser Val Ile Cys Asn Gln Leu Gly Cys Pro Thr
                85                  90                  95

Ala Ile Lys Ala Thr Gly Trp Ala Asn Ser Ser Ala Gly Ser Gly Arg
            100                 105                 110

Ile Trp Met Asp His Val Ser Cys Arg Gly Asn Glu Ser Ala Leu Trp
        115                 120                 125

Asp Cys Lys His Asp Gly Trp Gly Lys His Ser Asn Cys Thr His Gln
    130                 135                 140

Gln Asp Ala Gly Val Thr Cys Ser Asp Gly Ser Asp Leu Glu Met Arg
145                 150                 155                 160

Leu Thr Asn Gly Gly Asn Met Cys Ser Gly Arg Ile Glu Ile Lys Phe
                165                 170                 175

Gln Gly Gln Trp Gly Thr Val Cys Asp Asp Asn Phe Asn Ile Asn His
            180                 185                 190
```

```
Ala Ser Val Val Cys Lys Gln Leu Glu Cys Gly Ser Ala Val Ser Phe
        195                 200                 205

Ser Gly Ser Ala Asn Phe Gly Glu Gly Ser Gly Pro Ile Trp Phe Asp
    210                 215                 220

Asp Leu Ile Cys Asn Gly Asn Glu Ser Ala Leu Trp Asn Cys Lys His
225                 230                 235                 240

Gln Gly Trp Gly Lys His Asn Cys Asp His Ala Glu Asp Ala Gly Val
                245                 250                 255

Ile Cys Ser Lys Gly Ala Asp Leu Ser Leu Arg Leu Val Asp Gly Val
            260                 265                 270

Thr Glu Cys Ser Gly Arg Leu Glu Val Arg Phe Gln Gly Glu Trp Gly
        275                 280                 285

Thr Ile Cys Asp Asp Gly Trp Asp Ser His Asp Ala Ala Val Ala Cys
    290                 295                 300

Lys Gln Leu Gly Cys Pro Thr Ala Ile Thr Ala Ile Gly Arg Val Asn
305                 310                 315                 320

Ala Ser Glu Gly Phe Gly His Ile Trp Leu Asp Ser Val Ser Cys Gln
                325                 330                 335

Gly His Glu Pro Ala Val Trp Gln Cys Lys His His Glu Trp Gly Lys
            340                 345                 350

His Tyr Cys Asn His Asn Glu Asp Ala Gly Val Thr Cys Ser Asp Gly
        355                 360                 365

Ser Asp Leu Glu Leu Arg Leu Arg Gly Gly Gly Ser Arg Cys Ala Gly
    370                 375                 380

Thr Val Glu Val Glu Ile Gln Arg Leu Leu Gly Lys Val Cys Asp Arg
385                 390                 395                 400

Gly Trp Gly Leu Lys Glu Ala Asp Val Val Cys Arg Gln Leu Gly Cys
                405                 410                 415

Gly Ser Ala Leu Lys Thr Ser Tyr Gln Val Tyr Ser Lys Ile Gln Ala
            420                 425                 430

Thr Asn Met Trp Leu Phe Leu Ser Ser Cys Asn Gly Asn Glu Thr Ser
        435                 440                 445

Leu Trp Asp Cys Lys Asn Trp Gln Trp Gly Gly Leu Thr Cys Asp His
    450                 455                 460

Tyr Glu Glu Ala Lys Ile Thr Cys Ser Ala His Arg Glu Pro Arg Leu
465                 470                 475                 480

Val Gly Gly Asp Ile Pro Cys Ser Gly Arg Val Glu Val Lys His Gly
                485                 490                 495

Asp Thr Trp Gly Ser Val Cys Asp Ser Asp Phe Ser Leu Glu Ala Ala
            500                 505                 510

Ser Val Leu Cys Arg Glu Leu Gln Cys Gly Thr Val Val Ser Ile Leu
        515                 520                 525

Gly Gly Ala His Phe Gly Glu Gly Asn Gly Gln Ile Trp Ala Glu Glu
    530                 535                 540

Phe Gln Cys Glu Gly His Glu Ser His Leu Ser Leu Cys Pro Val Ala
545                 550                 555                 560

Pro Arg Pro Glu Gly Thr Cys Ser His Ser Arg Asp Val Gly Val Val
                565                 570                 575

Cys Ser Arg Tyr Thr Glu Ile Arg Leu Val Asn Gly Lys Thr Pro Cys
            580                 585                 590

Glu Gly Arg Val Glu Leu Lys Thr Leu Asn Ala Trp Gly Ser Leu Cys
        595                 600                 605

Asn Ser His Trp Asp Ile Glu Asp Ala His Val Leu Cys Gln Gln Leu
```

```
    610                 615                 620

Lys Cys Gly Val Ala Leu Ser Thr Pro Gly Gly Ala His Phe Gly Lys
625                 630                 635                 640

Gly Asn Gly Gln Val Trp Arg His Met Phe His Cys Thr Gly Thr Glu
                645                 650                 655

Gln His Met Gly Asp Cys Pro Val Thr Ala Leu Gly Ala Ser Leu Cys
            660                 665                 670

Pro Ser Gly Gln Val Ala Ser Val Ile Cys Ser Gly Asn Gln Ser Gln
        675                 680                 685

Thr Leu Ser Ser Cys Asn Ser Ser Ser Leu Gly Pro Thr Arg Pro Thr
    690                 695                 700

Ile Pro Glu Glu Ser Ala Val Ala Cys Ile Glu Ser Gly Gln Leu Arg
705                 710                 715                 720

Leu Val Asn Gly Gly Gly Arg Cys Ala Gly Arg Val Glu Ile Tyr His
                725                 730                 735

Glu Gly Ser Trp Gly Thr Ile Cys Asp Asp Ser Trp Asp Leu Ser Asp
            740                 745                 750

Ala His Val Val Cys Arg Gln Leu Gly Cys Gly Glu Ala Ile Asn Ala
        755                 760                 765

Thr Gly Ser Ala His Phe Gly Glu Gly Thr Gly Pro Ile Trp Leu Asp
    770                 775                 780

Glu Met Lys Cys Asn Gly Lys Glu Ser Arg Ile Trp Gln Cys His Ser
785                 790                 795                 800

His Gly Trp Gly Gln Gln Asn Cys Arg His Lys Glu Asp Ala Gly Val
                805                 810                 815

Ile Cys Ser Glu Phe Met Ser Leu Arg Leu Thr Ser Glu Ala Ser Arg
            820                 825                 830

Glu Ala Cys Ala Gly Arg Leu Glu Val Phe Tyr Asn Gly Ala Trp Gly
        835                 840                 845

Ser Val Gly Arg Ser Asn Met Ser Glu Thr Thr Val Gly Val Val Cys
    850                 855                 860

Arg Gln Leu Gly Cys Ala Asp Lys Gly Lys Ile Asn Pro Ala Ser Leu
865                 870                 875                 880

Asp Lys Ala Met Ser Ile Pro Met Trp Val Asp Asn Val Gln Cys Pro
                885                 890                 895

Lys Gly Pro Asp Thr Leu Trp Gln Cys Pro Ser Ser Pro Trp Glu Lys
            900                 905                 910

Arg Leu Ala Arg Pro Ser Glu Glu Thr Trp Ile Thr Cys Asp Asn Lys
        915                 920                 925

Met Arg Leu Gln Glu Gly Pro Thr Ser Cys Ser Gly Arg Val Glu Ile
    930                 935                 940

Trp His Gly Gly Ser Trp Gly Thr Val Cys Asp Asp Ser Trp Asp Leu
945                 950                 955                 960

Asn Asp Ala Gln Val Val Cys Gln Gln Leu Gly Cys Gly Pro Ala Leu
                965                 970                 975

Lys Ala Phe Lys Glu Ala Glu Phe Gly Gln Gly Thr Gly Pro Ile Trp
            980                 985                 990

Leu Asn Glu Val Lys Cys Lys Gly  Asn Glu Ser Ser Leu  Trp Asp Cys
        995                 1000                 1005

Pro Ala  Arg Arg Trp Gly His  Ser Glu Cys Gly His  Lys Glu Asp
    1010                 1015                 1020

Ala Ala  Val Asn Cys Thr Asp  Ile Ser Thr Asn Lys  Thr Pro Gln
    1025                 1030                 1035
```

```
Lys Ala  Thr Thr Gly Gln Ser  Ser Leu Ile Ala Val  Gly Ile Leu
    1040                 1045                 1050

Gly Val  Val Leu Leu Val Ile  Phe Val Ala Leu Phe  Leu Thr Gln
    1055                 1060                 1065

Lys Arg  Arg Gln Arg Gln Arg  Leu Thr Val Ser Ser  Arg Gly Glu
    1070                 1075                 1080

Asn Leu  Val His Gln Ile Gln  Tyr Arg Glu Met Asn  Ser Cys Leu
    1085                 1090                 1095

Asn Ala  Asp Asp Leu Asp Leu  Met Asn Ser Ser Gly  Gly His Ser
    1100                 1105                 1110

Glu Ala  His
    1115
```

<210> SEQ ID NO 33
<211> LENGTH: 3348
<212> TYPE: DNA
<213> ORGANISM: African green monkey

<400> SEQUENCE: 33

```
atgagcaaac tcagaatggt gctacttgaa gactctggat ctgctgacgt cagaagacat     60

tttgtcaact tgagtccctt cactattgct gtggtcttac ttctccgtgc ctgttttgtc    120

accagttctc ttggaggaac aaccaaggag ctgaggctag tggatggtga aaacaagtgt    180

agtgggagag tggaagtgaa aatccaggag gagtggggaa cggtgtgtaa taatggctgg    240

agcatggaag cagtctctgt gatttgtaac cagctgggat gtccaactgc tatcaaagcc    300

actggatggg ctaattccag tgcaggttct ggacgcattt ggatggatca tgtttcttgt    360

cgtgggaatg agtcagctct ttgggactgc aaacatgatg gatgggggaa gcatagtaac    420

tgtactcacc aacaagatgc tggagtaact tgctcagatg gatccgattt ggaaatgagg    480

ctgacgaatg gagggaatat gtgttctgga agaatagaga tcaaattcca aggacagtgg    540

ggaacagtgt gtgatgataa cttcaacatc aatcatgcat ctgtggtttg taaacaactt    600

gaatgtggaa gtgctgtcag tttctctggt tcagctaatt ttggagaagg ctctggacca    660

atctggtttg atgatcttat atgcaacgga aatgagtcag ctctctggaa ctgcaaacat    720

caaggatggg gaaagcataa ctgtgatcat gctgaggatg ctggagtgat ttgctcaaag    780

ggagcagatc tgagcctgag actggtagat ggagtcactg aatgttcagg aagattagaa    840

gtgagattcc aaggagaatg gggacaata tgtgatgacg gctgggacag tcatgatgct    900

gctgtggcat gcaagcaact gggatgtcca actgctatca ccgccattgg tcgagttaac    960

gccagtgagg gatttggaca catctggctt gacagtgttt cttgccaggg acatgaacct   1020

gcggtctggc aatgtaaaca ccatgaatgg ggaaagcatt attgcaatca caatgaagat   1080

gctggcgtaa catgttctga tggatcaggt ctggagctaa gacttagagg tggaggcagc   1140

cgctgtgctg ggacagttga ggtggagatt cagagactgt tagggaaggt gtgtgacaga   1200

ggctggggac tgaaagaagc tgatgtggtt tgcaggcagc tgggatgtgg atctgcactc   1260

aaaacatcct atcaagtata ctccaaaatc caggcaacaa acatgtggct gtttctaagt   1320

agctgtaacg gaaatgaaac ttctctttgg gactgcaaga actggcaatg ggtggactt    1380

acctgtgatc actatgaaga agccaaaatt acctgctcag cccacaggga acccagactg   1440

gttggaggag acattccctg ttctggacgc gttgaagtga agcatggtga cacatggggc   1500

tccgtctgtg attcggattt ctctctggaa gctgccagcg ttctatgcag ggaattacag   1560

tgtggcacag tcgtctctat cctgggggga gctcactttg gagagggaaa tggacagatc   1620
```

```
tggactgaag aattccagtg tgagggacat gagtcccatc tttcactctg cccagtagca   1680

ccccgcccag aaggaacttg tagccacagc agggatgttg gagtagtctg ctcaagatac   1740

acagaaattc gcttggtgaa tggcaagacc ccatgtgagg gcagagtgga gctcaaaacg   1800

cttaatgcct ggggatccct ctgcaactct cactgggaca tagaagatgc ccacgttctt   1860

tgccaacaac ttaaatgtgg agttgccctt tctaccccag gaggagcaca ttttggaaaa   1920

ggaaatggtc aggtctggag gcatatgttt cactgcactg ggactgagca gcacatggga   1980

gattgtcctg taactgctct gggtgcttca ctatgtcctt cagggcaagt ggcctctgta   2040

atttgctcag gaaaccagtc ccaaacactg tcctcgcgca attcatcatc tctgggccca   2100

acaaggccta ccattccaga agaaagtgct gtggcctgca tagagagtgg tcaacttcgc   2160

ttggtaaatg gaggaggtcg ctgtgctggg agagtagaga tttatcatga gggctcctgg   2220

ggcaccatct gtgatgacag ctgggacctg agcgatgccc acgtggtgtg cagacagctg   2280

ggctgtggag aggccattaa tgccactggt tctgctcatt ttggagaagg aacagggccc   2340

atctggctgg atgagatgaa atgcaatgga aaagaatccc gcatttggca gtgccattca   2400

catggctggg ggcagcaaaa ctgcaggcac aaggaggatg caggagttat ctgctcagag   2460

ttcatgtctc tgagactgac cagtgaagcc agcagagagg cctgtgcagg gcgtctagaa   2520

gtttttttaca acggagcttg gggcagtgtt ggcaggagta acatgtctga aaccactgtg   2580

ggtgtagtgt gcaggcagct gggctgtgca gacaaaggga aaatcaactc tgcatcttta   2640

gacaaggcca tgtccattcc catgtgggtg gacaatgttc agtgtccaaa aggacctgac   2700

acgctgtggc agtgcccatc atctccatgg gagaagagac tggccaggcc ctcggaggag   2760

acctggatca catgtgacaa caagatgaga ctacaagaag gacccacttc ctgttctgga   2820

cgtgtggaga tctggcacgg aggttcctgg gggacagtgt gtgatgactc ctgggacttg   2880

aacgatgctc aggtggtgtg tcaacaactt ggctgtggtc cagctttgaa agcattcaaa   2940

gaagcagagt ttggtcaggg gactggaccc atatggctca atgaagtgaa gtgcgaaggg   3000

aatgagtctt ccttgtggga ttgtcctgcc agacgctggg gccacagtga gtgtggacac   3060

aaggaagacg ctgcagtgaa ttgcacagat atttcaacgc gcaaaacccc acaaaaagcc   3120

acaacaggtc agtcatccct tattgcagtc ggaatccttg gagttgttct cttggccatt   3180

ttcgtcgcat tattcttgac tcaaaagcga agacagagac agcggcttac agtttcctca   3240

agaggagaga acttagtcca ccaaattcaa taccgggaga tgaattcttg cctgaatgca   3300

gatgatctgg acctaatgaa ttcctcagga ggccattctg aggcacac                 3348
```

```
<210> SEQ ID NO 34
<211> LENGTH: 1116
<212> TYPE: PRT
<213> ORGANISM: African Green Monkey

<400> SEQUENCE: 34

Met Ser Lys Leu Arg Met Val Leu Leu Glu Asp Ser Gly Ser Ala Asp
1               5                   10                  15

Val Arg Arg His Phe Val Asn Leu Ser Pro Phe Thr Ile Ala Val Val
            20                  25                  30

Leu Leu Leu Arg Ala Cys Phe Val Thr Ser Ser Leu Gly Gly Thr Thr
        35                  40                  45

Lys Glu Leu Arg Leu Val Asp Gly Glu Asn Lys Cys Ser Gly Arg Val
    50                  55                  60

Glu Val Lys Ile Gln Glu Glu Trp Gly Thr Val Cys Asn Asn Gly Trp
65                  70                  75                  80
```

```
Ser Met Glu Ala Val Ser Val Ile Cys Asn Gln Leu Gly Cys Pro Thr
                85                  90                  95

Ala Ile Lys Ala Thr Gly Trp Ala Asn Ser Ser Ala Gly Ser Gly Arg
            100                 105                 110

Ile Trp Met Asp His Val Ser Cys Arg Gly Asn Glu Ser Ala Leu Trp
        115                 120                 125

Asp Cys Lys His Asp Gly Trp Gly Lys His Ser Asn Cys Thr His Gln
    130                 135                 140

Gln Asp Ala Gly Val Thr Cys Ser Asp Gly Ser Asp Leu Glu Met Arg
145                 150                 155                 160

Leu Thr Asn Gly Gly Asn Met Cys Ser Gly Arg Ile Glu Ile Lys Phe
                165                 170                 175

Gln Gly Gln Trp Gly Thr Val Cys Asp Asp Asn Phe Asn Ile Asn His
            180                 185                 190

Ala Ser Val Val Cys Lys Gln Leu Glu Cys Gly Ser Ala Val Ser Phe
        195                 200                 205

Ser Gly Ser Ala Asn Phe Gly Glu Gly Ser Gly Pro Ile Trp Phe Asp
    210                 215                 220

Asp Leu Ile Cys Asn Gly Asn Glu Ser Ala Leu Trp Asn Cys Lys His
225                 230                 235                 240

Gln Gly Trp Gly Lys His Asn Cys Asp His Ala Glu Asp Ala Gly Val
                245                 250                 255

Ile Cys Ser Lys Gly Ala Asp Leu Ser Leu Arg Leu Val Asp Gly Val
            260                 265                 270

Thr Glu Cys Ser Gly Arg Leu Glu Val Arg Phe Gln Gly Glu Trp Gly
        275                 280                 285

Thr Ile Cys Asp Asp Gly Trp Asp Ser His Asp Ala Ala Val Ala Cys
    290                 295                 300

Lys Gln Leu Gly Cys Pro Thr Ala Ile Thr Ala Ile Gly Arg Val Asn
305                 310                 315                 320

Ala Ser Glu Gly Phe Gly His Ile Trp Leu Asp Ser Val Ser Cys Gln
                325                 330                 335

Gly His Glu Pro Ala Val Trp Gln Cys Lys His His Glu Trp Gly Lys
            340                 345                 350

His Tyr Cys Asn His Asn Glu Asp Ala Gly Val Thr Cys Ser Asp Gly
        355                 360                 365

Ser Gly Leu Glu Leu Arg Leu Arg Gly Gly Gly Ser Arg Cys Ala Gly
    370                 375                 380

Thr Val Glu Val Glu Ile Gln Arg Leu Leu Gly Lys Val Cys Asp Arg
385                 390                 395                 400

Gly Trp Gly Leu Lys Glu Ala Asp Val Val Cys Arg Gln Leu Gly Cys
                405                 410                 415

Gly Ser Ala Leu Lys Thr Ser Tyr Gln Val Tyr Ser Lys Ile Gln Ala
            420                 425                 430

Thr Asn Met Trp Leu Phe Leu Ser Ser Cys Asn Gly Asn Glu Thr Ser
        435                 440                 445

Leu Trp Asp Cys Lys Asn Trp Gln Trp Gly Gly Leu Thr Cys Asp His
    450                 455                 460

Tyr Glu Glu Ala Lys Ile Thr Cys Ser Ala His Arg Glu Pro Arg Leu
465                 470                 475                 480

Val Gly Gly Asp Ile Pro Cys Ser Gly Arg Val Glu Val Lys His Gly
                485                 490                 495

Asp Thr Trp Gly Ser Val Cys Asp Ser Asp Phe Ser Leu Glu Ala Ala
```

```
            500                 505                 510

Ser Val Leu Cys Arg Glu Leu Gln Cys Gly Thr Val Val Ser Ile Leu
        515                 520                 525

Gly Gly Ala His Phe Gly Glu Gly Asn Gly Gln Ile Trp Thr Glu Glu
    530                 535                 540

Phe Gln Cys Glu Gly His Glu Ser His Leu Ser Leu Cys Pro Val Ala
545                 550                 555                 560

Pro Arg Pro Glu Gly Thr Cys Ser His Ser Arg Asp Val Gly Val Val
                565                 570                 575

Cys Ser Arg Tyr Thr Glu Ile Arg Leu Val Asn Gly Lys Thr Pro Cys
            580                 585                 590

Glu Gly Arg Val Glu Leu Lys Thr Leu Asn Ala Trp Gly Ser Leu Cys
        595                 600                 605

Asn Ser His Trp Asp Ile Glu Asp Ala His Val Leu Cys Gln Gln Leu
    610                 615                 620

Lys Cys Gly Val Ala Leu Ser Thr Pro Gly Gly Ala His Phe Gly Lys
625                 630                 635                 640

Gly Asn Gly Gln Val Trp Arg His Met Phe His Cys Thr Gly Thr Glu
                645                 650                 655

Gln His Met Gly Asp Cys Pro Val Thr Ala Leu Gly Ala Ser Leu Cys
            660                 665                 670

Pro Ser Gly Gln Val Ala Ser Val Ile Cys Ser Gly Asn Gln Ser Gln
        675                 680                 685

Thr Leu Ser Ser Arg Asn Ser Ser Ser Leu Gly Pro Thr Arg Pro Thr
    690                 695                 700

Ile Pro Glu Glu Ser Ala Val Ala Cys Ile Glu Ser Gly Gln Leu Arg
705                 710                 715                 720

Leu Val Asn Gly Gly Gly Arg Cys Ala Gly Arg Val Glu Ile Tyr His
                725                 730                 735

Glu Gly Ser Trp Gly Thr Ile Cys Asp Asp Ser Trp Asp Leu Ser Asp
            740                 745                 750

Ala His Val Val Cys Arg Gln Leu Gly Cys Gly Glu Ala Ile Asn Ala
        755                 760                 765

Thr Gly Ser Ala His Phe Gly Glu Gly Thr Gly Pro Ile Trp Leu Asp
    770                 775                 780

Glu Met Lys Cys Asn Gly Lys Glu Ser Arg Ile Trp Gln Cys His Ser
785                 790                 795                 800

His Gly Trp Gly Gln Gln Asn Cys Arg His Lys Glu Asp Ala Gly Val
                805                 810                 815

Ile Cys Ser Glu Phe Met Ser Leu Arg Leu Thr Ser Glu Ala Ser Arg
            820                 825                 830

Glu Ala Cys Ala Gly Arg Leu Glu Val Phe Tyr Asn Gly Ala Trp Gly
        835                 840                 845

Ser Val Gly Arg Ser Asn Met Ser Glu Thr Thr Val Gly Val Val Cys
    850                 855                 860

Arg Gln Leu Gly Cys Ala Asp Lys Gly Lys Ile Asn Ser Ala Ser Leu
865                 870                 875                 880

Asp Lys Ala Met Ser Ile Pro Met Trp Val Asp Asn Val Gln Cys Pro
                885                 890                 895

Lys Gly Pro Asp Thr Leu Trp Gln Cys Pro Ser Ser Pro Trp Glu Lys
            900                 905                 910

Arg Leu Ala Arg Pro Ser Glu Glu Thr Trp Ile Thr Cys Asp Asn Lys
        915                 920                 925
```

```
Met Arg Leu Gln Glu Gly Pro Thr Ser Cys Ser Gly Arg Val Glu Ile
    930                 935                 940

Trp His Gly Gly Ser Trp Gly Thr Val Cys Asp Asp Ser Trp Asp Leu
945                 950                 955                 960

Asn Asp Ala Gln Val Val Cys Gln Gln Leu Gly Cys Gly Pro Ala Leu
                965                 970                 975

Lys Ala Phe Lys Glu Ala Glu Phe Gly Gln Gly Thr Gly Pro Ile Trp
            980                 985                 990

Leu Asn Glu Val Lys Cys Glu Gly  Asn Glu Ser Ser Leu  Trp Asp Cys
        995                 1000                 1005

Pro Ala  Arg Arg Trp Gly His  Ser Glu Cys Gly His  Lys Glu Asp
    1010                 1015                 1020

Ala Ala  Val Asn Cys Thr Asp  Ile Ser Thr Arg Lys  Thr Pro Gln
    1025                 1030                 1035

Lys Ala  Thr Thr Gly Gln Ser  Ser Leu Ile Ala Val  Gly Ile Leu
    1040                 1045                 1050

Gly Val  Val Leu Leu Ala Ile  Phe Val Ala Leu Phe  Leu Thr Gln
    1055                 1060                 1065

Lys Arg  Arg Gln Arg Gln Arg  Leu Thr Val Ser Ser  Arg Gly Glu
    1070                 1075                 1080

Asn Leu  Val His Gln Ile Gln  Tyr Arg Glu Met Asn  Ser Cys Leu
    1085                 1090                 1095

Asn Ala  Asp Asp Leu Asp Leu  Met Asn Ser Ser Gly  Gly His Ser
    1100                 1105                 1110

Glu Ala  His
    1115
```

<210> SEQ ID NO 35
<211> LENGTH: 3453
<212> TYPE: DNA
<213> ORGANISM: African Green Monkey

<400> SEQUENCE: 35

```
atgagcaaac tcagaatggt gctacttgaa gactctggat ctgctgacgt cagaagacat     60

tttgtcaact tgagtccctt cactattgct gtggtcttac ttctccgtgc ctgttttgtc    120

accagttctc ttggaggaac aaccaaggag ctgaggctag tggatggtga aaacaagtgt    180

agtgggagag tggaagtgaa aatccaggag gagtggggaa cggtgtgtaa taatggctgg    240

agcatggaag cagtctctgt gatttgtaac cagctgggat gtccaactgc tatcaaagcc    300

actggatggg ctaattccag tgcaggttct ggacgcattt ggatggatca tgtttcttgt    360

cgtgggaatg agtcagctct ttgggactgc aaacatgatg gatggggaaa gcatagtaac    420

tgtactcacc aacaagatgc tggagtaact tgctcagatg gatccgattt ggaaatgagg    480

ctgacgaatg gagggaatat gtgttctgga agaatagaga tcaaattcca aggacagtgg    540

ggaacagtgt gtgatgataa cttcaacatc aatcatgcat ctgtggtttg taaacaactt    600

gaatgtggaa gtgctgtcag tttctctggt tcagctaatt ttggagaagg ctctggacca    660

atctggtttg atgatcttat atgcaacgga aatgagtcag ctctctggaa ctgcaaacat    720

caaggatggg gaaagcataa ctgtgatcat gctgaggatg ctggagtgat ttgctcaaag    780

ggagcagatc tgagcctgag actggtagat ggagtcactg aatgttcagg aagattagaa    840

gtgagattcc aaggagaatg gggacaata tgtgatgacg gctgggacag tcatgatgct    900

gctgtggcat gcaagcaact gggatgtcca actgctatca ccgccattgg tcgagttaac    960

gccagtgagg gatttggaca catctggctt gacagtgttt cttgccaggg acatgaacct   1020
```

```
gcggtctggc aatgtaaaca ccatgaatgg ggaaagcatt attgcaatca caatgaagat   1080
gctggcgtaa catgttctga tggatcagat ctggagctaa gacttagagg tggaggcagc   1140
cgctgtgctg ggacagttga ggtggagatt cagagactgt tagggaaggt gtgtgacaga   1200
ggctggggac tgaaagaagc tgatgtggtt tgcaggcagc tgggatgtgg atctgcactc   1260
aaaacatcct atcaagtata ctccaaaatc caggcaacaa acatgtggct gtttctaagt   1320
agctgtaacg gaaatgaaac ttctctttgg gactgcaaga actggcaatg ggtggactt    1380
acctgtgatc actatgaaga agccaaaatt acctgctcag cccacaggga acccagactg   1440
gttggaggag acattccctg ttctggacgc gttgaagtga agcatggtga cacatggggc   1500
tccgtctgtg attcggattt ctctctggaa gctgccagcg ttctatgcag ggaattacag   1560
tgtggcacag tcgtctctat cctgggggga gctcactttg gagagggaaa tggacagatc   1620
tggactgaag aattccagtg tgagggacat gagtcccatc tttcactctg cccagtagca   1680
ccccgcccag aaggaacttg tagccacagc agggatgttg gagtagtctg ctcaagatac   1740
acagaaattc gcttggtgaa tggcaagacc ccatgtgagg gcagagtgga gctcaaaacg   1800
cttaatgcct ggggatccct ctgcaactct cactgggaca tagaagatgc ccacgttctt   1860
tgccaacaac ttaaatgtgg agttgccctt tctaccccag gaggagcaca ttttggaaaa   1920
ggaaatggtc aggtctggag gcatatgttt cactgcactg ggactgagca gcacatggga   1980
gattgtcctg taactgctct gggtgcttca ctatgtcctt cagggcaagt ggcctctgta   2040
atttgctcag gaaaccagtc ccaaacactg tcctcgtgca attcatcatc tctgggccca   2100
acaaggccta ccattccaga agaaagtgct gtggcctgca tagagagtgg tcaacttcgc   2160
ttggtaaatg gaggaggtcg ctgtgctggg agagtagaga tttatcatga gggctcctgg   2220
ggcaccatct gtgatgacag ctgggacctg agcgatgccc acgtggtgtg cagacagctg   2280
ggctgtggag aggccattaa tgccactggt tctgctcatt ttggagaagg aacagggccc   2340
atctggctgg atgagatgaa atgcaatgga aaagaatccc gcatttggca gtgccattca   2400
catggctggg ggcagcaaaa ctgcaggcac aaggaggatg caggagttat ctgctcagag   2460
ttcatgtctc tgagactgac cagtgaagcc agcagagagg cctgtgcagg gcgtctagaa   2520
gtttttttaca acggagcttg gggcagtgtt ggcaggagta acatgtctga aaccactgtg   2580
ggtgtagtgt gcaggcagct gggctgtgca gacaaaggga aaatcaactc tgcatcttta   2640
gacaaggcca tgtccattcc catgtgggtg gacaatgttc agtgtccaaa aggacctgac   2700
acgctgtggc agtgcccatc atctccatgg gagaagagac tggccaggcc ctcggaggag   2760
acctggatca catgtgacaa caagatgaga ctacaagaag gacccacttc ctgttctgga   2820
cgtgtggaga tctggcacgg aggttcctgg gggacagtgt gtgatgactc ctgggacttg   2880
aacgatgctc aggtggtgtg tcaacaactt ggctgtggtc cagctttgaa agcattcaaa   2940
gaagcagagt ttggtcaggg gactggaccc atatggctca atgaagtgaa gtgcaaaggg   3000
aatgagtctt ccttgtggga ttgtcctgcc agacgctggg gccacagtga gtgtggacac   3060
aaggaagacg ctgcagtgaa ttgcacagat atttcaacgc gcaaaacccc acaaaaagcc   3120
acaacaggtc agtcatccct tattgcagtc ggaatccttg gagttgttct cttggccatt   3180
ttcgtcgcat tattcttgac tcaaaagcga agacagagac agcggcttac agtttcctca   3240
agaggagaga acttagtcca ccaaattcaa taccgggaga tgaattcttg cctgaatgca   3300
gatgatctgg acctaatgaa ttcctcagaa aattccaatg agtcagctga tttcaatgct   3360
gctgaactaa tttctgtgtc taaatttctt cctatttctg gaatggaaaa ggaggccatt   3420
```

ctgaggcaca ctgaaaagga aaatgggaat tta 3453

<210> SEQ ID NO 36
<211> LENGTH: 1151
<212> TYPE: PRT
<213> ORGANISM: African Green Monkey

<400> SEQUENCE: 36

```
Met Ser Lys Leu Arg Met Val Leu Leu Glu Asp Ser Gly Ser Ala Asp
1               5                   10                  15

Val Arg Arg His Phe Val Asn Leu Ser Pro Phe Thr Ile Ala Val Val
            20                  25                  30

Leu Leu Leu Arg Ala Cys Phe Val Thr Ser Ser Leu Gly Gly Thr Thr
        35                  40                  45

Lys Glu Leu Arg Leu Val Asp Gly Glu Asn Lys Cys Ser Gly Arg Val
    50                  55                  60

Glu Val Lys Ile Gln Glu Glu Trp Gly Thr Val Cys Asn Asn Gly Trp
65                  70                  75                  80

Ser Met Glu Ala Val Ser Val Ile Cys Asn Gln Leu Gly Cys Pro Thr
                85                  90                  95

Ala Ile Lys Ala Thr Gly Trp Ala Asn Ser Ser Ala Gly Ser Gly Arg
            100                 105                 110

Ile Trp Met Asp His Val Ser Cys Arg Gly Asn Glu Ser Ala Leu Trp
        115                 120                 125

Asp Cys Lys His Asp Gly Trp Gly Lys His Ser Asn Cys Thr His Gln
    130                 135                 140

Gln Asp Ala Gly Val Thr Cys Ser Asp Gly Ser Asp Leu Glu Met Arg
145                 150                 155                 160

Leu Thr Asn Gly Gly Asn Met Cys Ser Gly Arg Ile Glu Ile Lys Phe
                165                 170                 175

Gln Gly Gln Trp Gly Thr Val Cys Asp Asp Asn Phe Asn Ile Asn His
            180                 185                 190

Ala Ser Val Val Cys Lys Gln Leu Glu Cys Gly Ser Ala Val Ser Phe
        195                 200                 205

Ser Gly Ser Ala Asn Phe Gly Glu Gly Ser Gly Pro Ile Trp Phe Asp
    210                 215                 220

Asp Leu Ile Cys Asn Gly Asn Glu Ser Ala Leu Trp Asn Cys Lys His
225                 230                 235                 240

Gln Gly Trp Gly Lys His Asn Cys Asp His Ala Glu Asp Ala Gly Val
                245                 250                 255

Ile Cys Ser Lys Gly Ala Asp Leu Ser Leu Arg Leu Val Asp Gly Val
            260                 265                 270

Thr Glu Cys Ser Gly Arg Leu Glu Val Arg Phe Gln Gly Glu Trp Gly
        275                 280                 285

Thr Ile Cys Asp Asp Gly Trp Asp Ser His Asp Ala Ala Val Ala Cys
    290                 295                 300

Lys Gln Leu Gly Cys Pro Thr Ala Ile Thr Ala Ile Gly Arg Val Asn
305                 310                 315                 320

Ala Ser Glu Gly Phe Gly His Ile Trp Leu Asp Ser Val Ser Cys Gln
                325                 330                 335

Gly His Glu Pro Ala Val Trp Gln Cys Lys His His Glu Trp Gly Lys
            340                 345                 350

His Tyr Cys Asn His Asn Glu Asp Ala Gly Val Thr Cys Ser Asp Gly
        355                 360                 365
```

```
Ser Asp Leu Glu Leu Arg Leu Arg Gly Gly Gly Ser Arg Cys Ala Gly
    370                 375                 380

Thr Val Glu Val Glu Ile Gln Arg Leu Leu Gly Lys Val Cys Asp Arg
385                 390                 395                 400

Gly Trp Gly Leu Lys Glu Ala Asp Val Val Cys Arg Gln Leu Gly Cys
                405                 410                 415

Gly Ser Ala Leu Lys Thr Ser Tyr Gln Val Tyr Ser Lys Ile Gln Ala
            420                 425                 430

Thr Asn Met Trp Leu Phe Leu Ser Ser Cys Asn Gly Asn Glu Thr Ser
        435                 440                 445

Leu Trp Asp Cys Lys Asn Trp Gln Trp Gly Gly Leu Thr Cys Asp His
    450                 455                 460

Tyr Glu Glu Ala Lys Ile Thr Cys Ser Ala His Arg Glu Pro Arg Leu
465                 470                 475                 480

Val Gly Gly Asp Ile Pro Cys Ser Gly Arg Val Glu Val Lys His Gly
                485                 490                 495

Asp Thr Trp Gly Ser Val Cys Asp Ser Asp Phe Ser Leu Glu Ala Ala
            500                 505                 510

Ser Val Leu Cys Arg Glu Leu Gln Cys Gly Thr Val Val Ser Ile Leu
        515                 520                 525

Gly Gly Ala His Phe Gly Glu Gly Asn Gly Gln Ile Trp Thr Glu Glu
    530                 535                 540

Phe Gln Cys Glu Gly His Glu Ser His Leu Ser Leu Cys Pro Val Ala
545                 550                 555                 560

Pro Arg Pro Glu Gly Thr Cys Ser His Ser Arg Asp Val Gly Val Val
                565                 570                 575

Cys Ser Arg Tyr Thr Glu Ile Arg Leu Val Asn Gly Lys Thr Pro Cys
            580                 585                 590

Glu Gly Arg Val Glu Leu Lys Thr Leu Asn Ala Trp Gly Ser Leu Cys
        595                 600                 605

Asn Ser His Trp Asp Ile Glu Asp Ala His Val Leu Cys Gln Gln Leu
    610                 615                 620

Lys Cys Gly Val Ala Leu Ser Thr Pro Gly Gly Ala His Phe Gly Lys
625                 630                 635                 640

Gly Asn Gly Gln Val Trp Arg His Met Phe His Cys Thr Gly Thr Glu
                645                 650                 655

Gln His Met Gly Asp Cys Pro Val Thr Ala Leu Gly Ala Ser Leu Cys
            660                 665                 670

Pro Ser Gly Gln Val Ala Ser Val Ile Cys Ser Gly Asn Gln Ser Gln
        675                 680                 685

Thr Leu Ser Ser Cys Asn Ser Ser Ser Leu Gly Pro Thr Arg Pro Thr
    690                 695                 700

Ile Pro Glu Glu Ser Ala Val Ala Cys Ile Glu Ser Gly Gln Leu Arg
705                 710                 715                 720

Leu Val Asn Gly Gly Gly Arg Cys Ala Gly Arg Val Glu Ile Tyr His
                725                 730                 735

Glu Gly Ser Trp Gly Thr Ile Cys Asp Asp Ser Trp Asp Leu Ser Asp
            740                 745                 750

Ala His Val Val Cys Arg Gln Leu Gly Cys Gly Glu Ala Ile Asn Ala
        755                 760                 765

Thr Gly Ser Ala His Phe Gly Glu Gly Thr Gly Pro Ile Trp Leu Asp
    770                 775                 780

Glu Met Lys Cys Asn Gly Lys Glu Ser Arg Ile Trp Gln Cys His Ser
785                 790                 795                 800
```

```
His Gly Trp Gly Gln Gln Asn Cys Arg His Lys Glu Asp Ala Gly Val
                805                 810                 815

Ile Cys Ser Glu Phe Met Ser Leu Arg Leu Thr Ser Glu Ala Ser Arg
            820                 825                 830

Glu Ala Cys Ala Gly Arg Leu Glu Val Phe Tyr Asn Gly Ala Trp Gly
        835                 840                 845

Ser Val Gly Arg Ser Asn Met Ser Glu Thr Thr Val Gly Val Val Cys
    850                 855                 860

Arg Gln Leu Gly Cys Ala Asp Lys Gly Lys Ile Asn Ser Ala Ser Leu
865                 870                 875                 880

Asp Lys Ala Met Ser Ile Pro Met Trp Val Asp Asn Val Gln Cys Pro
                885                 890                 895

Lys Gly Pro Asp Thr Leu Trp Gln Cys Pro Ser Ser Pro Trp Glu Lys
            900                 905                 910

Arg Leu Ala Arg Pro Ser Glu Glu Thr Trp Ile Thr Cys Asp Asn Lys
        915                 920                 925

Met Arg Leu Gln Glu Gly Pro Thr Ser Cys Ser Gly Arg Val Glu Ile
    930                 935                 940

Trp His Gly Gly Ser Trp Gly Thr Val Cys Asp Asp Ser Trp Asp Leu
945                 950                 955                 960

Asn Asp Ala Gln Val Val Cys Gln Gln Leu Gly Cys Gly Pro Ala Leu
                965                 970                 975

Lys Ala Phe Lys Glu Ala Glu Phe Gly Gln Gly Thr Gly Pro Ile Trp
            980                 985                 990

Leu Asn Glu Val Lys Cys Lys Gly  Asn Glu Ser Ser Leu  Trp Asp Cys
        995                 1000                1005

Pro Ala  Arg Arg Trp Gly His  Ser Glu Cys Gly His  Lys Glu Asp
    1010                1015                1020

Ala Ala  Val Asn Cys Thr Asp  Ile Ser Thr Arg Lys  Thr Pro Gln
    1025                1030                1035

Lys Ala  Thr Thr Gly Gln Ser  Ser Leu Ile Ala Val  Gly Ile Leu
    1040                1045                1050

Gly Val  Val Leu Leu Ala Ile  Phe Val Ala Leu Phe  Leu Thr Gln
    1055                1060                1065

Lys Arg  Arg Gln Arg Gln Arg  Leu Thr Val Ser Ser  Arg Gly Glu
    1070                1075                1080

Asn Leu  Val His Gln Ile Gln  Tyr Arg Glu Met Asn  Ser Cys Leu
    1085                1090                1095

Asn Ala  Asp Asp Leu Asp Leu  Met Asn Ser Ser Glu  Asn Ser Asn
    1100                1105                1110

Glu Ser  Ala Asp Phe Asn Ala  Ala Glu Leu Ile Ser  Val Ser Lys
    1115                1120                1125

Phe Leu  Pro Ile Ser Gly Met  Glu Lys Glu Ala Ile  Leu Arg His
    1130                1135                1140

Thr Glu  Lys Glu Asn Gly Asn  Leu
    1145                1150

<210> SEQ ID NO 37
<211> LENGTH: 3273
<212> TYPE: DNA
<213> ORGANISM: African Green Monkey

<400> SEQUENCE: 37

atgagcaaac tcagaatggt gctacttgaa gactctggat ctgctgacgt cagaagacat     60
```

-continued

```
tttgtcaact tgagtccctt cactattgct gtggtcttac ttctccgtgc ctgttttgtc    120
accagttctc ttggaggaac aaccaaggag ctgaggctag tggatggtga aaacaagtgt    180
agtgggagag tggaagtgaa aatccaggag gagtggggaa cggtgtgtaa taatggctgg    240
agcatggaag cagtctctgt gatttgtaac cagctgggat gtccaactgc tatcaaagcc    300
actggatggg ctaattccag tgcaggttct ggacgcattt ggatggatca tgtttcttgt    360
cgtgggaatg agtcagctct ttgggactgc aaacatgatg gatggggaaa gcatagtaac    420
tgtactcacc aacaagatgc tggagtaact tgctcagatg gatccgattt ggaaatgagg    480
ctgacgaatg gagggaatat gtgttctgga agaatagaga tcaaattcca aggacagtgg    540
ggaacagtgt gtgatgataa cttcaacatc aatcatgcat ctgtggtttg taaacaactt    600
gaatgtggaa gtgctgtcag tttctctggt tcagctaatt ttggagaagg ctctggacca    660
atctggtttg atgatcttat atgcaacgga aatgagtcag ctctctggaa ctgcaaacat    720
caaggatggg gaaagcataa ctgtgatcat gctgaggatg ctggagtgat ttgctcaaag    780
ggagcagatc tgagcctgag actggtagat ggagtcactg aatgttcagg aagattagaa    840
gtgagattcc aaggagaatg gggacaata tgtgatgacg gctgggacag tcatgatgct    900
gctgtggcat gcaagcaact gggatgtcca actgctatca ccgccattgg tcgagttaac    960
gccagtgagg gatttggaca catctggctt gacagtgttt cttgccaggg acatgaacct   1020
gcggtctggc aatgtaaaca ccatgaatgg ggaaagcatt attgcaatca caatgaagat   1080
gctggcgtaa catgttctga tggatcagat ctggagctaa gacttagagg tggaggcagc   1140
cgctgtgctg ggacagttga ggtggagatt cagagactgt tagggaaggt gtgtgacaga   1200
ggctggggac tgaaagaagc tgatgtggtt tgcaggcagc tgggatgtgg atctgcactc   1260
aaaacatcct atcaagtata ctccaaaatc caggcaacaa acatgtggct gtttctaagt   1320
agctgtaacg gaaatgaaac ttctctttgg gactgcaaga actggcaatg gggtggactt   1380
acctgtgatc actatgaaga agccaaaatt acctgctcag cccacaggga acccagactg   1440
gttggaggag acattccctg ttctggacgc gttgaagtga agcatggtga cacatggggc   1500
tccgtctgtg attcggattt ctctctggaa gctgccagcg ttctatgcag ggaattacag   1560
tgtggcacag tcgtctctat cctgggggga gctcactttg gagagggaaa tggacagatc   1620
tggactgaag aattccagtg tgagggacat gagtcccatc tttcactctg cccagtagca   1680
ccccgcccag aaggaacttg tagccacagc agggatgttg gagtagtctg ctcaagatac   1740
acagaaattc gcttggtgaa tggcaagacc ccatgtgagg gcagagtgga gctcaaaacg   1800
cttaatgcct ggggatccct ctgcaactct cactgggaca tagaagatgc ccacgttctt   1860
tgccaacaac ttaaatgtgg agttgccctt tctaccccag gaggagcaca ttttggaaaa   1920
ggaaatggtc aggtctggag gcatatgttt cactgcactg ggactgagca gcacatggga   1980
gattgtcctg taactgctct gggtgcttca ctatgtcctt cagggcaagt ggcctctgta   2040
atttgctcag gaaaccagtc ccaaacactg tcctcgtgca attcatcatc tctgggccca   2100
acaaggccta ccattccaga agaaagtgct gtggcctgca tagagagtgg tcaacttcgc   2160
ttggtaaatg gaggaggtcg ctgtgctggg agagtagaga tttatcatga gggctcctgg   2220
ggcaccatct gtgatgacag ctgggacctg agcgatgccc acgtggtgtg cagacagctg   2280
ggctgtggag aggccattaa tgccactggt tctgctcatt ttggagaagg aacagggccc   2340
atctggctgg atgagatgaa atgcaatgga aaagaatccc gcatttggca gtgccattca   2400
catggctggg ggcagcaaaa ctgcaggcac aaggaggatg caggagttat ctgctcagag   2460
```

```
ttcatgtctc tgagactgac cagtgaagcc agcagagagg cctgtgcagg gcgtctagaa   2520

gtttttttaca acggagcttg gggcagtgtt ggcaggagta acatgtctga aaccactgtg   2580

ggtgtagtgt gcaggcagct gggctgtgca gacaaaggga aaatcaactc tgcatcttta   2640

gacaaggcca tgtccattcc catgtgggtg gacaatgttc agtgtccaaa aggacctgac   2700

acgctgtggc agtgcccatc atctccatgg gagaagagac tggccaggcc ctcggaggag   2760

acctggatca catgtgacaa caagatgaga ctacaagaag gacccacttc ctgttctgga   2820

cgtgtggaga tctggcacgg aggttcctgg gggacagtgt gtgatgactc ctgggacttg   2880

aacgatgctc aggtggtgtg tcaacaactt ggctgtggtc cagctttgaa agcattcaaa   2940

gaagcagagt ttggtcaggg gactggaccc atatggctca atgaagtgaa gtgcaaaggg   3000

aatgagtctt ccttgtggga ttgtcctgcc agacgctggg gccacagtga gtgtggacac   3060

aaggaagacg ctgcggtgaa ttgcacagat atttcaacgc gcaaaacccc acaaaaagcc   3120

acaacggttt cctcaagagg agagaactta gtccaccaaa ttcaataccg ggagatgaat   3180

tcttgcctga atgcagatga tctgaaccta atgaattcct caggaggcca ttctgaggca   3240

cactgaaaag gaaaatggga atttataacc cag                                 3273
```

```
<210> SEQ ID NO 38
<211> LENGTH: 1081
<212> TYPE: PRT
<213> ORGANISM: African Green Monkey

<400> SEQUENCE: 38

Met Ser Lys Leu Arg Met Val Leu Leu Glu Asp Ser Gly Ser Ala Asp
1               5                   10                  15

Val Arg Arg His Phe Val Asn Leu Ser Pro Phe Thr Ile Ala Val Val
            20                  25                  30

Leu Leu Leu Arg Ala Cys Phe Val Thr Ser Ser Leu Gly Gly Thr Thr
        35                  40                  45

Lys Glu Leu Arg Leu Val Asp Gly Glu Asn Lys Cys Ser Gly Arg Val
    50                  55                  60

Glu Val Lys Ile Gln Glu Glu Trp Gly Thr Val Cys Asn Asn Gly Trp
65                  70                  75                  80

Ser Met Glu Ala Val Ser Val Ile Cys Asn Gln Leu Gly Cys Pro Thr
                85                  90                  95

Ala Ile Lys Ala Thr Gly Trp Ala Asn Ser Ser Ala Gly Ser Gly Arg
            100                 105                 110

Ile Trp Met Asp His Val Ser Cys Arg Gly Asn Glu Ser Ala Leu Trp
        115                 120                 125

Asp Cys Lys His Asp Gly Trp Gly Lys His Ser Asn Cys Thr His Gln
    130                 135                 140

Gln Asp Ala Gly Val Thr Cys Ser Asp Gly Ser Asp Leu Glu Met Arg
145                 150                 155                 160

Leu Thr Asn Gly Gly Asn Met Cys Ser Gly Arg Ile Glu Ile Lys Phe
                165                 170                 175

Gln Gly Gln Trp Gly Thr Val Cys Asp Asp Asn Phe Asn Ile Asn His
            180                 185                 190

Ala Ser Val Val Cys Lys Gln Leu Glu Cys Gly Ser Ala Val Ser Phe
        195                 200                 205

Ser Gly Ser Ala Asn Phe Gly Glu Gly Ser Gly Pro Ile Trp Phe Asp
    210                 215                 220

Asp Leu Ile Cys Asn Gly Asn Glu Ser Ala Leu Trp Asn Cys Lys His
225                 230                 235                 240
```

```
Gln Gly Trp Gly Lys His Asn Cys Asp His Ala Glu Asp Ala Gly Val
                245                 250                 255

Ile Cys Ser Lys Gly Ala Asp Leu Ser Leu Arg Leu Val Asp Gly Val
            260                 265                 270

Thr Glu Cys Ser Gly Arg Leu Glu Val Arg Phe Gln Gly Glu Trp Gly
        275                 280                 285

Thr Ile Cys Asp Asp Gly Trp Asp Ser His Asp Ala Ala Val Ala Cys
    290                 295                 300

Lys Gln Leu Gly Cys Pro Thr Ala Ile Thr Ala Ile Gly Arg Val Asn
305                 310                 315                 320

Ala Ser Glu Gly Phe Gly His Ile Trp Leu Asp Ser Val Ser Cys Gln
                325                 330                 335

Gly His Glu Pro Ala Val Trp Gln Cys Lys His His Glu Trp Gly Lys
            340                 345                 350

His Tyr Cys Asn His Asn Glu Asp Ala Gly Val Thr Cys Ser Asp Gly
        355                 360                 365

Ser Asp Leu Glu Leu Arg Leu Arg Gly Gly Gly Ser Arg Cys Ala Gly
    370                 375                 380

Thr Val Glu Val Glu Ile Gln Arg Leu Leu Gly Lys Val Cys Asp Arg
385                 390                 395                 400

Gly Trp Gly Leu Lys Glu Ala Asp Val Val Cys Arg Gln Leu Gly Cys
                405                 410                 415

Gly Ser Ala Leu Lys Thr Ser Tyr Gln Val Tyr Ser Lys Ile Gln Ala
            420                 425                 430

Thr Asn Met Trp Leu Phe Leu Ser Ser Cys Asn Gly Asn Glu Thr Ser
        435                 440                 445

Leu Trp Asp Cys Lys Asn Trp Gln Trp Gly Gly Leu Thr Cys Asp His
    450                 455                 460

Tyr Glu Glu Ala Lys Ile Thr Cys Ser Ala His Arg Glu Pro Arg Leu
465                 470                 475                 480

Val Gly Gly Asp Ile Pro Cys Ser Gly Arg Val Glu Val Lys His Gly
                485                 490                 495

Asp Thr Trp Gly Ser Val Cys Asp Ser Asp Phe Ser Leu Glu Ala Ala
            500                 505                 510

Ser Val Leu Cys Arg Glu Leu Gln Cys Gly Thr Val Val Ser Ile Leu
        515                 520                 525

Gly Gly Ala His Phe Gly Glu Gly Asn Gly Gln Ile Trp Thr Glu Glu
    530                 535                 540

Phe Gln Cys Glu Gly His Glu Ser His Leu Ser Leu Cys Pro Val Ala
545                 550                 555                 560

Pro Arg Pro Glu Gly Thr Cys Ser His Ser Arg Asp Val Gly Val Val
                565                 570                 575

Cys Ser Arg Tyr Thr Glu Ile Arg Leu Val Asn Gly Lys Thr Pro Cys
            580                 585                 590

Glu Gly Arg Val Glu Leu Lys Thr Leu Asn Ala Trp Gly Ser Leu Cys
        595                 600                 605

Asn Ser His Trp Asp Ile Glu Asp Ala His Val Leu Cys Gln Gln Leu
    610                 615                 620

Lys Cys Gly Val Ala Leu Ser Thr Pro Gly Gly Ala His Phe Gly Lys
625                 630                 635                 640

Gly Asn Gly Gln Val Trp Arg His Met Phe His Cys Thr Gly Thr Glu
                645                 650                 655

Gln His Met Gly Asp Cys Pro Val Thr Ala Leu Gly Ala Ser Leu Cys
```

```
            660                 665                 670

Pro Ser Gly Gln Val Ala Ser Val Ile Cys Ser Gly Asn Gln Ser Gln
        675                 680                 685

Thr Leu Ser Ser Cys Asn Ser Ser Ser Leu Gly Pro Thr Arg Pro Thr
    690                 695                 700

Ile Pro Glu Glu Ser Ala Val Ala Cys Ile Glu Ser Gly Gln Leu Arg
705                 710                 715                 720

Leu Val Asn Gly Gly Gly Arg Cys Ala Gly Arg Val Glu Ile Tyr His
                725                 730                 735

Glu Gly Ser Trp Gly Thr Ile Cys Asp Asp Ser Trp Asp Leu Ser Asp
            740                 745                 750

Ala His Val Val Cys Arg Gln Leu Gly Cys Gly Glu Ala Ile Asn Ala
        755                 760                 765

Thr Gly Ser Ala His Phe Gly Glu Gly Thr Gly Pro Ile Trp Leu Asp
    770                 775                 780

Glu Met Lys Cys Asn Gly Lys Glu Ser Arg Ile Trp Gln Cys His Ser
785                 790                 795                 800

His Gly Trp Gly Gln Gln Asn Cys Arg His Lys Glu Asp Ala Gly Val
                805                 810                 815

Ile Cys Ser Glu Phe Met Ser Leu Arg Leu Thr Ser Glu Ala Ser Arg
            820                 825                 830

Glu Ala Cys Ala Gly Arg Leu Glu Val Phe Tyr Asn Gly Ala Trp Gly
        835                 840                 845

Ser Val Gly Arg Ser Asn Met Ser Glu Thr Thr Val Gly Val Val Cys
    850                 855                 860

Arg Gln Leu Gly Cys Ala Asp Lys Gly Lys Ile Asn Ser Ala Ser Leu
865                 870                 875                 880

Asp Lys Ala Met Ser Ile Pro Met Trp Val Asp Asn Val Gln Cys Pro
                885                 890                 895

Lys Gly Pro Asp Thr Leu Trp Gln Cys Pro Ser Ser Pro Trp Glu Lys
            900                 905                 910

Arg Leu Ala Arg Pro Ser Glu Glu Thr Trp Ile Thr Cys Asp Asn Lys
        915                 920                 925

Met Arg Leu Gln Glu Gly Pro Thr Ser Cys Ser Gly Arg Val Glu Ile
    930                 935                 940

Trp His Gly Gly Ser Trp Gly Thr Val Cys Asp Asp Ser Trp Asp Leu
945                 950                 955                 960

Asn Asp Ala Gln Val Val Cys Gln Gln Leu Gly Cys Gly Pro Ala Leu
                965                 970                 975

Lys Ala Phe Lys Glu Ala Glu Phe Gly Gln Gly Thr Gly Pro Ile Trp
            980                 985                 990

Leu Asn Glu Val Lys Cys Lys Gly  Asn Glu Ser Ser Leu  Trp Asp Cys
        995                 1000                1005

Pro Ala  Arg Arg Trp Gly His  Ser Glu Cys Gly His  Lys Glu Asp
    1010                1015                1020

Ala Ala  Val Asn Cys Thr Asp  Ile Ser Thr Arg Lys  Thr Pro Gln
    1025                1030                1035

Lys Ala  Thr Thr Val Ser Ser  Arg Gly Glu Asn Leu  Val His Gln
    1040                1045                1050

Ile Gln  Tyr Arg Glu Met Asn  Ser Cys Leu Asn Ala  Asp Asp Leu
    1055                1060                1065

Asn Leu  Met Asn Ser Ser Gly  Gly His Ser Glu Ala  His
    1070                1075                1080
```

<210> SEQ ID NO 39
<211> LENGTH: 3279
<212> TYPE: DNA
<213> ORGANISM: African Green Monkey

<400> SEQUENCE: 39

```
atgagcaaac tcagaatggt gctacttgaa gactctggat ctgctgacgt cagaagacat      60
tttgtcaact tgagtccctt cactattgct gtggtcttac ttctccgtgc ctgttttgtc     120
accagttctc ttggaggaac aaccaaggag ctgaggctag tggatggtga aaacaagtgt     180
agtgggagag tggaagtgaa aatccaggag gagtggggaa cggtgtgtaa taatggctgg     240
agcatggaag cagtctctgt gatttgtaac cagctgggat gtccaactgc tatcaaagcc     300
actggatggg ctaattccag tgcaggttct ggacgcattt ggatggatca tgtttcttgt     360
cgtgggaatg agtcagctct ttgggactgc aaacatgatg gatggggaaa gcatagtaac     420
tgtactcacc aacaagatgc tggagtgact tgctcagatg gatccgattt ggaaatgagg     480
ctgacgaatg gagggaatat gtgttctgga agaatagaga tcaaattcca aggacagtgg     540
ggaacagtgt gtgatgataa cttcaacgtc aatcatgcat ctgtggtttg taaacaactt     600
gaatgtggaa gtgctgtcag tttctctggt tcagctaatt ttggagaagg ctctggacca     660
atctggtttg atgatcttat atgcaacgga aatgagtcag ctctctggaa ctgcaaacat     720
caaggatggg gaaagcataa ctgtgatcat gctgaggatg ctggagtgat ttgctcaaag     780
ggagcagatc tgagcctgag actggtagat ggagtcactg aatgttcagg aagattagaa     840
gtgagattcc aaggagaatg gggacaata tgtgatgacg gctgggacag tcatgatgct     900
gctgtggcat gcaagcaact gggatgtcca actgctatca ccgccattgg tcgagttaac     960
gccagtgagg gatttggaca catctggctt gacagtgttt cttgccaggg acatgaacct    1020
gcggtctggc aatgtaaaca ccatgaatgg ggaaagcatt attgcaatca caatgaagat    1080
gctggcgtaa catgttctga tggatcagat ctggagctaa gacttagagg tggaggcagc    1140
cgctgtgctg ggacagttga ggtggagatt cagagactgt tagggaaggt gtgtgacaga    1200
ggctggggac tgaaagaagc tgatgtggtt tgcaggcagc tgggatgtgg atctgcactc    1260
aaaacatcct atcaagtata ctccaaaatc caggcaacaa acatgtggct gtttctaagt    1320
agctgtaacg gaaatgaaac ttctctttgg gactgcaaga actggcaatg ggggtggactt   1380
acctgtgatc actatgaaga agccaaaatt acctgctcag cccacaggga acccagactg    1440
gttggaggag acattccctg ttctggacgc gttgaagtga agcatggtga cacatggggc    1500
tccgtctgtg attcggattt ctctctggaa gctgccagcg ttctatgcag ggaattacag    1560
tgtggcacag tcgtctctat cctgggggga gctcactttg gagagggaaa tggacagatc    1620
tgggctgaag aattccagtg tgagggacat gagtcccatc tttcactctg cccagtagca    1680
ccccgcccag aaggaacttg tagccacagc agggatgttg gagtagtctg ctcaagatac    1740
acagaaattc gcttggtgaa tggcaagacc ccatgtgagg gcagagtgga gctcaaaacg    1800
cttaatgcct ggggatccct ctgcaactct cactgggaca tagaagatgc ccacgttctt    1860
tgccaacaac ttaaatgtgg agttgccctt tctaccccag gaggagcaca ttttggaaaa    1920
ggaaatggtc aggtctggag gcatatgttt cactgcactg ggactgagca gcacatggga    1980
gattgtcctg taactgctct gggtgcttca ctatgtcctt cagggcaagt ggcctctgta    2040
atttgctcag gaaaccagtc ccaaacactg tcctcgtgca attcatcatc tctgggccca    2100
acaaggccta ccattccaga agaaagtgct gtggcctgca tagagagtgg tcaacttcgc    2160
```

```
ttggtaaatg gaggaggtcg ctgtgctggg agagtagaga tttatcatga gggctcctgg   2220

ggcaccatct gtgatgacag ctgggacctg agcgatgccc acgtggtgtg cagacagctg   2280

ggctgtggag aggccattaa tgccactggt tctgctcatt ttggagaagg aacagggccc   2340

atctggctgg atgagatgaa atgcaatgga aaagaatccc gtatttggca gtgccattca   2400

catggctggg ggcagcaaaa ctgcaggcac aaggaggatg caggagttat ctgctcagag   2460

ttcatgtctc tgagactgac cagtgaagcc agcagagagg cctgtgcagg gcgtctagaa   2520

gtttttttaca acggagcttg gggcagtgtt ggcaggagta acatgtctga aaccactgtg   2580

ggtgtggtgt gcaggcagct gggctgtgca gacaaaggga aaatcaactc tgcatcttta   2640

gacaaggcca tgtccattcc catgtgggtg gacaatgttc agtgtccaaa aggacctgac   2700

acgctgtggc agtgcccatc atctccatgg gagaagagac tggccaggcc ctcggaggag   2760

acctggatca catgtgacaa caagatgaga ctacaagaag gacccacttc ctgttctgga   2820

cgtgtggaga tctggcacgg aggttcctgg gggacagtgt gtgatgactc ctgggacttg   2880

aacgatgctc aggtggtgtg tcaacaactt ggctgtggtc cagctttgaa agcattcaaa   2940

gaagcagagt ttggtcaggg gactggaccc atatggctca atgaagtgaa gtgcaaaggg   3000

aatgagtctt ccttgtggga ttgtcctgcc agacgctggg gccacagtga gtgtggacac   3060

aaggaagacg ctgcagtgaa ttgcacagca caaaaaattt caacgcacaa aaccccacaa   3120

aaagccacaa cagtttcctc aagaggagag aacttagtcc accaaattca ataccgggag   3180

atgaattctt gcctgaatgc agatgatctg gacctaatga attcctcagg aggccattct   3240

gaggcacact gaaaaggaaa atgggaattt ataacccag                          3279
```

```
<210> SEQ ID NO 40
<211> LENGTH: 1083
<212> TYPE: PRT
<213> ORGANISM: African Green Monkey

<400> SEQUENCE: 40

Met Ser Lys Leu Arg Met Val Leu Leu Glu Asp Ser Gly Ser Ala Asp
1               5                   10                  15

Val Arg Arg His Phe Val Asn Leu Ser Pro Phe Thr Ile Ala Val Val
            20                  25                  30

Leu Leu Leu Arg Ala Cys Phe Val Thr Ser Ser Leu Gly Gly Thr Thr
        35                  40                  45

Lys Glu Leu Arg Leu Val Asp Gly Glu Asn Lys Cys Ser Gly Arg Val
    50                  55                  60

Glu Val Lys Ile Gln Glu Glu Trp Gly Thr Val Cys Asn Asn Gly Trp
65                  70                  75                  80

Ser Met Glu Ala Val Ser Val Ile Cys Asn Gln Leu Gly Cys Pro Thr
                85                  90                  95

Ala Ile Lys Ala Thr Gly Trp Ala Asn Ser Ser Ala Gly Ser Gly Arg
            100                 105                 110

Ile Trp Met Asp His Val Ser Cys Arg Gly Asn Glu Ser Ala Leu Trp
        115                 120                 125

Asp Cys Lys His Asp Gly Trp Gly Lys His Ser Asn Cys Thr His Gln
    130                 135                 140

Gln Asp Ala Gly Val Thr Cys Ser Asp Gly Ser Asp Leu Glu Met Arg
145                 150                 155                 160

Leu Thr Asn Gly Gly Asn Met Cys Ser Gly Arg Ile Glu Ile Lys Phe
                165                 170                 175

Gln Gly Gln Trp Gly Thr Val Cys Asp Asp Asn Phe Asn Val Asn His
```

```
            180                 185                 190

Ala Ser Val Val Cys Lys Gln Leu Glu Cys Gly Ser Ala Val Ser Phe
        195                 200                 205

Ser Gly Ser Ala Asn Phe Gly Glu Gly Ser Gly Pro Ile Trp Phe Asp
    210                 215                 220

Asp Leu Ile Cys Asn Gly Asn Glu Ser Ala Leu Trp Asn Cys Lys His
225                 230                 235                 240

Gln Gly Trp Gly Lys His Asn Cys Asp His Ala Glu Asp Ala Gly Val
                245                 250                 255

Ile Cys Ser Lys Gly Ala Asp Leu Ser Leu Arg Leu Val Asp Gly Val
            260                 265                 270

Thr Glu Cys Ser Gly Arg Leu Glu Val Arg Phe Gln Gly Glu Trp Gly
        275                 280                 285

Thr Ile Cys Asp Asp Gly Trp Asp Ser His Asp Ala Ala Val Ala Cys
    290                 295                 300

Lys Gln Leu Gly Cys Pro Thr Ala Ile Thr Ala Ile Gly Arg Val Asn
305                 310                 315                 320

Ala Ser Glu Gly Phe Gly His Ile Trp Leu Asp Ser Val Ser Cys Gln
                325                 330                 335

Gly His Glu Pro Ala Val Trp Gln Cys Lys His His Glu Trp Gly Lys
            340                 345                 350

His Tyr Cys Asn His Asn Glu Asp Ala Gly Val Thr Cys Ser Asp Gly
        355                 360                 365

Ser Asp Leu Glu Leu Arg Leu Arg Gly Gly Gly Ser Arg Cys Ala Gly
    370                 375                 380

Thr Val Glu Val Glu Ile Gln Arg Leu Leu Gly Lys Val Cys Asp Arg
385                 390                 395                 400

Gly Trp Gly Leu Lys Glu Ala Asp Val Val Cys Arg Gln Leu Gly Cys
                405                 410                 415

Gly Ser Ala Leu Lys Thr Ser Tyr Gln Val Tyr Ser Lys Ile Gln Ala
            420                 425                 430

Thr Asn Met Trp Leu Phe Leu Ser Ser Cys Asn Gly Asn Glu Thr Ser
        435                 440                 445

Leu Trp Asp Cys Lys Asn Trp Gln Trp Gly Gly Leu Thr Cys Asp His
    450                 455                 460

Tyr Glu Glu Ala Lys Ile Thr Cys Ser Ala His Arg Glu Pro Arg Leu
465                 470                 475                 480

Val Gly Gly Asp Ile Pro Cys Ser Gly Arg Val Glu Val Lys His Gly
                485                 490                 495

Asp Thr Trp Gly Ser Val Cys Asp Ser Asp Phe Ser Leu Glu Ala Ala
            500                 505                 510

Ser Val Leu Cys Arg Glu Leu Gln Cys Gly Thr Val Val Ser Ile Leu
        515                 520                 525

Gly Gly Ala His Phe Gly Glu Gly Asn Gly Gln Ile Trp Ala Glu Glu
    530                 535                 540

Phe Gln Cys Glu Gly His Glu Ser His Leu Ser Leu Cys Pro Val Ala
545                 550                 555                 560

Pro Arg Pro Glu Gly Thr Cys Ser His Ser Arg Asp Val Gly Val Val
                565                 570                 575

Cys Ser Arg Tyr Thr Glu Ile Arg Leu Val Asn Gly Lys Thr Pro Cys
            580                 585                 590

Glu Gly Arg Val Glu Leu Lys Thr Leu Asn Ala Trp Gly Ser Leu Cys
        595                 600                 605
```

```
Asn Ser His Trp Asp Ile Glu Asp Ala His Val Leu Cys Gln Gln Leu
    610                 615                 620

Lys Cys Gly Val Ala Leu Ser Thr Pro Gly Gly Ala His Phe Gly Lys
625                 630                 635                 640

Gly Asn Gly Gln Val Trp Arg His Met Phe His Cys Thr Gly Thr Glu
                645                 650                 655

Gln His Met Gly Asp Cys Pro Val Thr Ala Leu Gly Ala Ser Leu Cys
            660                 665                 670

Pro Ser Gly Gln Val Ala Ser Val Ile Cys Ser Gly Asn Gln Ser Gln
        675                 680                 685

Thr Leu Ser Ser Cys Asn Ser Ser Ser Leu Gly Pro Thr Arg Pro Thr
    690                 695                 700

Ile Pro Glu Glu Ser Ala Val Ala Cys Ile Glu Ser Gly Gln Leu Arg
705                 710                 715                 720

Leu Val Asn Gly Gly Gly Arg Cys Ala Gly Arg Val Glu Ile Tyr His
                725                 730                 735

Glu Gly Ser Trp Gly Thr Ile Cys Asp Asp Ser Trp Asp Leu Ser Asp
            740                 745                 750

Ala His Val Val Cys Arg Gln Leu Gly Cys Gly Glu Ala Ile Asn Ala
        755                 760                 765

Thr Gly Ser Ala His Phe Gly Glu Gly Thr Gly Pro Ile Trp Leu Asp
    770                 775                 780

Glu Met Lys Cys Asn Gly Lys Glu Ser Arg Ile Trp Gln Cys His Ser
785                 790                 795                 800

His Gly Trp Gly Gln Gln Asn Cys Arg His Lys Glu Asp Ala Gly Val
                805                 810                 815

Ile Cys Ser Glu Phe Met Ser Leu Arg Leu Thr Ser Glu Ala Ser Arg
            820                 825                 830

Glu Ala Cys Ala Gly Arg Leu Glu Val Phe Tyr Asn Gly Ala Trp Gly
        835                 840                 845

Ser Val Gly Arg Ser Asn Met Ser Glu Thr Thr Val Gly Val Val Cys
    850                 855                 860

Arg Gln Leu Gly Cys Ala Asp Lys Gly Lys Ile Asn Ser Ala Ser Leu
865                 870                 875                 880

Asp Lys Ala Met Ser Ile Pro Met Trp Val Asp Asn Val Gln Cys Pro
                885                 890                 895

Lys Gly Pro Asp Thr Leu Trp Gln Cys Pro Ser Ser Pro Trp Glu Lys
            900                 905                 910

Arg Leu Ala Arg Pro Ser Glu Glu Thr Trp Ile Thr Cys Asp Asn Lys
        915                 920                 925

Met Arg Leu Gln Glu Gly Pro Thr Ser Cys Ser Gly Arg Val Glu Ile
    930                 935                 940

Trp His Gly Gly Ser Trp Gly Thr Val Cys Asp Asp Ser Trp Asp Leu
945                 950                 955                 960

Asn Asp Ala Gln Val Val Cys Gln Gln Leu Gly Cys Gly Pro Ala Leu
                965                 970                 975

Lys Ala Phe Lys Glu Ala Glu Phe Gly Gln Gly Thr Gly Pro Ile Trp
            980                 985                 990

Leu Asn Glu Val Lys Cys Lys Gly  Asn Glu Ser Ser Leu  Trp Asp Cys
        995                 1000                1005

Pro Ala  Arg Arg Trp Gly His  Ser Glu Cys Gly His  Lys Glu Asp
    1010                1015                1020

Ala Ala  Val Asn Cys Thr Ala  Gln Lys Ile Ser Thr  His Lys Thr
    1025                1030                1035
```

```
Pro Gln  Lys Ala Thr Thr Val  Ser Ser Arg Gly Glu  Asn Leu Val
    1040                 1045                 1050

His Gln  Ile Gln Tyr Arg Glu  Met Asn Ser Cys Leu  Asn Ala Asp
    1055                 1060                 1065

Asp Leu  Asp Leu Met Asn Ser  Ser Gly Gly His Ser  Glu Ala His
    1070                 1075                 1080


<210> SEQ ID NO 41
<211> LENGTH: 3354
<212> TYPE: DNA
<213> ORGANISM: African Green Monkey

<400> SEQUENCE: 41

atgagcaaac tcagaatggt gctacttgaa gactctggat ctgctgacgt cagaagacat      60

tttgtcaact tgagtccctt cactattgct gtggtcttac ttctccgtgc ctgttttgtc     120

accagttctc ttggaggaac aaccaaggag ctgaggctag tggatggtga aaacaagtgt     180

agtgggagag tggaagtgaa aatccaggag gagtggggaa cggtgtgtaa taatggctgg     240

agcatggaag cagtctctgt gatttgtaac cagctgggat gtccaactgc tatcaaagcc     300

actggatggg ctaattccag tgcaggttct ggacgcattt ggatggatca tgtttcttgt     360

cgtgggaatg agtcagctct ttgggactgc aaacatgatg gatggggaaa gcatagtaac     420

tgtactcacc aacaagatgc tggagtgact tgctcagatg gatccgattt ggaaatgagg     480

ctgacgaatg gagggaatat gtgttctgga agaatagaga tcaaattcca aggacagtgg     540

ggaacagtgt gtgatgataa cttcaacatc aatcatgcat ctgtggtttg taaacaactt     600

gaatgtggaa gtgctgtcag tttctctggt tcagctaatt ttggagaagg ctctggacca     660

atctggtttg atgatcttat atgcaacgga aatgagtcag ctctctggaa ctgcaaacat     720

caaggatggg gaaagcataa ctgtgatcat gctgaggatg ctggagtgat ttgctcaaag     780

ggagcagatc tgagcctgag actggtagat ggagtcactg aatgttcagg aagattagaa     840

gtgagattcc aaggagaatg gggggacaata tgtgatgacg gctgggacag tcatgatgct     900

gctgtggcat gcaagcaact gggatgtcca actgctatca ccgccattgg tcgagttaac     960

gccagtgagg gatttggaca catctggctt gacagtgttt cttgccaggg acatgaacct    1020

gcggtctggc aatgtaaaca ccatgaatgg ggaaagcatt attgcaatca caatgaagat    1080

gctggcgtaa catgttctga tggatcagat ctggagctaa gacttagagg tggaggcagc    1140

cgctgtgctg ggacagttga ggtggagatt cagagactgt tagggaaggt gtgtgacaga    1200

ggctggggac tgaaagaagc tgatgtggtt tgcaggcagc tgggatgtgg atctgcactc    1260

aaaacatcct atcaagtata ctccaaaatc caggcaacaa acatgtggct gtttctaagt    1320

agctgtaacg gaaatgaaac ttctctttgg gactgcaaga actggcaatg ggggtggactt    1380

acctgtgatc actatgaaga agccaaaatt acctgctcag cccacaggga acccagactg    1440

gttggaggag acattccctg ttctggacgc gttgaagtga agcatggtga cacatggggc    1500

tccgtctgtg attcggattt ctctctggaa gctgccagcg ttctatgcag ggaattacag    1560

tgtggcacag tcgtctctat cctgggggga gctcactttg gagagggaaa tggacagatc    1620

tgggctgaag aattccagtg tgagggacat gagtcccatc tttcactctg cccagtagca    1680

ccccgcccag aaggaacttg tagccacagc agggatgttg gagtagtctg ctcaagatac    1740

acagaaattc gcttggtgaa tggcaagacc ccatgtgagg gcagagtgga gctcaaaacg    1800

cttaatgcct ggggatccct ctgcaactct cactgggaca tagaagatgc ccacgttctt    1860
```

```
tgccaacaac ttaaatgtgg agttgccctt tctaccccag gaggagcaca ttttggaaaa   1920
ggaaatggtc aggtctggag gcatatgttt cactgcactg ggactgagca gcacatggga   1980
gattgtcctg taactgctct gggtgcttca ctatgtcctt cagggcaagt ggcctctgta   2040
atttgctcag gaaaccagtc ccaaacactg tcctcgtgca attcatcatc tctgggccca   2100
acaaggccta ccattccaga agaaagtgct gtggcctgca tagagagtgg tcaacttcgc   2160
ttggtaaatg gaggaggtcg ctgtgctggg agagtagaga tttatcatga gggctcctgg   2220
ggcaccatct gtgatgacag ctgggacctg agcgatgccc acgtggtgtg cagacagctg   2280
ggctgtggag aggccattaa tgccactggt tctgctcatt ttggagaagg aacagggccc   2340
atctggctgg atgagatgaa atgcaatgga aaagaatccc gtatttggca gtgccattca   2400
catggctggg ggcagcaaaa ctgcaggcac aaggaggatg caggagttat ctgctcagag   2460
ttcatgtctc tgagactgac cagtgaagcc agcagagagg cctgtgcagg gcgtctagaa   2520
gtttttttaca acggagcttg gggcagtgtt ggcaggagta acatgtctga aaccactgtg   2580
ggtgtggtgt gcaggcagct gggctgtgca gacaaaggga aaatcaactc tgcatcttta   2640
gacaaggcca tgtccattcc catgtgggtg gacaatgttc agtgtccaaa aggacctgac   2700
acgctgtggc agtgcccatc atctccatgg gagaagagac tggccaggcc ctcggaggag   2760
acctggatca catgtgacaa caagatgaga ctacaagaag gacccacttc ctgttctgga   2820
cgtgtggaga tctggcacgg aggttcctgg gggacagtgt gtgatgactc ctgggacttg   2880
aacgatgctc aggtggtgtg tcaacaactt ggctgtggtc cagctttgaa agcattcaaa   2940
gaagcagagt ttggtcaggg gactggaccc atatggctca atgaagtgaa gtgcaaaggg   3000
aatgagtctt ccttgtggga ttgtcctgcc agacgctggg gccacagtga gtgtggacac   3060
aaggaagacg ctgcagtgaa ttgcacagca caaaaaattt caacgcacaa aaccccacaa   3120
aaagccacaa caggtcggtc attccttatt gcattcggaa tccttggagt tgttctcttg   3180
gccattttcg tcgcattatt cttgactcaa aagcgaagac agagacagcg gcttacagtt   3240
tcctcaagag gagagaactt agtccaccaa attcaatacc gggagatgaa ttcttgcctg   3300
aatgcagatg atctggacct aatgaattcc tcaggaggcc attctgaggc acac         3354
```

```
<210> SEQ ID NO 42
<211> LENGTH: 1118
<212> TYPE: PRT
<213> ORGANISM: African Green Monkey

<400> SEQUENCE: 42

Met Ser Lys Leu Arg Met Val Leu Leu Glu Asp Ser Gly Ser Ala Asp
1               5                   10                  15

Val Arg Arg His Phe Val Asn Leu Ser Pro Phe Thr Ile Ala Val Val
            20                  25                  30

Leu Leu Leu Arg Ala Cys Phe Val Thr Ser Ser Leu Gly Gly Thr Thr
        35                  40                  45

Lys Glu Leu Arg Leu Val Asp Gly Glu Asn Lys Cys Ser Gly Arg Val
    50                  55                  60

Glu Val Lys Ile Gln Glu Glu Trp Gly Thr Val Cys Asn Asn Gly Trp
65                  70                  75                  80

Ser Met Glu Ala Val Ser Val Ile Cys Asn Gln Leu Gly Cys Pro Thr
                85                  90                  95

Ala Ile Lys Ala Thr Gly Trp Ala Asn Ser Ser Ala Gly Ser Gly Arg
            100                 105                 110

Ile Trp Met Asp His Val Ser Cys Arg Gly Asn Glu Ser Ala Leu Trp
```

```
        115                 120                 125

Asp Cys Lys His Asp Gly Trp Gly Lys His Ser Asn Cys Thr His Gln
    130                 135                 140

Gln Asp Ala Gly Val Thr Cys Ser Asp Gly Ser Asp Leu Glu Met Arg
145                 150                 155                 160

Leu Thr Asn Gly Gly Asn Met Cys Ser Gly Arg Ile Glu Ile Lys Phe
                165                 170                 175

Gln Gly Gln Trp Gly Thr Val Cys Asp Asp Asn Phe Asn Ile Asn His
            180                 185                 190

Ala Ser Val Val Cys Lys Gln Leu Glu Cys Gly Ser Ala Val Ser Phe
        195                 200                 205

Ser Gly Ser Ala Asn Phe Gly Glu Gly Ser Gly Pro Ile Trp Phe Asp
    210                 215                 220

Asp Leu Ile Cys Asn Gly Asn Glu Ser Ala Leu Trp Asn Cys Lys His
225                 230                 235                 240

Gln Gly Trp Gly Lys His Asn Cys Asp His Ala Glu Asp Ala Gly Val
                245                 250                 255

Ile Cys Ser Lys Gly Ala Asp Leu Ser Leu Arg Leu Val Asp Gly Val
            260                 265                 270

Thr Glu Cys Ser Gly Arg Leu Glu Val Arg Phe Gln Gly Glu Trp Gly
        275                 280                 285

Thr Ile Cys Asp Asp Gly Trp Asp Ser His Asp Ala Ala Val Ala Cys
    290                 295                 300

Lys Gln Leu Gly Cys Pro Thr Ala Ile Thr Ala Ile Gly Arg Val Asn
305                 310                 315                 320

Ala Ser Glu Gly Phe Gly His Ile Trp Leu Asp Ser Val Ser Cys Gln
                325                 330                 335

Gly His Glu Pro Ala Val Trp Gln Cys Lys His His Glu Trp Gly Lys
            340                 345                 350

His Tyr Cys Asn His Asn Glu Asp Ala Gly Val Thr Cys Ser Asp Gly
        355                 360                 365

Ser Asp Leu Glu Leu Arg Leu Arg Gly Gly Gly Ser Arg Cys Ala Gly
    370                 375                 380

Thr Val Glu Val Glu Ile Gln Arg Leu Leu Gly Lys Val Cys Asp Arg
385                 390                 395                 400

Gly Trp Gly Leu Lys Glu Ala Asp Val Val Cys Arg Gln Leu Gly Cys
                405                 410                 415

Gly Ser Ala Leu Lys Thr Ser Tyr Gln Val Tyr Ser Lys Ile Gln Ala
            420                 425                 430

Thr Asn Met Trp Leu Phe Leu Ser Ser Cys Asn Gly Asn Glu Thr Ser
        435                 440                 445

Leu Trp Asp Cys Lys Asn Trp Gln Trp Gly Gly Leu Thr Cys Asp His
    450                 455                 460

Tyr Glu Glu Ala Lys Ile Thr Cys Ser Ala His Arg Glu Pro Arg Leu
465                 470                 475                 480

Val Gly Gly Asp Ile Pro Cys Ser Gly Arg Val Glu Val Lys His Gly
                485                 490                 495

Asp Thr Trp Gly Ser Val Cys Asp Ser Asp Phe Ser Leu Glu Ala Ala
            500                 505                 510

Ser Val Leu Cys Arg Glu Leu Gln Cys Gly Thr Val Val Ser Ile Leu
        515                 520                 525

Gly Gly Ala His Phe Gly Glu Gly Asn Gly Gln Ile Trp Ala Glu Glu
    530                 535                 540
```

```
Phe Gln Cys Glu Gly His Glu Ser His Leu Ser Leu Cys Pro Val Ala
545                 550                 555                 560

Pro Arg Pro Glu Gly Thr Cys Ser His Ser Arg Asp Val Gly Val Val
                565                 570                 575

Cys Ser Arg Tyr Thr Glu Ile Arg Leu Val Asn Gly Lys Thr Pro Cys
            580                 585                 590

Glu Gly Arg Val Glu Leu Lys Thr Leu Asn Ala Trp Gly Ser Leu Cys
        595                 600                 605

Asn Ser His Trp Asp Ile Glu Asp Ala His Val Leu Cys Gln Gln Leu
    610                 615                 620

Lys Cys Gly Val Ala Leu Ser Thr Pro Gly Gly Ala His Phe Gly Lys
625                 630                 635                 640

Gly Asn Gly Gln Val Trp Arg His Met Phe His Cys Thr Gly Thr Glu
                645                 650                 655

Gln His Met Gly Asp Cys Pro Val Thr Ala Leu Gly Ala Ser Leu Cys
            660                 665                 670

Pro Ser Gly Gln Val Ala Ser Val Ile Cys Ser Gly Asn Gln Ser Gln
        675                 680                 685

Thr Leu Ser Ser Cys Asn Ser Ser Ser Leu Gly Pro Thr Arg Pro Thr
    690                 695                 700

Ile Pro Glu Glu Ser Ala Val Ala Cys Ile Glu Ser Gly Gln Leu Arg
705                 710                 715                 720

Leu Val Asn Gly Gly Gly Arg Cys Ala Gly Arg Val Glu Ile Tyr His
                725                 730                 735

Glu Gly Ser Trp Gly Thr Ile Cys Asp Asp Ser Trp Asp Leu Ser Asp
            740                 745                 750

Ala His Val Val Cys Arg Gln Leu Gly Cys Gly Glu Ala Ile Asn Ala
        755                 760                 765

Thr Gly Ser Ala His Phe Gly Glu Gly Thr Gly Pro Ile Trp Leu Asp
    770                 775                 780

Glu Met Lys Cys Asn Gly Lys Glu Ser Arg Ile Trp Gln Cys His Ser
785                 790                 795                 800

His Gly Trp Gly Gln Gln Asn Cys Arg His Lys Glu Asp Ala Gly Val
                805                 810                 815

Ile Cys Ser Glu Phe Met Ser Leu Arg Leu Thr Ser Glu Ala Ser Arg
            820                 825                 830

Glu Ala Cys Ala Gly Arg Leu Glu Val Phe Tyr Asn Gly Ala Trp Gly
        835                 840                 845

Ser Val Gly Arg Ser Asn Met Ser Glu Thr Thr Val Gly Val Val Cys
    850                 855                 860

Arg Gln Leu Gly Cys Ala Asp Lys Gly Lys Ile Asn Ser Ala Ser Leu
865                 870                 875                 880

Asp Lys Ala Met Ser Ile Pro Met Trp Val Asp Asn Val Gln Cys Pro
                885                 890                 895

Lys Gly Pro Asp Thr Leu Trp Gln Cys Pro Ser Ser Pro Trp Glu Lys
            900                 905                 910

Arg Leu Ala Arg Pro Ser Glu Glu Thr Trp Ile Thr Cys Asp Asn Lys
        915                 920                 925

Met Arg Leu Gln Glu Gly Pro Thr Ser Cys Ser Gly Arg Val Glu Ile
    930                 935                 940

Trp His Gly Gly Ser Trp Gly Thr Val Cys Asp Asp Ser Trp Asp Leu
945                 950                 955                 960

Asn Asp Ala Gln Val Val Cys Gln Gln Leu Gly Cys Gly Pro Ala Leu
                965                 970                 975
```

```
Lys Ala Phe Lys Glu Ala Glu Phe Gly Gln Gly Thr Gly Pro Ile Trp
            980                 985                 990

Leu Asn Glu Val Lys Cys Lys Gly  Asn Glu Ser Ser Leu  Trp Asp Cys
        995                 1000                1005

Pro Ala  Arg Arg Trp Gly His  Ser Glu Cys Gly His  Lys Glu Asp
    1010                 1015                 1020

Ala Ala  Val Asn Cys Thr Ala  Gln Lys Ile Ser Thr  His Lys Thr
    1025                 1030                 1035

Pro Gln  Lys Ala Thr Thr Gly  Arg Ser Phe Leu Ile  Ala Phe Gly
    1040                 1045                 1050

Ile Leu  Gly Val Val Leu Leu  Ala Ile Phe Val Ala  Leu Phe Leu
    1055                 1060                 1065

Thr Gln  Lys Arg Arg Gln Arg  Gln Arg Leu Thr Val  Ser Ser Arg
    1070                 1075                 1080

Gly Glu  Asn Leu Val His Gln  Ile Gln Tyr Arg Glu  Met Asn Ser
    1085                 1090                 1095

Cys Leu  Asn Ala Asp Asp Leu  Asp Leu Met Asn Ser  Ser Gly Gly
    1100                 1105                 1110

His Ser  Glu Ala His
    1115
```

<210> SEQ ID NO 43
<211> LENGTH: 3459
<212> TYPE: DNA
<213> ORGANISM: African Green Monkey

<400> SEQUENCE: 43

```
atgagcaaac tcagaatggt gctacttgaa gactctggat ctgctgacgt cagaagacat     60

tttgtcaact tgagtccctt cactattgct gtggtcttac ttctccgtgc ctgttttgtc    120

accagttctc ttggaggaac aaccaaggag ctgaggctag tggatggtga aaacaagtgt    180

agtgggagag tggaagtgaa aatccaggag gagtggggaa cggtgtgtaa taatggctgg    240

agcatggaag cagtctctgt gatttgtaac cagctgggat gtccaactgc tatcaaagcc    300

actggatggg ctaattccag tgcaggttct ggacgcattt ggatggatca tgtttcttgt    360

cgtgggaatg agtcagctct ttgggactgc aaacatgatg gatggggaaa gcatagtaac    420

tgtactcacc aacaagatgc tggagtgact tgctcagatg gatccgattt ggaaatgagg    480

ctgacgaatg gagggaatat gtgttctgga agaatagaga tcaaattcca aggacagtgg    540

ggaacagtgt gtgatgataa cttcaacatc aatcatgcat ctgtggtttg taaacaactt    600

gaatgtggaa gtgctgtcag tttctctggt tcagctaatt ttggagaagg ctctggacca    660

atctggtttg atgatcttat atgcaacgga aatgagtcag ctctctggaa ctgcaaacat    720

caaggatggg gaaagcataa ctgtgatcat gctgaggatg ctggagtgat ttgctcaaag    780

ggagcagatc tgagcctgag actggtagat ggagtcactg aatgttcagg aagattagaa    840

gtgagattcc aaggagaatg gggacaata tgtgatgacg gctgggacag tcatgatgct    900

gctgtggcat gcaagcaact gggatgtcca actgctatca ccgccattgg tcgagttaac    960

gccagtgagg gatttggaca catctggctt gacagtgttt cttgccaggg acatgaacct   1020

gcggtctggc aatgtaaaca ccatgaatgg ggaaagcatt attgcaatca caatgaagat   1080

gctggcgtaa catgttctga tggatcagat ctggagctaa gacttagagg tggaggcagc   1140

cgctgtgctg ggacagttga ggtggagatt cagagactgt tagggaaggt gtgtgacaga   1200

ggctggggac tgaaagaagc tgatgtggtt tgcaggcagc tgggatgtgg atctgcactc   1260
```

```
aaaacatcct atcaagtata ctccaaaatc caggcaacaa acatgtggct gtttctaagt   1320
agctgtaacg gaaatgaaac ttctctttgg gactgcaaga actggcaatg ggtggactt    1380
acctgtgatc actatgaaga agccaaaatt acctgctcag cccacaggga acccagactg   1440
gttggaggag acattccctg ttctggacgc gttgaagtga agcatggtga cacatggggc   1500
tccgtctgtg attcggattt ctctctggaa gctgccagcg ttctatgcag ggaattacag   1560
tgtggcacag tcgtctctat cctgggggga gctcactttg gagagggaaa tggacagatc   1620
tgggctgaag aattccagtg tgagggacat gagtcccatc tttcactctg cccagtagca   1680
ccccgcccag aaggaacttg tagccacagc agggatgttg gagtagtctg ctcaagatac   1740
acagaaattc gcttggtgaa tggcaagacc ccatgtgagg gcagagtgga gctcaaaacg   1800
cttaatgcct ggggatccct ctgcaactct cactgggaca tagaagatgc ccacgttctt   1860
tgccaacaac ttaaatgtgg agttgccctt tctaccccag gaggagcaca ttttggaaaa   1920
ggaaatggtc aggtctggag gcatatgttt cactgcactg ggactgagca gcacatggga   1980
gattgtcctg taactgctct gggtgcttca ctatgtcctt cagggcaagt ggcctctgta   2040
atttgctcag gaaaccagtc ccaaacactg tcctcgtgca attcatcatc tctgggccca   2100
acaaggccta ccattccaga agaaagtgct gtggcctgca tagagagtgg tcaacttcgc   2160
ttggtaaatg gaggaggtcg ctgtgctggg agagtagaga tttatcatga gggctcctgg   2220
ggcaccatct gtgatgacag ctgggacctg agcgatgccc acgtggtgtg cagacagctg   2280
ggctgtggag aggccattaa tgccactggt tctgctcatt ttggagaagg aacagggccc   2340
atctggctgg atgagatgaa atgcaatgga aaagaatccc gtatttggca gtgccattca   2400
catggctggg ggcagcaaaa ctgcaggcac aaggaggatg caggagttat ctgctcagag   2460
ttcatgtctc tgagactgac cagtgaagcc agcagagagg cctgtgcagg gcgtctagaa   2520
gtttttttaca acggagcttg gggcagtgtt ggcaggagta acatgtctga aaccactgtg   2580
ggtgtggtgt gcaggcagct gggctgtgca gacaaaggga aaatcaactc tgcatcttta   2640
gacaaggcca tgtccattcc catgtgggtg gacaatgttc agtgtccaaa aggacctgac   2700
acgctgtggc agtgcccatc atctccatgg gagaagagac tggccaggcc ctcggaggag   2760
acctggatca catgtgacaa caagatgaga ctacaagaag gacccacttc ctgttctgga   2820
cgtgtggaga tctggcacgg aggttcctgg gggacagtgt gtgatgactc ctgggacttg   2880
aacgatgctc aggtggtgtg tcaacaactt ggctgtggtc cagctttgaa agcattcaaa   2940
gaagcagagt ttggtcaggg gactggaccc atatggctca atgaagtgaa gtgcaaaggg   3000
aatgagtctt ccttgtggga ttgtcctgcc agacgctggg gccacagtga gtgtggacac   3060
aaggaagacg ctgcagtgaa ttgcacagca caaaaaaattt caacgcacaa aaccccacaa  3120
aaagccacaa caggtcagtc attccttatt gcattcggaa tccttggagt tgttctcttg   3180
gccattttcg tcgcattatt cttgactcaa aagcgaagac agagacagcg gcttacagtt   3240
tcctcaagag gagagaactt agtccaccaa attcaatacc gggagatgaa ttcttgcctg   3300
aatgcagatg atctggacct aatgaattcc tcagaaaatt ccaatgagtc agctgatttc   3360
aatgctgctg aactaatttc tgtgtctaaa tttcttccta tttctggaat ggaaaaggag   3420
gccattctga ggcacactga aaaggaaaat gggaattta                          3459
```

<210> SEQ ID NO 44
<211> LENGTH: 1153
<212> TYPE: PRT
<213> ORGANISM: African Green Monkey

<400> SEQUENCE: 44

```
Met Ser Lys Leu Arg Met Val Leu Leu Glu Asp Ser Gly Ser Ala Asp
1               5                   10                  15

Val Arg Arg His Phe Val Asn Leu Ser Pro Phe Thr Ile Ala Val Val
            20                  25                  30

Leu Leu Leu Arg Ala Cys Phe Val Thr Ser Ser Leu Gly Gly Thr Thr
        35                  40                  45

Lys Glu Leu Arg Leu Val Asp Gly Glu Asn Lys Cys Ser Gly Arg Val
    50                  55                  60

Glu Val Lys Ile Gln Glu Glu Trp Gly Thr Val Cys Asn Asn Gly Trp
65                  70                  75                  80

Ser Met Glu Ala Val Ser Val Ile Cys Asn Gln Leu Gly Cys Pro Thr
                85                  90                  95

Ala Ile Lys Ala Thr Gly Trp Ala Asn Ser Ser Ala Gly Ser Gly Arg
            100                 105                 110

Ile Trp Met Asp His Val Ser Cys Arg Gly Asn Glu Ser Ala Leu Trp
        115                 120                 125

Asp Cys Lys His Asp Gly Trp Gly Lys His Ser Asn Cys Thr His Gln
    130                 135                 140

Gln Asp Ala Gly Val Thr Cys Ser Asp Gly Ser Asp Leu Glu Met Arg
145                 150                 155                 160

Leu Thr Asn Gly Gly Asn Met Cys Ser Gly Arg Ile Glu Ile Lys Phe
                165                 170                 175

Gln Gly Gln Trp Gly Thr Val Cys Asp Asp Asn Phe Asn Ile Asn His
            180                 185                 190

Ala Ser Val Val Cys Lys Gln Leu Glu Cys Gly Ser Ala Val Ser Phe
        195                 200                 205

Ser Gly Ser Ala Asn Phe Gly Glu Gly Ser Gly Pro Ile Trp Phe Asp
    210                 215                 220

Asp Leu Ile Cys Asn Gly Asn Glu Ser Ala Leu Trp Asn Cys Lys His
225                 230                 235                 240

Gln Gly Trp Gly Lys His Asn Cys Asp His Ala Glu Asp Ala Gly Val
                245                 250                 255

Ile Cys Ser Lys Gly Ala Asp Leu Ser Leu Arg Leu Val Asp Gly Val
            260                 265                 270

Thr Glu Cys Ser Gly Arg Leu Glu Val Arg Phe Gln Gly Glu Trp Gly
        275                 280                 285

Thr Ile Cys Asp Asp Gly Trp Asp Ser His Asp Ala Ala Val Ala Cys
    290                 295                 300

Lys Gln Leu Gly Cys Pro Thr Ala Ile Thr Ala Ile Gly Arg Val Asn
305                 310                 315                 320

Ala Ser Glu Gly Phe Gly His Ile Trp Leu Asp Ser Val Ser Cys Gln
                325                 330                 335

Gly His Glu Pro Ala Val Trp Gln Cys Lys His His Glu Trp Gly Lys
            340                 345                 350

His Tyr Cys Asn His Asn Glu Asp Ala Gly Val Thr Cys Ser Asp Gly
        355                 360                 365

Ser Asp Leu Glu Leu Arg Leu Arg Gly Gly Gly Ser Arg Cys Ala Gly
    370                 375                 380

Thr Val Glu Val Glu Ile Gln Arg Leu Leu Gly Lys Val Cys Asp Arg
385                 390                 395                 400

Gly Trp Gly Leu Lys Glu Ala Asp Val Val Cys Arg Gln Leu Gly Cys
                405                 410                 415
```

```
Gly Ser Ala Leu Lys Thr Ser Tyr Gln Val Tyr Ser Lys Ile Gln Ala
            420                 425                 430

Thr Asn Met Trp Leu Phe Leu Ser Ser Cys Asn Gly Asn Glu Thr Ser
        435                 440                 445

Leu Trp Asp Cys Lys Asn Trp Gln Trp Gly Gly Leu Thr Cys Asp His
    450                 455                 460

Tyr Glu Glu Ala Lys Ile Thr Cys Ser Ala His Arg Glu Pro Arg Leu
465                 470                 475                 480

Val Gly Gly Asp Ile Pro Cys Ser Gly Arg Val Glu Val Lys His Gly
                485                 490                 495

Asp Thr Trp Gly Ser Val Cys Asp Ser Asp Phe Ser Leu Glu Ala Ala
            500                 505                 510

Ser Val Leu Cys Arg Glu Leu Gln Cys Gly Thr Val Val Ser Ile Leu
        515                 520                 525

Gly Gly Ala His Phe Gly Glu Gly Asn Gly Gln Ile Trp Ala Glu Glu
    530                 535                 540

Phe Gln Cys Glu Gly His Glu Ser His Leu Ser Leu Cys Pro Val Ala
545                 550                 555                 560

Pro Arg Pro Glu Gly Thr Cys Ser His Ser Arg Asp Val Gly Val Val
                565                 570                 575

Cys Ser Arg Tyr Thr Glu Ile Arg Leu Val Asn Gly Lys Thr Pro Cys
            580                 585                 590

Glu Gly Arg Val Glu Leu Lys Thr Leu Asn Ala Trp Gly Ser Leu Cys
        595                 600                 605

Asn Ser His Trp Asp Ile Glu Asp Ala His Val Leu Cys Gln Gln Leu
    610                 615                 620

Lys Cys Gly Val Ala Leu Ser Thr Pro Gly Gly Ala His Phe Gly Lys
625                 630                 635                 640

Gly Asn Gly Gln Val Trp Arg His Met Phe His Cys Thr Gly Thr Glu
                645                 650                 655

Gln His Met Gly Asp Cys Pro Val Thr Ala Leu Gly Ala Ser Leu Cys
            660                 665                 670

Pro Ser Gly Gln Val Ala Ser Val Ile Cys Ser Gly Asn Gln Ser Gln
        675                 680                 685

Thr Leu Ser Ser Cys Asn Ser Ser Ser Leu Gly Pro Thr Arg Pro Thr
    690                 695                 700

Ile Pro Glu Glu Ser Ala Val Ala Cys Ile Glu Ser Gly Gln Leu Arg
705                 710                 715                 720

Leu Val Asn Gly Gly Gly Arg Cys Ala Gly Arg Val Glu Ile Tyr His
                725                 730                 735

Glu Gly Ser Trp Gly Thr Ile Cys Asp Asp Ser Trp Asp Leu Ser Asp
            740                 745                 750

Ala His Val Val Cys Arg Gln Leu Gly Cys Gly Glu Ala Ile Asn Ala
        755                 760                 765

Thr Gly Ser Ala His Phe Gly Glu Gly Thr Gly Pro Ile Trp Leu Asp
    770                 775                 780

Glu Met Lys Cys Asn Gly Lys Glu Ser Arg Ile Trp Gln Cys His Ser
785                 790                 795                 800

His Gly Trp Gly Gln Gln Asn Cys Arg His Lys Glu Asp Ala Gly Val
                805                 810                 815

Ile Cys Ser Glu Phe Met Ser Leu Arg Leu Thr Ser Glu Ala Ser Arg
            820                 825                 830

Glu Ala Cys Ala Gly Arg Leu Glu Val Phe Tyr Asn Gly Ala Trp Gly
```

```
        835                 840                 845

Ser Val Gly Arg Ser Asn Met Ser Glu Thr Thr Val Gly Val Val Cys
    850                 855                 860

Arg Gln Leu Gly Cys Ala Asp Lys Gly Lys Ile Asn Ser Ala Ser Leu
865                 870                 875                 880

Asp Lys Ala Met Ser Ile Pro Met Trp Val Asp Asn Val Gln Cys Pro
                885                 890                 895

Lys Gly Pro Asp Thr Leu Trp Gln Cys Pro Ser Ser Pro Trp Glu Lys
            900                 905                 910

Arg Leu Ala Arg Pro Ser Glu Glu Thr Trp Ile Thr Cys Asp Asn Lys
        915                 920                 925

Met Arg Leu Gln Glu Gly Pro Thr Ser Cys Ser Gly Arg Val Glu Ile
    930                 935                 940

Trp His Gly Gly Ser Trp Gly Thr Val Cys Asp Asp Ser Trp Asp Leu
945                 950                 955                 960

Asn Asp Ala Gln Val Val Cys Gln Gln Leu Gly Cys Gly Pro Ala Leu
                965                 970                 975

Lys Ala Phe Lys Glu Ala Glu Phe Gly Gln Gly Thr Gly Pro Ile Trp
            980                 985                 990

Leu Asn Glu Val Lys Cys Lys Gly  Asn Glu Ser Ser Leu  Trp Asp Cys
        995                 1000                1005

Pro Ala  Arg Arg Trp Gly His  Ser Glu Cys Gly His  Lys Glu Asp
    1010                1015                1020

Ala Ala  Val Asn Cys Thr Ala  Gln Lys Ile Ser Thr  His Lys Thr
    1025                1030                1035

Pro Gln  Lys Ala Thr Thr Gly  Gln Ser Phe Leu Ile  Ala Phe Gly
    1040                1045                1050

Ile Leu  Gly Val Val Leu Leu  Ala Ile Phe Val Ala  Leu Phe Leu
    1055                1060                1065

Thr Gln  Lys Arg Arg Gln Arg  Gln Arg Leu Thr Val  Ser Ser Arg
    1070                1075                1080

Gly Glu  Asn Leu Val His Gln  Ile Gln Tyr Arg Glu  Met Asn Ser
    1085                1090                1095

Cys Leu  Asn Ala Asp Asp Leu  Asp Leu Met Asn Ser  Ser Glu Asn
    1100                1105                1110

Ser Asn  Glu Ser Ala Asp Phe  Asn Ala Ala Glu Leu  Ile Ser Val
    1115                1120                1125

Ser Lys  Phe Leu Pro Ile Ser  Gly Met Glu Lys Glu  Ala Ile Leu
    1130                1135                1140

Arg His  Thr Glu Lys Glu Asn  Gly Asn Leu
    1145                1150
```

<210> SEQ ID NO 45
<211> LENGTH: 3345
<212> TYPE: DNA
<213> ORGANISM: Canis familiaris

<400> SEQUENCE: 45

```
atgagcaaac tcagaatggt cccacatgga aactctggat ctgctgactt tagaagatgt      60

tttgccctct tgtgtccctc tgctgtggct gtggtctcca ttctcagtac ctgtttgatg     120

accaattctc ttgggagagc agataaagag atgaggctaa cggatggtga agacaattgc     180

tccgggagag tggaagtgaa agtccaggag gagtggggaa cggtgtgtaa taatggctgg     240

ggcatggatg aagtctctgt gatttgcagg cagctgggat gtcccactgc tatcaaagcc     300
```

-continued

```
gctggatggg ccaattccag ggcaggctct ggacgaatct ggatggatca tgtttcttgt    360
cgagggaatg aatctgctct ctgggactgc aaacatgatg gatggggaaa gcacaactgc    420
agtcatcaac aggatgctgg agtaacctgt tcagatggat ccagtttgga gatgaggttg    480
atgaacggcg gaaaccagtg ttctggcaga atagaagtca agttccaggg acagtgggga    540
acagtgtgtg atgacaactt caacatagat catgcttctg tggtttgtaa acagctcgaa    600
tgtggaagtg ctgtcagttt ctctggttca gctaattttg gagaaggttc tgggccaatc    660
tggtttgatg atcttgtgtg cagtggaaat gagtcagctc tctggaactg caagcatgaa    720
ggatggggaa agcataactg tgatcacgct gaggatgttg gagtgatttg cttggatgga    780
gcagatctga gcctgagact ggtagatgga gtcactgaat gttcaggaag attagaagta    840
aaattccaag gggaatgggg gacagtgtgt gatgatggct gggatagtaa tgatgctgct    900
gtggtatgta aacaactggg atgcccaact gctgtcaccg ccattggtcg agttaacgcc    960
agtgagggaa gtggacacat ttggcttgac aatctttcct gccaaggaga cgaatctgct   1020
ctctggcagt gtagacacca tgaatgggga aagcattatt gcaatcataa tgaagatgct   1080
ggtgtgacat gttctgatgg atcagacctg gagctgagac ttgtcggtgg aggcagccgc   1140
tgtgctggga cagtggaggt tgaaattcag aaactgctag ggaaagtatg tgatagaggc   1200
tggggactga aagaagccga tgtggtttgc aagcagttgg gatgtggatc tgctctcaaa   1260
acgtcctatc agcgttattc caaagttaag gcaacaaaca catggctgtt tttaagccgc   1320
tgtagtggca atgaaacttc cctttgggac tgcaagaact ggcagtgggg tggactgagc   1380
tgtgatcact atgaagaagc taaagttacc tgctcagccc acagggaacc cagactagtt   1440
ggaggagata ttccctgctc tggtcgtgtt gaagtgaaac atggtgacac atggggcacc   1500
gtctgtgatt ccgacttctc tttggaagct gccagtgtgc tgtgcagaga gttacagtgt   1560
ggcacagtca tctccatcct aggggggagct cactttggag aaggaaatgg acagatctgg   1620
gctgaagaat tccagtgtga ggggcaggag tcccatcttt cactctgttc agtagcctct   1680
cgcccagatg ggacctgtag ccacagcagg gatgttggag tcgtctgctc aagatacacg   1740
gaaatccgct tggtgaatgg ccagtccccg tgtgaaggaa gagtggagct caagatactt   1800
gggaactggg gatccctctg caactctcac tgggacatag aagatgccca tgttttctgt   1860
cagcagctca aatgtggagt tgccctttct attccgggag gagcacattt tgggaaagga   1920
agtggtcaga tctggaggca catgtttcac tgcactggga ctgagcagca catgggagat   1980
tgccctgtaa ctgctctggg cgcgacgctg tgttctgctg ggcaagtggc ctctgtaatc   2040
tgctcaggaa atcagagcca gacgctatcc ccatgcaatt caacatctct ggacccaaca   2100
agatctacca cttcggaaga aagtgctgtt gcttgtattg cgagtgggca acttcgcctg   2160
gtaaatggag gcggtcgctg tgctgggaga atagaggtct accatgaggg ctcctggggc   2220
accatctgtg atgacagctg ggacctgagt gatgcccatg tggtgtgcag acagctgggc   2280
tgtggagtgg ccattaatgc cactggctct gctcattttg ggaaggaac agggcccatc   2340
tggctggacg aggtgaactg taatggaaag gaatctcata tctggcaatg ccgctcacac   2400
ggctgggggc aacacaactg cagacataag gaggatgcag gagttatctg ctcagagttc   2460
atgtctctca gactgattga tgaaaccagc agagacatct gtgcagggcg tcttgaagtt   2520
ttttacaatg gagcttgggg cagcgttggc aagagtaata tgtctgcaac cactgtggag   2580
gtggtatgca ggcaactggg ttgtgcagac aaggggagca tcaaccctgc atcttcagac   2640
aagcccatgt ccaggcacat gtgggtggac aatgtccagt gtccaaaagg acctgacacc   2700
```

```
ttatggcagt gcccatcttc tccatggaaa cagagagtgg ccagttcttc agaggagacc   2760

tggatcacat gtgccaacaa gataagactt caagaaggaa cctctaattg ttctggacgt   2820

gtggagctct ggcacggagg ttcctggggg acagtgtgcg atgactcctg ggaccttgaa   2880

gatgcacaag tggtgtgtcg acagctgggc tgtggcccag cattagaagc actaaaagag   2940

gcagcatttg gtcaggggac tgggcctata tggctcaatg acgtgaagtg caaagggaat   3000

gagtcttcct tgtgggattg tcctgctaga ccctgggggc acagtgactg tggccacaag   3060

gaagatgctg ctgtgaggtg ctcagaaatt gcaatggccc aaagatcatc aaatcctaga   3120

ggtcactcat cccttgttgc attggggatc tttggtgtca ttcttctggc ctttctcatc   3180

gctctcctct tgtggactca aaggcgaaga cagcaacagc ggcttacagt ttccttgaga   3240

ggagagaatt ctgtccacca aattcaatac cgggaaatga attcttccct gaaagcagat   3300

gatctggacg tgctgacttc ctcagaagac cattttgagg tacac                   3345
```

<210> SEQ ID NO 46
<211> LENGTH: 1115
<212> TYPE: PRT
<213> ORGANISM: Canis familiaris

<400> SEQUENCE: 46

```
Met Ser Lys Leu Arg Met Val Pro His Gly Asn Ser Gly Ser Ala Asp
1               5                   10                  15

Phe Arg Arg Cys Phe Ala Leu Leu Cys Pro Ser Ala Val Ala Val Val
            20                  25                  30

Ser Ile Leu Ser Thr Cys Leu Met Thr Asn Ser Leu Gly Arg Ala Asp
        35                  40                  45

Lys Glu Met Arg Leu Thr Asp Gly Glu Asp Asn Cys Ser Gly Arg Val
    50                  55                  60

Glu Val Lys Val Gln Glu Glu Trp Gly Thr Val Cys Asn Asn Gly Trp
65                  70                  75                  80

Gly Met Asp Glu Val Ser Val Ile Cys Arg Gln Leu Gly Cys Pro Thr
                85                  90                  95

Ala Ile Lys Ala Ala Gly Trp Ala Asn Ser Arg Ala Gly Ser Gly Arg
            100                 105                 110

Ile Trp Met Asp His Val Ser Cys Arg Gly Asn Glu Ser Ala Leu Trp
        115                 120                 125

Asp Cys Lys His Asp Gly Trp Gly Lys His Asn Cys Ser His Gln Gln
    130                 135                 140

Asp Ala Gly Val Thr Cys Ser Asp Gly Ser Ser Leu Glu Met Arg Leu
145                 150                 155                 160

Met Asn Gly Gly Asn Gln Cys Ser Gly Arg Ile Glu Val Lys Phe Gln
                165                 170                 175

Gly Gln Trp Gly Thr Val Cys Asp Asp Asn Phe Asn Ile Asp His Ala
            180                 185                 190

Ser Val Val Cys Lys Gln Leu Glu Cys Gly Ser Ala Val Ser Phe Ser
        195                 200                 205

Gly Ser Ala Asn Phe Gly Glu Gly Ser Gly Pro Ile Trp Phe Asp Asp
    210                 215                 220

Leu Val Cys Ser Gly Asn Glu Ser Ala Leu Trp Asn Cys Lys His Glu
225                 230                 235                 240

Gly Trp Gly Lys His Asn Cys Asp His Ala Glu Asp Val Gly Val Ile
                245                 250                 255

Cys Leu Asp Gly Ala Asp Leu Ser Leu Arg Leu Val Asp Gly Val Thr
            260                 265                 270
```

```
Glu Cys Ser Gly Arg Leu Glu Val Lys Phe Gln Gly Glu Trp Gly Thr
        275                 280                 285

Val Cys Asp Asp Gly Trp Asp Ser Asn Asp Ala Ala Val Val Cys Lys
    290                 295                 300

Gln Leu Gly Cys Pro Thr Ala Val Thr Ala Ile Gly Arg Val Asn Ala
305                 310                 315                 320

Ser Glu Gly Ser Gly His Ile Trp Leu Asp Asn Leu Ser Cys Gln Gly
                325                 330                 335

Asp Glu Ser Ala Leu Trp Gln Cys Arg His His Glu Trp Gly Lys His
            340                 345                 350

Tyr Cys Asn His Asn Glu Asp Ala Gly Val Thr Cys Ser Asp Gly Ser
        355                 360                 365

Asp Leu Glu Leu Arg Leu Val Gly Gly Gly Ser Arg Cys Ala Gly Thr
    370                 375                 380

Val Glu Val Glu Ile Gln Lys Leu Leu Gly Lys Val Cys Asp Arg Gly
385                 390                 395                 400

Trp Gly Leu Lys Glu Ala Asp Val Val Cys Lys Gln Leu Gly Cys Gly
                405                 410                 415

Ser Ala Leu Lys Thr Ser Tyr Gln Arg Tyr Ser Lys Val Lys Ala Thr
            420                 425                 430

Asn Thr Trp Leu Phe Leu Ser Arg Cys Ser Gly Asn Glu Thr Ser Leu
        435                 440                 445

Trp Asp Cys Lys Asn Trp Gln Trp Gly Gly Leu Ser Cys Asp His Tyr
    450                 455                 460

Glu Glu Ala Lys Val Thr Cys Ser Ala His Arg Glu Pro Arg Leu Val
465                 470                 475                 480

Gly Gly Asp Ile Pro Cys Ser Gly Arg Val Glu Val Lys His Gly Asp
                485                 490                 495

Thr Trp Gly Thr Val Cys Asp Ser Asp Phe Ser Leu Glu Ala Ala Ser
            500                 505                 510

Val Leu Cys Arg Glu Leu Gln Cys Gly Thr Val Ile Ser Ile Leu Gly
        515                 520                 525

Gly Ala His Phe Gly Glu Gly Asn Gly Gln Ile Trp Ala Glu Glu Phe
    530                 535                 540

Gln Cys Glu Gly Gln Glu Ser His Leu Ser Leu Cys Ser Val Ala Ser
545                 550                 555                 560

Arg Pro Asp Gly Thr Cys Ser His Ser Arg Asp Val Gly Val Val Cys
                565                 570                 575

Ser Arg Tyr Thr Glu Ile Arg Leu Val Asn Gly Gln Ser Pro Cys Glu
            580                 585                 590

Gly Arg Val Glu Leu Lys Ile Leu Gly Asn Trp Gly Ser Leu Cys Asn
        595                 600                 605

Ser His Trp Asp Ile Glu Asp Ala His Val Phe Cys Gln Gln Leu Lys
    610                 615                 620

Cys Gly Val Ala Leu Ser Ile Pro Gly Gly Ala His Phe Gly Lys Gly
625                 630                 635                 640

Ser Gly Gln Ile Trp Arg His Met Phe His Cys Thr Gly Thr Glu Gln
                645                 650                 655

His Met Gly Asp Cys Pro Val Thr Ala Leu Gly Ala Thr Leu Cys Ser
            660                 665                 670

Ala Gly Gln Val Ala Ser Val Ile Cys Ser Gly Asn Gln Ser Gln Thr
        675                 680                 685

Leu Ser Pro Cys Asn Ser Thr Ser Leu Asp Pro Thr Arg Ser Thr Thr
```

```
    690                 695                 700

Ser Glu Glu Ser Ala Val Ala Cys Ile Ala Ser Gly Gln Leu Arg Leu
705                 710                 715                 720

Val Asn Gly Gly Gly Arg Cys Ala Gly Arg Ile Glu Val Tyr His Glu
                725                 730                 735

Gly Ser Trp Gly Thr Ile Cys Asp Asp Ser Trp Asp Leu Ser Asp Ala
            740                 745                 750

His Val Val Cys Arg Gln Leu Gly Cys Gly Val Ala Ile Asn Ala Thr
        755                 760                 765

Gly Ser Ala His Phe Gly Glu Gly Thr Gly Pro Ile Trp Leu Asp Glu
    770                 775                 780

Val Asn Cys Asn Gly Lys Glu Ser His Ile Trp Gln Cys Arg Ser His
785                 790                 795                 800

Gly Trp Gly Gln His Asn Cys Arg His Lys Glu Asp Ala Gly Val Ile
                805                 810                 815

Cys Ser Glu Phe Met Ser Leu Arg Leu Ile Asp Glu Thr Ser Arg Asp
            820                 825                 830

Ile Cys Ala Gly Arg Leu Glu Val Phe Tyr Asn Gly Ala Trp Gly Ser
        835                 840                 845

Val Gly Lys Ser Asn Met Ser Ala Thr Thr Val Glu Val Val Cys Arg
    850                 855                 860

Gln Leu Gly Cys Ala Asp Lys Gly Ser Ile Asn Pro Ala Ser Ser Asp
865                 870                 875                 880

Lys Pro Met Ser Arg His Met Trp Val Asp Asn Val Gln Cys Pro Lys
                885                 890                 895

Gly Pro Asp Thr Leu Trp Gln Cys Pro Ser Ser Pro Trp Lys Gln Arg
            900                 905                 910

Val Ala Ser Ser Ser Glu Glu Thr Trp Ile Thr Cys Ala Asn Lys Ile
        915                 920                 925

Arg Leu Gln Glu Gly Thr Ser Asn Cys Ser Gly Arg Val Glu Leu Trp
    930                 935                 940

His Gly Gly Ser Trp Gly Thr Val Cys Asp Asp Ser Trp Asp Leu Glu
945                 950                 955                 960

Asp Ala Gln Val Val Cys Arg Gln Leu Gly Cys Gly Pro Ala Leu Glu
                965                 970                 975

Ala Leu Lys Glu Ala Ala Phe Gly Gln Gly Thr Gly Pro Ile Trp Leu
            980                 985                 990

Asn Asp Val Lys Cys Lys Gly Asn  Glu Ser Ser Leu Trp  Asp Cys Pro
        995                 1000                1005

Ala Arg  Pro Trp Gly His Ser  Asp Cys Gly His Lys  Glu Asp Ala
    1010                1015                1020

Ala Val  Arg Cys Ser Glu Ile  Ala Met Ala Gln Arg  Ser Ser Asn
    1025                1030                1035

Pro Arg  Gly His Ser Ser Leu  Val Ala Leu Gly Ile  Phe Gly Val
    1040                1045                1050

Ile Leu  Leu Ala Phe Leu Ile  Ala Leu Leu Leu Trp  Thr Gln Arg
    1055                1060                1065

Arg Arg  Gln Gln Gln Arg Leu  Thr Val Ser Leu Arg  Gly Glu Asn
    1070                1075                1080

Ser Val  His Gln Ile Gln Tyr  Arg Glu Met Asn Ser  Ser Leu Lys
    1085                1090                1095

Ala Asp  Asp Leu Asp Val Leu  Thr Ser Ser Glu Asp  His Phe Glu
    1100                1105                1110
```

Val His
1115

<210> SEQ ID NO 47
<211> LENGTH: 3399
<212> TYPE: DNA
<213> ORGANISM: Canis familiaris

<400> SEQUENCE: 47
atgagcaaac tcagaatggt cccacatgga aactctggat ctgctgactt tagaagatgt 60
tttgccctct tgtgtccctc tgctgtggct gtggtctcca ttctcagtac ctgtttgatg 120
accaattctc ttgggagagc agataaagag atgaggctaa cggatggtga agacaattgc 180
tccgggagag tggaagtgaa agtccaggag gagtggggaa cggtgtgtaa taatggctgg 240
ggcatggatg aagtctctgt gatttgcagg cagctgggat gtcccactgc tatcaaagcc 300
gctggatggg ccaattccag ggcaggctct ggacgaatct ggatggatca tgtttcttgt 360
cgagggaatg aatctgctct ctgggactgc aaacatgatg gatggggaaa gcacaactgc 420
agtcatcaac aggatgctgg agtaacctgt tcagatggat ccagtttgga gatgaggttg 480
atgaacggcg gaaaccagtg ttctggcaga atagaagtca agttccaggg acagtgggga 540
acagtgtgtg atgacaactt caacatagat catgcttctg tggtttgtaa acagctcgaa 600
tgtggaagtg ctgtcagttt ctctggttca gctaattttg gagaaggttc tgggccaatc 660
tggtttgatg atcttgtgtg cagtggaaat gagtcagctc tctggaactg caagcatgaa 720
ggatggggaa agcataactg tgatcacgct gaggatgttg gagtgatttg cttggatgga 780
gcagatctga gcctgagact ggtagatgga gtcactgaat gttcaggaag attagaagta 840
aaattccaag gggaatgggg gacagtgtgt gatgatggct gggatagtaa tgatgctgct 900
gtggtatgta aacaactggg atgcccaact gctgtcaccg ccattggtcg agttaacgcc 960
agtgagggaa gtggacacat ttggcttgac aatctttcct gccaaggaga cgaatctgct 1020
ctctggcagt gtagacacca tgaatgggga aagcattatt gcaatcataa tgaagatgct 1080
ggtgtgacat gttctgatgg atcagacctg gagctgagac ttgtcggtgg aggcagccgc 1140
tgtgctggga cagtggaggt tgaaattcag aaactgctag ggaaagtatg tgatagaggc 1200
tggggactga aagaagccga tgtggtttgc aagcagttgg gatgtggatc tgctctcaaa 1260
acgtcctatc agcgttattc caaagttaag gcaacaaaca catggctgtt tttaagccgc 1320
tgtagtggca atgaaacttc cctttgggac tgcaagaact ggcagtgggg tggactgagc 1380
tgtgatcact atgaagaagc taaagttacc tgctcagccc acagggaacc cagactagtt 1440
ggaggagata ttccctgctc tggtcgtgtt gaagtgaaac atggtgacac atggggcacc 1500
gtctgtgatt ccgacttctc tttggaagct gccagtgtgc tgtgcagaga gttacagtgt 1560
ggcacagtca tctccatcct agggggagct cactttggag aaggaaatgg acagatctgg 1620
gctgaagaat tccagtgtga ggggcaggag tcccatcttt cactctgttc agtagcctct 1680
cgcccagatg ggacctgtag ccacagcagg gatgttggag tcgtctgctc aagatacacg 1740
gaaatccgct tggtgaatgg ccagtccccg tgtgaaggaa gagtggagct caagatactt 1800
gggaactggg gatccctctg caactctcac tgggacatag aagatgccca tgttttctgt 1860
cagcagctca aatgtggagt tgccctttct attccgggag gagcacattt tgggaaagga 1920
agtggtcaga tctggaggca catgtttcac tgcactggga ctgagcagca catgggagat 1980
tgccctgtaa ctgctctggg cgcgacgctg tgttctgctg ggcaagtggc ctctgtaatc 2040
tgctcaggaa atcagagcca gacgctatcc ccatgcaatt caacatctct ggacccaaca 2100

```
agatctacca cttcggaaga aagtgctgtt gcttgtattg cgagtgggca acttcgcctg   2160

gtaaatggag gcggtcgctg tgctgggaga atagaggtct accatgaggg ctcctggggc   2220

accatctgtg atgacagctg ggacctgagt gatgcccatg tggtgtgcag acagctgggc   2280

tgtggagtgg ccattaatgc cactggctct gctcattttg ggaaggaac agggcccatc   2340

tggctggacg aggtgaactg taatggaaag gaatctcata tctggcaatg ccgctcacac   2400

ggctgggggc aacacaactg cagacataag gaggatgcag gagttatctg ctcagagttc   2460

atgtctctca gactgattga tgaaaccagc agagacatct gtgcagggcg tcttgaagtt   2520

ttttacaatg gagcttgggg cagcgttggc aagagtaata tgtctgcaac cactgtggag   2580

gtggtatgca ggcaactggg ttgtgcagac aaggggagca tcaaccctgc atcttcagac   2640

aagcccatgt ccaggcacat gtgggtggac aatgtccagt gtccaaaagg acctgacacc   2700

ttatggcagt gcccatcttc tccatggaaa cagagagtgg ccagttcttc agaggagacc   2760

tggatcacat gtgccaacaa gataagactt caagaaggaa cctctaattg ttctggacgt   2820

gtggagctct ggcacggagg ttcctggggg acagtgtgcg atgactcctg ggaccttgaa   2880

gatgcacaag tggtgtgtcg acagctgggc tgtggcccag cattagaagc actaaaagag   2940

gcagcatttg gtcaggggac tgggcctata tggctcaatg acgtgaagtg caaagggaat   3000

gagtcttcct tgtgggattg tcctgctaga ccctgggggc acagtgactg tggccacaag   3060

gaagatgctg ctgtgaggtg ctcagaaatt gcaatggccc aaagatcatc aaatcctaga   3120

ggtcactcat cccttgttgc attggggatc tttggtgtca ttcttctggc ctttctcatc   3180

gctctcctct tgtggactca aaggcgaaga cagcaacagc ggcttacagt ttccttgaga   3240

ggagagaatt ctgtccacca aattcaatac cgggaaatga attcttccct gaaagcagat   3300

gatctggacg tgctgacttc ctcagaatat cccaatgagt cagatgattt taatgatgct   3360

gggctaattt ctgtgtctaa atctcttcct atttctgga                          3399
```

<210> SEQ ID NO 48
<211> LENGTH: 1133
<212> TYPE: PRT
<213> ORGANISM: Canis familiaris

<400> SEQUENCE: 48

```
Met Ser Lys Leu Arg Met Val Pro His Gly Asn Ser Gly Ser Ala Asp
1               5                   10                  15

Phe Arg Arg Cys Phe Ala Leu Leu Cys Pro Ser Ala Val Ala Val Val
            20                  25                  30

Ser Ile Leu Ser Thr Cys Leu Met Thr Asn Ser Leu Gly Arg Ala Asp
        35                  40                  45

Lys Glu Met Arg Leu Thr Asp Gly Glu Asp Asn Cys Ser Gly Arg Val
    50                  55                  60

Glu Val Lys Val Gln Glu Glu Trp Gly Thr Val Cys Asn Asn Gly Trp
65                  70                  75                  80

Gly Met Asp Glu Val Ser Val Ile Cys Arg Gln Leu Gly Cys Pro Thr
                85                  90                  95

Ala Ile Lys Ala Ala Gly Trp Ala Asn Ser Arg Ala Gly Ser Gly Arg
            100                 105                 110

Ile Trp Met Asp His Val Ser Cys Arg Gly Asn Glu Ser Ala Leu Trp
        115                 120                 125

Asp Cys Lys His Asp Gly Trp Gly Lys His Asn Cys Ser His Gln Gln
    130                 135                 140
```

```
Asp Ala Gly Val Thr Cys Ser Asp Gly Ser Ser Leu Glu Met Arg Leu
145                 150                 155                 160

Met Asn Gly Gly Asn Gln Cys Ser Gly Arg Ile Glu Val Lys Phe Gln
                165                 170                 175

Gly Gln Trp Gly Thr Val Cys Asp Asp Asn Phe Asn Ile Asp His Ala
            180                 185                 190

Ser Val Val Cys Lys Gln Leu Glu Cys Gly Ser Ala Val Ser Phe Ser
        195                 200                 205

Gly Ser Ala Asn Phe Gly Glu Gly Ser Gly Pro Ile Trp Phe Asp Asp
    210                 215                 220

Leu Val Cys Ser Gly Asn Glu Ser Ala Leu Trp Asn Cys Lys His Glu
225                 230                 235                 240

Gly Trp Gly Lys His Asn Cys Asp His Ala Glu Asp Val Gly Val Ile
                245                 250                 255

Cys Leu Asp Gly Ala Asp Leu Ser Leu Arg Leu Val Asp Gly Val Thr
            260                 265                 270

Glu Cys Ser Gly Arg Leu Glu Val Lys Phe Gln Gly Glu Trp Gly Thr
        275                 280                 285

Val Cys Asp Asp Gly Trp Asp Ser Asn Asp Ala Ala Val Val Cys Lys
    290                 295                 300

Gln Leu Gly Cys Pro Thr Ala Val Thr Ala Ile Gly Arg Val Asn Ala
305                 310                 315                 320

Ser Glu Gly Ser Gly His Ile Trp Leu Asp Asn Leu Ser Cys Gln Gly
                325                 330                 335

Asp Glu Ser Ala Leu Trp Gln Cys Arg His His Glu Trp Gly Lys His
            340                 345                 350

Tyr Cys Asn His Asn Glu Asp Ala Gly Val Thr Cys Ser Asp Gly Ser
        355                 360                 365

Asp Leu Glu Leu Arg Leu Val Gly Gly Gly Ser Arg Cys Ala Gly Thr
    370                 375                 380

Val Glu Val Glu Ile Gln Lys Leu Leu Gly Lys Val Cys Asp Arg Gly
385                 390                 395                 400

Trp Gly Leu Lys Glu Ala Asp Val Val Cys Lys Gln Leu Gly Cys Gly
                405                 410                 415

Ser Ala Leu Lys Thr Ser Tyr Gln Arg Tyr Ser Lys Val Lys Ala Thr
            420                 425                 430

Asn Thr Trp Leu Phe Leu Ser Arg Cys Ser Gly Asn Glu Thr Ser Leu
        435                 440                 445

Trp Asp Cys Lys Asn Trp Gln Trp Gly Gly Leu Ser Cys Asp His Tyr
    450                 455                 460

Glu Glu Ala Lys Val Thr Cys Ser Ala His Arg Glu Pro Arg Leu Val
465                 470                 475                 480

Gly Gly Asp Ile Pro Cys Ser Gly Arg Val Glu Val Lys His Gly Asp
                485                 490                 495

Thr Trp Gly Thr Val Cys Asp Ser Asp Phe Ser Leu Glu Ala Ala Ser
            500                 505                 510

Val Leu Cys Arg Glu Leu Gln Cys Gly Thr Val Ile Ser Ile Leu Gly
        515                 520                 525

Gly Ala His Phe Gly Glu Gly Asn Gly Gln Ile Trp Ala Glu Glu Phe
    530                 535                 540

Gln Cys Glu Gly Gln Glu Ser His Leu Ser Leu Cys Ser Val Ala Ser
545                 550                 555                 560

Arg Pro Asp Gly Thr Cys Ser His Ser Arg Asp Val Gly Val Val Cys
                565                 570                 575
```

```
Ser Arg Tyr Thr Glu Ile Arg Leu Val Asn Gly Gln Ser Pro Cys Glu
            580                 585                 590

Gly Arg Val Glu Leu Lys Ile Leu Gly Asn Trp Gly Ser Leu Cys Asn
        595                 600                 605

Ser His Trp Asp Ile Glu Asp Ala His Val Phe Cys Gln Gln Leu Lys
    610                 615                 620

Cys Gly Val Ala Leu Ser Ile Pro Gly Gly Ala His Phe Gly Lys Gly
625                 630                 635                 640

Ser Gly Gln Ile Trp Arg His Met Phe His Cys Thr Gly Thr Glu Gln
                645                 650                 655

His Met Gly Asp Cys Pro Val Thr Ala Leu Gly Ala Thr Leu Cys Ser
            660                 665                 670

Ala Gly Gln Val Ala Ser Val Ile Cys Ser Gly Asn Gln Ser Gln Thr
        675                 680                 685

Leu Ser Pro Cys Asn Ser Thr Ser Leu Asp Pro Thr Arg Ser Thr Thr
    690                 695                 700

Ser Glu Glu Ser Ala Val Ala Cys Ile Ala Ser Gly Gln Leu Arg Leu
705                 710                 715                 720

Val Asn Gly Gly Gly Arg Cys Ala Gly Arg Ile Glu Val Tyr His Glu
                725                 730                 735

Gly Ser Trp Gly Thr Ile Cys Asp Asp Ser Trp Asp Leu Ser Asp Ala
            740                 745                 750

His Val Val Cys Arg Gln Leu Gly Cys Gly Val Ala Ile Asn Ala Thr
        755                 760                 765

Gly Ser Ala His Phe Gly Glu Gly Thr Gly Pro Ile Trp Leu Asp Glu
    770                 775                 780

Val Asn Cys Asn Gly Lys Glu Ser His Ile Trp Gln Cys Arg Ser His
785                 790                 795                 800

Gly Trp Gly Gln His Asn Cys Arg His Lys Glu Asp Ala Gly Val Ile
                805                 810                 815

Cys Ser Glu Phe Met Ser Leu Arg Leu Ile Asp Glu Thr Ser Arg Asp
            820                 825                 830

Ile Cys Ala Gly Arg Leu Glu Val Phe Tyr Asn Gly Ala Trp Gly Ser
        835                 840                 845

Val Gly Lys Ser Asn Met Ser Ala Thr Thr Val Glu Val Val Cys Arg
    850                 855                 860

Gln Leu Gly Cys Ala Asp Lys Gly Ser Ile Asn Pro Ala Ser Ser Asp
865                 870                 875                 880

Lys Pro Met Ser Arg His Met Trp Val Asp Asn Val Gln Cys Pro Lys
                885                 890                 895

Gly Pro Asp Thr Leu Trp Gln Cys Pro Ser Ser Pro Trp Lys Gln Arg
            900                 905                 910

Val Ala Ser Ser Ser Glu Glu Thr Trp Ile Thr Cys Ala Asn Lys Ile
        915                 920                 925

Arg Leu Gln Glu Gly Thr Ser Asn Cys Ser Gly Arg Val Glu Leu Trp
    930                 935                 940

His Gly Gly Ser Trp Gly Thr Val Cys Asp Asp Ser Trp Asp Leu Glu
945                 950                 955                 960

Asp Ala Gln Val Val Cys Arg Gln Leu Gly Cys Gly Pro Ala Leu Glu
                965                 970                 975

Ala Leu Lys Glu Ala Ala Phe Gly Gln Gly Thr Gly Pro Ile Trp Leu
            980                 985                 990

Asn Asp Val Lys Cys Lys Gly Asn  Glu Ser Ser Leu Trp  Asp Cys Pro
```

-continued

```
        995                 1000                1005

Ala Arg  Pro Trp Gly His Ser  Asp Cys Gly His Lys  Glu Asp Ala
    1010                 1015                1020

Ala Val  Arg Cys Ser Glu Ile  Ala Met Ala Gln Arg  Ser Ser Asn
    1025                 1030                1035

Pro Arg  Gly His Ser Ser Leu  Val Ala Leu Gly Ile  Phe Gly Val
    1040                 1045                1050

Ile Leu  Leu Ala Phe Leu Ile  Ala Leu Leu Leu Trp  Thr Gln Arg
    1055                 1060                1065

Arg Arg  Gln Gln Gln Arg Leu  Thr Val Ser Leu Arg  Gly Glu Asn
    1070                 1075                1080

Ser Val  His Gln Ile Gln Tyr  Arg Glu Met Asn Ser  Ser Leu Lys
    1085                 1090                1095

Ala Asp  Asp Leu Asp Val Leu  Thr Ser Ser Glu Tyr  Pro Asn Glu
    1100                 1105                1110

Ser Asp  Asp Phe Asn Asp Ala  Gly Leu Ile Ser Val  Ser Lys Ser
    1115                 1120                1125

Leu Pro  Ile Ser Gly
    1130
```